(12) United States Patent
Jaenisch et al.

(10) Patent No.: US 12,060,588 B2
(45) Date of Patent: Aug. 13, 2024

(54) METHODS OF EDITING DNA METHYLATION

(71) Applicant: Whitehead Institute for Biomedical Research, Cambridge, MA (US)

(72) Inventors: Rudolf Jaenisch, Brookline, MA (US); X. Shawn Liu, Cambridge, MA (US); Hao Wu, Newton, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 17/858,758

(22) Filed: Jul. 6, 2022

(65) Prior Publication Data
US 2023/0096554 A1    Mar. 30, 2023

Related U.S. Application Data

(62) Division of application No. 16/326,700, filed as application No. PCT/US2017/047674 on Aug. 18, 2017, now Pat. No. 11,434,476.

(60) Provisional application No. 62/377,520, filed on Aug. 19, 2016.

(51) Int. Cl.
| | | |
|---|---|---|
| *C12N 9/22* | (2006.01) | |
| *A61K 35/30* | (2015.01) | |
| *A61K 35/33* | (2015.01) | |
| *A61P 3/10* | (2006.01) | |
| *A61P 9/00* | (2006.01) | |
| *A61P 9/10* | (2006.01) | |
| *A61P 9/12* | (2006.01) | |
| *C12N 9/10* | (2006.01) | |
| *C12N 15/11* | (2006.01) | |
| *C12N 15/86* | (2006.01) | |
| *C12N 15/90* | (2006.01) | |

(52) U.S. Cl.
CPC ............... *C12N 9/22* (2013.01); *A61K 35/30* (2013.01); *A61K 35/33* (2013.01); *C12N 9/1007* (2013.01); *C12N 15/11* (2013.01); *C12N 15/86* (2013.01); *C12N 15/907* (2013.01); *C12Y 201/01037* (2013.01); *C12N 2310/20* (2017.05); *C12N 2740/15031* (2013.01); *C12N 2800/80* (2013.01)

(58) Field of Classification Search
None
See application file for complete search history.

(56) References Cited

U.S. PATENT DOCUMENTS

| | | |
|---|---|---|
| 6,780,986 B1 | 8/2004 | Heintz et al. |
| 8,513,207 B2 | 8/2013 | Brown |
| 9,801,877 B2 | 10/2017 | Yao et al. |
| 10,378,027 B2 | 8/2019 | Joung et al. |
| 11,312,955 B2 | 4/2022 | Berry et al. |
| 11,434,476 B2 | 9/2022 | Jaenisch et al. |
| 11,873,496 B2 | 1/2024 | Young et al. |
| 2008/0311039 A1 | 12/2008 | Bonavida et al. |
| 2009/0082470 A1 | 3/2009 | Farjo |
| 2012/0115227 A1 | 5/2012 | Cohen-Haguenauer et al. |
| 2014/0273226 A1 | 9/2014 | Wu |
| 2014/0322707 A1 | 10/2014 | He et al. |
| 2015/0071906 A1 | 3/2015 | Liu et al. |
| 2015/0353885 A1 | 12/2015 | Sourdive |
| 2015/0376612 A1 | 12/2015 | Lee et al. |
| 2016/0010076 A1 | 1/2016 | Joung et al. |
| 2016/0024474 A1 | 1/2016 | Conway et al. |
| 2016/0186208 A1 | 6/2016 | Jaenisch et al. |
| 2016/0215280 A1 | 7/2016 | Fanucchi et al. |
| 2016/0340749 A1 | 11/2016 | Stelzer et al. |
| 2017/0014449 A1 | 1/2017 | Bangera et al. |
| 2017/0130247 A1 | 5/2017 | Dowen et al. |
| 2017/0362649 A1 | 12/2017 | Lieberman-Aiden et al. |
| 2018/0245079 A1 | 8/2018 | Lieberman Aiden et al. |
| 2019/0024086 A1 | 1/2019 | Lande et al. |
| 2019/0127713 A1 | 5/2019 | Gersbach |
| 2019/0241964 A1 | 8/2019 | Hunter et al. |
| 2019/0309291 A1 | 10/2019 | Lee et al. |
| 2019/0352648 A1 | 11/2019 | Young et al. |
| 2019/0359959 A1 | 11/2019 | Jaenisch et al. |
| 2020/0002558 A1 | 1/2020 | Iwasaki et al. |
| 2020/0149039 A1 | 5/2020 | Schuijers et al. |
| 2020/0224274 A1 | 7/2020 | Bernstein et al. |
| 2024/0014133 A1 | 5/2024 | Schuijers et al. |

FOREIGN PATENT DOCUMENTS

| | | |
|---|---|---|
| EP | 3382018 A1 | 10/2018 |
| WO | WO-2006/025802 A1 | 3/2006 |
| WO | WO-2009/146033 A2 | 12/2009 |
| WO | WO-2012/019168 A3 | 7/2012 |
| WO | WO-2013176772 A1 | 11/2013 |
| WO | WO-2014/071247 A1 | 5/2014 |
| WO | WO-2014172470 A2 | 10/2014 |
| WO | WO-2015/033293 A1 | 3/2015 |

(Continued)

OTHER PUBLICATIONS

Kim, S., et al., "CTCF as a multifunctional protein in genome regulation and gene expression," *Experimental & Molecular Medicine*, 47, e166 (2015).

(Continued)

*Primary Examiner* — Manjunath N Rao
*Assistant Examiner* — Jae W Lee
(74) *Attorney, Agent, or Firm* — Morse, Barnes-Brown & Pendleton, P.C.; Lisa M. Warren, Esq.; Erin E. Bryan, Esq.

(57) ABSTRACT

The invention relates to methods of modifying DNA methylation by contacting a cell with a catalytically inactive site specific nuclease fused to an effector domain having methylation or demethylation activity and one or more guide sequences.

14 Claims, 48 Drawing Sheets
Specification includes a Sequence Listing.

(56) References Cited

FOREIGN PATENT DOCUMENTS

| | | |
|---|---|---|
| WO | WO-2015/038892 A1 | 3/2015 |
| WO | WO-2015/191780 A2 | 12/2015 |
| WO | WO-2015/196128 A2 | 12/2015 |
| WO | WO-2016/063264 A1 | 4/2016 |
| WO | WO-2016/022363 A3 | 5/2016 |
| WO | WO-2016/081798 A1 | 5/2016 |
| WO | WO-2016/070037 A3 | 6/2016 |
| WO | WO-2016103233 A2 | 6/2016 |
| WO | WO-2016/115326 A1 | 7/2016 |
| WO | WO-2016/073990 A3 | 8/2016 |
| WO | WO-2016130600 A2 | 8/2016 |
| WO | WO-2016/154330 A1 | 9/2016 |
| WO | WO-2016/164356 A1 | 10/2016 |
| WO | WO-2016/174250 A1 | 11/2016 |
| WO | WO-2016/130600 A9 | 12/2016 |
| WO | WO-2017/031370 A1 | 2/2017 |
| WO | WO-2017/040793 A1 | 3/2017 |
| WO | WO-2017/011710 A3 | 4/2017 |
| WO | WO-2017064546 A1 | 4/2017 |
| WO | WO-2017/106290 A1 | 6/2017 |
| WO | WO-2017/143042 A3 | 10/2017 |
| WO | WO-2017208247 A1 | 12/2017 |
| WO | WO-2018/035495 A1 | 2/2018 |
| WO | WO-2018/049073 A1 | 3/2018 |
| WO | WO-2018/049075 A1 | 3/2018 |
| WO | WO-2018/049077 A1 | 3/2018 |
| WO | WO-2018/049079 A1 | 3/2018 |
| WO | WO-2018/111944 A1 | 6/2018 |
| WO | WO-2018/129544 A1 | 7/2018 |
| WO | WO-2018/204764 A1 | 11/2018 |
| WO | WO-2019/036430 A1 | 2/2019 |
| WO | WO-2019/071054 A1 | 4/2019 |

OTHER PUBLICATIONS

Choudhury, et al., "CRISPR-dCas9 mediated TET1 targeting for selective DNA demethylation at BRCA1 promoter," *Oncotarget*, 7(29):46545-46556, (published Jun. 23, 2016).

Votja, et al., "Repurposing the CRISPR-Cas9 system for targeted DNA methylation," *Nucleic Acids Research*, 44(12):5615-5628, (Mar. 11, 2016).

Stelzer, et al., "Tracing dynamic changes of DNA methylation at single-cell resolution," *Cell*, 163:218-229, (2015).

Chen, et al., "Derepression of BDNF transcription involves calcium-dependent phosphorylation of MeCP2," Science, 302:885-889, (2003).

Martinowich, et al., "DNA methylation-related chromatin remodeling in activity-dependent BDNF gene regulation," *Science*, 302:890-893, (2003).

Wu, et al., "Reversing DNA methylation: mechanisms, genomics, and biological functions," *Cell* 156:45-68, (2014).

Schultz, et al., "Human body epigenome maps reveal noncanonical DNA methylation variation," *Nature*, 523:212-216, (2015).

Wang, et al., "Widespread plasticity in CTCF occupancy linked to DNA methylation," *Genome Res* 22:1680-1688, (2012).

Sweatt, J.D., "The emerging field of neuroepigenetics," *Neuron*, 80:624-632, (2013).

Kang, et al., "Disruption of CTCF/cohesin-mediated high-order chromatin structures by DNA methylation downregulates PTGS2 expression," *Oncogene*, 34:5677-5684, (2015).

Bell, et al., "Methylation of a CTCF-dependent boundary controls imprinted expression of the Igf2 gene," *Nature*, 405: 482-485, (2000).

Jaenish, "Nuclear Cloning and the Reprogramming of the Genome," HD045022; Funding date: Jul. 28, 2003-May 1, 2007.

Jaenish, "In Vitro Reprogramming of Somatic Cells Into Pluripotent ES-Like Cells," HD045022; Funding date: Jun. 15, 2008-Jun. 1, 2017.

Xu, et al., "A CRISPR-based approach for targeted DNA demethylation," *Cell discovery*, 2.1:1-12, (2016).

Kungulovski, et al., "Epigenome editing: state of the art, concepts, and perspectives," *Trends in Genetics*, 32.2:101-113, (2015).

McDonald, et al., "Reprogrammable CBISPR/Cas9-based system for inducing site-specific DNA methylation," *Biology open*, 5.6:866-874, (2016).

Xiong, et al., "Targeted DNA methylation in human cells using engineered dCas9-methyltransferases," *Scientific Reports*, 7.1:1-14, (2017).

Morita, et al., "Targeted DNA demethylation in vivo using dCas9-peptide repeat and scFv-TET1 catalytic domain fusions," *Nature Biotechnology*, 34.10:1060-1065, (2016).

Stepper, et al., "Efficient targeted DNA methylation with chimeric dCas9-Dnmt3a-Dnmt3L methyltransferase," *Nucleic Acids Research*, 45.4:1703-1713, (2016).

Lo, et al., "Genetic and epigenetic control of gene expression by CRISPR-Cas systems," *F1000 Research*, 6:747, (2017).

Dávalos-Salas, et al. "Gain of DNA methylation is enhanced in the absence of CTCF at the human retinoblastoma gene promoter," *BMC cancer*, 11.1:1-11, (2011).

Ishimaru, et al., "Differential epigenetic regulation of BDNF and NT-3 genes by trichostatin A and 5-aza-2'-deoxycytidine in Neuro-2a cells," *Biochemical and biophysical research communications*, 394.1:173-177, (2010).

Brunk, et al., "Regulated demethylation of themyoddistal enhancer during skeletal myogenesis," *Developmental Biology*, 177.2:490-503, (1996).

International Search Report for International Application No. PCT/US17/47674, dated Jan. 4, 2018.

Amabile, A. et al., "Inheritable Silencing of Endogenous Genes by Hit-and-Run Targeted Epigenetic Editing," Cell, 167:219-232 (2016).

Banani et al. "Biomolecular condensates: organizers of cellular biochemistry," Nature Reviews Molecular Cell Biology (2017) vol. 18, No. 5, pp. 285-298.

Barrera, L. et al., "Survey of variation in human transcription factors reveals prevalent DNA binding changes," Science, 351 (6280):1450-1454 (2016).

Beagan JA, et al. "YY1 and CTCF orchestrate a 3D chromatin looping switch during early neural lineage commitment," *Genome Res.* 2017;27(7):1139-1152.

Bonavida, Benjamin, "Therapeutic YY1 inhibitors in cancer: All in One," Critical Reviews ™ in Oncogenesis 22.1-2 (2017).

Cho et al., "Antisense Transcription and Short Article Heterochromatin at the DMI CTG Repeats Are Constrained by CTCF," Molecular Cell (2005) vol. 20, pp. 483-489.

Cong et al., "Multiplex Genome Engineering Using CRISPR/Cas Systems," Science (2013) vol. 339, pp. 819-823.

De Groote, et al. "Epigenetic Editing: targeted rewriting of epigenetic marks to modulate expression of selected target genes," Nucleic Acids Res. (2012) vol. 40, No. 21, p. 10596-10613.

De Souza, et al., "DNA methylation profiling in human Huntington's disease brain," Human Molecular Genetics (2016) vol. 25, No. 10, pp. 2013-2030.

De Wit, et al. "CTCF Binding Polarity Determines Chromatin Looping," Molecular Cell, vol. 60. No. 4, pp. 676-684, 2015.

Deng et al., "Controlling Long-Range Genomic Interactions at a Native Locus by Targeted Tethering of a Looping Factor," Cell (2012) vol. 149, pp. 1233-1244.

Dowen, J. et al., "Control of Cell Identity Genes Occurs in Insulated Neighborhoods in Mammalian Chromosomes," Cell, 159:374-387 (2014).

Ecker et al., "Genomics: Encode explained," Nature (2012) Sep. 6; vol. 489 (7414) pp. 52-55.

Extended European Search Report for Application No. 17849560.2 dated Mar. 31, 2020.

Filippova, et al., "Tumor-associated Zinc Finger Mutations in the CTCF Transcription Factor Selectively Alter Its DNA-binding Specificity," Cancer Research, 62, 48-52, 2002.

Final Office Action for U.S. Appl. No. 16/469,131 dated Feb. 3, 2023.

Final Office Action for U.S. Appl. No. 16/476,868 dated Feb. 6, 2023.

(56) References Cited

OTHER PUBLICATIONS

Flavahan, et al. "Insulator dysfunction and oncogene activation in IDH mutant gliomas," (Nature) 2015, vol. 529, No. 7584, pp. 110-114.
Guo et al., "YY1 Target DB: an integral information resource for Yin Yang 1 target loci," Database, 2013 vol., pp. 1-10.
Guo, C. et al., "CTCF Binding Elements Mediate Control of V(D)J Recombination," Nature, 477(7365):424-430, 2011.
Herold, M., et al., "CTCF: insights into insulator function during development," Development, 139:1045-1057, 2012.
Hnisz, D. et al., "Activation of proto-oncogenes by disruption of chromosome neighborhoods," Science, 351(6280): 1454-1458, 2016.
Hnisz, D. et al., "Convergence of Developmental and Oncogenic Signaling Pathways at Transcriptional Super-Enhancers," Molecular Cell, 58:362-370, 2015.
Hnisz, D. et al., "Super-Enhancers in the Control of Cell Identity and Disease," Cell, 155:934-947, 2013.
Hsu, "Completion of a Programmable DNA-Binding Small Molecule Library," Thesis, California Institute of Technology (2008) retrieved from thesis.library.caltech.edu/4398, 153 pages.
International Preliminary Report on Patentability for International Application No. PCT/US2017/047674, issued Feb. 19, 2019.
International Preliminary Report on Patentability for International Application No. PCT/US2017/050553, issued Mar. 12, 2019.
International Preliminary Report on Patentability for International Application No. PCT/US2017/065918, issued Jun. 18, 2019.
International Search Report and Written Opinion issued in PCT/US2017/050553, dated Jan. 30, 2018.
International Search Report for International Application No. PCT/US2017/065918, dated Apr. 30, 2018.
International Search Report for PCT/US2017/50553 (Methods and Compositions for Modulating Gene Expression, filed Sep. 7, 2017), issued by ISA/US, 6 pages (Jan. 30, 2018).
International Search Report for PCT/US2017/50556 (Methods and Compositions for Modulating Gene Expression, filed Sep. 7, 2017), issued by ISA/US, 5 pages (Dec. 26, 2017).
International Search Report for PCT/US2017/50558 (Methods and Compositions for Modulating Gene Expression, filed Sep. 7, 2017), issued by ISA/US, 5 pages (Dec. 18, 2017).
International Search Report for PCT/US2017/50561 (Methods and Compositions for Modulating Gene Expression, filed Sep. 7, 2017), issued by ISA/US, 5 pages (Dec. 18, 2017).
International Search Report issued in PCT/US2018/013003 dated Jun. 1, 2018.
Issad, et al., "O—GlcNAc modification of transcription factors, glucose sensing and glucotoxicity," Trends in Endocrinology and Metabolism, 19, 10, 2008, 380-389.
Ji, X. et al., "3D Chromosome Regulatory Landscape of Human Pluripotent Cells," Cell Stem Cell, 18:262-275 (2016).
Ji, X. et al., "Chromatin proteomic profiling reveals novel proteins associated with histone-marked genomic regions," PNAS, 112(12):3841-3846 (2015).
Jinek et al., "A Programmable Dual-RNA-Guided DNA Endonuclease in Adaptive Bacterial Immunity," Science, 2012, vol. 337, pp. 816-821.
Kearns et al., "Functional annotation of native enhancers with a Cas9-histone demethylase fusion," Nature Methods, vol. 12, No. 5, pp. 401-403, 2015.
Kim, et al., "Genome-wide target specificities of CRISPR RNA-guided programmable deaminases," Nat Biotechnol, vol. 35, pp. 475-480, 2017.
Koferle, et al., "Brave new epigenomes: the dawn of epigenetic engineering" Genome Medicine, vol. 7, No. 59, pp. 1-3, 2015.
Komor, et al., "Programmable editing of a target base in genomic DNA without double-stranded DNA cleavage," Nature, vol. 533, pp. 420-424, Supplement, 2016.
Krylov, et al., "A general method to design dominant negatives to B-HLHZip proteins that abolish DNA binding," PNAS, vol. 94, No. 23, p. 12274-12279, 1997.
Lee, Jeng-Shin, et al., "Evidence for physical interaction between the zinc-finger transcription factors YY1 and Sp1," Proceedings of the National Academy of Sciences, 90.13: 6145-6149, 1993.
Lei, et al., "Targeted DNA methylation in vivo using an engineered dCas9-MQ1 fusion protein," Nature Communications, 8, Article No. 16026, 2017.
Li, et al., "An alternative CTCF isoform antagonizes canonical CTCF occupancy and changes chromatin architecture to promote apoptosis," Nature Communications, Article No. 1535; pp. 1-13, 2019.
Lin, et al., "Formation and Maturation of Phase-Separated Liquid Droplets by RNA-Binding Proteins," Molecular Cell, vol. 60, pp. 208-219, 2015.
Ling, et al. "Long-range DNA interactions are specifically altered by locked nucleic acid-targeting of a CTFC binding site," Biochimica et Biophysica Acta. Gene Regulatory Mechanisms, vol. 1809, No. 1. pp. 24-33, 2011.
Liu, et al., "Editing DNA Methylation in the Mammalian Genome," Cell, 167(1):233-247, 2016.
Lopez-Bertoni, et al., "DNMT-dependent suppression of microRNA regulates the induction of GBM tumor-propagating phenotype by Oct4 and Sox2," Oncogene, 2015, 34, 3994-4004.
Ma, et al. "Targeted Gene Suppression by Inducing De Novo DNA Methylation in the Gene Promotor," Epigenetics & Chromatin, vol. 7:20, pp. 1-11, 2014.
Mansour, M. et al., "An oncogenic super-enhancer formed through somatic mutation of a noncoding intergenic element," Science, 346(6215):1373-7, Nov. 13, 2014.
McClellan, Michael J., et al., "Modulation of enhancer looping and differential gene targeting by Epstein-Barr virus transcription factors directs cellular reprogramming," PLOS Pathog 9.9: e1003636, 2013.
McDonald, James I., et al., "Reprogrammable CRISPR/Cas9-based system for inducing site-specific DNA methylation," Biology open, 5.6: 866-874, 2016.
Morgan et al., "Manipulation of nuclear architecture through CRISPR-mediated chromosomal looping," Nature Communications, vol. 8, Article 15993, 9 pages, 2017.
Narenda et al., "CTCF establishes discrete functional chromatin domains at the Hox clusters during differentiation," Science, vol. 347, No. 6225, pp. 1017-1021, 2015.
Narlikar, et al., "Identifying regulatory elements in eukaryotic genomes," Briefings in functional genomics and proteomics 8.4,: 215-230, 2009.
Non-Final Office Action for U.S. Appl. No. 16/326,700 dated Dec. 7, 2021.
Non-Final Office Action for U.S. Appl. No. 16/469,131 dated Jun. 20, 2022.
Non-Final Office Action for U.S. Appl. No. 16/476,868 dated Jul. 6, 2022.
Non-Final Office Action for U.S. Appl. No. 18/329,541 dated Feb. 27, 2024.
Notice of Allowance for U.S. Appl. No. 16/476,868 dated Sep. 19, 2023.
Notice of Allowance for U.S. Appl. No. 16/476,868, dated Jun. 1, 2023.
Patterson et al., "DNA Methylation: Bisulphite Modification and Analysis" J Vis Exp., vol. 56, e3170, pp. 1-9, 2011.
Phillips, J.E., et al., "CTCF: master weaver of the genome," Cell 137, 1194-1211, 2009.
Rada-Iglesias et al., "Whole-genome maps of USF1 and USF2 binding and histone H3 acetylation reveal new aspects of promoter structure and candidate genes for common human disorders," Genome Research, vol. 18(3), pp. 380-392, 2008.
Ran et al., "Genome engineering using the CRISPR-Cas9 system," Nature Protocols, vol. 8, No. 11, pp. 2281-2308, 2013.
Rodriguez, et al., "CTCF is a DNA methylation-sensitive positive regulator of the INK/ARF locus," Biochem. Biophys. Res. Commun., 392(2):129-34, 2010.
Sabari et al., "Coactivator condensation at super-enhancers links phase separation and gene control," Science, 361(6400): eaar3958, pp. 1-16, 2018.

(56) References Cited

OTHER PUBLICATIONS

Shin et al., "Spatiotemporal control of intracellular phase transitions using light-activated optoDroplets," Cell, vol. 168, No. 1-2, pp. 159-171, 2017.

Singh, et al., "Protein Engineering Approaches in the Post-Genomic Era," Current Protein and Peptide Science, 18, 1-11, 2017.

Spencer, R. et al., "A Boundary Element Between Tsix and Xist Binds the Chromatin Insulator CTCF and Contributes to Initiation of X-Chromosome Inactivation," Genetics, 189:441-454, 2011.

Subramaniam, et al., "DNA methyltransferases: a novel target for prevention and therapy," Frontiers in Oncology, 4, May 1, 2014.

Supplementary Partial European Search Report in Application No. EP 17 88 1835, dated Jul. 30, 2020.

Szabó, P. et al., "Role of CTCF Binding Sites in the Igf2/H19 Imprinting Control Region," Molecular and Cellular Biology, 24(11):4791-4800, 2004.

Tang, Z. et al., "CTCF-Mediated Human 3D Genome Architecture Reveals Chromatin Topology for Transcription," Cell, 163:1-17, 2015.

Thakore, et al., "Highly Specific Epigenome Editing by CRISPR/Cas9 Repressors for Silencing of Distal Regulatory Elements," Nat Methods, vol. 12, No. 12, pp. 1143-1149, 2015.

The Encode Project Consortium. "An Integrated Encyclopedia of DNA Elements in the Human Genome" Nature, vol. 6; 489 (7414):57-74, 2012.

Torres, A. et al., "Potent and sustained cellular inhibition of miR-122 by lysine-derivatized peptide nucleic acids (PNA) and phosphorothioate locked nucleic acid (LNA)/2'-O-methyl (OMe) mixmer anti-miRs in the absence of transfection agents," Artificial DNA: PNA & XNA, 2(3):71-78, 2011.

Viscidi, et al., "Novel Chemical Method for the Preparation of Nucleic Acids for Nonisotopic Hybridization," J Clin Microbiol, vol. 23, No. 2, pp. 311-317, 1986.

Weintraub, Abraham S., et al. "YY1 is a structural regulator of enhancer-promoter loops." Cell 171.7 (2017): 1573-1588.

Woloszynska-Read, et al., "DNA Methylation-dependent Regulation of BORIS/CTCFL Expression in Ovarian Cancer," Cancer Immunity, vol. 7, 1 pp. 1-10, 2007.

Written Opinion for PCT/US2017/50553 (Methods and Compositions for Modulating Gene Expression, filed Sep. 7, 2017), issued by ISA/US, 12 pages (dated Jan. 30, 2018).

Written Opinion for PCT/US2017/50556 (Methods and Compositions for Modulating Gene Expression, filed Sep. 7, 2017), issued by ISA/US, 8 pages (dated Dec. 26, 2017).

Written Opinion for PCT/US2017/50558 (Methods and Compositions for Modulating Gene Expression, filed Sep. 7, 2017), issued by ISA/US, 6 pages (dated Dec. 18, 2017).

Written Opinion for PCT/US2017/50561 (Methods and Compositions for Modulating Gene Expression, filed Sep. 7, 2017), issued by ISA/US, 6 pages (dated Dec. 18, 2017).

Wu et al., "MicroRNAs direct rapid deadenylation of mRNA" Proc Natl Acad Sci, vol. 103, pp. 4034-4039, 2006.

Yan, et al., "DNA methylation reactivates GAD1 expression in cancer by preventing CTCF-mediated polycomb repressive complex 2 recruitment," Oncogene, 35(30):3995-4008, 2016.

Young et al., Abstract "Transcriptional Regulatory Networks in Living Cells," National Institutes of Health Grant No. HG002668 (Funding Start Date: May 2, 2003).

Young et al., Abstract "Transcriptional Regulatory Networks in Living Cells," National Institutes of Health Grant No. HG002668 (Funding Start Date: Apr. 17, 2007).

Young et al., Abstract, "Epigenomic Changes in Normal T-cell Development and Leukemogenesis," National Institutes of Health Grant No. CA109901 (Funding Start Date: Apr. 15, 2010).

Zhang, et al., "Propagated Perturbations from a Peripheral Mutation Show Interactions Supporting WW Domain Thermostability," Structure, 26, 1474-1485, 2018.

Zhao, et al., "CTCF cooperates with noncoding RNA MYCNOS to promote neuroblastoma progression through facilitating MYCN expression," Oncogene, 35, 3565-3576, 2016.

Ziebarth et al., "CTCFBSDB 2.0: a database for CTCF-binding sites and genome organization," Nucleic Acid Research, vol. 41; D188-94, 2013.

Zheng, "Cellular and Molecular Biology of Tumors," Military Medical Press, pp. 265-273, 2014 (English translation of excerpt of the named reference attached).

2G

2H

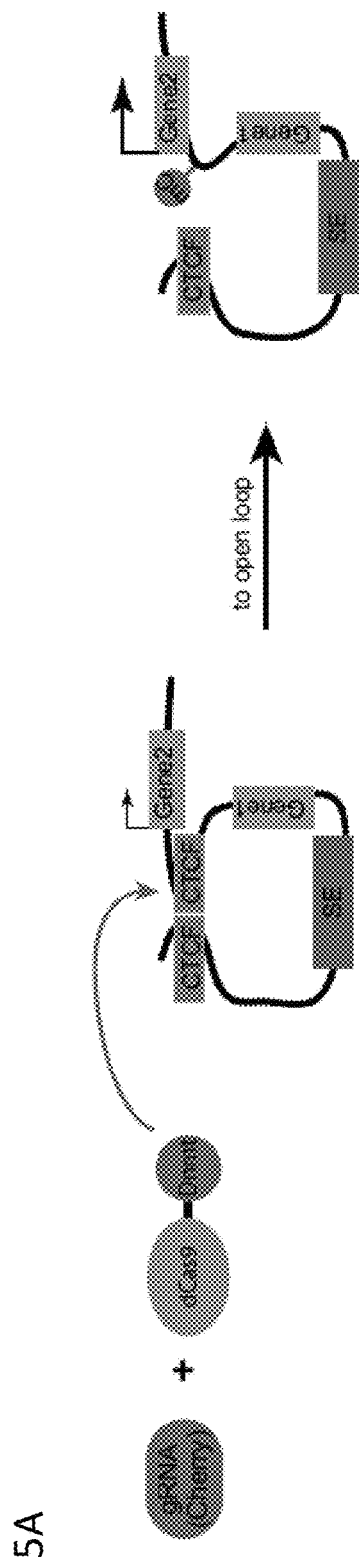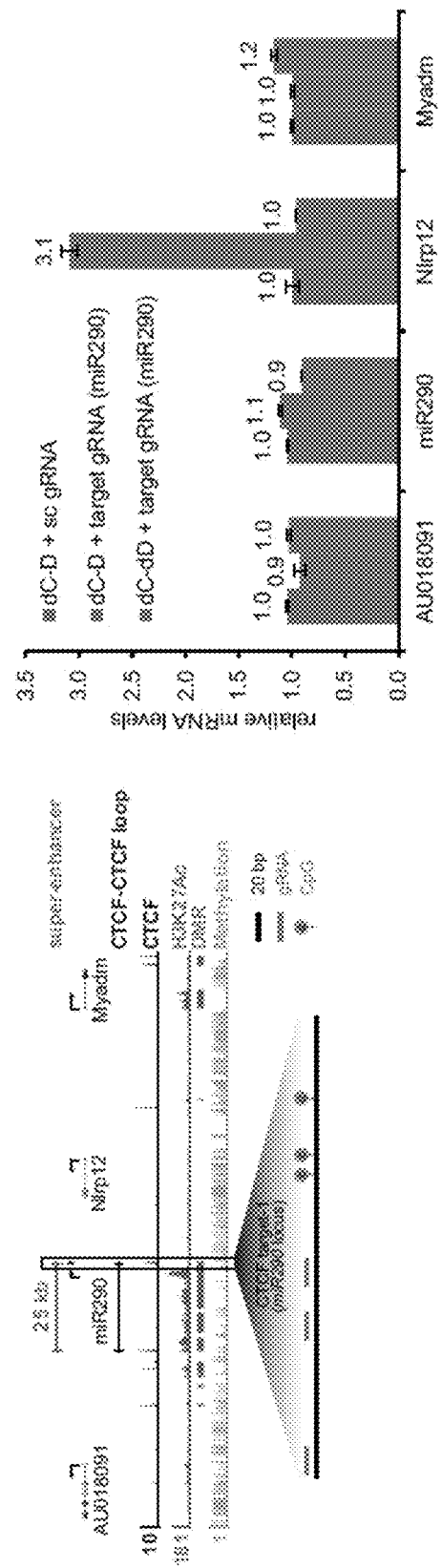
FIGS. 5A-5C

6A

6B

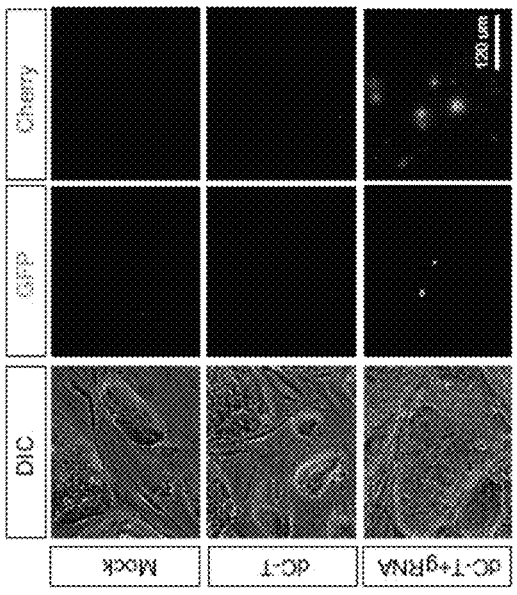
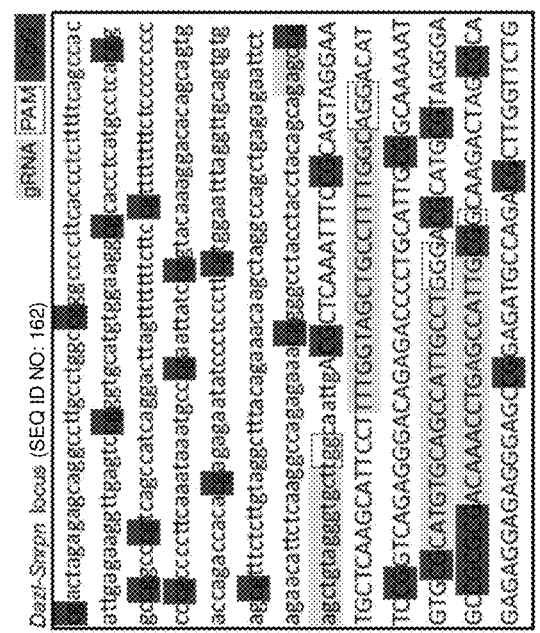
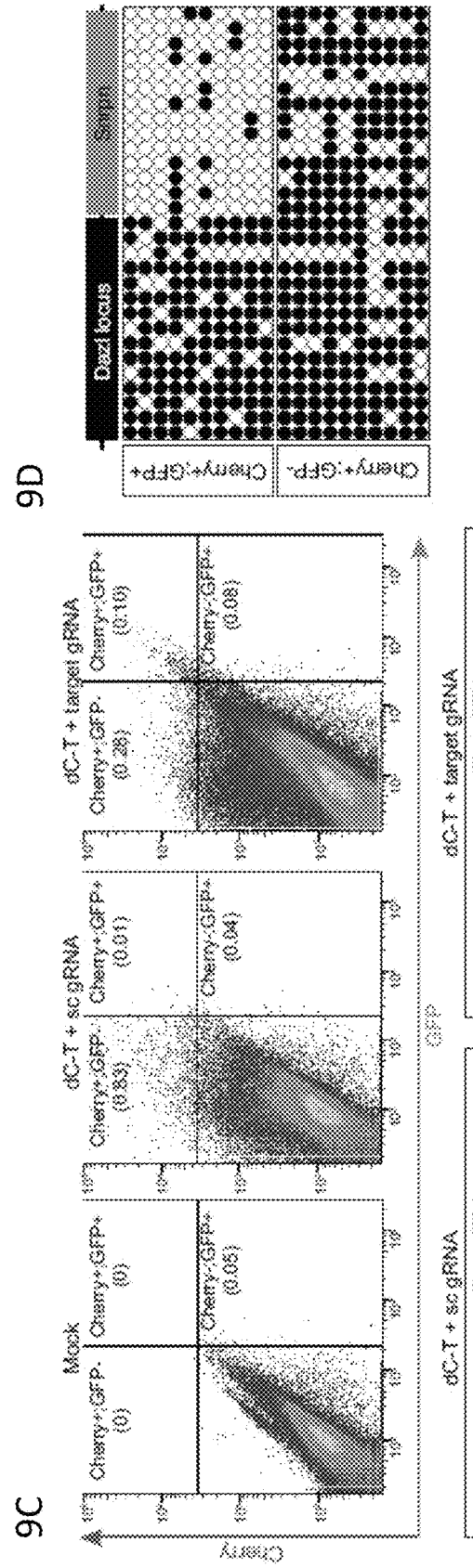
FIGS. 9A-9D

12A
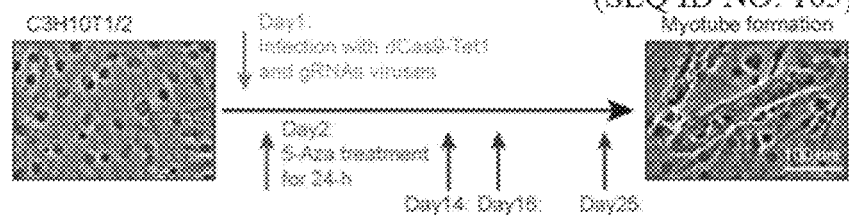
12B
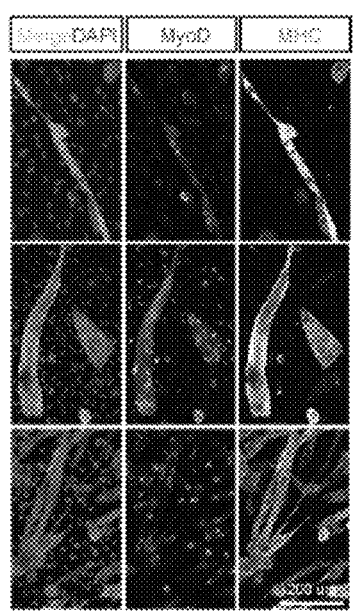
12C
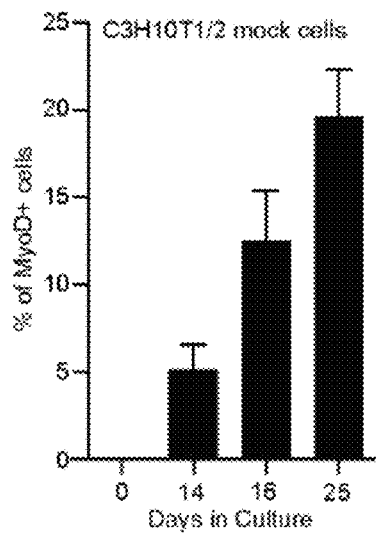
12D
12E
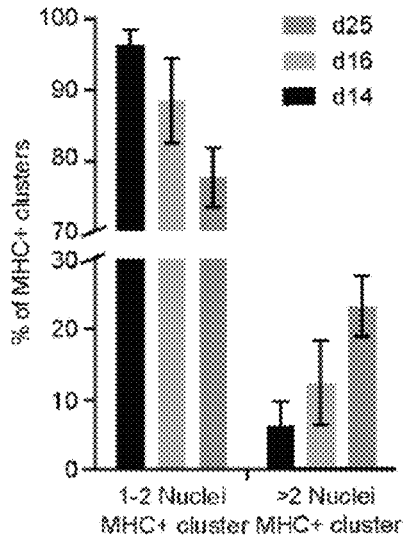
FIGS. 12A-12E

METHODS OF EDITING DNA METHYLATION

RELATED APPLICATIONS

This application is a divisional of U.S. application Ser. No. 16/326,700, filed on Feb. 19, 2019, which is a national stage filing under 35 U.S.C. 371 of International Application No. PCT/US2017/047674, filed Aug. 18, 2017, which claims the benefit of U.S. Provisional Application Ser. No. 62/377,520, filed Aug. 19, 2016, the contents of which are hereby incorporated by reference in their entirety. International Application No. PCT/US2017/047674 was published under PCT Article 21(2) in English.

GOVERNMENT SUPPORT

This invention was made with government support under Grant Nos. HD045022 awarded by the National Institutes of Health. The government has certain rights in the invention.

STATEMENT REGARDING SEQUENCE LISTING

The Sequence Listing associated with this application is provided in .xml format in lieu of a paper copy and is hereby incorporated by reference into the specification. The name of the .xml file containing the Sequence Listing is WIBR-158-102.xml. The xml file is 2,27,220 bytes, was created on Dec. 6, 2022, and is being submitted electronically via Patent Center.

BACKGROUND OF THE INVENTION

Mammalian DNA methylation at 5-cytosine plays critical roles in many biological processes, including genomic imprinting, cell fate determination, chromatin architecture organization, maintenance of cell identity, and regulation of gene expression (Bird, 2002; Cedar and Bergman, 2012; Jaenisch and Bird, 2003; Smith and Meissner, 2013). Genetic studies have revealed that DNA methylation is essential for mammalian development and adaptation to environmental signals (Jaenisch and Bird, 2003; Li et al., 1992; Smith and Meissner, 2013). Abnormal DNA methylation has been observed in cancer and neurological disorders (Laird and Jaenisch, 1996; Robertson, 2005). Owing to the advancement in sequencing technologies, single-nucleotide resolution methylation maps for many types of human and mouse cells and tissues have been depicted (Lister et al., 2009; Schultz et al., 2015). Importantly, these maps have allowed for the identification of differentially methylated regions (DMRs) at base pair resolution during different stages of normal development (Lister et al., 2013) as well as disease (De Jager et al., 2014; Doi et al., 2009; Landau et al., 2014). However, investigation of the functional significance of these DMRs remains a challenge due to lack of appropriate molecular tools that enable efficient editing of DNA methylation in a targeted manner.

SUMMARY OF THE INVENTION

Mammalian DNA methylation is a epigenetic mechanism orchestrating gene expression networks in many biological processes. However, investigation of the functions of specific methylation events remains challenging. It is demonstrated that fusion of Tet1 or Dnmt3a with a catalytically inactive Cas9 (dCas9) enables targeted DNA methylation editing. Targeting of the dCas9-Tet1 or -Dnmt3a fusion protein to methylated or unmethylated promoter sequences caused activation or silencing, respectively, of an endogenous reporter. Targeted demethylation of the BDNF promoter IV or the MyoD distal enhancer by dCas9-Tet1 induced BDNF expression in post-mitotic neurons or activated MyoD facilitating reprogramming of fibroblasts into myoblasts, respectively. Targeted de novo methylation of a CTCF loop anchor site by dCas9-Dnmt3a blocked CTCF binding and interfered with DNA looping, causing altered gene expression in the neighboring loop. Finally, it is shown that these tools can edit DNA methylation in mice demonstrating their wide utility for functional studies of epigenetic regulation. These tools will be useful to gain insight into the functional significance of DNA methylation in diverse biological processes such as gene expression, cell fate determination, and organization of high-order chromatin structures. Furthermore, these tools would be useful to build a screening platform to identify functionally specified differentially methylated regions (DMRs) when combined with different sgRNA libraries, and to generate transgenic mice to study specific DNA methylation events in vivo.

Disclosed herein are methods of modifying one or more genomic sequences in a cell, the methods comprising introducing into the cell a catalytically inactive site specific nuclease fused to an effector domain having methylation activity; and one or more guide sequences, thereby modifying one or more genomic sequences in the cell.

Also disclosed herein are methods of modifying one or more genomic sequences in a cell, the methods comprising introducing into the cell a catalytically inactive site specific nuclease fused to an effector domain having demethylation activity; and one or more guide sequences, thereby modifying one or more genomic sequences in the cell.

Also disclosed herein are methods of modulating the methylation of one or more genomic sequences in a cell, the methods comprising introducing into the cell a catalytically inactive site specific nuclease fused to an effector domain having methylation or demethylation activity; and a guide sequence or a nucleic acid that encodes a guide sequence, thereby modulating the methylation of one or more genomic sequences in a cell.

In certain aspects, the genomic sequence comprises a differentially methylated region, an enhancer (e.g., an enhancer of MyoD), a promoter (e.g., a BDNF promoter), or a CTCF binding site. In some aspects, the effector domain comprises Tet1. In other aspects, the effector domain comprises Dnmt3a.

In some aspects, the catalytically inactive site specific nuclease is a catalytically inactive Cas protein (e.g., a Cas9 protein or a Cpf1 protein). The guide sequences may be ribonucleic acid guide sequences. In certain aspects, the guide sequence is from about 10 base pairs to about 150 base pairs in length. The one or more guide sequences may comprise two or more guide sequences.

In some embodiments, 2, 3, 4, 5, 6, 7, 8, 9, 10, 11, 12, 13, 14, 15, 16, 17, 18, 19, or 20 genomic sequences are modified in the cell. The cell may be a stem cell, a neuron, a post-mitotic cell, or a fibroblast. In some aspects, the cell is a human cell or a mouse cell.

In some aspects, one or more nuclear localization sequences are fused between the catalytically inactive site specific nuclease and the effector domain. In certain aspects, one or more of the genomic sequences are associated with a disease or condition.

In certain aspects, the methods further comprise contacting the cell with an agent that inhibits or enhances DNA methylation. The agent may be a small molecule. For example, the agent is 5-azacytidine or 5-azadeoxycytidine.

In certain embodiments, the methods further comprise introducing the cell into a non-human mammal. The non-human mammal may be a mouse.

Also disclosed are isolated modified cell produced by the methods described herein.

Also disclosed herein are methods of treating a patient in need thereof, the method comprising administering a modified cell described herein to a patient in need of such cells.

Also disclosed are method of modulating the methylation of one or more genomic sequences that cause a disease in an individual in need thereof comprising introducing into the individual a catalytically inactive site specific nuclease fused to an effector domain having methylation or demethylation activity; and one or more guide sequences, thereby modulating the methylation of one or more genomic sequences that cause a disease in the individual.

Also disclosed are modified cells having a modified genome comprising a first genomic modification in which the methylation of a genomic sequence has been modulated, wherein the modulation occurs by contacting a cell with a catalytically inactive site specific nuclease fused to an effector domain having methylation or demethylation activity, and one or more guide sequences.

Also disclosed herein are methods of modulating the methylation of one or more genomic sequences in a cell, the methods comprising contacting the cell with a nucleic acid that encodes a polypeptide comprising a catalytically inactive site specific nuclease fused to an effector domain having methylation or demethylation activity; and a guide sequence or a nucleic acid that encodes a guide sequence.

Also disclosed herein, are methods of modulating the methylation of one or more genomic sequences in an individual, the methods comprising administering to the individual a nucleic acid that encodes a polypeptide comprising a catalytically inactive site specific nuclease fused to an effector domain having methylation or demethylation activity; and a guide sequence or a nucleic acid that encodes a guide sequence.

In some aspects, the guide sequence targets the polypeptide to the one or more genomic sequences. The genomic sequence may comprise a differentially methylated region, an enhancer, a promoter, or a CTCF binding site. In certain aspects, the method comprises modulating the methylation of at least two genomic sequences in a cell, wherein the genomic sequences are selected from differentially methylated regions, enhancers, promoters, and CTCF binding sites.

In some embodiments, the effector domain comprises Tet1 or Dnmt3a. In some aspects, the catalytically inactive site specific nuclease is a catalytically inactive Cas protein (e.g., a dCas9 protein).

In certain aspects, the methods further comprise administering to the individual an agent that inhibits or enhances DNA methylation. The agent may be a small molecule. For example, the agent is 5-azacytidine or 5-azadeoxycytidine.

Also disclosed herein, are methods of treating a patient in need thereof, the methods comprising administering to the patient a nucleic acid that encodes a polypeptide comprising a catalytically inactive site specific nuclease fused to an effector domain having methylation activity; and a guide sequence or a nucleic acid that encodes a guide sequence.

Also disclosed are methods of modulating the expression of one or more genes of interest in a cell, wherein a differentially methylated region is located within 50 kB of the transcription start site of the gene, the methods comprising contacting the cell with a nucleic acid that encodes a polypeptide comprising a catalytically inactive site specific nuclease fused to an effector domain having methylation or demethylation activity; a guide sequence or a nucleic acid that encodes a guide sequence, wherein the guide sequence targets the polypeptide to the differentially methylated region.

In some aspects, the differentially methylated region is hypermethylated in the cell and the effector domain (e.g., Tet1) has demethylation activity. In other aspects, the differentially methylated region is unmethylated in the cell and the effector domain (e.g., Dnmt3a) has methylation activity. In some embodiments, the cell is a stem cell, a post-mitotic cell, a neuron, or a fibroblast.

Also disclosed herein are methods of identifying a genomic sequence whose methylation status affects expression of a gene of interest, the methods comprising contacting a cell with a nucleic acid that encodes a polypeptide comprising a catalytically inactive site specific nuclease fused to an effector domain having methylation or demethylation activity; a guide sequence or a nucleic acid that encodes a guide sequence, wherein the guide sequence targets the polypeptide to a candidate genomic sequence; and measuring expression of the gene, wherein the genomic sequence is identified as one whose methylation status affects expression of the gene of interest if expression of the gene in the cell contacted with the nucleic acid differs from the level of methylation of said genomic region in a control cell not contacted with the nucleic acid.

In some aspects, the genomic sequence comprises a differentially methylated region, an enhancer, a promoter, or a CTCF binding site. In certain aspects, the method comprises modulating the methylation of at least two genomic sequences selected from: differentially methylated regions, enhancers, promoters, and CTCF binding sites. The one or more genomic sequences may be located within 50 kB of the transcription start site (TSS) of the gene.

In certain aspects, the effector domain has methylation activity. For example, the effector domain is Dnmt3a. In other aspects, the effector domain has demethylation activity. For example, the effector domain is Tet1. In some aspects, the cell is a stem cell, a post-mitotic cell, a neuron, or a fibroblast. In certain embodiments, one or more nuclear localization sequences is fused between the polypeptide comprising the catalytically inactive site specific nuclease and the effector domain.

Also disclosed herein are methods comprising identifying a genomic region whose methylation status affects expression of a gene of interest according to the method described herein; contacting a cell with a test agent; and measuring methylation of the identified genomic region in the cell, wherein the test agent is identified as a modulator of methylation of the genomic region if the level of methylation of the genomic region in the cell contacted with the test agent differs from the level of methylation of said genomic region in a control cell not contacted with the test agent (e.g., a small molecule).

The above discussed, and many other features and attendant advantages of the present inventions will become better understood by reference to the following detailed description of the invention.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A Upper panel: provides schematic representation of a catalytic inactive mutant Cas9 (dCas9) fused with Tet1 for erasing DNA methylation, and with Dnmt3a for de novo methylation of specific sequences. Lower panel: shows optimized dCas9-effector construct with nuclear localization signal (NLS) linking dCas9 with Tet1, and a guide RNA construct with puro and Cherry cassettes. FIG. 1B is a schematic representation of targeting the Snrpn promoter region by dCas9-Tet1 with specific gRNAs to erase methylation and activate GFP expression. FIG. 1C shows Dazl-Snrpn-GFP mESCs were infected with lentiviruses expressing dCas9-Tet1 (dC-T) with a scrambled gRNA (sc gRNA) or 4 gRNAs targeting the Snrpn promoter region (target gRNA). Percentage of GFP positive cells were calculated by flow cytometric analysis of these cells 3-day post infection, and shown as the mean percentages of GFP positive cells±SD of two biological replicates. Note that the percentages of GFP-positive cells are expressed as the fraction of infected Cherry-positive cells. FIG. 1D Left: shows representative fluorescence images of the sorted Cherry positive cells in FIG. 1C after culturing for 1 week. Scale bar: 250 um. Right: provides percentages of GFP positive colonies were quantified, and shown as the mean percentages of GFP positive cells±SD of two biological replicates. FIG. 1E shows the bisulfite sequencing of cells described in FIG. 1C. FIG. 1F provides methylation levels of individual CpGs in the Snrpn promoter region and the adjacent Dazl locus. Shown is the mean percentage±SD of two biological replicates.

FIGS. 2A-2H depicts silencing of the Gapdh-Snrpn-GFP reporter by dCas9-Dnmt3a. FIG. 2A shows a schematic representation of targeting the Snrpn promoter region by dCas9-Dnmt3a with specific gRNAs to methylate the promoter and silence GFP expression. FIG. 2B shows Gapdh-Snrpn-GFP mESCs were infected with lentiviruses expressing dCas9-Dnmt3a (dC-D) with a scrambled gRNA (sc gRNA) or gRNAs targeting the Snrpn promoter region (target gRNA). Percentage of GFP negative cells was calculated by flow cytometric analysis 3-days after infection, and is shown as the mean percentages of GFP negative cells±SD of two biological replicates. Note that the percentages of GFP-positive cells are expressed as the fraction of infected Cherry-positive cells. FIG. 2C Left: shows representative fluorescence images of the sorted Cherry-positive cells in B after culturing for 1 week. Scale bar: 250 um. Right: shows percentages of GFP negative colonies were quantified, and are shown as the mean percentages of GFP negative cells±SD of two biological replicates. FIG. 2D provides bisulfite sequencing of cells described in FIG. 2B. FIG. 2E depicts methylation levels of individual CpGs in the Snrpn promoter region and the adjacent Gapdh locus. Shown is the mean percentage±SD of two biological replicates. FIG. 2F shows Gapdh-Snrpn-GFP mESCs with Doxycycline-inducible dCas9-Dnmt3a were infected with lentiviruses expressing gRNAs targeting the Snrpn promoter region in the presence of Doxycycline (2 ug/ml). Percentages of GFP negative cells were calculated by flow cytometric analysis 3-day after infection, and are shown as the mean percentages of GFP negative cells±SD of two biological replicates. Note that the percentages of GFP-positive cells are expressed as the fraction of infected Cherry-positive cells. FIG. 2G Left: depicts representative fluorescence images of the sorted Cherry-positive population in FIG. 2F after culturing for 1 week with or without Doxycycline. Scale bar: 250 um. Right: shows percentages of GFP negative colonies were quantified, and are shown as the mean percentages of GFP negative cells±SD of two biological replicates. FIG. 2H depicts methylation level of each individual CpG in the Snrpn promoter region and the adjacent Gapdh locus from cells in FIG. 2G. Shown is mean percentage±SD of two biological replicates.

FIG. 3A provides a schematic representation of targeting BDNF promoter IV by dCas9-Tet1 (dC-T) with specific gRNAs to erase methylation and activate BDNF expression. FIG. 3B shows mouse cortical neurons cultured in vitro for 3 days (DIV3) were infected with lentiviruses expressing dC-T with or without gRNAs targeting the BDNF promoter IV, or a catalytic dead form of Tet1 (dC-dT, with mutations at H1672Y and D1674A) with BDNF gRNAs for 2 days, and then treated with or without KCl (50 mM) for 6 hours before harvesting for RT-qPCR analysis. Bars are mean t SD of three biological replicates. FIG. 3C provides representative confocal images for BDNF induction in FIG. 3B. Top panel: BDNF expression was induced by 50 mM KCl treatment for 6 hrs. Lower panels: BDNF expression was significantly induced when dC-T was co-expressed with gRNAs targeting BDNF promoter IV region. Note that co-expression of dC-dT with BDNF gRNAs did not activate BDNF expression. Stained in red for MAP2 (top two panels) or Cherry (bottom two panels), green for BDNF, blue for DAPI and grey for dCas9. Scale bar: 50 um. FIG. 3D depicts bisulfite sequencing of neurons in FIG. 3C. FIG. 3E shows methylation levels of each individual CpGs in the BDNF promoter IV region. Shown is the mean percentage±SD of two biological replicates.

FIG. 4A provides a schematic representation of targeting the MyoD distal enhancer (DE) region in DMR-5 by dCas9-Tet1 (dC-T) with specific gRNAs. FIG. 4B shows C3H10T1/2 mouse embryonic fibroblast cells were infected with lentiviruses expressing dC-T with target gRNAs, or a catalytic dead form of Tet1 (dC-dT) with target gRNAs for 2 days. Cherry positive cells were FACS sorted for RT-qPCR analysis. Bars represent mean±SD of three experimental replicates. FIG. 4C bisulfite sequencing of cells in FIG. 4B. FIG. 4D shows methylation level of individual CpGs in the MyoD DE region. Shown is the mean percentage±SD of two biological replicates. FIG. 4E shows representative confocal images for C3H10T1/2 cells on day 14 in the fibroblast-to-myoblast conversion assay. C3H10T1/2 cells were plated as 1×104 cells per well in 6-well plate, and then infected with lentiviruses expressing dC-T and gRNAs targeting DMR-5, or a catalytic dead form of Tet1 (dC-dT) with target gRNAs. 24-hour post infection, cells were treated with vehicle control (HEPES buffer) or 5-Azacytidine (1 uM) for 24-hour, and then harvested after 14 days for immunofluorescence staining. Stained in green for MyoD, magenta for MHC and blue for DAPI. Scale bar: 200 um. FIG. 4F provides quantification of MyoD positive cell ratio 14-day post infection with lentiviruses expressing dC-T alone, dC-T with gRNAs targeting DMR-5, and dC-dT with the target gRNAs. FIG. 4G shows a distribution profile of MHC positive cell clusters based on nuclei number per MHC+ cluster (grouped as 2-5, 6-10, 11-20 and >20 nuclei per MHC+ cluster) 14-days post infection. When treated with 5-Aza, co-expression of dC-T and the target gRNAs, but not of the other combinations significantly facilitates formation of more matured, larger MHC+ clusters compared to mock control or dC-T alone. FIG. 4H provides quantification of myotube density in MHC positive clusters with more than 2 or 5 nuclei at 14-days after infection. Addition of 5-Aza induces MHC+ myotube formation. Co-expression of dC-T and the target gRNAs synergizes with 5-Aza significantly, inducing more and larger myotubes (>5 nuclei MHC+ clusters). Data are quantified from 3-5 representative images for F-H. Bars represent mean±SD.

FIGS. 5A-5I depict targeted methylation of CTCF binding sites. FIG. 5A provides a schematic representation of targeting the CTCF binding site by dCas9-Dnmt3a with specific gRNAs to induce de novo methylation, blocking CTCF recruitment, and opening CTCF loops which alters gene expression in the adjacent loop. FIG. 5B provides a schematic representation of CTCF target-1 (miR290 locus) with super-enhancer and miR290 in the loop, AU018091 gene in the left neighboring loop, and Nlrp12 gene in the right neighboring loop (close to the targeted CTCF binding site). The Myadm gene is in the adjacent loop right to the loop containing Nlrp12. The super-enhancer domain is indicated as a red bar. The targeted CTCF site is highlighted with a box. ChIP-seq binding profiles (reads per million per base pair) for CTCF in black and H3K27Ac (super-enhancer) in red, and methylation track in yellow with DMR in blue are also shown. FIGS. 5C-5E show doxycycline-inducible dCas9-Dnmt3a mESCs were infected with lentiviruses expressing a scrambled gRNA or CTCF target-1 gRNAs, and dC-dT with CTCF target-1 gRNAs for 3 days, and then Cherry-positive cells were FACS sorted. After cultured in the presence of Doxycycline for 3 day, these cells were plated on gelatin-coated plates for 1 hour to remove feeder cells and then harvested for RT-qPCR analysis in FIG. 5C, for bisulfite-sequencing analysis in FIG. 5D & FIG. 5E. Bars represent mean±SD of three experimental replicates. FIG. 5F provides a schematic representation of CTCF target-2 with super-enhancer and Pou5f1 gene in this loop, H2Q10 gene in the left neighboring loop (close to the targeted CTCF binding site), and Tcf19 in the right neighboring loop. The super-enhancer domain is indicated as a red bar. The targeted CTCF site is highlighted with a box. ChIP-seq binding profiles (reads per million per base pair) for CTCF in black and H3K27Ac (super-enhancer) in red, and methylation track in yellow with DMR in blue are also shown. FIGS. 5G-5I show the same set of experiments performed as described in FIGS. 5C-5E for CTCF target-2, and cells were harvested for RT-qPCR analysis as in FIG. 5C and for bisulfite sequencing as in FIG. 5D and FIG. 5E. Bars represent mean±SD of three experimental replicates.

FIG. 6A provides Quantitative Chromosome Conformation Capture (3C) analysis of cells described in C at the miR290 locus. The super-enhancer domain is indicated as a red bar. The targeted CTCF site is highlighted with a box. Arrows indicate the chromosomal positions between which the interaction frequency was assayed. Asterisk indicates the 3C anchor site. ChIP-seq binding profiles (reads per million base pair) for CTCF in black and H3K27Ac (super-enhancer) in red, and methylation track in yellow with DMR in blue are also shown. The interaction frequencies between the indicated chromosomal positions and the 3C anchor sites are displayed as a bar chart (mean±SD) on the bottom panel. qPCR reactions were run in duplicates, and values are normalized against the mean interaction frequency in cells with a scrambled gRNA. ($p<0.05$ for all three regions; Student's t test, ns stands for non-significant, NC stands for negative control.) FIG. 6B shows anti-CTCF ChIP experiment was performed using cells in FIG. 6A followed by quantitative PCR analysis. Bars represent mean±SD of three experimental replicates. FIG. 6C provides Quantitative Chromosome Conformation Capture (3C) analysis of cells described in FIG. 5G at the Pou5f1 locus. The super-enhancer domain is indicated as a red bar. The targeted CTCF site is highlighted with a box. Arrows indicate the chromosomal positions between which the interaction frequency was assayed. Asterisk indicates the 3C anchor site. ChIP-seq binding profiles (reads per million per base pair) for CTCF in black and H3K27Ac (super-enhancer) in red, and methylation track in yellow with DMR in blue are also shown. The interaction frequencies between the indicated chromosomal positions and the 3C anchor sites are displayed as a bar chart (mean±SD) on the bottom panel. qPCR reactions were run in duplicates, and values are normalized against the mean interaction frequency in cells with a scrambled gRNA. ($p<0.05$; Student's t test, ns stands for non-significant.). FIG. 6D shows anti-CTCF ChIP experiment was performed using cells in C followed by quantitative PCR analysis. Bars represent mean±SD of three experimental replicates.

FIG. 7A provides a schematic diagram illustrating the experimental procedure for the ex vivo activation of a silenced GFP reporter in mouse fibroblast cells. Mouse tail fibroblast cells were derived from a genetically modified mouse line carrying a paternal IG-DMR-Snrpn-GFP allele (IG-DMRGFP/Pat) in the Dlk1-Dio3 locus. The IG-DMR-Snrpn promoter on the paternal allele is hypermethylated so that the GFP reporter is constitutively silenced. The cultured fibroblast cells were infected with lentiviral vectors expressing dCas9-Tet1 and gRNAs to demethylate the Snrpn promoter and activate the GFP reporter. Cells are subject to imaging and FACS analysis. FIG. 7B shows representative immunohistochemical images of IG-DMR$^{GFP/Pat}$ fibroblasts infected with lentiviruses expressing dCas9-Tet1 (dC-T) with a sc gRNA, an inactive form of dCas9-Tet1 (dC-dT) with Snrpn target gRNA, or dCas9-Tet1 with Snrpn target gRNA. Stained in red for Cherry, green for GFP and DAPI for nuclei. Scale bar: 100 um. Note that in order to turn on the Snrpn-GFP methylation reporter, both dCas9-Tet1 and target gRNA lentiviral vectors have to be transduced into the same cells. Therefore, the number of Cherry-positive cells (target gRNA) is expected to be greater than the number of GFP-positive cells (demethylation of the Snrpn promoter) in this experiment. FIG. 7C provides quantification of the percentage of IG-DMR$^{GFP/Pat}$ mouse fibroblast cells with GFP activation in Cherry (gRNAs) positive cells. ~80% cells with the Snrpn target gRNAs expression turned on GFP expression. dC-T with a sc gRNA and an inactive form of dC-T (dC-dT) with Snrpn target gRNAs cannot turn on GFP reporter expression. Bars represent mean±SD of three experimental replicates. FIG. 7D provides a schematic diagram illustrating the experimental procedure for in vivo activation of GFP reporter in the IG-DMR$^{GFP/Pat}$ mouse brain. Lentiviral vectors expressing dC-T and sc gRNA, dC-dT and Snrpn target gRNAs, and dC-T and Snrpn target gRNAs were delivered with stereotaxic microinjection approach. Brains were sliced and analyzed by immunohistochemical approaches. FIG. 7E provides representative confocal micrographs for the IG-DMR$^{GFP/Pat}$ mouse brains infected with dC-T and sc gRNA, dC-dT and Snrpn target gRNAs, and dC-T and Snrpn target gRNAs. Only dC-T with the target gRNAs activated the GFP expression. Scale bar: 100 um. FIGS. 7G-7H provide quantification of the percentage of IG-DMR$^{GFP/Pat}$ cells with GFP activation in Cherry (gRNAs) positive cells in the in vivo lentiviral delivery experiment in the brain (FIG. 7G) and in the skin epidemis (FIG. 7H). About 70% neurons and 85% skin dermal cells transduced with the Snrpn target gRNAs expression turned on GFP expression in vivo. In contrast, dC-T with a scrambled gRNA and an inactive form of Tet1 (dC-dT) with Snrpn target gRNAs did not activate GFP reporter expression. Bars represent mean±SD of more than four representative images from 2 animals.

FIG. 8A depicts design of dCas9-effector constructs with nuclear localization signal (NLS) located at different positions, and guide RNA (gRNA) or enhanced guide RNA (E-gRNA) with CMV-driven puro-T2A-Cherry cassette. Ub: human Ubiquitin C promoter. FIG. 8B shows expression of dCas-NLS-Tet1 and NLS-dCas9-NLS-Tet1 was analyzed by immunoblotting with anti-Cas9 antibody after transfection with these constructs in HEK293T cells for 2 days. α-tubulin was used as a loading control. FIG. 8C provides comparison of the cellular localization of dCas9-NLS-Tet1 and NLS-dCas9-NLS-Tet1 in HEK293T cells with or without co-expression of a gRNA or E-gNRA targeting the same position in the MyoD locus. In the absence of sgRNAs, dCas9-NLS-Tet1 is predominantly excluded from the nuclear compartment, and NLS-dCas9-NLS-Tet1 shows weak nuclear localization in transfected HEK293T cells. Co-expression of either gRNA or E-gRNA induced cytoplasm-to-nucleus translocation of these two proteins. Stained in green for dCas9, red for Cherry and blue for DAPI in the merged images. The red dashed lines in the first two panels indicate the cross section of the images for GFP intensity quantification. Scale bar: 10 um. FIG. 8D provides quantification of the nuclear-cytoplasmic ratio of dCas9-NLS-Tet1 and NLS-dCas9-NLS-Tet1 in HEK293T cells in the absence or presence of a gRNA, or an E-gNRA in a Box and Whiskers plot. Average dCas9 intensity of cytoplasmic and nuclear domain along a cross-sectional line as illustrated in C was used for the quantification. "+" denotes mean value of the 20 data points in each group; the boxes indicate the extreme data points (top and bottom bars), the 25-75% interval (box), and the median (central line). FIG. 8E shows quantification of induction index (defined as the nuclear-cytoplasmic ratio with sgRNA normalized to that without sgRNA) for dCas9-NLS-Tet1 and NLS-dCas9-NLS-Tet1. gRNA and E-gRNA induced 3.17 and 3.22 folds of nuclear localization for dCas9-NLS-Tet1, and 1.73 and 1.77 folds for NLS-dCas9-NLS-Tet1, respectively. We reasoned that the combination with the highest induction index would result in the best signal-to-noise ratio for targeted DNA methylation editing.

FIGS. 9A-9J depict targeted promoter methylation editing to activate Dazle-Snrpn-GFP reporter by dCas9-Tet1 and repress Gapdh-Snrpn-GFP reporter by dCas9-Dnmt3a. FIG. 9A provides genomic sequence of the Dazl-Snrpn locus with gRNA sequences labeled in yellow and CpGs in green. PAM for each gRNA is highlighted by a red box. The Dazl sequence is in lower case, and the Snrpn sequence is in upper case. FIG. 9B provides fluorescence images of Dazl-Snrpn-GFP mESCs infected with lentiviruses expressing dCas9-Tet1 (dC-T) with or without target gRNAs for the Snrpn promoter for 3 days. Scale bar: 120 um. FIG. 9C provides flow cytometric analysis of Dazl-Snrpn-GFP mESCs 3-day after infection with lentiviruses to express dCas9-Tet1 (dC-T) with a scrambled gRNA or 4 gRNAs targeting the Snrpn promoter region. Activation efficiency was calculated by the listed equation and shown as the mean percentages of Cherry and GFP double positive cells±SD of two biological replicates. FIG. 9D depicts bisulfite sequencing of the Dazl-Snrpn region in Cherry+; GFP+ or Cherry+; GFP− cell populations after FACS sorting of Dazl-Snrpn mouse ES cells infected with lentiviruses expressing dC-T and Snrpn gRNAs. FIG. 9E provide genomic sequence of the Gapdh-Snrpn locus with gRNA sequences labeled in yellow and CpGs in green. PAM for each gRNA is highlighted by a red box. The Gapdh sequence is in lower case, and the Snrpn sequence is in upper case. FIG. 9F provide flow cytometric analysis of Gapdh-Snrpn-GFP mESCs at 3-days after infection with lentiviruses to express dCas9-Dnmt3a (dC-D) and 3 gRNAs targeting the Snrpn promoter region. Inactivation efficiency was calculated by the listed equation and shown as the mean percentage of Cherry positive and GFP negative cells±SD of two biological replicates. FIG. 9G depict bisulfite sequencing of the Gapdh-Snrpn region in Cherry+; GFP+ or Cherry+; GFP− cell populations after FACS sorting of Gapdh-Snrpn mouse ES cells infected with lentiviruses expressing dC-D and Snrpn gRNAs. FIG. 9H shows mESCs with stably integrated Doxycycline-inducible dCas9-Dnmt3a cassette were analyzed by RT-qPCR after Doxycycline (2 ug/ml) treatment for 48 hours. Bars represent mean±SD of three experimental replicates. FIG. 9I provide flow cytometric analysis of Gapdh-Snrpn-GFP mESCs with Doxycycline-inducible dCas9-Dnmt3a after 3-day infection with lentiviruses expressing the same 3 gRNAs as in F in the presence of Doxycycline (2 ug/ml). Inactivation efficiency was calculated as shown at the bottom and is expressed as the mean percentage of Cherry positive and GFP negative cells±SD of two biological replicates. FIG. 9J Left panel: shows a schematic diagram of dCas9-Dnmt3a-P2A-BFP construct and gRNA-Cherry constructs. Middle panel: provides percentages of BFP-positive only, Cherry-positive only, and double positive cell populations by FACS analysis of Gapdh-Snrpn-GFP mESCs after infection with lentiviruses expressing dCas9-Dnmt3a-P2A-BFP and Snrpn gRNAs. Right panel: depicts FACS analysis of the percentages of GFP− or GFP+ cells within BFP+; Cherry+ cell population.

FIG. 10A shows HeLa cells were transfected with dCas9-Dnmt3a and one p16 target gRNA (cherry) or TALE-Dnmt3a-GFP. Transfection positive cell populations (cherry+) or (GFP+) were FACS sorted 48-hour post-transfection. Methylation levels of each individual CpG in the p16 promoter region were analyzed by bisulfite sequencing. Shown is the mean percentage±SD of two biological replicates with a total of 34 single colonies sequenced for dCas9-Dnmt3a and 31 single colonies sequenced for TALE-Dnmt3a. Red arrow indicates the position of p16 target gRNA, and purple arrow indicates the binding site for TALE-Dnmt3a. FIG. 10B depicts HEK293T cells were co-transfected with dCas9-Tet1 and one RHOXF2 target gRNA (with puro cassette) or TALE-Tet1 with a puro cassette expressing plasmid. Puromycin (2 ug/ml) was added to the culture medium to select for transfection positive cells. Cells were harvested after 2-day selection for analysis of methylation levels for individual CpGs in the RHOXF2 promoter region by bisulfite sequencing. Shown is the mean percentage±SD of two biological replicates with a total of 34 single colonies sequenced for dCas9-Tet1 and 38 single colonies sequenced for TALE-Tet1. Red arrow indicates the position of RHOXF2 target gRNA, and purple arrow indicates the binding site for TALE-Dnmt3a. FIG. 10C provides a summary of methylation level analysis in A and B. The effective range was determined by the distance of CpGs that were significantly edited by dCas9-Dnmt3a/

Tet1 (change of methylation greater than 10%) from the site of gRNA targeting. The resolution is defined as the effective range of dCas9-Dnmt3a/Tet1 with one single gRNA, and better resolution is referred to the shorter effective range of dCas9-Dnmt3a/Tet1 which will allow for more precise editing of DNA methylation. FIG. 10D shows Dox-inducible dCas9-Dnmt3a expression mouse ES cells described in FIG. 9H were infected with a scrambled gRNA or gRNAs targeting the miR290 locus or Dazl-Snrpn locus. FACS sorted Cherry-positive cells were cultured with Dox (2 ug/ml) for 3 days. Then these cells were harvested for anti-dCas9 ChIP-seq analysis. Peaks were called with the pairwise peak calling procedure described previously (Wu et al., 2014), and presented in a Manhattan plot depicting genome-wide ChIP-seq peaks. All peaks with p<0.001 are shown. Each dot represents a peak, with the X-axis showing genomic location and Y-axis showing the peak summit height output by Model-based Analysis of ChIP-Seq (MACS) (Zhang et al., 2008). The size of each dot is proportional to its Y-axis value, and individual chromosome is colored differently for visualization. FIG. 10E depicts ChIP-seq peaks at the targeted loci (miR290 or Dazl-Snrpn) with the highest level of signal and at two off-target loci with the second and third highest signals (Vac14 and Tenm4 loci for miR290 gRNAs; Vrk1 and Gm42619 loci for Dazl-Snrpn gRNAs) are illustrated with the nearby genes listed below. Note that the 4 Dad-Snrpn gRNAs recognize the promoter sequences of Dad and Snrpn as described in FIG. 9A, so the peaks for this group of gRNAs were mapped to both loci. FIG. 10F shows genomic DNA from cells used in FIG. 5C was subject to bisulfite sequencing of the off-target binding sites at Vac14 and Tenm4 loci. Shown is the mean percentage±SD of two biological replicates. FIG. 10G shows genomic DNA from cells used in FIG. 1D and FIG. 2C was subject to bisulfite sequencing of the off-target binding sites at Vrk1 and Gm42619 loci. Shown is the mean percentage±SD of two biological replicates.

FIG. 11A shows genomic sequence of the BDNF promoter IV region with gRNA sequences labeled in yellow and CpGs in green. PAM for each gRNA is highlighted by a red box. FIG. 11B Left panel: shows a schematic diagram depicting the KCl treatment and lentiviral delivery experiment on E17.5 mouse primary cortical neurons to investigate BDNF expression. Note that cultured neurons were treated with AraC on DIV2 to halt cell division in glial cells and neural progenitors. Right panel: shows DIV3 mouse cortical neurons were treated with 50 mM of KCl, and harvested at different time points for BDNF expression analysis by RT-qPCR. FIG. 11C provides EDU labeling analysis for the mouse primary neurons over the course of KCl treatment for 24 hrs. Note that extremely few EDU positive cells were observed. Stained in red for EDU, green for MAP2 and DAPI for nuclei. Scale bar: 500 um. FIG. 11D Upper panel: provides quantification of neuronal density over the course of KCl treatment. The post-mitotic neuron density remains steadily around 4.5×10$^4$/cm$^2$ over time. Bars represent mean±SD of three experimental replicates. Lower panel: provides quantification of the EDU positive cells over the course of KCl treatment. Less than 2% of the cells are EDU-positive over 24 hrs. Bars represent mean±SD of three experimental replicates. FIG. 11E provides confocal micrographs of BDNF induction by ectopic expression of dCas9-Tet1 and a set of 4 gRNAs targeting BDNF promoter IV. Stained in green for BDNF, magenta for MAP2, red for Cherry and blue for DAPI. Note that the lentiviral infection efficiency is close to 100% in these neurons. Scale bar: 50 um. FIG. 11F shows neurons harvested from B and E were subjected to RT-qPCR analysis for Npas4 expression. Bars represent mean±SD of three experimental replicates. FIG. 11G shows DIV3 mouse cortical neurons were infected with dC-T alone or together with 4 gRNAs targeting BDNF promoter IV or individual BDNF gRNA, and then subject to qPCR analysis for BDNF expression. FIGS. 11H-11I shows Tet Assisted Bisulfite sequencing (TAB-Seq) analysis of neurons infected with lentiviruses expressing dC-T or dC-dT with 4 BDNF gRNAs for 40 and 60 hours in H, or neurons after KCl treatment for 6 hours in FIG. 11I. FIG. 11J depicts DIV3 mouse cortical neurons were treated with ABT (50 uM) for 6 hours and then treated with KCl (50 mM) for 6-hour before harvest for RT-qPCR analysis. Bars represent mean±SD of three experimental replicates. FIG. 11K depicts DIV3 mouse cortical neurons were treated with 2-Hydroxyglutarate (10 mM) for 2 hours and then treated with KCl (50 mM) for 6-hour before harvest for RT-qPCR analysis. Bars represent mean±SD of three experimental replicates. FIG. 11L depicts DIV3 mouse cortical neurons derived from wild-type or Tet1 knockout E17.5 embryos were subject to time course KCl treatment experiments (6, 9 and 12 h). Bars represent mean±SD of three experimental replicates.

FIGS. 12A-12J depict targeted demethylation of the MyoD DMR-5 by dCas9-Tet1 and conversion of fibroblasts to myoblasts. FIG. 12A shows genomic sequence of the MyoD distal enhancer region with gRNA sequences labeled in yellow and CpGs in green. PAM for each sgRNA is highlighted by a red box. FIG. 12B provides experimental scheme of the fibroblast-to-myoblast conversion assay. Briefly, C3H10T1/2 mouse embryonic fibroblast cells were plated as 1×10$^4$ cells per well in 6-well plate, and then infected with lentiviruses expressing dCas9-Tet1 and target gRNAs. 24-hour post infection, cells were optionally treated with 5-Azacytidine (1 uM) for 24-hour (labeled in red), and harvested for immunofluorescence staining at different time points (day-14, -16 and -25, labeled in dark blue) with medium change every other day. Scale bar: 100 um. FIG. 12C shows representative confocal micrographs of myotube formation for C3H10T1/2 fibroblast cells after 5-Aza treatment. Upper panel: shows a clonal field contains sparsely distributed small and mid-size myotubes. Middle panel: shows a clonal field contains sparsely distributed large size myotubes. Bottom panel: shows a clonal field contains high density of myotubes with heterogeneous size. Stained in green for MHC, red for MyoD and blue for DAPI. Scale bar: 200 um. FIG. 12D depicts a fraction of mock C3H10T1/2 cells expressing MyoD at different times after 5-Aza treatment. The fraction of cells expressing MyoD increases from around 6% at day 14 to around 13% at day 16 and reached around 20% at day 25. Bars represent mean±SD. FIG. 12E provides number of nuclei in MHC+ cell clusters (grouped as 1-2 and >2 nuclei per MHC+ cluster). Formation of larger myotubes was observed at later time points after 5-Aza treatment. Bars represent mean±SD. Data was quantified from 3-5 representative images for each group in FIG. 12D and FIG. 12E. FIG. 12F shows C3H10T1/2 cells were infected with lentiviruses expressing dC-T with MyoD gRNAs for 24-hour, and treated with or without 5-Aza for 48-hour before harvested for qPCR analysis. Bars represent mean±SD of three experimental replicates. FIG. 12G provides representative images for C3H10T1/2 cells 16 days after infection with lentiviruses expressing dC-T and gRNAs targeting DMR-5 (MyoD distal enhancer) in a fibroblast-to-myoblast conversion assay as described in FIG. 12B. Note that a modest level of MyoD activation (compared to the cells treated by 5-Aza) was observed in cells with dC-T and target gRNA, but not myosin heavy chain (MHC) expression or myotube formation. Stained in magenta for MHC, green for MyoD and blue for DAPI. Scale bar: 200 um. FIG. 12H depicts a fraction of MyoD positive cells 16 days after infection with lentiviruses expressing dC-T alone or with gRNAs targeting DMR-5. FIG. 12I show a number of nuclei in MHC+ cell clusters (grouped as 2-5, 6-10, 11-20 and >20 nuclei per MHC+ cluster) 16 days after infection. When treated with 5-Aza, co-expression of gRNAs and dC-T significantly facilitated formation of larger and more maturated MHC+ clusters compared to mock control or dC-T alone. FIG. 12J shows myotube density of MHC positive clusters with more than 2 or 5 nuclei 16 days after infection. Addition of 5-Aza induces MHC+ myotube formation. Co-expression of dC-T and gRNAs significantly induced more and larger myotubes (>5 nuclei MHC+ clusters). Data are quantified from 3-5 representative images for FIGS. 12H-12J. Bars represent mean±SD.

FIG. 13A provides genomic sequence of the CTCF target 1 region (miR290 locus) with gRNA sequences labeled in yellow and CpGs in green. PAM for each sgRNA is highlighted by a red box, predicted CTCF binding motif is highlighted in a blue box. FIG. 13B provides genomic sequence of the CTCF target 2 region (H2Q10-Pou5f1 locus) with gRNA sequences labeled in yellow and CpGs in green. PAM for each sgRNA is highlighted by a red box, predicted CTCF binding motif is highlighted in blue boxes.

FIG. 14A provides a schematic diagram illustrating the experimental procedure for ex vivo activation of the silenced GFP reporter in IG-DMR$^{GFP/Pat}$ mouse fibroblasts. The cultured fibroblasts were infected with lentiviral vectors expressing dCas9-Tet1 and gRNAs to demethylate the Snrpn promoter and activate the GFP reporter. FIG. 14B provides FACS analysis of the infected IG-DMR$^{GFP/Pat}$ mouse fibroblasts. FIG. 14C shows quantification of the percent of GFP+ cells in Cherry positive cell population in FIG. 14B. FIG. 14D provides a schematic diagram illustrating the lentiviral delivery approach for each site on the ventral side of the IG-DMR$^{GFP/Pat}$ mouse. FIG. 14E provides representative confocal micrographs for the IG-DMR$^{GFP/Pat}$ mouse skin infected with dCas9-Tet1 and sc gRNA, an inactive form of Tet1 (dC-dT) and the Snrpn gRNAs, and dCas9-Tet1 with Snrpn gRNAs. Arrowheads indicate that only dC-T with Snrpn gRNAs activated the GFP expression. Note red auto-fluorescence on the left edges of the epidermis. FIG. 14F provides representative confocal micrographs of 2 hair follicles with lentiviral delivery for dC-T and Snrpn gRNAs to activate the GFP expression.

FIG. 19A demonstrates the demethylation of DazI-Snrpn-GFP reporter and methylation of Gapdh-Snrpn-GFP reporter. FIG. 19B demonstrates targeted demethylation of BDNF promoter IV by dCas9-Tet1 to activate BDNF. FIG. 19C demonstrates targeted demethylation of the MyoD distal enhancer by dCas9-Tet1 to facilitate muscle cell transdifferentiation. FIG. 19D demonstrates targeted methylation of CTCF binding sites.

FIG. 19E demonstrates targeted in vivo DNA methylation editing by dCas9-Tet1 to activate a silenced GFP reporter.

FIG. 23A demonstrates a three-dimensional structure of a chromosome. FIG. 23B shows gene expression level of the indicated genes in wild type and CTCF site-deleted cells measured by qRT-PCR. FIG. 23C shows anti-CTCF ChIP experiment was performed using cells in C followed by quantitative PCR analysis. Bars represent mean±SD of three experimental replicates.

DETAILED DESCRIPTION OF THE INVENTION

Figure 1A:
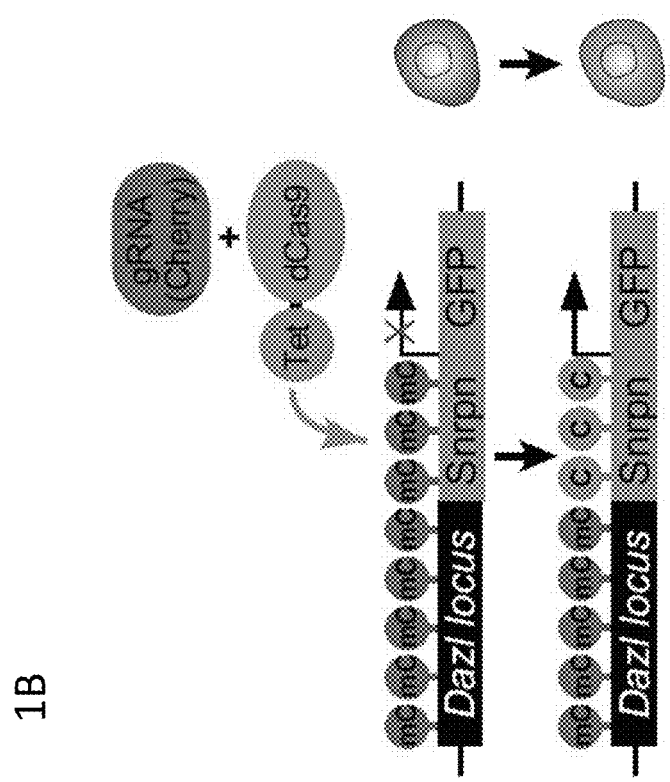
FIGS. 1A-1F depict activation of the Dazl-Snrpn-GFP reporter by dCas9-Tet1.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, ncbi.nlm.nih.gov/omim/and in Online Mendelian Inheritance in Animals (OMIA), a database of genes, inherited disorders and traits in animal species (other than human and mouse), at omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

In one aspect, the invention is directed to a method of modifying or modulating one or more genomic sequences in a cell comprising introducing into the cell a catalytically inactive site specific nuclease fused to an effector domain having methylation activity or demethylation activity, and one or more guide sequences. The method can result in the modification of the one or more genomic sequences in the cell. An isolated modified cell may be produced by the described method. The catalytically inactive site specific nuclease may bind to each of the one or more guide sequences and the effector domain modulates the methylation or demethylation (e.g., DNA methylation or DNA demethylation) of the genomic sequence. One or more guide sequences, catalytically inactive site specific nucleases and effector domains can be introduced into a cell, zygote, embryo or non-human mammal.

In other aspects, the invention is directed to a method of modulating the methylation of one or more genomic sequences in a cell. The method may comprise contacting the cell with a nucleic acid that encodes a polypeptide comprising a catalytically inactive site specific nuclease fused to an effector domain having methylation or demethylation activity. The cell is further contacted with a guide sequence or a nucleic acid that encodes a guide sequence. In some aspects, the guide sequence targets the polypeptide to the one or more genomic sequences. In some embodiments, the contacting of the cell may include introducing directly into the cell. In other aspects, the contacting of the cell includes expressing in the cell or inducing expression in the cell. Reporters of genomic methylation are described in U.S. application Ser. No. 15/078,851, which is incorporated herein by reference in its entirety.

There are various ways that a polypeptide comprising a catalytically inactive site specific nuclease fused to an effector domain having methylation or demethylation activity can be delivered to a cell or subject, e.g., by administering a nucleic acid that encodes the polypeptide, which nucleic acid may be, e.g., a viral vector or may be a translatable nucleic acid (e.g, synthetic modified mRNA. Examples of modified mRNA are described in Warren et al. (Cell Stem Cell 7(5):618-30, 2010, Mandal P K, Rossi D J. Nat Protoc. 2013 8(3):568-82, US Pat. Pub. No. 20120046346 and/or PCT/US2011/032679 (WO/2011/130624). Additional examples are found in numerous PCT and US applications and issued patents to Moderna Therapeutics, e.g., PCT/US2011/046861; PCT/US2011/054636, PCT/US2011/054617, U.S. Ser. No. 14/390,100 (and additional patents and patent applications mentioned in these.) Also, the guide sequence can be delivered as a nucleic acid that encodes the guide sequence. For example, administration can be performed by direct administration to a tissue or organ (e.g., skin, heart, liver, lung, kidney, brain, eye, muscle, bone, nerve) or tumor. Administration may be by any route (e.g., oral, intravenous, intraperitoneal, gavage, topical, transdermal, intramuscular, enteral, subcutaneous), may be systemic or local, may include any dose (e.g., from about 0.01 mg/kg to about 500 mg/kg), may involve a single dose or multiple doses. The nucleic acids may be encapsulated, e.g., in liposomes, polymeric particles (e.g., PLGA particles).

The methods described herein can be used to modify or modulate one or more genomic sequences in a variety of cells, which includes somatic cells, stem cells, mitotic or post-mitotic cells, neurons, fibroblasts, or zygotes. A cell, zygote, embryo, or post-natal mammal can be of vertebrate (e.g., mammalian) origin. In some aspects, the vertebrates are mammals or avians. Particular examples include primate (e.g., human), rodent (e.g., mouse, rat), canine, feline, bovine, equine, caprine, porcine, or avian (e.g., chickens, ducks, geese, turkeys) cells, zygotes, embryos, or post-natal mammals. In some embodiments, the cell, zygote, embryo, or post-natal mammal is isolated (e.g., an isolated cell; an isolated zygote; an isolated embryo). In some embodiments, a mouse cell, mouse zygote, mouse embryo, or mouse post-natal mammal is used. In some embodiments, a rat cell, rat zygote, rat embryo, or rat post-natal mammal is used. In some embodiments, a human cell, human zygote or human embryo is used. The methods described herein can be used to modify or modulate one or more genomic sequences (e.g., methylate or demethylate a genomic sequence) in a mammal (e.g., a mouse) in vivo.

Stem cells may include totipotent, pluripotent, multipotent, oligipotent and unipotent stem cells. Specific examples of stem cells include embryonic stem cells, fetal stem cells, adult stem cells, and induced pluripotent stem cells (iPSCs) (e.g., see U.S. Published Application Nos. 2010/0144031, 2011/0076678, 2011/0088107, 2012/0028821 all of which are incorporated herein by reference).

Somatic cells may be primary cells (non-immortalized cells), such as those freshly isolated from an animal, or may be derived from a cell line capable of prolonged proliferation in culture (e.g., for longer than 3 months) or indefinite proliferation (immortalized cells). Adult somatic cells may be obtained from individuals, e.g., human subjects, and cultured according to standard cell culture protocols available to those of ordinary skill in the art. Somatic cells of use in aspects of the invention include mammalian cells, such as, for example, human cells, non-human primate cells, or rodent (e.g., mouse, rat) cells. They may be obtained by well-known methods from various organs, e.g., skin, lung, pancreas, liver, stomach, intestine, heart, breast, reproductive organs, muscle, blood, bladder, kidney, urethra and other urinary organs, etc., generally from any organ or tissue containing live somatic cells. Mammalian somatic cells useful in various embodiments include, for example, fibroblasts, Sertoli cells, granulosa cells, neurons, pancreatic cells, epidermal cells, epithelial cells, endothelial cells, hepatocytes, hair follicle cells, keratinocytes, hematopoietic cells, melanocytes, chondrocytes, lymphocytes (B and T lymphocytes), macrophages, monocytes, mononuclear cells, cardiac muscle cells, skeletal muscle cells, etc.

In some aspects, one or more guide sequences include sequences that recognize DNA in a site-specific manner. For example, guide sequences can include guide ribonucleic acid (RNA) sequences utilized by a CRISPR system or sequences within a TALEN or zinc finger system that recognize DNA in a site-specific manner. The guide sequences comprise a portion that is complementary to a portion of each of the one or more genomic sequences and comprise a binding site for the catalytically inactive site specific nuclease. In some embodiments, the RNA sequence is referred to as guide RNA (gRNA) or single guide RNA (sgRNA).

In some aspects, a single RNA sequence can be complementary to one or more (e.g., all) of the genomic sequences that are being modulated or modified. In one aspect, a single RNA is complementary to a single target genomic sequence.

In a particular aspect in which two or more target genomic sequences are to be modulated or modified, multiple (e.g., 2, 3, 4, 5, 6, 7, 8, 9, 10, or more) RNA sequences are introduced wherein each RNA sequence is complementary to (specific for) one target genomic sequence. In some aspects, two or more, three or more, four or more, five or more, or six or more RNA sequences are complementary to (specific for) different parts of the same target sequence. In one aspect, two or more RNA sequences bind to different sequences of the same region of DNA. In some aspects, a single RNA sequence is complementary to at least two target or more (e.g., all) of the genomic sequences. It will also be apparent to those of skill in the art that the portion of the RNA sequence that is complementary to one or more of the genomic sequences and the portion of the RNA sequence that binds to the catalytically inactive site specific nuclease can be introduced as a single sequence or as 2 (or more) separate sequences into a cell, zygote, embryo or nonhuman animal. In some embodiments the sequence that binds to the catalytically inactive site specific nuclease comprises a stem-loop.

In some embodiments, an RNA sequence used to modify gene expression in a nonhuman mammal is a naturally occurring RNA sequence, a modified RNA sequence (e.g., a RNA sequence comprising one or more modified bases), a synthetic RNA sequence, or a combination thereof. As used herein a "modified RNA" is an RNA comprising one or more modifications (e.g., RNA comprising one or more non-standard and/or non-naturally occurring bases) to the RNA sequence (e.g., modifications to the backbone and or sugar). Methods of modifying bases of RNA are well known in the art. Examples of such modified bases include those contained in the nucleosides 5-methylcytidine (5mC), pseudouridine (T), 5-methyluridine, 2'0-methyluridine, 2-thiouridine, N-6 methyladenosine, hypoxanthine, dihydrouridine (D), inosine (I), and 7- methylguanosine (m7G). It should be noted that any number of bases in a RNA sequence can be substituted in various embodiments. It should further be understood that combinations of different modifications may be used.

In some aspects, the RNA sequence is a morpholino. Morpholinos are typically synthetic molecules, of about 25 bases in length and bind to complementary sequences of RNA by standard nucleic acid base-pairing. Morpholinos have standard nucleic acid bases, but those bases are bound to morpholine rings instead of deoxyribose rings and are linked through phosphorodiamidate groups instead of phosphates. Morpholinos do not degrade their target RNA molecules, unlike many antisense structural types (e.g., phosphorothioates, siRNA). Instead, morpholinos act by steric blocking and bind to a target sequence within a RNA and block molecules that might otherwise interact with the RNA.

Each RNA sequence can vary in length from about 8 base pairs (bp) to about 200 bp. In some embodiments, the RNA sequence can be about 9 to about 190 bp; about 10 to about 150 bp; about 15 to about 120 bp; about 20 to about 100 bp; about 30 to about 90 bp; about 40 to about 80 bp; about 50 to about 70 bp in length.

The portion of each genomic sequence to which each RNA sequence is complementary can also vary in size. In particular aspects, the portion of each genomic sequence to which the RNA is complementary can be about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 39, 40, 41, 42, 43, 44, 45, 46 47, 48, 49, 50, 51, 52, 53, 54, 55, 56, 57, 58, 59 60, 61, 62, 63, 64, 65, 66, 67, 68, 69, 70, 71, 72, 73, 74, 75, 76, 77, 78, 79, 80 81, 82, 83, 84, 85, 86, 87 88, 89, 90, 81, 92, 93, 94, 95, 96, 97, 98, or 100 nucleotides (contiguous nucleotides) in length. In some embodiments, each RNA sequence can be at least about 70%, 75%, 80%, 85%, 90%, 95%, 100%, etc. identical or similar to the portion of each genomic sequence. In some embodiments, each RNA sequence is completely or partially identical or similar to each genomic sequence. For example, each RNA sequence can differ from perfect complementarity to the portion of the genomic sequence by about 1, 2, 3, 4, 5, 6, 7, 8, 9, 10, 11, 12, 13, 14, 15, 16, 17, 18, 19, 20, etc. nucleotides. In some embodiments, one or more RNA sequences are perfectly complementary (100%) across at least about 10 to about 25 (e.g., about 20) nucleotides of the genomic sequence.

The one or more guide sequences (e.g., RNA sequences) can be complementary to any of a variety of all or a portion of a target genomic sequence that is to be modified. In some aspects, the target genomic sequence comprises a differentially methylated region, an enhancer (e.g., MyoD distal enhancer), a promoter (e.g., BDNF promoter), a reporter, or a CTCF binding site.

In some aspects of the invention, the method of modulating one or more genomic sequences comprises introducing one or more guide sequences that are complementary to all or a portion of a (one or more) regulatory region, an open reading frame (ORF; a splicing factor), an intronic sequence, a chromosomal region (e.g., telomere, centromere) of the one or more genomic sequences into a cell. In some aspects, the genomic sequence is all or a portion of a plasmid or linear double stranded DNA (dsDNA). In some aspects, the regulatory region targeted by the one or more genomic sequences is a promoter, enhancer, and/or operator region. In some aspects, all or a portion of the regulatory region is targeted by the one or more genomic sequences. All or a portion of the region targeted by the one or more genomic sequences may be a differentially methylated region. In some aspects, the differentially methylated region is exactly or within about 25 bases, 50 bases, 100 bases, 200 bases, 300 bases, 400 bases, 500 bases, 600 bases, 700 bases, 800 bases, 900 bases, 1000 bases, 1500 bases, 2000 bases, 5000 bases, 10000 bases, 20000 bases, 50000 bases or more upstream to the one or more genes (e.g., endogenous genes; exogenous genes) or a (one or more) transcription start site (TSS). In some aspects, the differentially methylated region is exactly or within about 25 bases, 50 bases, 100 bases, 200 bases, 300 bases, 400 bases, 500 bases, 600 bases, 700 bases, 800 bases, 900 bases, 1000 bases, 1500 bases, 2000 bases, 5000 bases, 10000 bases, 20000 bases, 50000 bases, or more downstream to the one or more genes (e.g., endogenous genes; exogenous genes) or a TSS. As will be appreciated by one of ordinary skill in the art, the regulatory region targeted by one or more genomic sequences can be entirely or partially found at or about the 5' end of the gene (e.g., endogenous or exogenous) or a TSS. The 5' end of a gene can include untranscribed (flanking) regions (e.g., all or a portion of a promoter) and a portion of the transcribed region.

As will be apparent to those of ordinary skill in the art, the one or more RNA sequences can further comprise one or more expression control elements. For example, in some embodiments the RNA sequences comprises a promoter, suitable to direct expression in cells, wherein the portion of the RNA sequence is operably linked to the expression control element(s). The promoter can be a viral promoter (e.g., a CMV promoter) or a mammalian promoter (e.g., a PGK promoter). The RNA sequence can comprise other genetic elements, e.g., to enhance expression or stability of a transcript. In some embodiments the additional coding region encodes a selectable marker (e.g., a reporter gene such as green fluorescent protein (GFP)).

As described herein, the one or more RNA sequences also comprise a (one or more) binding site for a (one or more) catalytically inactive site specific nuclease. The catalytically inactive site specific nuclease may be a catalytically inactive CRISPR associated (Cas) protein. In a particular aspect, upon hybridization of the one or more RNA sequences to the one or more genomic sequences, the catalytically inactive site specific nuclease binds to the one or more RNA sequences.

In some aspects, the method of modulating one or more genomic sequences comprises adjusting the level of modulation of one or more genomic sequences by adjusting the amount (e.g. grams, milligrams, micrograms, nanograms, moles, millimoles, micromoles, nanomoles, stoichiometric amount, molar ratio) of the one or more guide sequences introduced into the cell or zygote. In some aspects, the level of modulation of one genomic sequence is the same or different compared to the level of modulation of another genomic sequence in the same cell or zygote. In one aspect, multiple genomic sequences are modulated (e.g. multiplexed activation).

In one aspect, the method further comprises introducing one or more catalytically inactive Cas (dCas) nucleic acid or variant thereof into the cell, embryo, zygote, or non-human mammal. In some aspects, a dCas protein or variant thereof is introduced into the cell, embryo, zygote, or non-human mammal. In some aspects, a cell, e.g., post-mitotic cell, neuron, fibroblast, stem cell (ES or iPS cell), zygote, embryo, or animal may already harbor a nucleic acid that encodes dCas (may be constitutive or inducible) and/or may already contain dCas protein. For example, in some embodiments a cell, zygote, embryo, or animal, may be descended from a cell or organism into which a nucleic acid encoding a dCas protein has been introduced by a process involving the hand of man.

A variety of CRISPR associated (Cas) genes or proteins which are known in the art can be used in the methods of the invention and the choice of Cas protein will depend upon the particular conditions of the method (e.g., ncbi.nlm.nih.gov/gene/?term=cas9). Specific examples of Cas proteins include Cas1, Cas2, Cas3, Cas4, Cas5, Cas6, Cas7, Cas8, Cas9 and Cas10. In a particular aspect, the Cas nucleic acid or protein used in the methods is Cas9. In some embodiments a Cas protein, e.g., a Cas9 protein, may be from any of a variety of prokaryotic species. In some embodiments a particular Cas protein, e.g., a particular Cas9 protein, may be selected to recognize a particular protospacer-adjacent motif (PAM) sequence. In certain embodiments a Cas protein, e.g., a Cas9 protein, may be obtained from a bacteria or archaea or synthesized using known methods. In certain embodiments, a Cas protein may be from a gram positive bacteria or a gram negative bacteria. In certain embodiments, a Cas protein may be from a *Streptococcus*, (e.g., a *S. pyogenes*, a *S. thermophilus*) a *Crptococcus*, a *Corynebacterium*, a *Haemophilus*, a *Eubacterium*, a *Pasteurella*, a *Prevotella*, a *VeiUonella*, or a *Marinobacter*. In some embodiments nucleic acids encoding two or more different Cas proteins, or two or more Cas proteins, may be introduced into a cell, zygote, embryo, or animal, e.g., to allow for recognition and modification of sites comprising the same, similar or different PAM motifs.

In some embodiments, the Cas protein is Cpf1 protein or a functional portion thereof. In some embodiments, the Cas protein is Cpf1 from any bacterial species or functional portion thereof. In certain embodiments, a Cpf1 protein is a *Francisella novicida* U112 protein or a functional portion thereof, a *Acidaminococcus* sp. BV3L6 protein or a functional portion thereof, or a *Lachnospiraceae* bacterium ND2006 protein or a function portion thereof. Cpf1 protein is a member of the type V CRISPR systems. Cpf1 protein is a polypeptide comprising about 1300 amino acids. Cpf1 contains a RuvC-like endonuclease domain.

In some embodiments a Cas9 nickase may be generated by inactivating one or more of the Cas9 nuclease domains. In some embodiments, an amino acid substitution at residue 10 in the RuvC I domain of Cas9 converts the nuclease into a DNA nickase. For example, the aspartate at amino acid residue 10 can be substituted for alanine (Cong et al, Science, 339:819-823). Other amino acids mutations that create a catalytically inactive Cas9 protein includes mutating at residue 10 and/or residue 840. Mutations at both residue 10 and residue 840 can create a catalytically inactive Cas9 protein, sometimes referred herein as dCas9. For example, a D10A and a H840A Cas9 mutant is catalytically inactive.

Modulating one or more genomic sequences may comprise introducing one or more effector domains. As used herein an "effector domain" is a molecule (e.g., protein) that modulates the expression and/or activation of a genomic sequence (e.g., gene). The effector domain may have methylation activity or demethylation activity (e.g., DNA methylation or DNA demethylation activity). In some aspects, the effector domain targets one or both alleles of a gene. The effector domain can be introduced as a nucleic acid sequence and/or as a protein. In some aspects, the effector domain can be a constitutive or an inducible effector domain. In some aspects, a Cas (e.g., dCas) nucleic acid sequence or variant thereof and an effector domain nucleic acid sequence are introduced into the cell as a chimeric sequence. In some aspects, the effector domain is fused to a molecule that associates with (e.g., binds to) Cas protein (e.g., the effector molecule is fused to an antibody or antigen binding fragment thereof that binds to Cas protein). In some aspects, a Cas (e.g., dCas) protein or variant thereof and an effector domain are fused or tethered creating a chimeric protein and are introduced into the cell as the chimeric protein. In some aspects, the Cas (e.g., dCas) protein and effector domain bind as a protein-protein interaction. In some aspects, the Cas (e.g., dCas) protein and effector domain are covalently linked. In some aspects, the effector domain associates non-covelently with the Cas (e.g., dCas) protein. In some aspects, a Cas (e.g., dCas) nucleic acid sequence and an effector domain nucleic acid sequence are introduced as separate sequences and/or proteins. In some aspects, the Cas (e.g., dCas) protein and effector domain are not fused or tethered.

As shown herein, fusions of a catalytically inactive (D10A; H840A) Cas9 protein (dCas9) tethered with all or a portion of (e.g., biologically active portion of) an (one or more) effector domain create chimeric proteins that can be guided to specific DNA sites by one or more RNA sequences (sgRNA) to modulate activity and/or expression of one or more genomic sequences (e.g., exert certain effects on transcription or chromatin organization, or bring specific kind of molecules into specific DNA loci, or act as sensor of local histone or DNA state). In specific aspects, fusions of a dCas9 tethered with all or a portion of an effector domain create chimeric proteins that can be guided to specific DNA sites by one or more RNA sequences to modulate or modify methylation or demethylation of one or more genomic sequences. As used herein, a "biologically active portion of an effector domain" is a portion that maintains the function (e.g. completely, partially, minimally) of an effector domain (e.g., a "minimal" or "core" domain). The fusion of the Cas9 (e.g., dCas9) with all or a portion of one or more effector domains created a chimeric protein.

Examples of effector domains include a transcription(al) activating domain, a coactivator domain, a transcription factor, a transcriptional pause release factor domain, a negative regulator of transcriptional elongation domain, a transcriptional repressor domain, a chromatin organizer domain, a remodeler domain, a histone modifier domain, a DNA modification domain, a RNA binding domain, a protein interaction input devices domain (Grunberg and Serrano, Nucleic Acids Research, 3 '8 (8): '2663-267 '5 (2010)), and a protein interaction output device domain (Grunberg and Serrano, Nucleic Acids Research, 3 '8 (8): '2663-267 '5 (2010)). As used herein a "protein interaction input device" and a "protein interaction output device" refers to a protein-protein interaction (PPI). In some embodiments the PPI is regulatable, e.g., by a small molecule or by light. In some aspect, binding partners are targeted to different sites in the genome using the inactive Cas protein. The binding partners interact, thereby bringing the targeted loci into proximity. A protein interaction output device is a system for detecting/monitoring occurrence of a PPI, generally by producing a detectable signal when the PPI occurs (e.g., by reconstituting a fluorescent protein) or to trigger specific cellular responses {e.g., by reconstituting a caspase protein to induce apoptosis). The idea in this context is to target different sites in the genome with the components of the "output device". If the interaction occurs, the "output device" generates a signal. This can be used to determine or monitor the proximity of the targeted loci. In some aspects, cells are treated with an agent and the effect of the agent on the cell is determined. Other examples of effector domains include histone marks readers/interactors (cell.com/abstract/S0092-8674(10)00951-7) and DNA modification readers/interactors.

In some aspects, the effector domain is a DNA modifier. Specific examples of DNA modifiers include 5hmc conversion from 5mC such as Tet1 (Tet1CD); DNA demethylation by Tet1, ACID A, MBD4, Apobec1, Apobec2, Apobec3, Tdg, Gadd45a, Gadd45b, ROS1; DNA methylation by Dnmt1, Dnmt3a, Dnmt3b, CpG Methyltransferase M.SssI, and/or M.EcoHK31I. In specific aspects, an effector domain is Tet1. In other specific aspects, as effector domain is Dmnt3a. In some embodiments, dCas9 is fused to Tet1. In other embodiments, dCas9 is fused to Dnmt3a.

DNA methylation is established by two de novo DNA methyltransferases (Dnmt3a/b), and is maintained by Dnmt1 (Smith and Meissner, 2013). Gene activation during development is associated with demethylation of promoter and enhancer sequences. In addition, demethylation can be achieved through oxidation of the methyl group by TET (ten-eleven translocation) dioxygenases to form 5-hydroxymethylcytosine (5-hmC), and then restoration into unmodified cytosines by either DNA replication-dependent dilution or DNA glycosylase-initiated base excision repair (BER), a process termed as active demethylation and proposed to operate during specific developmental stages such as preimplantation embryos or in post-mitotic neurons (Wu and Zhang, 2014).

In one aspect of the invention, fusion of the dCas9 to an effector domain can be to that of a single copy or multiple/tandem copies of full-length or partial-length effectors. Other fusions can be with split (functionally complementary) versions of the effector domains. Effector domains for use in the methods include any one of the following classes of proteins: proteins that mediate drug inducible looping of DNA and/or contacts of genomic loci, proteins that aid in the three-dimensional proximity of genomic loci bound by dCas9 with different sgRNA.

Other examples of effector domains are described in PCT Application No. PCT/US2014/034387 and U.S. application Ser. No. 14/785,031, which are incorporated herein by reference in their entirety.

In some aspects the invention is directed to (e.g., a composition comprising, consisting essentially of, consisting of) a nucleic acid sequence that encodes a fusion protein (chimeric protein) comprising all or a portion of a Cas (e.g., dCas) protein fused to all or a portion of an effector domain. In some aspects, the invention is directed to (e.g., a composition comprising, consisting essentially of, consisting of) a fusion protein comprising all or a portion of a Cas (e.g., dCas) protein fused to all or a portion of an effector domain. In some aspects all or a portion of the Cas (e.g., dCas) protein targets but does not cleave a nucleic acid sequence. In some aspects, the Cas (e.g., dCas) protein can be fused to the N-terminus or C-terminus of the effector domain. In some aspects, the portion of the effector domain modulates the methylation of the genomic sequence (e.g., demethylates or methylates the genomic sequence).

In some aspects, the nucleic acid sequence encoding the fusion protein and/or the fusion protein are isolated. An "isolated," "substantially pure," or "substantially pure and isolated" nucleic acid sequence, as used herein, is one that is separated from nucleic acids that normally flank the gene or nucleotide sequence (as in genomic sequences) and/or has been completely or partially purified from other transcribed sequences (e.g., as in an RNA or cDNA library). For example, an isolated nucleic acid of the invention may be substantially isolated with respect to the complex cellular milieu in which it naturally occurs, or culture medium when produced by recombinant techniques, or chemical precursors or other chemicals when chemically synthesized. An "isolated," "substantially pure," or "substantially pure and isolated" protein (e.g., chimeric protein; fusion protein), as used herein, is one that is separated from or substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system, or reagent mix. In other circumstances, the material may be purified to essential homogeneity, for example, as determined by agarose gel electrophoresis or column chromatography such as HPLC. Preferably, an isolated nucleic acid molecule comprises at least about 50%, 80%, 90%, 95%, 98% or 99% (on a molar basis) of all macromolecular species present.

In one aspect, fusion of Cas9 with all or a portion of one or more effector domains comprise one or more linkers. As used herein, a "linker" is something that connects or fuses two or more effector domains (e.g see Hermanson, Bioconjugate Techniques, $2^{nd}$ Edition, which is hereby incorporated by reference in its entirety). As will be appreciated by one of ordinary skill in the art, a variety of linkers can be used. In one aspect, a linker comprises one or more amino acids. In some aspects, a linker comprises two or more amino acids. In one aspect, a linker comprises the amino acid sequence GS. In some aspects, fusion of Cas9 (e.g., dCas9) with two or more effector domains comprises one or more interspersed linkers (e.g., GS linkers) between the domains. In some aspects, one or more nuclear localization sequences may be located between the catalytically inactive nuclease (e.g., dCas9) and the effector domain. For example, a fusion protein may include dCas9-NLS-Tet1 or dCas9-NLS-Dnmt3a.

In some aspects of the invention, the method of modulating one or more genomic sequences in a cell can further comprise introducing an effector molecule. As used herein, an "effector molecule" is a molecule (e.g., nucleic acid sequence; protein; organic molecule; inorganic molecule, small molecule) or physical trigger that associates with (e.g., binds to; specifically binds to) the effector domain to modulate the methylation or demethylation of a genomic sequence (e.g., an inducer molecule; a trigger molecule). The effector molecule can be contacted with the cell and/or introduced into the cell (e.g., as a nucleic acid sequence or as protein sequence). In some embodiments, the effector molecule is endogenous. In other embodiments, the effector molecule is exogenous. For example, an exogenous effector molecule can be introduced to the cell. In some aspects, the effector molecule binds to the effector domain. In some aspects, the effector molecule is a nucleic acid, protein, drug, small organic molecule and derivatives/variants thereof. In some aspects of the invention, the effector molecule is an antibiotic or derivatives/variants thereof.

As will be apparent to those of skill in the art, the method can further comprise introducing other molecules or factors into the cell to facilitate methylation or demethylation of the genomic sequence. An agent that inhibits or enhances DNA methylation may be an inhibitor of an endogenous DNA methylase or DNA demethylase. For example, an inhibitor of DNA methylation may be a small molecule, e.g., a cytidine analog, such as 5-azacytidine (azacitidine) and 5-azadeoxycytidine (decitabine). In other methods, the agent that inhibits or enhances DNA methylation may be administered to an individual.

A variety of genomic sequences can be modulated or modified using the methods described herein and will depend upon the desired results. In one aspect, the target genomic sequence is a gene sequence. In particular aspects, the methods described herein can be used to genetically modify two or more different genes in the same gene family, two or more genes that have a redundant function (e.g., redundant may mean that one needs to inactivate at least two of the genes to produce a particular phenotype, e.g., a detectable phenotype), two or more genes at least 80%, 85%, 90%, 95%, 96%, 97%, 98%, 99%, or more identical, two or more copies of the same gene, two or more genes in same biological pathway (e.g., signaling pathway, metabolic pathway), two or more genes that share at least one biological activity and/or act on at least one common substrate and/or are part of the same protein or protein-nucleic acid complex (e.g., a heteroligomeric protein, spliceosome, proteasome, RISC, transcription complex, replication complex, kinetochore, channel, transporter). In some aspects, two or more guide sequences may guide a polypeptide comprising a catalytically inactive site specific nuclease fused to an effector domain to different sites located within the genomic sequence.

"Modulate" or "modify" is used consistently with its use in the art, i.e., meaning to cause or facilitate a qualitative or quantitative change, alteration, or modification in a process, pathway, or phenomenon of interest. Without limitation, such change may be an increase, decrease, or change in relative strength or activity of different components or branches of the process, pathway, or phenomenon. A "modulator" or "modifier" is an agent that causes or facilitates a qualitative or quantitative change, alteration, or modification in a process, pathway, or phenomenon of interest.

In some aspects, "modulating" or "modifying" the methylation of a genomic sequence refers to any of a variety of alterations to the methylation status of the one or more genomic sequences. For example, the method of modulating the methylation of the one or more genomic sequences includes methylating or demethylating the genomic sequence (e.g., the genomic sequence may be methylated or the genomic sequence may be demethylated).

The methods provided herein can also be used to modify or modulate one or more genomic sequences in cells that are present in cell compositions such as embryos, zygotes, fetuses, and post-natal mammals. In some embodiments, a cell (e.g., a post-mitotic cell, a neuron, a fibroblast, a stem cell, etc.), zygote, embryo, or post-natal mammal is already genetically modified (already harbors one or more genetic modifications, e.g., epigenetic modifications) prior to being subjected to the methods described herein. For example, the cell, zygote, embryo, or post-natal mammal may be one into which an exogenous nucleic acid has been introduced by a process involving the hand of man (or may be descended at least in part from a cell or organism into which an exogenous nucleic acid has been introduced by a process involving the hand of man). The nucleic acid may for example contain a sequence that is exogenous to the cell, it may contain native sequences (i.e., sequences naturally found in the cells) but in a non-naturally occurring arrangement (e.g., a coding region linked to a promoter from a different gene), or altered versions of native sequences, etc. In some embodiments, a cell, zygote, embryo, or post-natal mammal is not already genetically modified (does not already harbor one or more genetic modifications) prior to being subjected to the methods described herein.

In some aspects, the invention is directed to a method of producing a nonhuman mammal carrying modifications in one or more genomic sequences comprising introducing into a zygote or an embryo a catalytically inactive site specific nuclease fused to an effector domain having methylation or demethylation activity, and one or more guide sequences. The zygote or the embryo is maintained under conditions in which the guide sequence hybridizes to a portion of each of the one or more genomic sequences, and the catalytically inactive site specific nuclease fused to an effector domain either methylates or demethylates the genomic sequence, thereby producing an embryo having one or more modified genomic sequences. The embryo having one or more modified genomic sequences may be transferred into a foster nonhuman mammalian mother. The foster nonhuman mammalian mother is maintained under conditions in which one or more offspring carrying the one or more modified genomic sequences are produced, thereby producing a nonhuman mammal carrying modifications in one or more genomic sequences.

As will be apparent to those of skill in the art, the nonhuman mammals can also be produced using methods described herein and/or with conventional methods, see for example, U.S. Published Application No. 2011/0302665. A method of producing a non-human mammalian embryo can comprise injecting non-human mammalian ES cells (e.g., iPSCs) into non-human tetraploid blastocysts and maintaining said resulting tetraploid blastocysts under conditions that result in formation of embryos, thereby producing a non-human mammalian embryo. In some embodiments, said non-human mammalian cells are mouse cells and said non-human mammalian embryo is a mouse. In some embodiments, said mouse cells are mutant mouse cells and are injected into said non-human tetraploid blastocysts by microinjection. In some embodiments laser-assisted micromanipulation or piezo injection is used. In some embodiments, a non-human mammalian embryo comprises a mouse embryo.

Another example of such conventional techniques is two step cloning which involves introducing embryonic stem (ES) and/or induced pluripotent stem (iPS) cells comprising the one or more mutations into a blastocyst (e.g., a tetraploid blastocyst) and maintaining the blastocyst under conditions that result in development of an embryo. The embryo is then transferred (impregnated) into an appropriate foster mother, such as a pseudopregnant female (e.g., of the same species as the embryo). The foster mother is then maintained under conditions that result in development of live offspring that harbor the one or more mutations.

Another example is the use of the tetraploid complementation assay in which cells of two mammalian embryos are combined to form a new embryo (Tarn and Rossant, Develop, 750:6156-6163 (2003)). The assay involves producing a tetraploid cell in which every chromosome exists fourfold. This is done by taking an embryo at the two-cell stage and fusing the two cells by applying an electrical current. The resulting tetraploid cell continues to divide, and all daughter cells will also be tetraploid. Such a tetraploid embryo develops normally to the blastocyst stage and will implant in the wall of the uterus. In the tetraploid complementation assay, a tetraploid embryo (either at the morula or blastocyst stage) is combined with normal diploid embryonic stem cells (ES) from a different organism. The embryo develops normally; the fetus is exclusively derived from the ES cell, while the extraembryonic tissues are exclusively derived from the tetraploid cells.

Another conventional method used to produce nonhuman mammals includes pronuclear microinjection. DNA is introduced directly into the male pronucleus of a nonhuman mammal egg just after fertilization. Similar to the two-step cloning described above, the egg is implanted into a pseudopregnant female. Offspring are screened for the integrated transgene. Heterozygous offspring can be subsequently mated to generate homozygous animals.

A variety of nonhuman mammals can be used in the methods described herein. For example, the nonhuman mammal can be a rodent (e.g., mouse, rat, guinea pig, hamster), a nonhuman primate, a canine, a feline, a bovine, an equine, a porcine or a caprine.

In some aspects, various mouse strains and mouse models of human disease are used in conjunction with the methods of producing a nonhuman mammal carrying mutations in one or more target nucleic acid sequences described herein. One of ordinary skill in the art appreciates the thousands of commercially and non-commercially available strains of laboratory mice for modeling human disease. Mice models exist for diseases such as cancer, cardiovascular disease, autoimmune diseases and disorders, inflammatory diseases, diabetes (type 1 and 2), neurological diseases, and other diseases. Examples of commercially available research strains include, and is not limited to, 11BHSD2 Mouse, GSK3B Mouse, 129-E Mouse HSD1 1B1 Mouse, AK Mouse Immortomouse®, Athymic Nude Mouse, LCAT Mouse, B6 Albino Mouse, Lox-1 Mouse, B6C3F1 Mouse, Ly5 Mouse, B6D2F1 (BDF1) Mouse, MMP9 Mouse, BALB/c Mouse, NIH-III Nude Mouse, BALB/c Nude Mouse, NOD Mouse, NOD SCID Mouse, Black Swiss Mouse, NSE-p25 Mouse, C3H Mouse, NU/NU Nude Mouse, C57BUJ6-E Mouse, PCSK9 Mouse, C57BUJ6N Mouse, PGP Mouse (P-glycoprotein Deficient), CB6F1 Mouse, repTOP™ ERE-Luc Mouse, CD-I® Mouse, repTOP™ mitoIRE Mouse, CD-I® Nude Mouse, repTOP™ PPRE-Luc Mouse, CD1-E Mouse, Rip-HAT Mouse, CD2F1 (CDF1) Mouse, SCID Hairless Congenic (SHC™) Mouse, CF-1™ Mouse, SCID Hairless Outbred (SHO™) Mouse, DBA/2 Mouse, SJL-E Mouse, Fox Chase CB 17™ M Mouse, SKH1-E Mouse, Fox Chase SCID® Beige Mouse, Swiss Webster (CFW®) Mouse, Fox Chase SCID® Mouse, TARGATT™ Mouse, FVB Mouse, THE POUND MOUSE™, and GLUT 4 Mouse. Other mouse strains include BALB/c, C57BU/6, C57BL/10, C3H, ICR, CBA, A/J, NOD, DBA/1, DBA/2, MOLD, 129, HRS, MRL, NZB, NIH, AKR, SJL, NZW, CAST, KK, SENCAR, C57L, SAMR1, SAMP1, C57BR, and NZO.

In some aspects, the method of producing a nonhuman mammal carrying modifications in one or more genomic sequences further comprises mating one or more commercially and/or non-commercially available nonhuman mammal with the nonhuman mammal carrying modifications in one or more genomic sequences produced by the methods described herein. The invention is also directed to nonhuman mammals produced by the methods described herein.

In some aspects, the genomic sequence is associated with a disease or condition (e.g., see van der Weyden et al, Genome Biol, 12:224 (2011)). Specific examples of genetic modifications of interest include modifying sequence(s), (e.g., gene(s)) to match sequence in different species (e.g., change mouse sequence to human sequence for any gene(s) of interest), alter sites of potential or known post-translational modification of proteins (e.g., phosphorylation, glycosylation, lipidation, acylation, acetylation), alter sites of potential or known epigenetic modification, alter sites of potential or known protein-protein or protein-nucleic acid interaction, inserting tag, e.g., epitope tag, and/or inserting or deleting splice sites.

In some aspects, one copy of the one or more genomic sequences is modified. In some aspects, both copies of one or more of the genomic sequences in the cell are modified. In some aspects, the one or more genomic sequences that are modified are endogenous to the cell.

In particular aspects, at least two of the genomic sequences are endogenous genomic sequences. In some aspects, at least two of the genomic sequences are exogenous genomic sequences. In some aspects where there are at least two genomic sequences, at least one of the genomic sequences is an endogenous genomic sequence and at least one of the genomic sequences is an exogenous genomic sequence. In some aspects, at least two of the genomic sequences are endogenous genes. In some aspects, at least two of the genomic sequences are exogenous genes. In some aspects where there are at least two genomic sequences, at least one of the genomic sequences is an endogenous gene and at least one of the genomic sequences is an exogenous gene. In some aspects, at least two of the genomic sequences are at least 1 kB apart. In some aspects, at least two of the genomic sequences are on different chromosomes. A genomic sequence may comprises a tag (e.g., an epitope tag or a fluorescent tag) or a transgene (e.g., a reporter gene).

The methods provided herein provide for multiplexed genome editing in cells, embryos, zygotes and nonhuman mammals. As shown herein, cells, embryos, zygotes and non-human mammals carrying modifications in multiple genes can be generated in a single step. In some aspects, the methods described herein allow for the modification of 1, 2, 3, 4, 5, 6, 7, 8, 9, 10, 11, 12, 13, 14, 15, 16, 17, 18, 19, 2021, 22, 23, 24, 25, 26, 27, 28, 29, 30, etc. genomic sequences (e.g., genes) in a (single) cell, zygote, embryo or nonhuman mammal using the methods described herein. In a particular aspect, one genomic sequence is modified in a (single) cell, zygote, embryo or nonhuman mammal. In some aspects, two genomic sequences are modified in a (single) cell, zygote, embryo or nonhuman mammal. In some aspects, three genomic sequences are modified in a (single) cell, zygote, embryo or nonhuman mammal. In some aspects, four genomic sequences are modified in a (single) cell, zygote, embryo or nonhuman mammal. In some aspects, five genomic sequences are modified in a (single) cell, zygote, embryo or nonhuman mammal, etc.

As will be apparent to those of skill in the art, a variety of methods can be used to introduce nucleic acid and/or protein into a cell, zygote, embryo, and or mammal. Suitable methods include calcium phosphate or lipid-mediated transfection, electroporation, injection, and transduction or infection using a vector (e.g., a viral vector such as an adenoviral vector). In some aspects, the nucleic acid and/or protein is complexed with a vehicle, e.g., a cationic vehicle, that facilitates uptake of the nucleic acid and/or protein, e.g., via endocytosis.

The method described herein can further comprise isolating the cell or zygote produced by the methods. Thus, in some aspects, the invention is directed to a cell or zygote (an isolated cell or zygote) produced by the methods described herein. In some aspects, the disclosure provides a clonal population of cells harboring the modification(s), replicating cultures comprising cells harboring the modification(s) and cells isolated from the generated animals.

The methods described herein can further comprise crossing the generated animals with other animals harboring genetic modifications (optionally in same strain background) and/or having one or more phenotypes of interest (e.g., disease susceptibility—such as NOD mice). In addition, the methods may comprise modifying a cell, zygote, and/or animal from a strain that harbors one or more genetic modifications and/or has one or more phenotypes of interest (e.g., disease susceptibility). In some aspects, the genetic modifications are epigenetic modifications.

The methods described herein can further comprise assessing whether the one or more target nucleic acids have been modified and/or modulated using a variety of known methods.

In some embodiments methods described herein are used to produce multiple genetic modifications in a cell, zygote, embryo, or animal, wherein at least one of the genetic modifications methylates or demethylates a gene, and at least one of the genetic modifications is in a different gene or genomic location. In some embodiments, a genetic modification further includes epigenetic modifications. The resulting cell, zygote, embryo, or animal, or a cell, zygote, embryo, or animal generated therefrom, is analyzed. In some embodiments at least one of the genetic modifications may be conditional (e.g., the effect of the modification, such as gene methylation or demethylation, only becomes manifest under certain conditions, which are typically under control of the artisan). In some embodiments animals are permitted to develop at least to post-natal stage, e.g., to adult stage. The appropriate conditions for the modification to produce an effect (sometimes termed "inducing conditions") are imposed, and the phenotype of the animal is subsequently analyzed. A phenotype may be compared to that of an unmodified animal or to the phenotype prior to the imposition of the inducing conditions.

Analysis may comprise any type of phenotypic analysis known in the art, e.g., examination of the structure, size, development, weight, or function, of any tissue, organ, or organ system (or the entire organism), analysis of behavior, activity of any biological pathway or process, level of any particular substance or gene product, etc. In some embodiments analysis comprises gene expression analysis, e.g., at the level of mRNA or protein. In some embodiments such analysis may comprise, e.g., use of microarrays (e.g., oligonucleotide microarrays, sometimes termed "chips"), high throughput sequencing (e.g., RNASeq), ChIP on Chip analysis, ChIPSeq analysis, etc. In some embodiments high content screening may be used, in which elements of high throughput screening may be applied to the analysis of individual cells through the use of automated microscopy and image analysis (see, e.g., Zanella et al, (2010). High content screening: seeing is believing. Trends Biotechnol. 28:237-245). In some embodiments analysis comprises quantitative analyses of components of cells such as spatiotemporal distributions of individual proteins, cytoskeletal structures, vesicles, and organelles, e.g., when contacted with test agents, e.g., chemical compounds. In some embodiments activation or inhibition of individual proteins and protein-protein interactions and/or changes in biological processes and cell functions may be assessed. A range of fluorescent probes for biological processes, functions, and cell components are available and may be used, e.g., with fluorescence microscopy. In some embodiments cells or animals generated according to methods herein may comprise a reporter, e.g., a fluorescent reporter or enzyme (e.g., a luciferase such as *Gaussia, Renilla*, or firefly luciferase) that, for example, reports on the expression or activity of particular genes. Such reporter may be fused to a protein, so that the protein or its activity is rendered detectable, optionally using a non-invasive detection means, e.g., an imaging or detection means such as PET imaging, MRI, fluorescence detection. Multiplexed genome editing according to the invention may allow installation of reporters for detection of multiple proteins, e.g., 2-20 different proteins, e.g., in a cell, tissue, organ, or animal, e.g., in a living animal.

Multiplexed genome editing according to the present invention may be useful to determine or examine the biological role(s) and/or roles in disease of genes of unknown function. For example, discovery of synthetic effects caused by modifications in first and second genes may pinpoint a genetic or biochemical pathway in which such gene(s) or encoded gene product(s) is involved.

In some embodiments it is contemplated to use, in methods described herein, cells or zygotes generated in or derived from animals produced in projects such as the International Knockout Mouse Consortium (IKMC), the website of which is knockoutmouse.org). In some embodiments it is contemplated to cross animals generated as described herein with animals generated by or available through the IKMC. For example, in some embodiments a mouse gene to be modified according to methods described herein is any gene from the Mouse Genome Informatics (MGI) database for which sequences and genome coordinates are available, e.g., any gene predicted by the NCBI. Ensembl, and Vega (Vertebrate Genome Annotation) pipelines for mouse Genome Build 37 (NCBI) or Genome Reference Consortium GRCm38.

In some embodiments a gene or genomic location to be modified is included in a genome of a species for which a fully sequenced genome exists. Genome sequences may be obtained, e.g., from the UCSC Genome Browser (genome.ucsc.edu/index.html). For example, in some embodiments a human gene or sequence to be modified according to methods described herein may be found in Human Genome Build hg19 (Genome Reference Consortium). In some embodiments a gene is any gene for which a Gene ID has been assigned in the Gene Database of the NCBI (ncbi.nlm.nih.gov/gene). In some embodiments a gene is any gene for which a genomic, cDNA, mRNA, or encoded gene product (e.g., protein) sequence is available in a database such as any of those available at the National Center for Biotechnology Information (ncbi.nih.gov) or Universal Protein Resource (uniprot.org). Databases include, e.g., GenBank, RefSeq, Gene, UniProtKB/SwissProt, UniProtKB/Trembl, and the like.

In some embodiments it is of interest to genetically modify a known or suspected differentially methylated region (DMR). There are various examples of differentially methylated regions. A differentially methylated region may be differentially methylated between cells of different cell types (e.g., muscle cells vs neuron or skin cells vs hepatocytes). A differentially methylated region may also be differentially methylated between diseased vs non-diseased cells (e.g., cancer vs non-cancer cells). A differentially methylated region may also be differentially methylated between differentiation states (e.g., progenitor cells vs terminally differentiated cells). The effect on expression of one or more genes (e.g., within up to about 0.5, 1, 2, 5, 10, 20, 50, 100, 500 kb or within about 1, 2, 5, or 10 MB from the modification) may be assessed. A genetic modification may be made in the sequence to determine whether such genetic modification alters the phenotype of a cell or animal or affects product of an RNA or protein or alters susceptibility to a disease. A genetic modification may include epigenetic modifications. In some aspects, the differentially methylated region may be hypermethylated or unmethylated.

In some aspects, it is of interest to demethylate a genomic sequence that is aberrantly hypermethylated or to methylate a genomic sequence that is aberrantly unmethylated. In some aspects, an aberrantly hypermethylated sequence or aberrantly unmethylated sequence may occur in a disease or disorder. In other aspects, it is of interest to methylate a CTCF site (e.g., a CTCF binding site) that is aberrantly unmethylated or remove methylation of a CTCF site that is aberrantly methylated. Modifying the methylation or demethylation of the CTCF site may treat or prevent a disease or disorder that exhibits an aberrantly unmethylated sequence or region or an aberrantly hypermethylated sequence or region. For example, a CTCF loop may be opened by methylating a CTCF binding site and thereby bring a gene that is outside the loop under control of an enhancer inside the loop if one wanted to increase expression of that gene (e.g., if expression of the gene is aberrantly low and/of if increased expression is desired for therapeutic or other purposes).

In some aspects, methods described herein may be used to produce cells having a modification in a promoter sequence. Targeting of dCas9-Tet1 or dCas9-Dnmt3a fusion proteins to methylated or unmethylated promoter sequences causes activation or silencing, respectively, of an endogenous reporter. For example, dCas9-Tet1 fusion protein targets the BDNF promoter IV and demethylates the promoter, thereby inducing BDNF expression in post-mitotic neurons.

In some aspects, methods described herein may be used to produce cells having a modification in an enhancer sequence. Targeting of dCas9-Tet1 or dCas9-Dnmt3a fusion proteins to methylated or unmethylated enhancer sequences causes activation or silencing, respectively, of an endogenous enhancer. For example, dCas9-Tet1 fusion protein targets the MyoD distal enhancer in fibroblasts and demethylates the enhancer, thereby facilitating reprogramming of fibroblasts into myoblasts.

In other aspects, methods described herein may be used to produce cells having a modification in a CTCF binding site. Targeting of dCas9-Tet1 or dCas9-Dnmt3a fusion proteins to CTCF binding sites may affect CTCF binding and interfere with DNA looping. For example, dCas9-Dnmt3a fusion protein performs targeted de novo methylation of a CTCF loop anchor site blocks CTCF binding and interferes with DNA looping, thereby causing altered gene expression in the neighboring loop.

In some embodiments any method described herein may comprise isolating one or more cells, samples, or substances from an animal generated according to methods described herein, e.g., any genetically modified animal generated as described herein. In some embodiments a method may further comprise analyzing the one or more cells, samples, or substances. Such analysis may, for example assess the effect of a genetic modification(s) introduced according to the methods. Genetic modifications may include the methylation or demethylation of a genomic sequence and/or may include epigenetic modifications.

In some embodiments animals generated according to methods described herein may be useful in the identification of candidate agents for treatment of disease and/or for testing agents for potential toxicity or side effects. In some embodiments any method described herein may comprise contacting an animal generated according to methods described herein, e.g., any genetically modified animal generated as described herein, with a test agent (e.g., a small molecule, nucleic acid, polypeptide, lipid, etc.). In some embodiments contacting comprises administering the test agent. Administration may be by any route (e.g., oral, intravenous, intraperitoneal, gavage, topical, transdermal, intramuscular, enteral, subcutaneous), may be systemic or local, may include any dose (e.g., from about 0.01 mg/kg to about 500 mg/kg), may involve a single dose or multiple doses. In some embodiments a method may further comprise analyzing the animal. Such analysis may, for example assess the effect of the test agent in an animal having a genetic modification(s) introduced according to the methods. In some embodiments a test agent that reduces or enhances an effect of one or more genetic modification(s) may be identified. In some embodiments if a test agent reduces or inhibits development of a disease associated with or produced by the genetic modification(s), (or reduces or inhibits one or more symptoms or signs of such a disease) the test agent may be identified as a candidate agent for treatment of a disease associated with or produced by the genetic modification(s) or associated with or produced by naturally occurring mutations in a gene or genomic location harboring the genetic modification.

In some embodiments a cell may be a diseased cell or may originate from a subject suffering from a disease, e.g., a disease affecting the cell or organ from which the cell was obtained. In some embodiments a mutation is introduced into a genomic region of the cell that is associated with a disease (e.g., any disease of interest, such as diseases mentioned herein). For example, in some embodiments it is of interest to methylate or demethylate a gene or genomic location that is known or suspected to be involved in disease pathogenesis and/or known or suspected to be associated with increased or decreased risk of developing a disease or particular manifestation(s) of a disease. In some embodiments it is of interest to methylate or demethylate a gene or genomic location and determine whether such modification alters the risk of developing a disease or one or more manifestations of a disease, alters progression of the disease, or alters the response of a subject to therapy or candidate therapy for a disease. In some embodiments it is of interest to modify an abnormal or disease-associated nucleotide or sequence to one that is normal or not associated with disease. In some embodiments this may allow production of genetically matched cells or cell lines (e.g., iPS cells or cell lines) that differ only at one or more selected sites of genetic modification. Multiplexed genome editing as described herein may allow for production of cells or cell lines that are isogenic except with regard to, e.g., between 2 and 20 selected sites of genetic alterations. This may allow for the study of the combined effect of multiple modifications that are suspected of or known to play a role in disease risk, development or progression.

The terms "disease", "disorder" or "condition" are used interchangeably and may refer to any alteration from a state of health and/or normal functioning of an organism, e.g., an abnormality of the body or mind that causes pain, discomfort, dysfunction, distress, degeneration, or death to the individual afflicted. Diseases include any disease known to those of ordinary skill in the art. In some embodiments a disease is a chronic disease, e.g., it typically lasts or has lasted for at least 3-6 months, or more, e.g., 1, 2, 3, 5, 10 or more years, or indefinitely. Disease may have a characteristic set of symptoms and/or signs that occur commonly in individuals suffering from the disease. Diseases and methods of diagnosis and treatment thereof are described in standard medical textbooks such as Longo, D., et al. (eds.), Harrison's Principles of Internal Medicine, 18th Edition; McGraw-Hill Professional, 2011 and/or Goldman's Cecil Medicine, Saunders; 24 edition (Aug. 5, 2011). In certain embodiments a disease is a multigenic disorder (also referred to as complex, multifactorial, or polygenic disorder). Such diseases may be associated with the effects of multiple genes, sometimes in combination with environmental factors (e.g., exposure to particular physical or chemical agents or biological agents such as viruses, lifestyle factors such as diet, smoking, etc.). A multigenic disorder may be any disease for which it is known or suspected that multiple genes (e.g., particular alleles of such genes, particular polymorphisms in such genes) may contribute to risk of developing the disease and/or may contribute to the way the disease manifests (e.g., its severity, age of onset, rate of progression, etc.) In some embodiments a multigenic disease is a disease that has a genetic component as shown by familial aggregation (occurs more commonly in certain families than in the general population) but does not follow Mendelian laws of inheritance, e.g., the disease does not clearly follow a dominant, recessive, X-linked, or Y-linked inheritance pattern. In some embodiments a multigenic disease is one that is not typically controlled by variants of large effect in a single gene (as is the case with Mendelian disorders). In some embodiments a multigenic disease may occur in familial form and sporadically. Examples include, e.g., Parkinson's disease, Alzheimer's disease, and various types of cancer. Examples of multigenic diseases include many common diseases such as hypertension, diabetes mellitus (e.g., type II diabetes mellitus), cardiovascular disease, cancer, and stroke (ischemic, hemorrhagic). In some embodiments a disease, e.g., a multigenic disease is a psychiatric, neurological, neurodevelopmental disease, neurodegenerative disease, cardiovascular disease, autoimmune disease, cancer, metabolic disease, or respiratory disease. In some embodiments at least one gene is implicated in a familial form of a multigenic disease.

In some embodiments a disease is cancer, which term is generally used interchangeably to refer to a disease characterized by one or more tumors, e.g., one or more malignant or potentially malignant tumors. The term "tumor" as used herein encompasses abnormal growths comprising aberrantly proliferating cells. As known in die art, tumors are typically characterized by excessive cell proliferation that is not appropriately regulated (e.g., that does not respond normally to physiological influences and signals that would ordinarily constrain proliferation) and may exhibit one or more of the following properties: dysplasia (e.g., lack of normal cell differentiation, resulting in an increased number or proportion of immature cells); anaplasia (e.g., greater loss of differentiation, more loss of structural organization, cellular pleomorphism, abnormalities such as large, hyperchromatic nuclei, high nuclearxytoplasmic ratio, atypical mitoses, etc.): invasion of adjacent tissues (e.g., breaching a basement membrane); and/or metastasis. Malignant tumors have a tendency for sustained growth and an ability to spread, e.g., to invade locally and/or metastasize regionally and/or to distant locations, whereas benign tumors often remain localized at the site of origin and are often self-limiting in terms of growth. The term "tumor" includes malignant solid tumors, e.g., carcinomas (cancers arising from epithelial cells), sarcomas (cancers arising from cells of mesenchymal origin), and malignant growths in which there may be no detectable solid tumor mass (e.g., certain hematologic malignancies). Cancer includes, but is not limited to: breast cancer; biliary tract cancer; bladder cancer: brain cancer (e.g., glioblastomas, medulloblastomas); cervical cancer: choriocarcinoma; colon cancer; endometrial cancer; esophageal cancer; gastric cancer; hematological neoplasms including acute lymphocytic leukemia and acute myelogenous leukemia; T-cell acute lymphoblastic leukemia/lymphoma; hairy cell leukemia; chronic lymphocytic leukemia, chronic myelogenous leukemia, multiple myeloma; adult T-cell leukemia/lymphoma; intraepithelial neoplasms including Bowen's disease and Paget's disease; liver cancer; lung cancer; lymphomas including Hodgkin's disease and lymphocytic lymphomas; neuroblastoma; melanoma, oral cancer including squamous cell carcinoma: ovarian cancer including ovarian cancer arising from epithelial cells, stromal cells, germ cells and mesenchymal cells; neuroblastoma, pancreatic cancer; prostate cancer; rectal cancer; sarcomas including angiosarcoma, gastrointestinal stromal tumors, leionyosarcoma, rhabdomyosarcoma, liposarcoma, fibrosarcoma, and osteosarcoma; renal cancer including renal cell carcinoma and Wilms tumor; skin cancer including basal cell carcinoma and squamous cell cancer; testicular cancer including germinal tumors such as seminoma, non-seminoma (teratomas, choriocarcinomas), stromal tumors, and germ cell tumors: thyroid cancer including thyroid adenocarcinoma and medullary carcinoma. It will be appreciated that a variety of different tumor types can arise in certain organs, which may differ with regard to, e.g., clinical and/or pathological features and/or molecular markers. Tumors arising in a variety of different organs are discussed, e.g., the WHO Classification of Tumours series, $4^{th}$ ed, or $3^{rd}$ ed (Pathology and Genetics of Tumours series), by the International Agency for Research on Cancer (IARC), WHO Press, Geneva, Switzerland, all volumes of which are incorporated herein by reference. In some embodiments a cancer is one for which mutation or overexpression of particular genes is known or suspected to play a role in development, progression, recurrence, etc., of a cancer. In some embodiments such genes are targets for genetic modification according to methods described herein. In some embodiments a gene is an oncogene, proto-oncogene, or tumor suppressor gene. The term "oncogene" encompasses nucleic acids that, when expressed, can increase the likelihood of or contribute to cancer initiation or progression. Normal cellular sequences ("proto-oncogenes") can be activated to become oncogenes (sometimes termed "activated oncogenes") by mutation and/or aberrant expression. In various embodiments an oncogene can comprise a complete coding sequence for a gene product or a portion that maintains at least in part the oncogenic potential of the complete sequence or a sequence that encodes a fusion protein. Oncogenic mutations can result, e.g., in altered (e.g., increased) protein activity, loss of proper regulation, or an alteration (e.g., an increase) in R A or protein level. Aberrant expression may occur, e.g., due to chromosomal rearrangement resulting in juxtaposition to regulatory elements such as enhancers, epigenetic mechanisms, or due to amplification, and may result in an increased amount of proto-oncogene product or production in an inappropriate cell type. Proto-oncogenes often encode proteins that control or participate in cell proliferation, differentiation, and/or apoptosis. These proteins include. e.g., various transcription factors, chromatin remodelers, growth factors, growth factor receptors, signal transducers, and apoptosis regulators. A TSG may be any gene wherein a loss or reduction in function of an expression product of the gene can increase the likelihood of or contribute to cancer initiation or progression. Loss or reduction in function can occur, e.g., due to mutation or epigenetic mechanisms. Many TSGs encode proteins that normally function to restrain or negatively regulate cell proliferation and/or to promote apoptosis. Exemplary oncogenes include, e.g., MYC, SRC, FOS, JUN, MYB, RAS, RAF, ABL, ALK, AKT, TRK, BCL2, WNT, HER2/NEU, EGFR, MAPK, ERK, MDM2, CDK4, GLI1, GLI2, IGF2, TP53, etc. Exemplary TSGs include, e.g., RB, TP53, APC, NF1, BRCA1, BRCA2, PTEN, CDK inhibitory proteins (e.g., p16, p21), PTCH, WT1, etc. It will be understood that a number of these oncogene and TSG names encompass multiple family members and that many other TSGs are known.

In some embodiments a disease is a cardiovascular disease, e.g., atherosclerotic heart disease or vessel disease, congestive heart failure, myocardial infarction, cerebrovascular disease, peripheral artery disease, cardiomyopathy.

In some embodiments a disease is a psychiatric, neurological, or neurodevelopmental disease, e.g., schizophrenia, depression, bipolar disorder, epilepsy, autism, addiction. Neurodegenerative diseases include, e.g., Alzheimer's disease. Parkinson's disease, amyotrophic lateral sclerosis, frontotemporal dementia. In some embodiments a disease is an autoimmune diseases e.g., acute disseminated encephalomyelitis, alopecia areata, antiphospholipid syndrome, autoimmune hepatitis, autoimmune myocarditis, autoimmune pancreatitis, autoimmune polyendocrine syndrome-sautoimmune uveitis, inflammatory bowel disease (Crohn's disease, ulcerative colitis), type I diabetes mellitus (e.g., juvenile onset diabetes), multiple sclerosis, scleroderma, ankylosing spondylitis, sarcoid, pemphigus vulgaris, pemphigoid, psoriasis, myasthenia gravis, systemic lupus erythemotasus, rheumatoid arthritis, juvenile arthritis, psoriatic arthritis, Behcet's syndrome, Reiter's disease, Berger's disease, dermatomyositis, polymyositis, antineutrophil cytoplasmic antibody-associated vasculitides (e.g., granulomatosis with polyangiitis (also known as Wegener's granulomatosis), microscopic polyangiitis, and Churg-Strauss syndrome), scleroderma, Sjogren's syndrome, anti-glomerular basement membrane disease (including Goodpasture's syndrome), dilated cardiomyopathy, primary biliary cirrhosis, thyroiditis (e.g., Hashimoto's thyroiditis, Graves' disease), transverse myelitis, and Guillane-Barre syndrome.

In some embodiments a disease is a respiratory disease, e.g., allergy affecting the respiratory system, asthma, chronic obstructive pulmonary disease, pulmonary hypertension, pulmonary fibrosis, and sarcoidosis.

In some embodiments a disease is a renal disease. e.g., polycystic kidney disease, lupus, nephropathy (nephrosis or nephritis) or glomerulonephritis (of any kind).

In some embodiments a disease is vision loss or hearing loss, e.g., associated with advanced age.

In some embodiments a disease is an infectious disease, e.g., any disease caused by a virus, bacteria, fungus, or parasite.

In some embodiments, a disease exhibits hypermethylation (e.g., aberrant hypermethylation) or unmethylation (e.g., aberrant unmethylation) in a genomic sequence. For example, Fragile X Syndrome exhibits hypermethylation of FMR-1. A dCas9-Tet1 fusion protein may be used to specifically demethylate CCG hypermethylation and to reactivate FMG-1, thereby treating Fragile X Syndrome. The methods described herein may be used to treat or prevent diseases or disorders exhibiting aberrant methylation (e.g., hypermethylation or unmethylation).

It will be understood that classification of diseases herein is not intended to be limiting. One of ordinary skill in the art will appreciate that various diseases may be appropriately classified in multiple different groups.

In some embodiments a disease is one for which at least one genome-wide association (GWA) study (GWAS) has been performed. In some embodiments a GWAS types multiple "cases" (subjects having a disease of interest or particular manifestations thereof) and "controls" (subjects not having the disease or manifestations) for several thousand to millions, e.g., 1 million or more, e.g., 1.5 million or more, alleles (e.g., single nucleotide polymorphisms) positioned throughout the genome or a substantial portion thereof (e.g., at least 80%, 90%, 95%, or more of the genome). It will be understood that control data may be obtained from historical data. Genotyping may be performed using microarrays or other methods. Alleles associated (e.g., in a statistically significant manner) with increased (or decreased) risk of a disease (or particular manifestations) may thereby be identified. It will be appreciated that statistical results may be corrected for multiple hypothesis testing, e.g., using methods known in the art. In some embodiments a p value of less than about $10^7$, $10^8$, or $10^9$ is considered evidence of association. In some embodiments a gene or allele or polymorphism has been identified as contributing to disease risk or severity in at least one GWAS. See, e.g., genome.gov/gwastudies for examples of GWAS studies and genetic variants (alleles, polymorphisms) associated with various diseases. In some embodiments a gene (or any sequence) is one for which an allele or polymorphism is associated with an increased or decreased risk of developing a disease of at least 1.1, 1.2, 1.5, 2, 3, 4, 5, 7.5, 10, or more, relative to individuals not having the allele or polymorphism. In some embodiments an allele or polymorphism is associated with an increased or decreased risk of developing a disease of at least 1.1, 1.2, 1.5, 2, 3, 4, 5, 7.5, 10, or more, relative to individuals not having the allele or polymorphism. Genes, alleles, polymorphisms, or genetic loci that may contribute to any phenotypic trait of interest such as longevity, weight, resistance to infection, response or lack thereof to various therapeutic agents, resistance or susceptibility to potentially harmful substances such as toxins or infectious agents (e.g., viruses, bacteria, fungi, parasites), are of interest. A phenotypic trait may be a physical sign (such as blood pressure), a biochemical marker, which in some embodiments may be detectable in a body fluid such as blood, saliva, urine, tears, etc., such as level of a metabolite, LDL, etc., wherein an abnormally low or high level of the marker may correlate with having or not having the disease or with susceptibility to or protection from a disease.

In some embodiments a sequence to be inserted into a genome encodes a tag. The sequence may be inserted into a gene in an appropriate position such that a fusion protein comprising the tag is produced. The term "tag" is used in a broad sense to encompass any of a wide variety of polypeptides. In some embodiments, a tag comprises a sequence useful for purifying, expressing, solubilizing, and/or detecting a polypeptide. In some embodiments a tag may serve multiple functions. In some embodiments a tag is a relatively small polypeptide, e.g., ranging from a few amino acids up to about 100 amino acids long. In some embodiments a tag is more than 100 amino acids long. e.g., up to about 500 amino acids long, or more. In some embodiments, a tag comprises an HA, TAP, Myc, 6xHis, Flag, V5, or GST tag, to name few examples. A tag (e.g., any of the aforementioned tags) that comprises an epitope against which an antibody, e.g., a monoclonal antibody, is available (e.g., commercially available) or known in the art may be referred to as an "epitope tag". In some embodiments a tag comprises a solubility-enhancing tag (e.g., a SUMO tag, NUS A tag, SN UT tag, a Strep tag, or a monomeric mutant of the Ocr protein of bacteriophage T7). See, e.g., Esposito D and Chatterjee D K. Curr Opin Biotechnol; 17(4):353-8 (2006). In some embodiments, a tag is cleavable, so that at least a portion of it can be removed, e.g., by a protease. In some embodiments, this is achieved by including a protease cleavage site in the tag, e.g., adjacent or linked to a functional portion of the tag. Exemplary proteases include, e.g., thrombin, TEV protease, Factor Xa, PreScission protease, etc. In some embodiments, a "self-cleaving" tag is used. See, e.g., PCT/US05/05763. In some embodiments, a tag comprises a fluorescent polypeptide (e.g., GFP or a derivative thereof such as enhanced GFP (EGFP)) or an enzyme that can act on a substrate to produce a detectable signal, e.g., a fluorescence or colorimetric signal. Luciferase (e.g., a firefly, *Renilla*, or *Gaussia* luciferase) is an example of such an enzyme. Examples of fluorescent proteins include GFP and derivatives thereof, proteins comprising chromophores that emit light of different colors such as red, yellow, and cyan fluorescent proteins, etc. A tag, e.g., a fluorescent protein, may be monomeric. In certain embodiments a fluorescent protein is e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mK02, mOrange, mOrange2, TagRFP, TagRFP-T, mStrawberry, mRuby, mCherry, mRaspberry, mKate2, mPlum, niNeptune, mTomato, T-Sapphire, mAmetrine, mKeima. See, e.g., Chalfie, M. and Kain, S R (eds.) Green fluorescent protein: properties, applications, and protocols (Methods of biochemical analysis, v. 47). Wiley-Interscience, Hoboken, N.J., 2006, and/or Chudakov, D M. et al, Physiol Rev. 90(3): 1103-63, 2010 for discussion of GFP and numerous other fluorescent or luminescent proteins. In some embodiments a tag may comprise a domain that binds to and/or acts a sensor of a small molecule (e.g., a metabolite) or ion, e.g., calcium, chloride, or of intracellular voltage, pH, or other conditions. Any genetically encodable sensor may be used: a number of such sensors are known in the art. In some embodiments a FRET-based sensor may be used. In some embodiments different genes are modified to incorporate different tags, so that proteins encoded by the genes are distinguishably labeled. For example, between 2 and 20 distinct tags may be introduced. In some embodiments the tags have distinct emission and/or absorption spectra. In some embodiments a tag may absorb and/or emit light in the infrared or near-infrared region. It will be understood that any nucleic acid sequence encoding a tag may be codon-optimized for expression in a cell, zygote, embryo, or animal into which it is to be introduced.

in some embodiments it may be of interest to express fragments or domains of a protein, which may act in a dominant negative manner and may, for example, disrupt normal function or interaction of the protein.

In some embodiments a gene of interest encodes a protein the aggregation of which is associated with one or more diseases, which may be referred to as protein misfolding diseases. Examples include, e.g., alpha-synuclein (Parkinson's disease and related disorders), amyloid beta or tau (Alzheimer's disease), TDP-43 (frontotemporal dementia, ALS).

In some embodiments a gene of interest encodes a transcription factor, a transcriptional co-activator or co-repressor, an enzyme, a chaperone, a heat shock factor, a heat shock protein, a receptor, a secreted protein, a transmembrane protein, a histone (e.g., HI, H2A, H2B, H3, H4), a peripheral membrane protein, a soluble protein, a nuclear protein, a mitochondrial protein, a growth factor, a cytokine (e.g., an interleukin, e.g., any of IL-1-IL-33), an interferon (e.g., alpha, beta, or gamma), a chemokine (e.g., a CXC, CX3C, C (or XC), or CX3C chemokine). A chemokine may be CCL1-CCL28, CXCL1-CXCL17, XCL1 or XCL2, or CXC3L1). In some embodiments a gene encodes a colony-stimulating factor, a hormone (e.g., insulin, thyroid hormone, growth hormone, estrogen, progesterone, testosterone), an extracellular matrix protein (e.g., collagen, fibronectin), a motor protein (e.g., dynein, myosin), cell adhesion molecule, a major or minor histocomnpatibility (MIC) gene, a transporter, a channel (e.g., an ion channel), an imnmunoglobulin (Ig) superfamily (IgSF) gene (e.g., a gene encoding an antibody. T cell receptor, B cell receptor), tumor necrosis factor, an NF-kappaB protein, an integrin, a cadherin superfamily member (e.g., a cadherin), a selectin, a clotting factor, a complement factor, a plasminogen, plasminogen activating factor. Growth factors include, e.g., members of the vascular endothelial growth factor (VEGF. e.g., VEGF-A, VEGF-B, VEGF-C, VEGF-D), epidermal growth factor (EGF), insulin-like growth factor (IGF; IGF-1, IGF-2), fibroblast growth factor (FGF, e.g., FGF1-FGF22), platelet derived growth factor (PDGF), or nerve growth factor (NGF) families. It will be understood that the aforementioned protein families comprise multiple members. Any such member may be used in various embodiments. In some embodiments a growth factor promotes proliferation and/or differentiation of one or more hematopoietic cell types. For example, a growth factor may be CSF1 (macrophage colony-stimulating factor). CSF2 (granulocyte macrophage colony-stimulating factor. GM-CSF), or CSF3 (granulocyte colony-stimulating factors, G-CSF). In some embodiments a gene encodes erythropoietin (EPO). In some embodiments, a gene encodes a neurotrophic factor. i.e., a factor that promotes survival, development and/or function of neural lineage cells (which term as used herein includes neural progenitor cells, neurons, and glial cells, e.g., astrocytes, oligodendrocytes, microglia). For example, in some embodiments, the protein is a factor that promotes neurite outgrowth. In some embodiments, the protein is ciliary neurotrophic factor (CNTF) or brain-derived neurotrophic factor (BDNF).

In some embodiments a gene of interest encodes a polypeptide that is a subunit of any protein that is comprised of multiple subunits.

An enzyme may be any protein that catalyzes a reaction of a type that has been assigned an Enzyme Commission number (EC number) by the Nomenclature Committee of the International Union of Biochemistry and Molecular Biology (NC-IUBMB). Enzymes include, e.g., oxidoreductases, transferases, hydrolases, lyases, isomerases, ligases. Examples include, e.g., kinases (protein kinases, e.g., Ser/Thr kinase, Tyr kinase), lipid kinases (e.g., phosphatidylmositide 3-kinases (PI 3-kinases or PI3Ks)), phosphatases, acetyltransferases, methyltransferases, deacetylases, demethylases, lipases, cytochrome P450s, glucuronidases, recombinases (e.g., Rag-1, Rag-2). An enzyme may participate in the biosynthesis, modification, or degradation of nucleotides, nucleic acids, amino acids, proteins, neurotransmitters, xenobiotics (e.g., drugs) or other macromolecules.

The mammalian genome encodes at least about 500 different kinases. Kinases can be classified based on the nature of their typical substrates and include protein kinases (i.e., kinases that transfer phosphate to one or more protein(s)), lipid kinases (i.e., kinases that transfer a phosphate group to one or more lipid(s)), nucleotide kinases, etc. Protein kinases (PKs) are of particular interest in certain aspects of the invention. PKs are often referred to as serine/threonine kinases (S/TKs) or tyrosine kinases (TKs) based on their substrate preference. Serine/threonine kinases (EC 2.7.11.1) phosphorylate serine and/or threonine residues while TKs (EC 2.7.10.1 and EC 2.7.10.2) phosphorylate tyrosine residues. A number of "dual specificity" kinases (EC 2.7.12.1) that are capable of phosphorylating both serine/threonine and tyrosine residues are known. The human protein kinase family can be further divided based on sequence/structural similarity into the following groups: (1) AGC kinases-containing PKA, PKC and PKG; (2) CaM kinases-containing the calcium/calmodulin-dependent protein kinases; (3) CK1-containing the casein kinase 1 group; (4) CMGC-containing CDK, MAPK, GSK3 and CLK kinases; (5) STE-containing the homologs of yeast Sterile 7, Sterile 11, and Sterile 20 kinases; (6) TK-containing the tyrosine kinases; (7) TKL-containing the tyrosine-kinase like group of kinases. A further group referred to as "atypical protein kinases" contains proteins that lack sequence homology to the other groups but are known or predicted to have kinase activity, and in some instances are predicted to have a similar structural fold to typical kinases.

Receptors include. e.g., G protein coupled receptors, tyrosine kinase receptors, serine/threonine kinase receptors, Toll-like receptors, nuclear receptor, immune cell surface receptor. In some embodiments a receptor is a receptor for any of the hormones, cytokines, growth factors, or secreted proteins mentioned herein. Numerous G protein coupled receptors (GPCRs) are known in the art. See, e.g., Vroling B, GPCRDB: information system for G protein-coupled receptors. Nucleic Acids Res. 2011 January; 39(Database issue): D309-19. Epub 2010 Nov. 2. The GPCRDB can be found online at gpcr.org/7tm/. G protein coupled receptors include, e.g., adrenergic, cannabinoid, purinergic receptors, neuropeptide receptors, olfactory receptors. Transcription factors (TFs) (sometimes called sequence-specific DNA-binding factors) bind to specific DNA sequences and (alone or in a complex with other proteins), regulate transcription, e.g., activating or repressing transcription. Exemplary TFs are listed, for example, in the TRANSFAC® database, Gene Ontology (geneonlology.org/) or DBD (transcriptionfactor.org) (Wilson, et al, DBD—taxonomically broad transcription factor predictions: new content and functionality Nucleic Acids Research 2008 doi: 10.1093/nar/gkm964). TFs can be classified based on the structure of their DNA binding domains (DBD). For example in certain embodiments a TF is a helix-loop-helix, helix-turn-helix, winged helix, leucine zipper, bZIP, zinc finger, homeodomain, or beta-scaffold factor with minor groove contacts protein. Transcription factors include, e.g., p53, STAT3, PAS family transcription factors (e.g., HIF family: HIF1A, HIF2A, HIF3A), aryl hydrocarbon receptor.

Other methods of modifying or modulating nucleic acids in a cell or nonhuman mammal are described in PCT Application No. PCT/US2014/034387 and U.S. application Ser. No. 14/785,031, which are incorporated herein by reference in their entirety.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more nucleic acids, polypeptides, cells, species or types of organism, disorders, subjects, or combinations thereof, can be excluded.

Where the claims or description relate to a composition of matter, e.g., a nucleic acid, polypeptide, cell, or non-human transgenic animal, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

Specific examples of these methods are set forth below in the Examples.

EXAMPLES

In this study, we demonstrate that fusion of dCas9 with the Tet1 enzymatic domain or Dnmt3a allows for targeted erasure or establishment of DNA methylation, respectively. As a proof of principle, we first induced alterations to DNA methylation in two synthetic methylation reporters integrated in mouse embryonic stem cells (mESCs). With application of dCas9-Tet1, we re-visited some long-standing questions in the DNA methylation field. Our results show that targeted demethylation of BDNF promoter IV is sufficient to activate its expression in mouse cortical neurons, and that targeted demethylation of a MyoD distal enhancer promotes reprogramming of fibroblasts into myoblasts and facilitates myotube formation. With dCas9-Dnmt3a, we demonstrate that targeted methylation at CTCF binding sites is able to block CTCF recruitment and to alter the expression of genes in the neighborhood loop by increasing their interaction frequencies with the super-enhancers insulated in the targeted loops. Furthermore, lentiviral delivery of dCas9-Tet1 with target gRNAs into mice enabled in vivo activation of a methylation reporter by demethylation of its promoter. Thus, dCas9-Tet1 and dCas9-Dnmt3a provide powerful tools to investigate the functional significance of DNA methylation in a locus-specific manner.

A Modified CRISPR System to Edit DNA Methylation

Figure 8A:
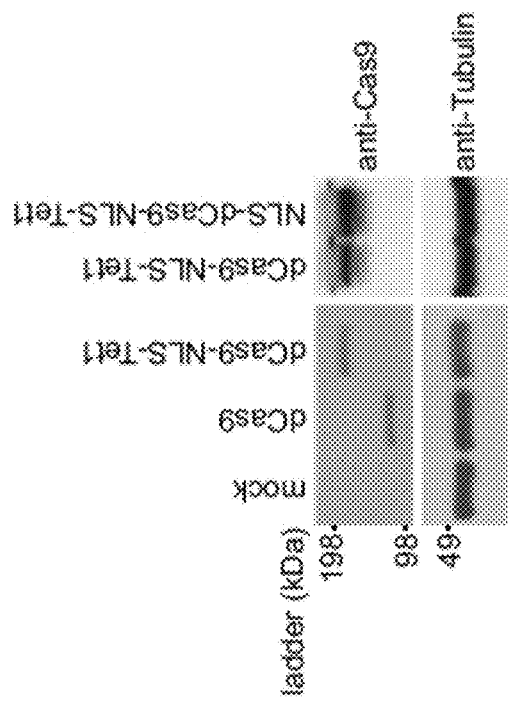
FIGS. 8A-8E depict a modified CRISPR system for editing 5-cytosine DNA methylation in the mammalian genome.
Figure 8B:
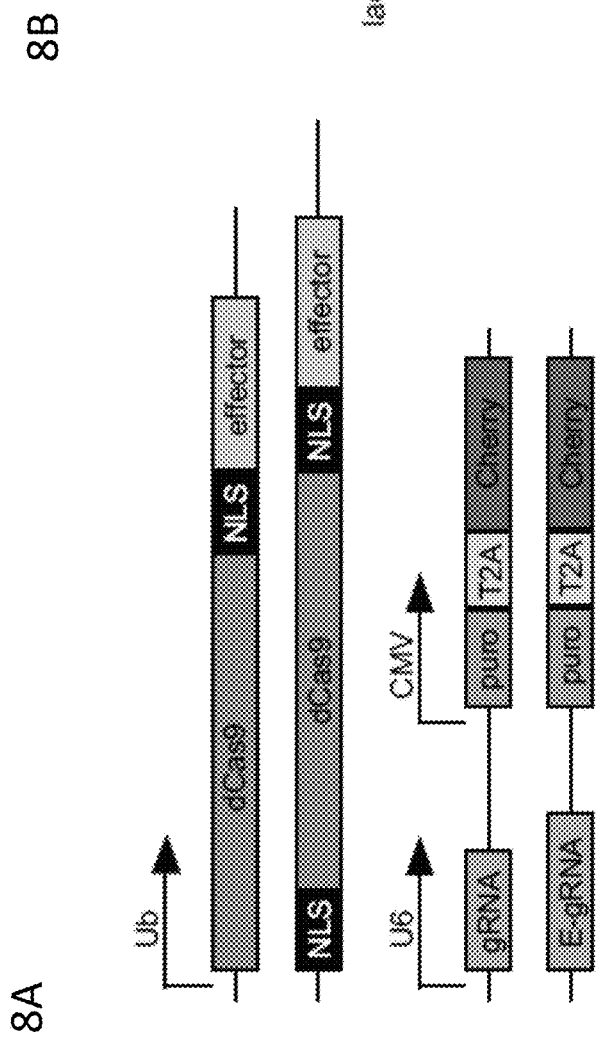
Figure 8C:
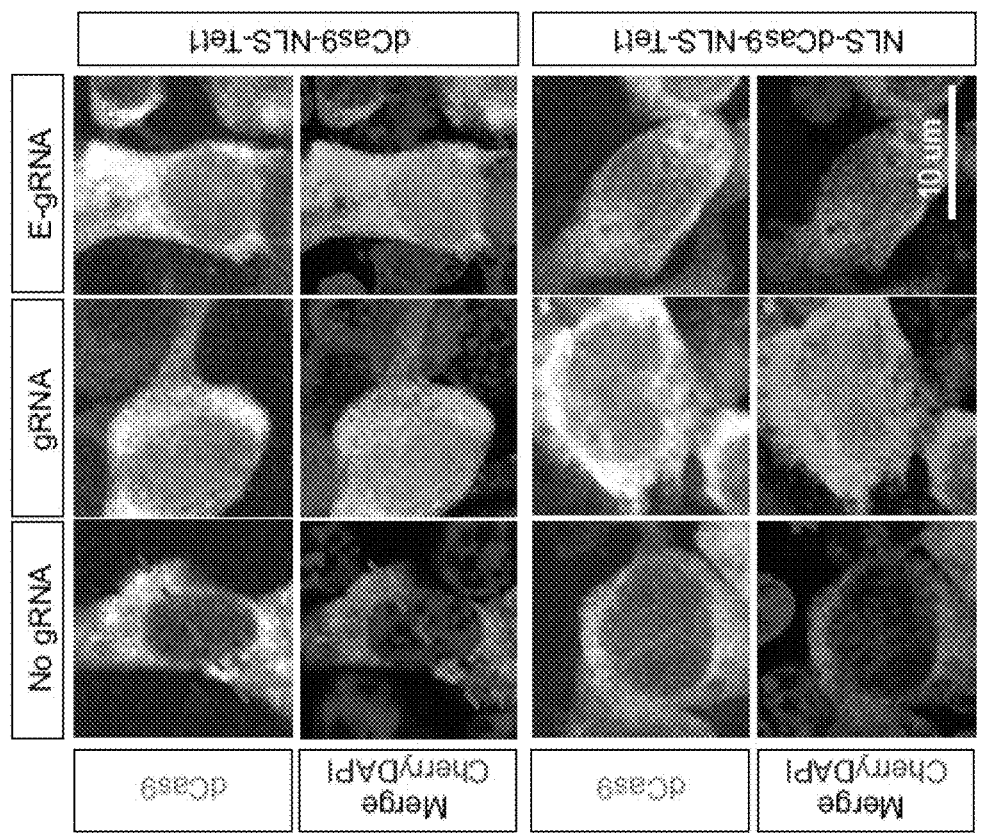
Figure 8D:
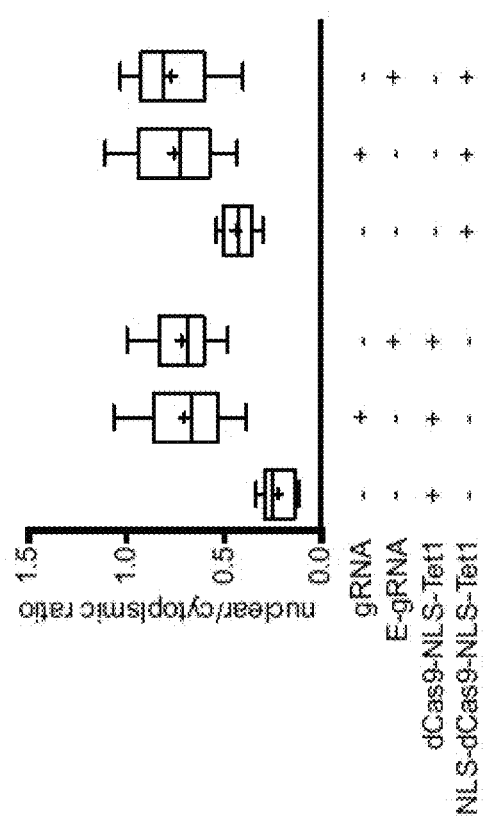
Figure 8E:
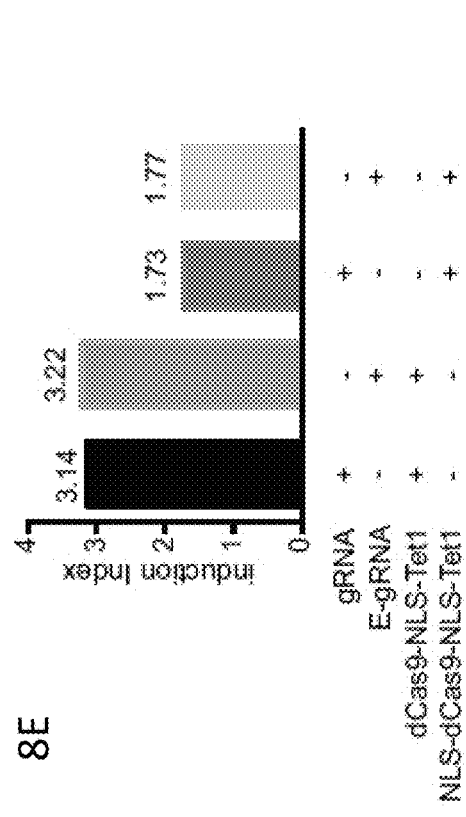

To achieve targeted editing of DNA methylation, we fused dCas9 with enzymes in the methylation/demethylation pathway (FIG. 1A). Based on previous studies using the TALE system to target specific CpGs (Bernstein et al., 2015; Maeder et al., 2013), Tet1 and Dnmt3a were chosen as the effectors in our system. Co-expression of sequence-specific guide RNA (gRNA) would be expected to target dCas9-Tet1 or dCas9-Dnmt3a to the specific locus and mediate modification of DNA methylation status without altering the DNA sequence. To optimize this chimeric CRISPR/dCas9-effector system, we tested two types of dCas9-Tet1 lentiviral constructs with nuclear localization signal (NLS) at different positions: dCas9-NLS-Tet1 and NLS-dCas9-NLS-Tet1 (FIGS. 8A and 8B). We also tested two types of gRNA lentiviral constructs, a widely used chimeric single-guide RNA referred as gRNA (Jinek et al., 2012) and a modified guide RNA with enhanced capacity to guide Cas9 to the designed genomic locus referred as E-gRNA (Chen et al., 2013). Both gRNA constructs contain a puro selection cassette and a Cherry fluorescence protein cassette driven by an independent CMV promoter that allows for Fluorescence Activated Cell Sorting (FACS) of gRNA-expressing cells after lentiviral transduction (FIG. 8A). Characterization of these constructs showed a robust gRNA-induced nuclear translocation for the dCas9- NLS-Tet1 construct (FIGS. 8C-8E), and thus this construct was chosen for all experiments in order to minimize non-specific modifications of DNA. Two types of gRNA behaved similarly (FIGS. 8C-8E) and thus were used interchangeably.

dCas9-Tet1 and dCas9-Dnmt3a Enable Targeted Alterations of CpG Methylation State To assess whether the dCas9-Tet1 and -Dnmt3a fusion constructs would induce demethylation or de novo methylation, respectively, of specific sequences, we utilized a methylation reporter system previously developed in our laboratory (Stelzer et al., 2015). This reporter system consists of a synthetic methylation-sensing promoter (conserved sequence elements from the promoter of an imprinted gene, Snrpn) that controls the expression of a green fluorescence protein (GFP). Insertion of this reporter construct into a genomic locus was shown to faithfully report on the methylation state of the adjacent sequences (Stelzer et al, 2015).

Figure 1B:
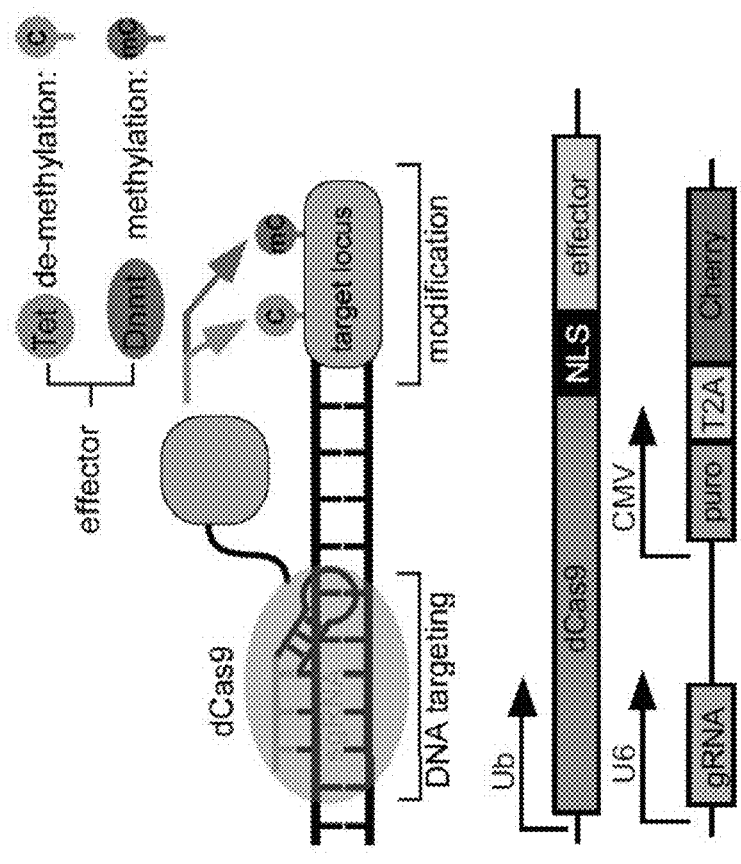
Figure 1C:
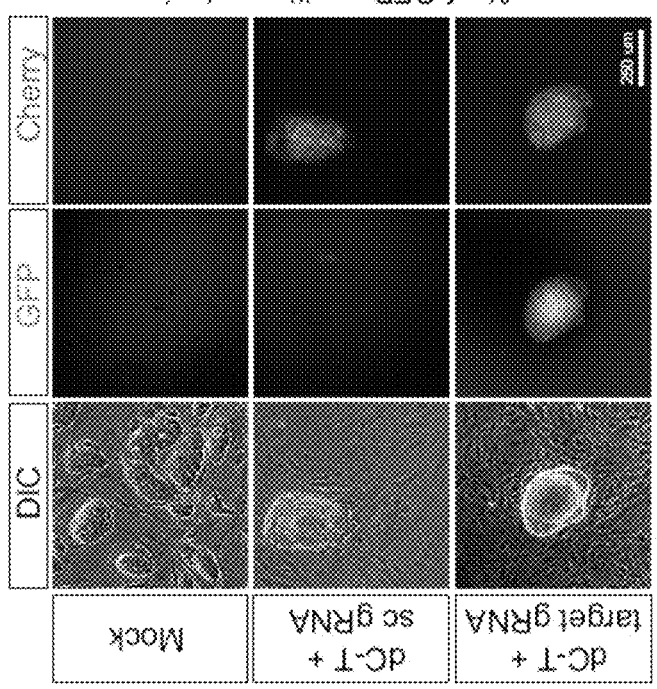
Figure 1D:
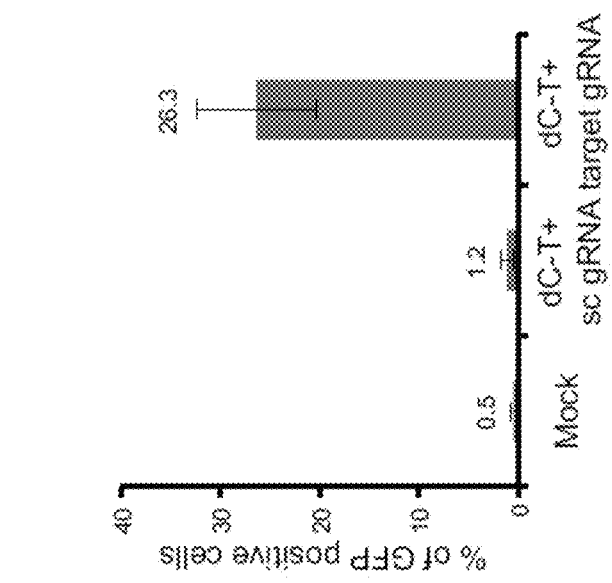
Figure 1E:
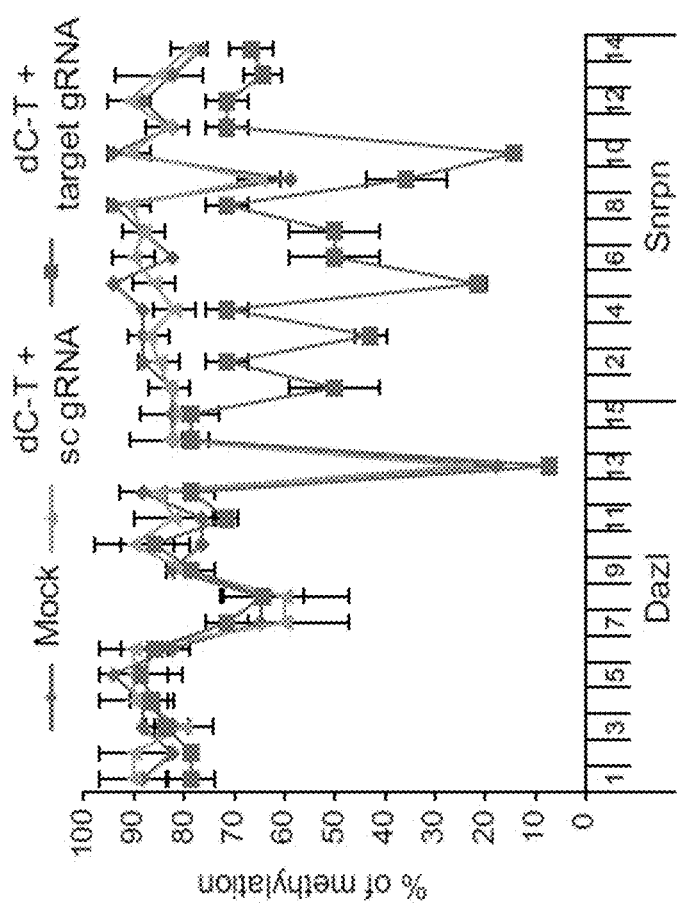
Figure 1F:
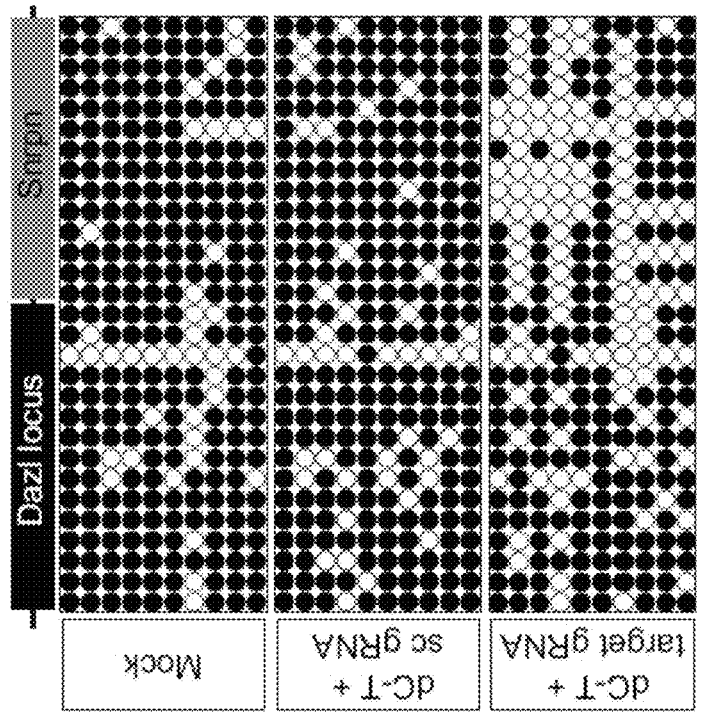

Demethylation of specific CpGs: To test whether defined sequences could be demethylated, we introduced the dCas9-Tet1 construct in combination with gRNAs to target the Snrpn-GFP reporter inserted into the Dazl promoter (FIG. 1B and FIG. 9A). Dazl is a germ cell specific gene, which is hypermethylated and not active in ES cells, and thus the GFP reporter is not expressed. To activate GFP expression by dCas9-Tet1 we designed 4 gRNAs targeting all 14 CpGs in the Snrpn promoter region. After infection with lentiviral vectors co-expressing dCas9-Tet1 and the 4 gRNAs for three days, some infection-positive cells as labeled by Cherry positive signal expressed from gRNA construct began to turn on GFP (FIG. 9B). To assess the activation efficiency by dCas9-Tet1 with target gRNAs, we analyzed the cells infected by both viruses using FACS. Among the Cherry positive population, about 26% of cells with target gRNAs activated GFP, whereas only 1% of cells with a scrambled gRNA were GFP positive (FIG. 1C and FIG. 9C). These Cherry positive single cells were further cultured to allow for formation of ES cell colonies. Cells with target gRNAs, but not the scrambled gRNA, expressed GFP (FIG. 1D). To confirm that the activation of GFP in these cells is caused by demethylation of the Snrpn promoter, we performed bisulfite sequencing of genomic DNA from these samples. As illustrated in FIGS. 1E and 1F, samples from cells with target gRNAs showed robust demethylation only in the Snrpn promoter region but not the adjacent Dad locus, and samples from the cells with the scrambled gRNA showed a similar methylation status to the uninfected (Mock) control. We further analyzed the GFP-positive and -negative populations within infected Cherry-positive cells. As shown in FIG. 9D, a more robust demethylation of the Snrpn promoter region was observed in double positive cells (Cherry+; GFP+). These results confirm the targeted erasure of DNA methylation by dCas9-Tet1 with gRNAs in proliferative cells.

Figure 2A:
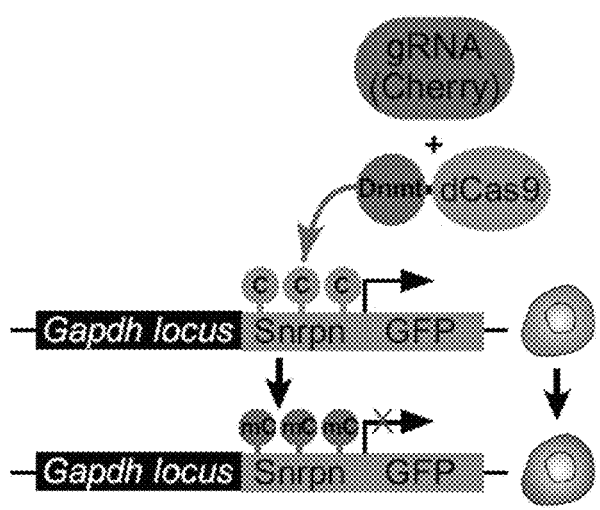
Figure 2B:
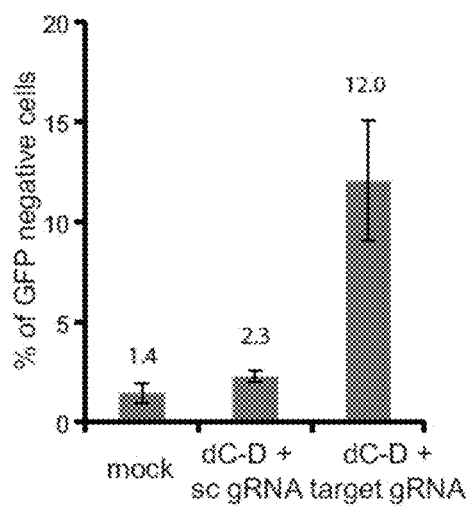
Figure 2C:
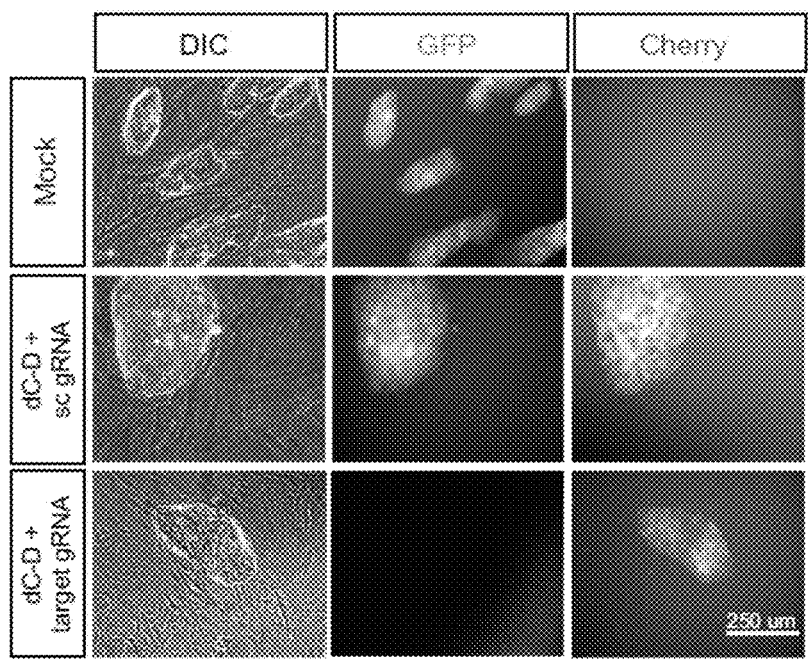
Figure 2D:
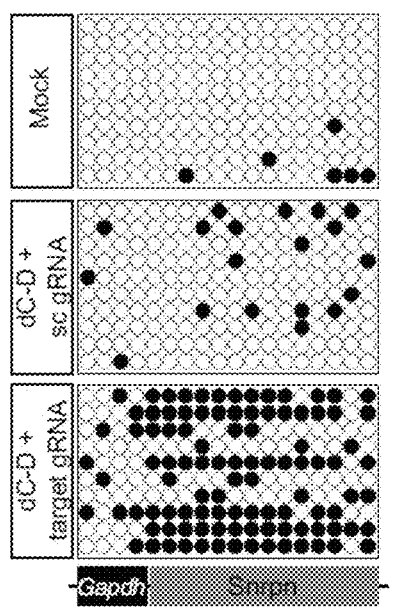
Figure 2E:
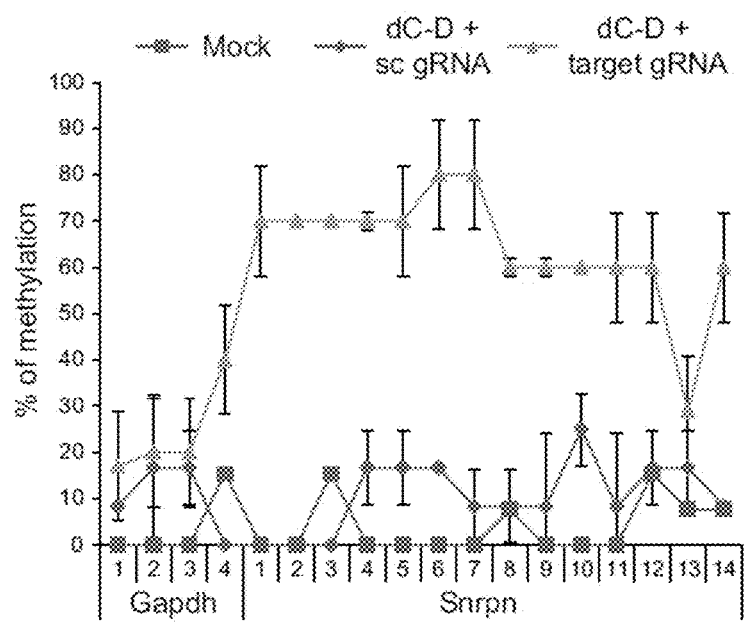
Figure 2F:
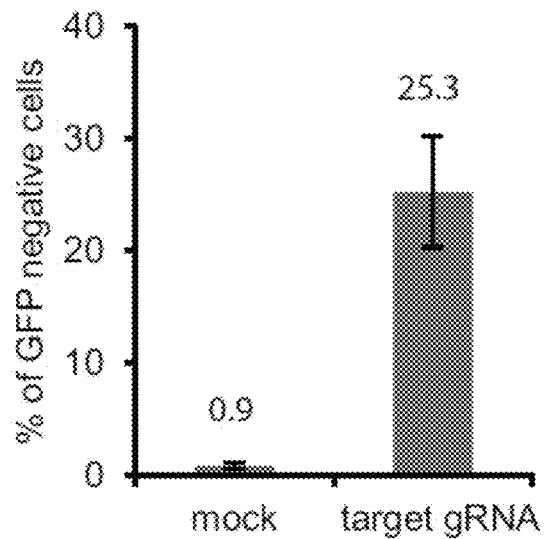
Figure 2G:
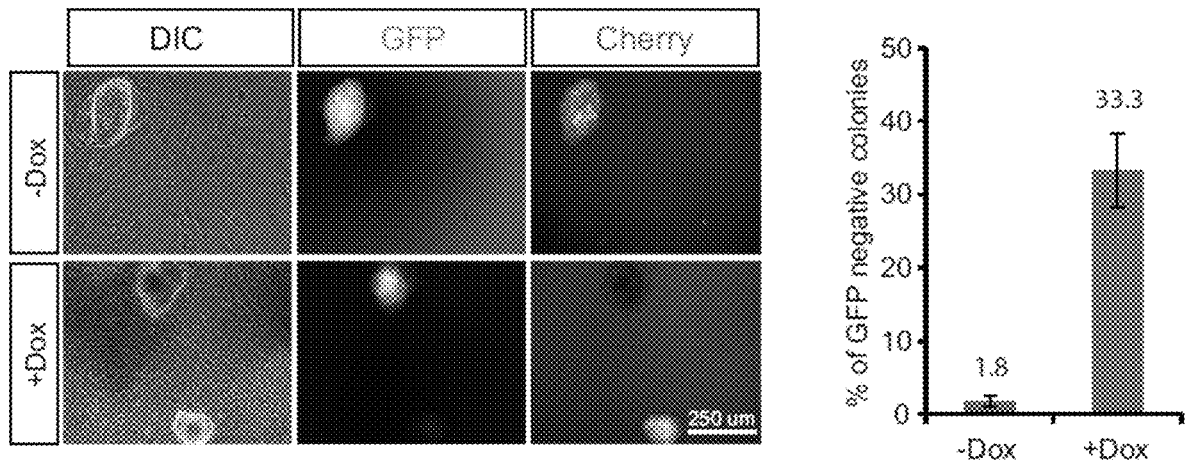
Figure 2H:
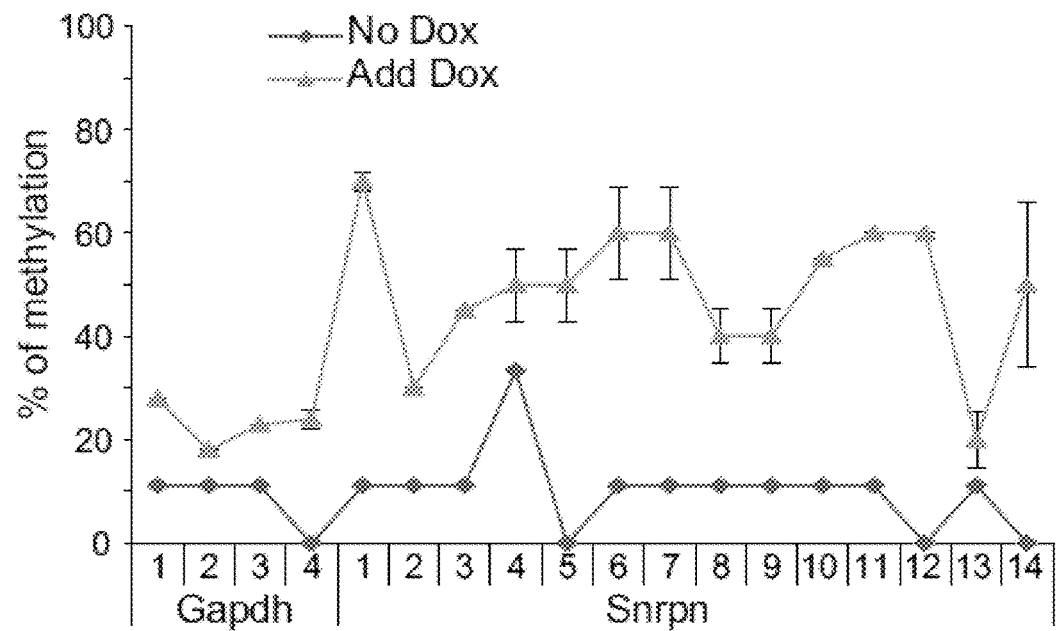
Figures 9E, 9F, 9G, 9H, 9I:
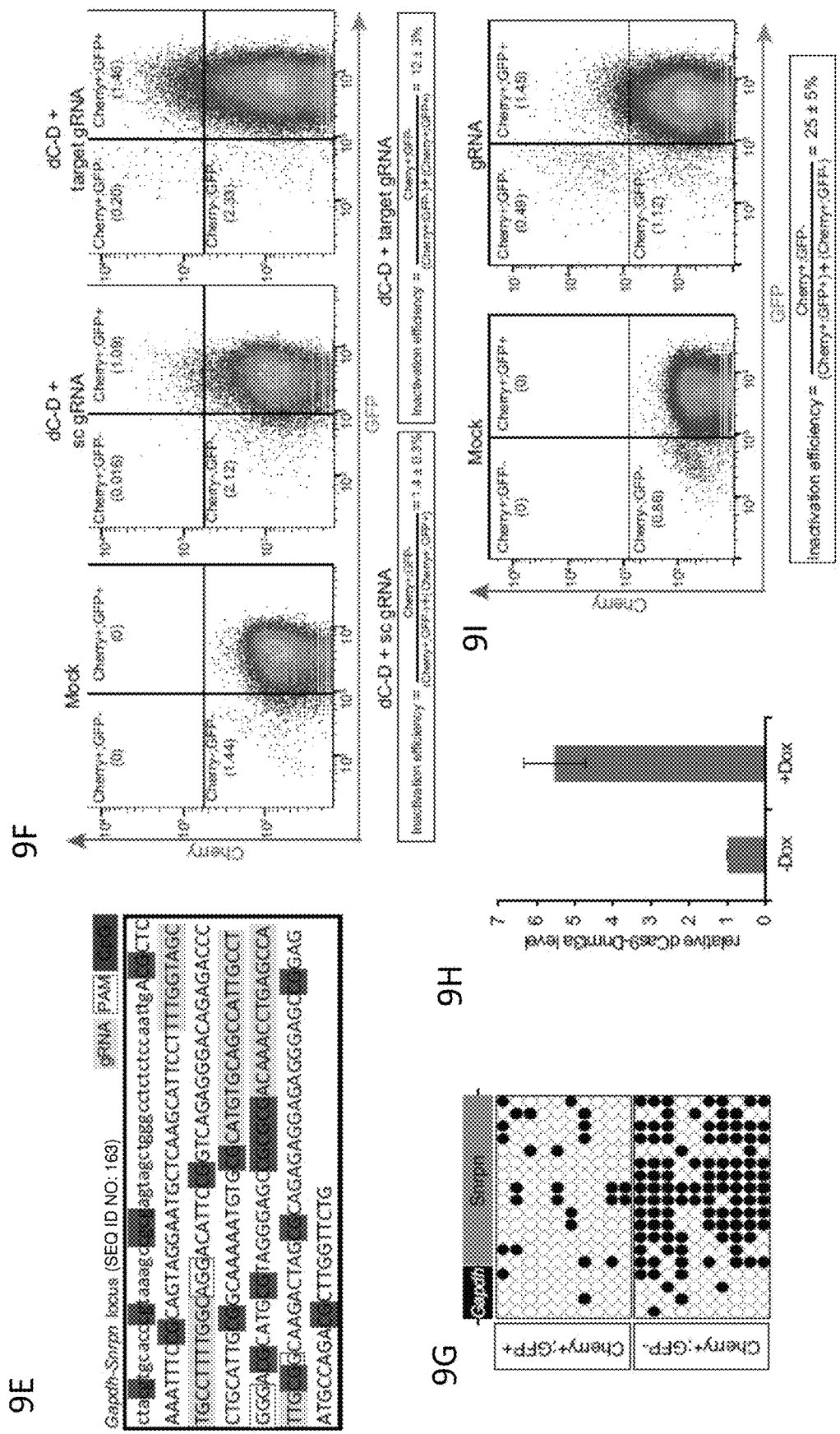
Figure 9J:
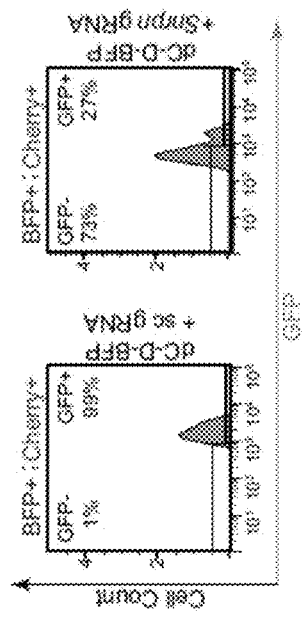
Figure 9J:
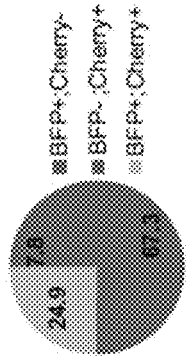
Figure 9J:
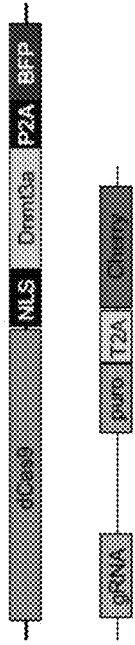

De novo methylation of specific CpGs: To assess whether a dCas9-Dnmt3a fusion protein could de novo methylate promoter sequences and silence gene expression, we used cells carrying the Snrpn-GFP reporter in the Gapdh promoter. These cells are GFP positive because Gapdh is unmethylated and expressed in ES cells (Stelzer et al., 2015). We infected the Gapdh-Snrpn-GFP ESCs with lentiviruses expressing dCas9-Dnmt3a and gRNAs targeting the Snrpn promoter or a scrambled gRNA (FIG. 2A and FIG. 9E), followed by FACS analysis. Among infection-positive (Cherry positive) population, about 12% of cells with target gRNAs inactivated GFP, whereas only 2% of cells with the scrambled gRNA were GFP negative (FIG. 2B and FIG. 9F). When the Cherry positive cells were grown in culture, GFP expression of cells with target gRNAs remained off whereas cells with the scrambled gRNA and mock controls remained GFP positive (FIG. 2C). Furthermore, bisulfite sequencing showed that transduction of dCas9- Dnmt3a/gRNAs resulted in a significant increase of DNA methylation in the Snrpn promoter region but not in the adjacent Gapdh region (FIGS. 2D-2E). Further analysis of the GFP-positive and -negative populations within infected Cherry-positive cells showed a more robust methylation of the Snrpn promoter region in Cherry+; GFP-cells (FIG. 9G). To overcome the possible limitation caused by low co-transduction efficiency of both dCas9-Dnmt3a and gRNA lentiviruses, a Doxycycline-inducible dCas9- Dnmt3a expression cassette was integrated into the Gapdh-Snrpn-GFP mES cell line by using a PiggyBac transposon system (FIG. 9H). After delivery of the same group of target gRNAs, FACS analysis showed that GFP inactivation efficiency was increased to 25% (FIG. 2F and FIG. 9I). Sorted Cherry-positive cells showed loss of GFP expression upon Doxycycline treatment (FIG. 2G) and were robustly methylated in the Snrpn promoter region (FIG. 2H). We also generated a new construct of dCas9-Dnmt3a-P2A-BFP which enables isolation of dCas9-Dnmt3a expressing cells by FACS. ~70% of GFP inactivation efficiency was achieved in FACS sorted double positive cells (BFP+; Cherry+) after lentiviral delivery of this construct together with gRNAs (FIG. 9J).

In summary, our results indicate that the dCas9 fusion constructs described above either efficiently demethylate methylated sequences (dCas9-Tet1) or de novo methylate unmethylated sequences (dCas9-Dnmt3a) in dividing cells when targeted by specific guide RNAs.

Comparison of dCas9- and TALE-Based Methylation Editing

Figures 10A, 10B, 10C, 10D:
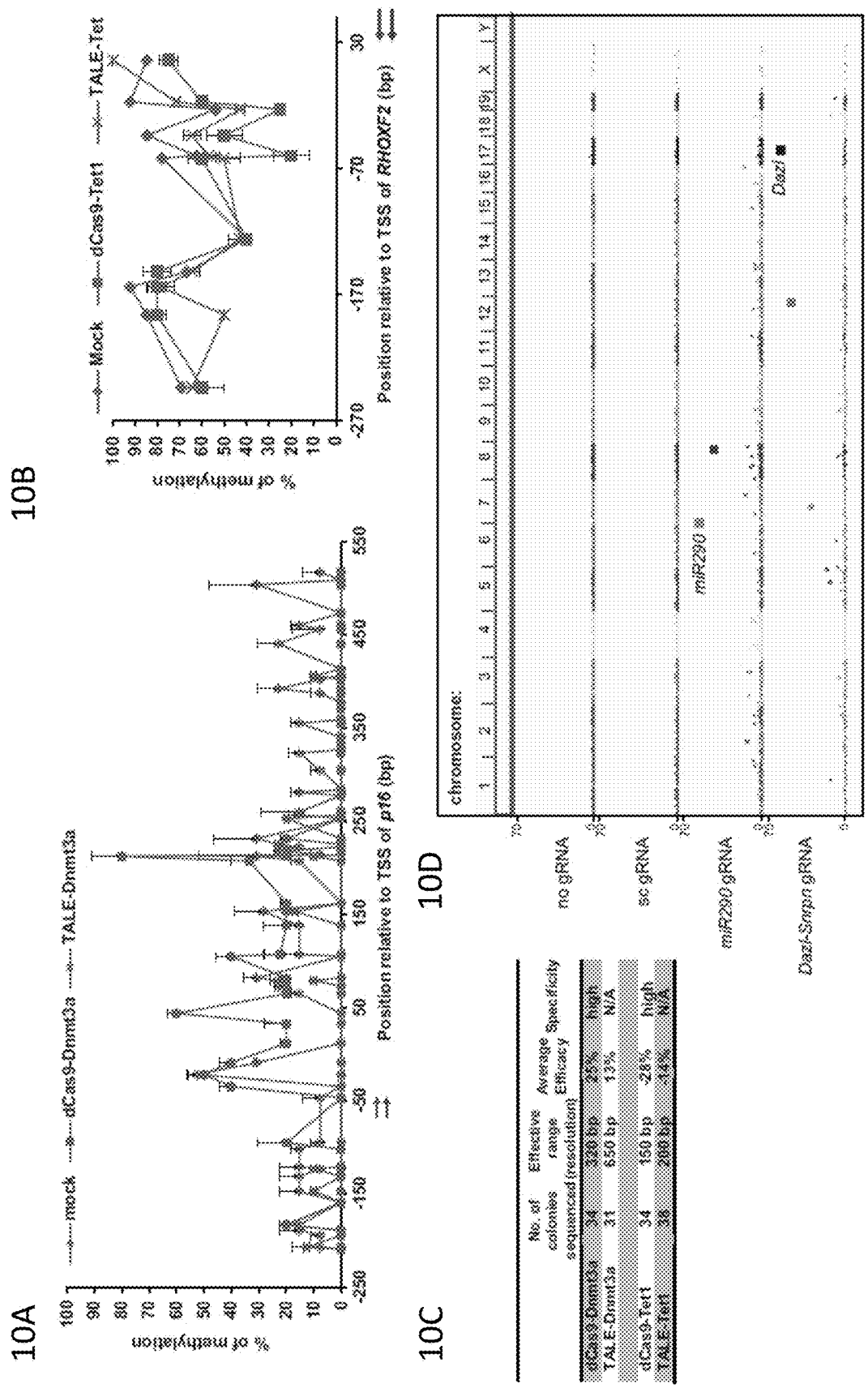
FIGS. 10A-10G depict comparison of TALE- and dCas9-based methylation editing.

To compare the methylation editing efficacy and effective range by dCas9-Tet1/Dnmt3a with TALE-based methods, we chose two previously reported loci edited by TALE-based method (Bernstein et al., 2015; Maeder et al., 2013) and designed a single gRNA targeting dCas9-Tet1/Dnmt3 to the same site bound by the TALE-Tet1/Dnmt3a. As shown in FIG. 10A and FIG. 10C, dCas9-Dnmt3a with one single gRNA targeting the p16 locus induced an average of 25% increase of methylation within a 320 bp region of the p16 promoter whereas TALE-Dnmt3a only induced 13% increase within a 650 bp region. Similarly, dCas9-Tet1 with one single gRNA targeting the RHOXF2 locus induced an average of 28% decrease of methylation within a 150 bp region of the RHOXF2 promoter whereas TALE-Tet1 only induced 14% decrease within a 200 bp region (FIGS. 10B-10C). These results suggest that dCas9-Tet1/Dnmt3a system has higher efficacy and resolution for methylation editing than TALE-based method.

Figures 10E, 10F, 10G:
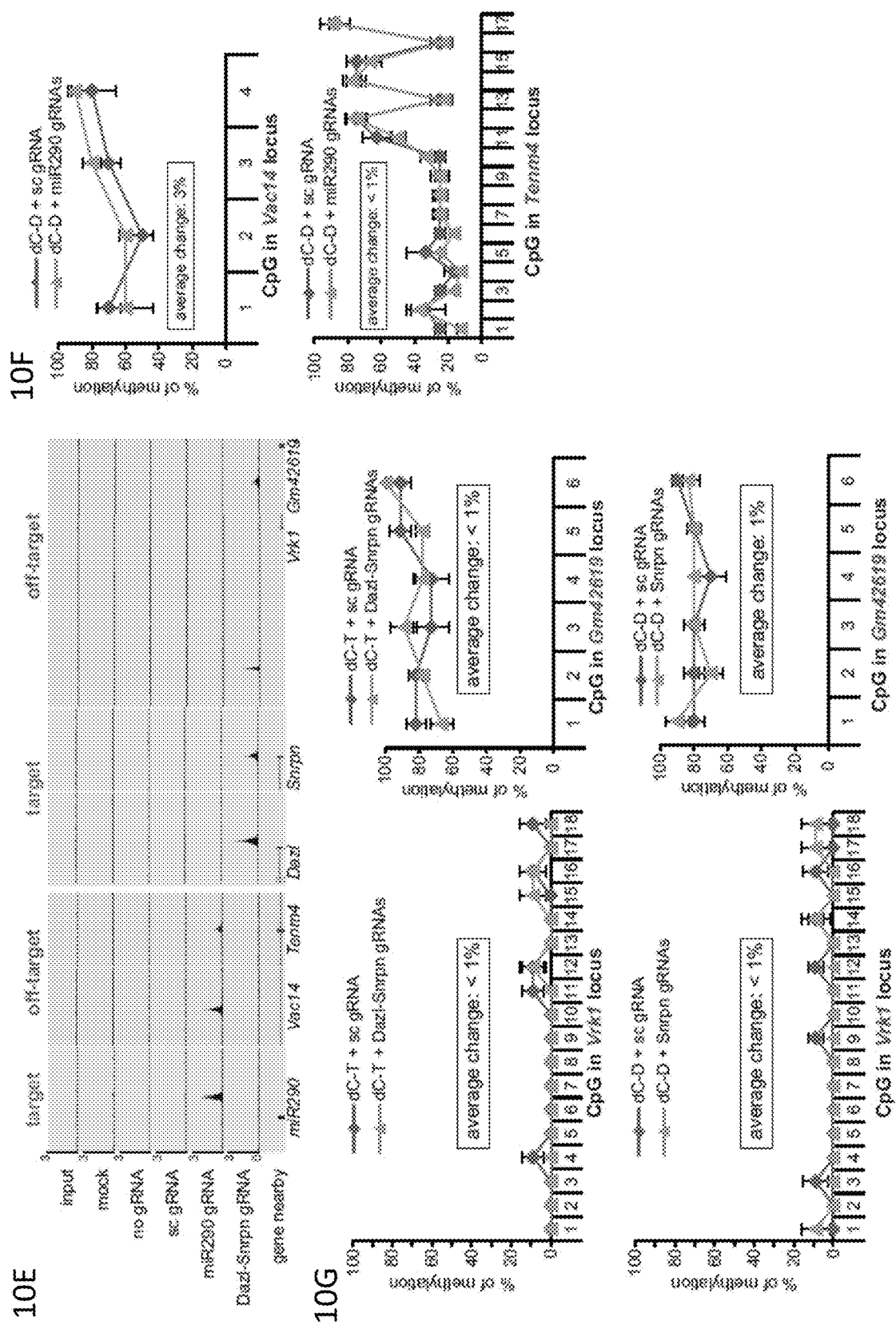
Figure 13A:
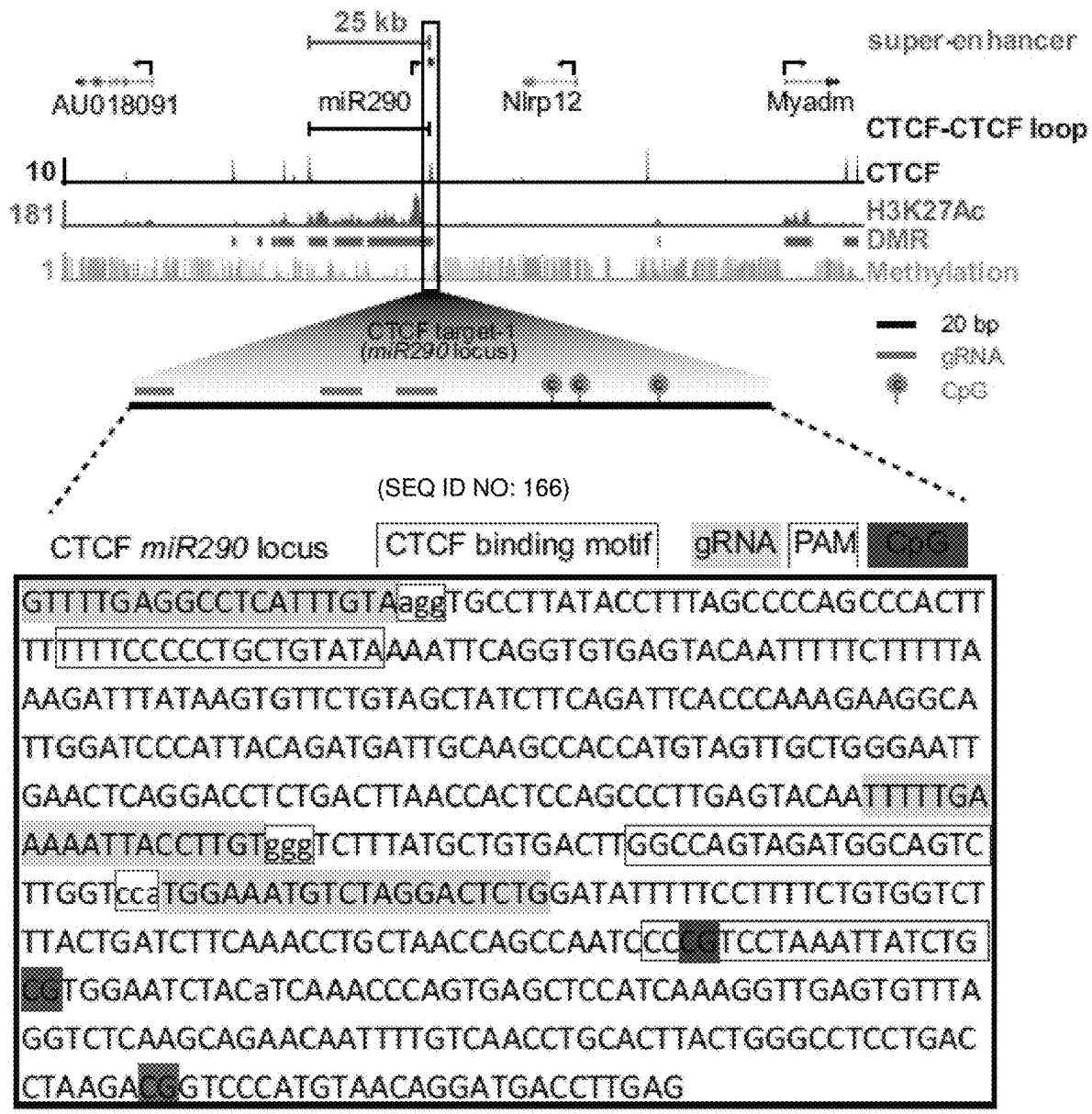
FIGS. 13A-13B depict gRNA design for targeted methylation of CTCF binding sites for miR290 and Pou5f1 loci.
Figure 18:
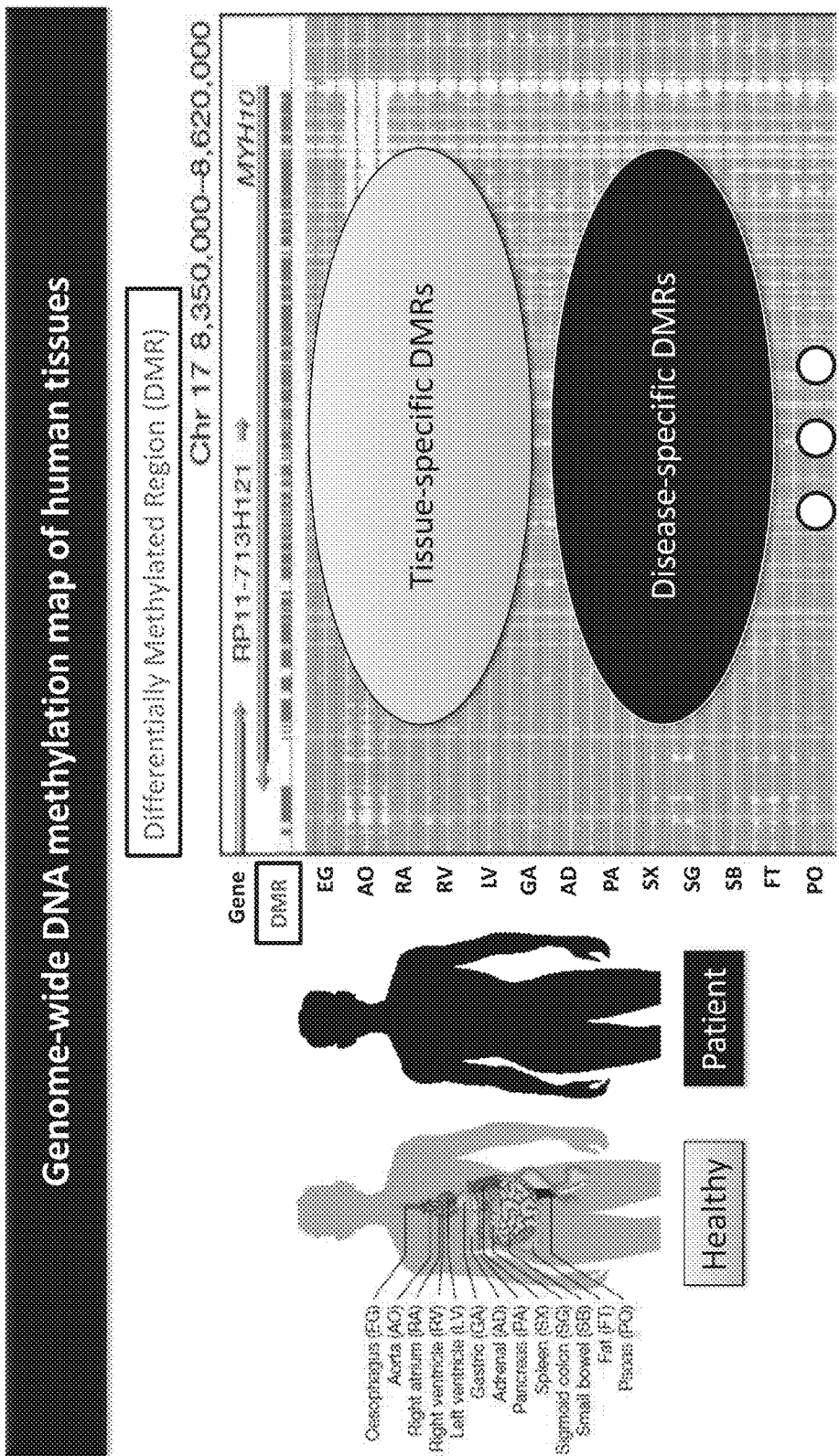
FIG. 18 provides an example of a DNA methylation map of human tissues.
Figure 19A:
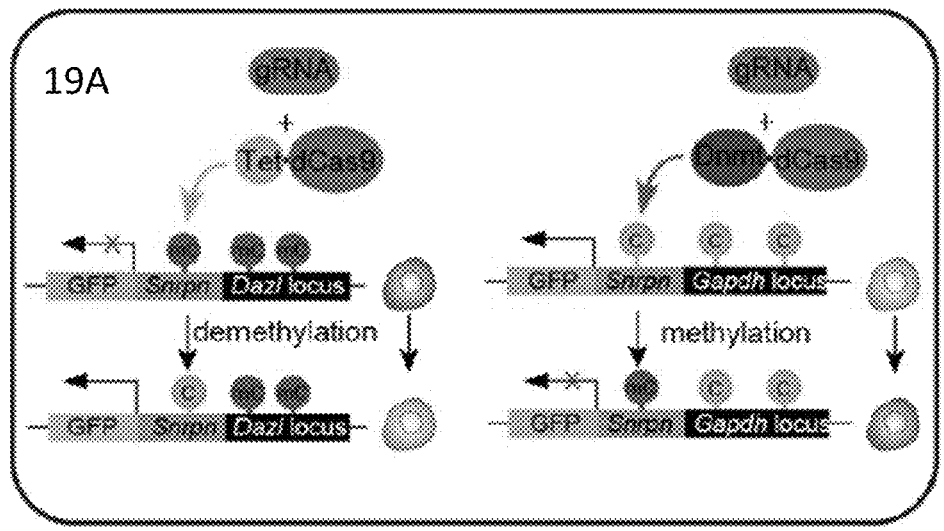
FIGS. 19A-19E depict a summary of methylation and demethylation activities.
Figure 19B:
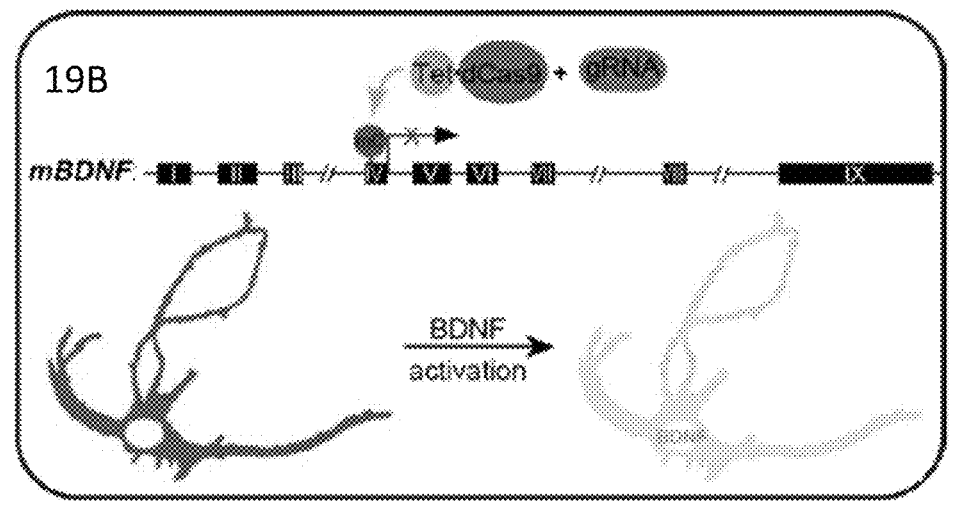
Figure 19C:
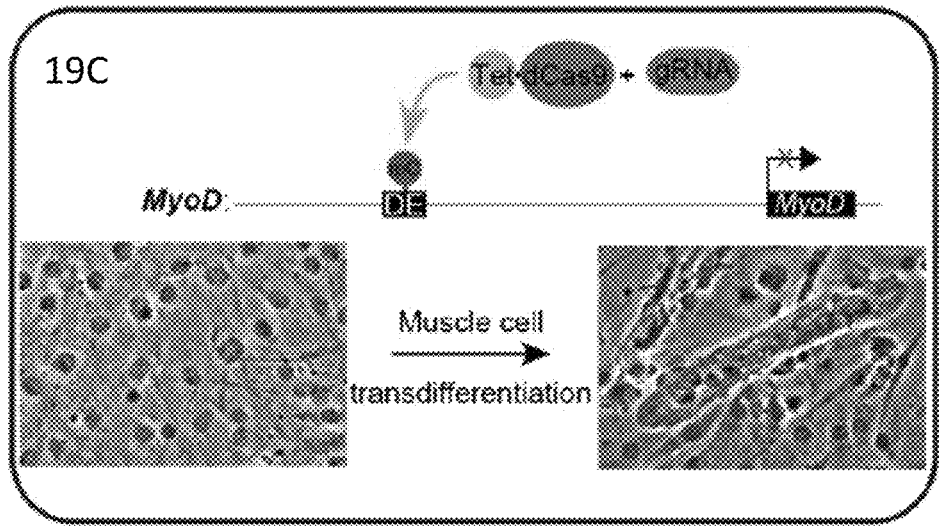
Figure 19D:
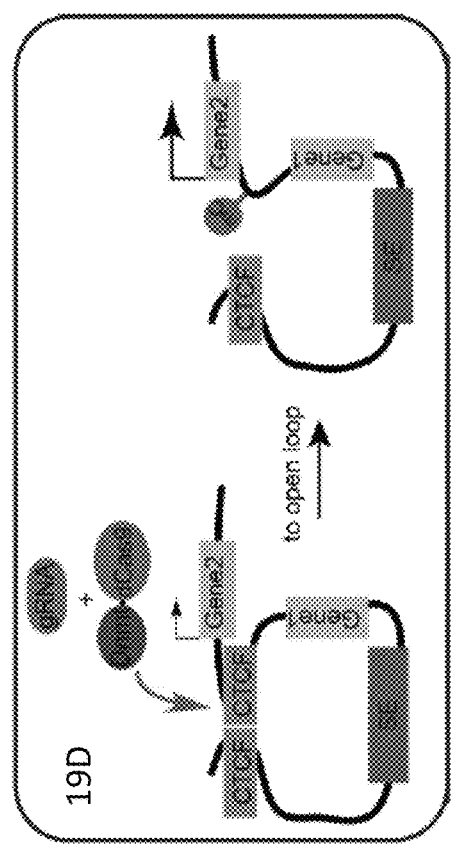
Figure 19E:
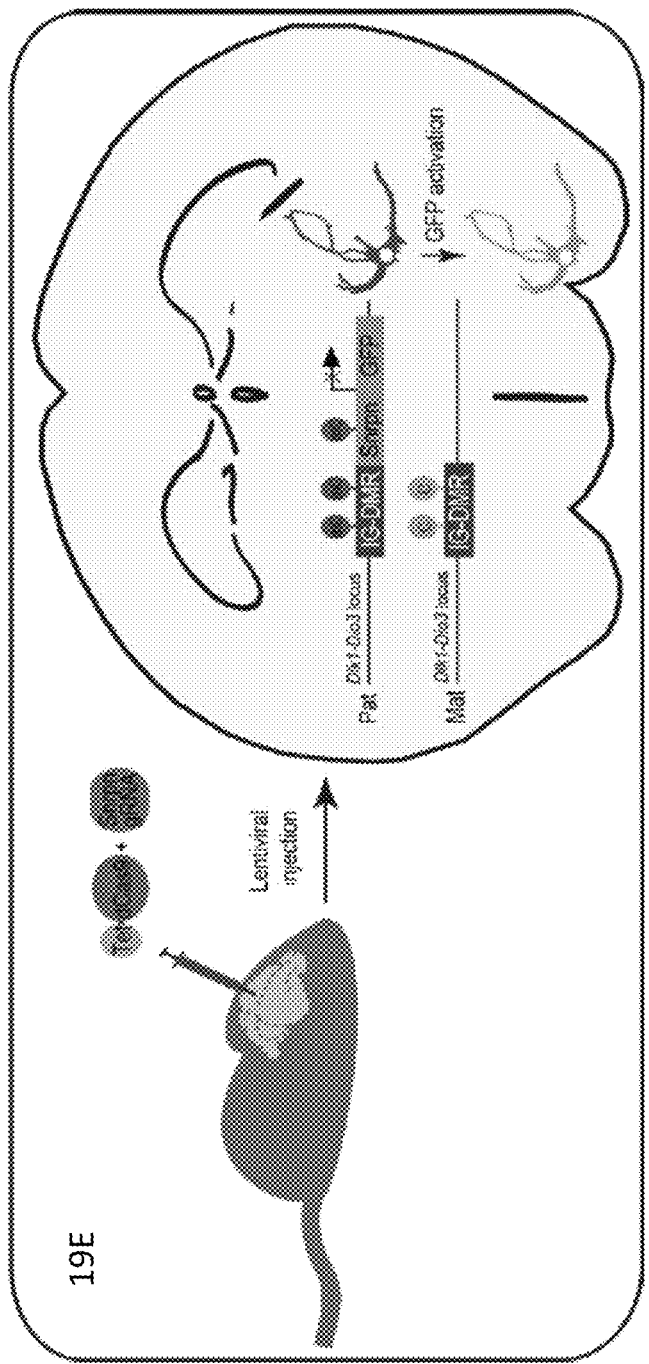
Figure 20:
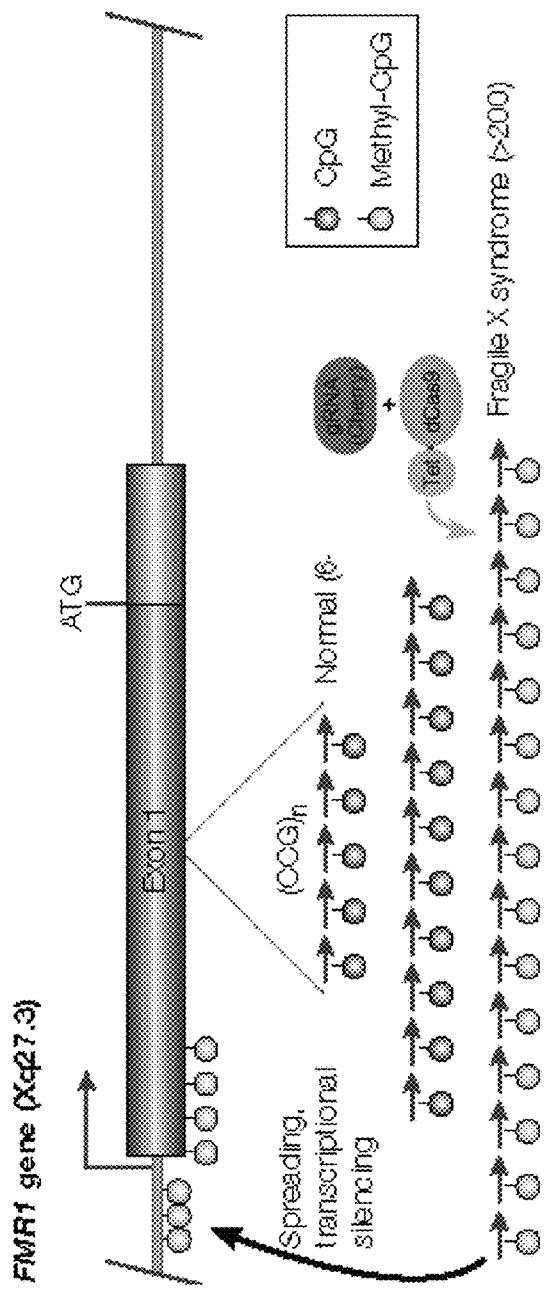
FIG. 20 depicts the reversal of hypermethylation of FMR-1 in Fragile X Syndrome. A cell exhibiting Fragile X Syndrome is contacted with dCas9-Tet1 fusion protein to specifically demethylate CCG hypermethylation so as to reactivate FMR-1.
Figure 21:
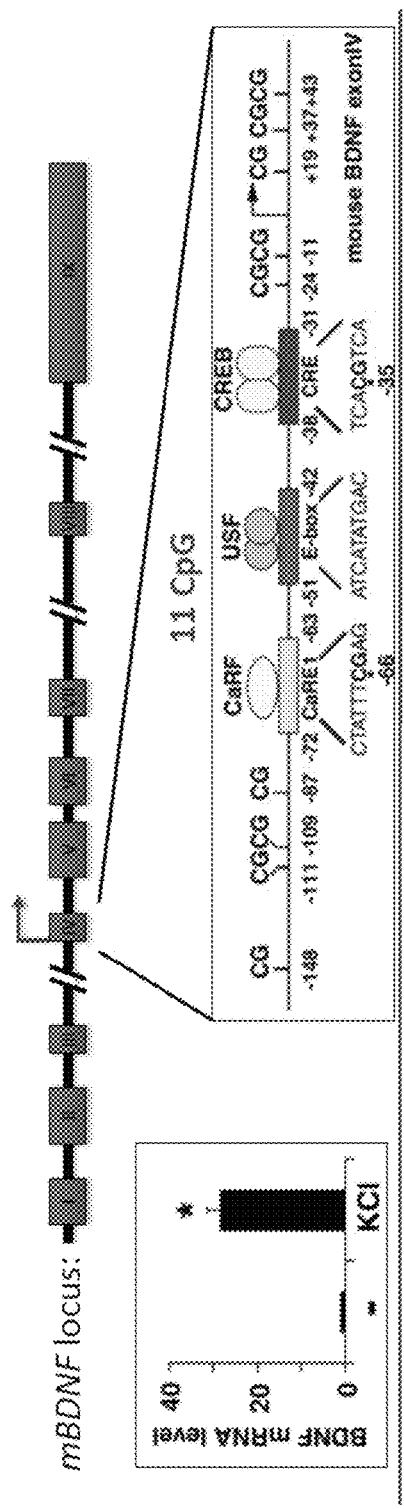
FIG. 21 demonstrates proposal of demethylation of BDNF to operate in post-mitotic neurons.
Figure 22:
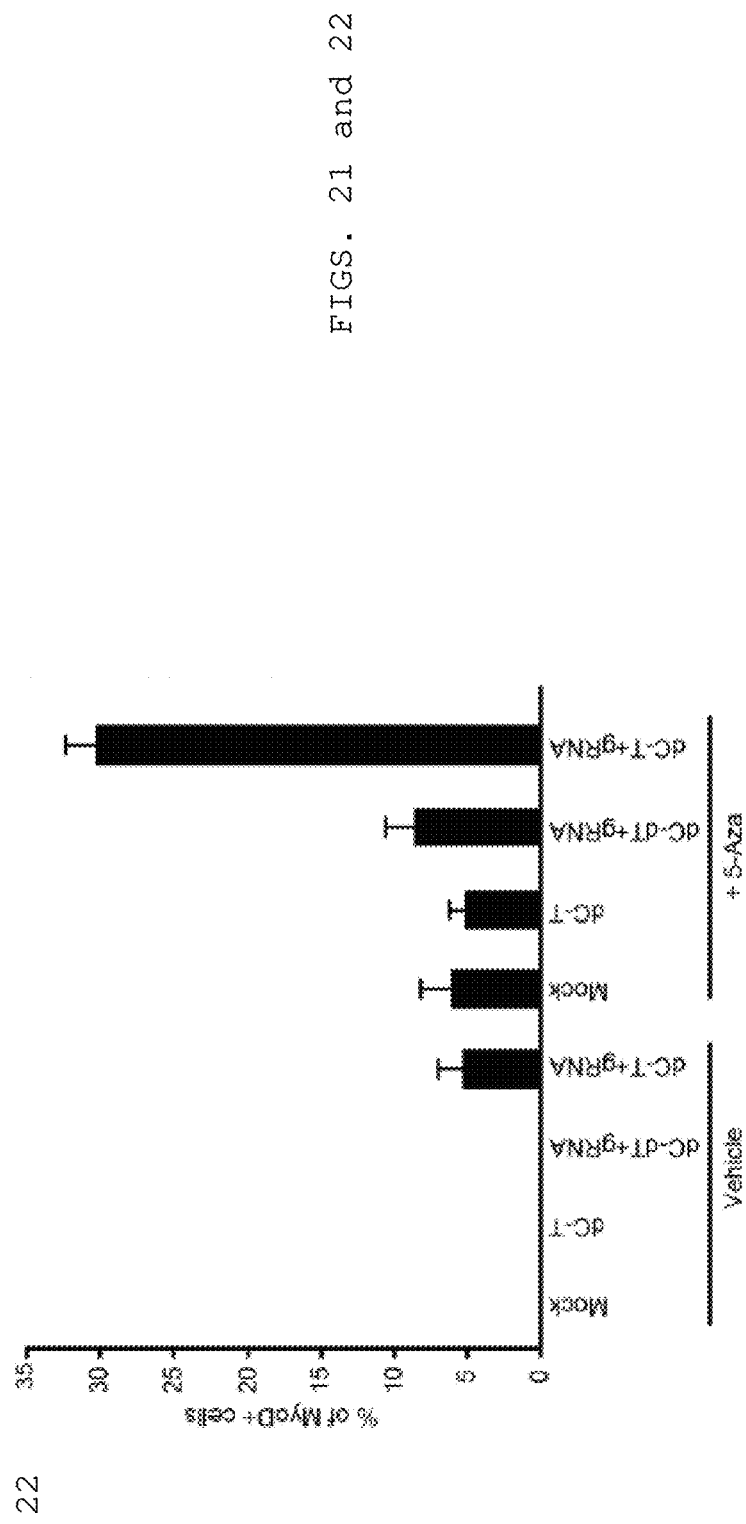
FIG. 22 depicts quantification of MyoD positive cell ratio after infection with lentiviruses expressing dC-T alone, dC-T with target gRNA, and dC-dT with target gRNAs.
Figure 23A:
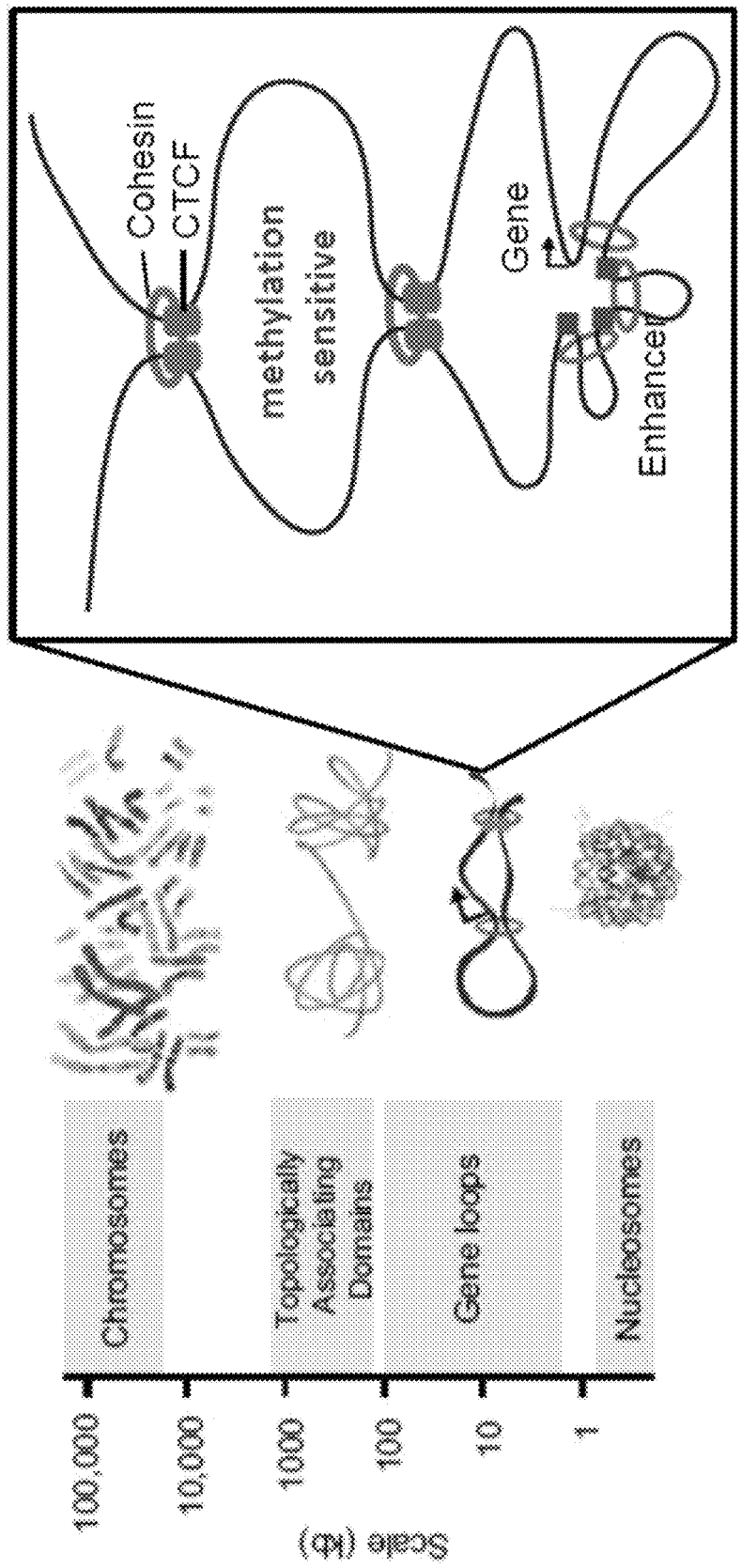
FIGS. 23A-23C depict targeted methylation of CTCF binding sites.
Figures 23B, 23C:
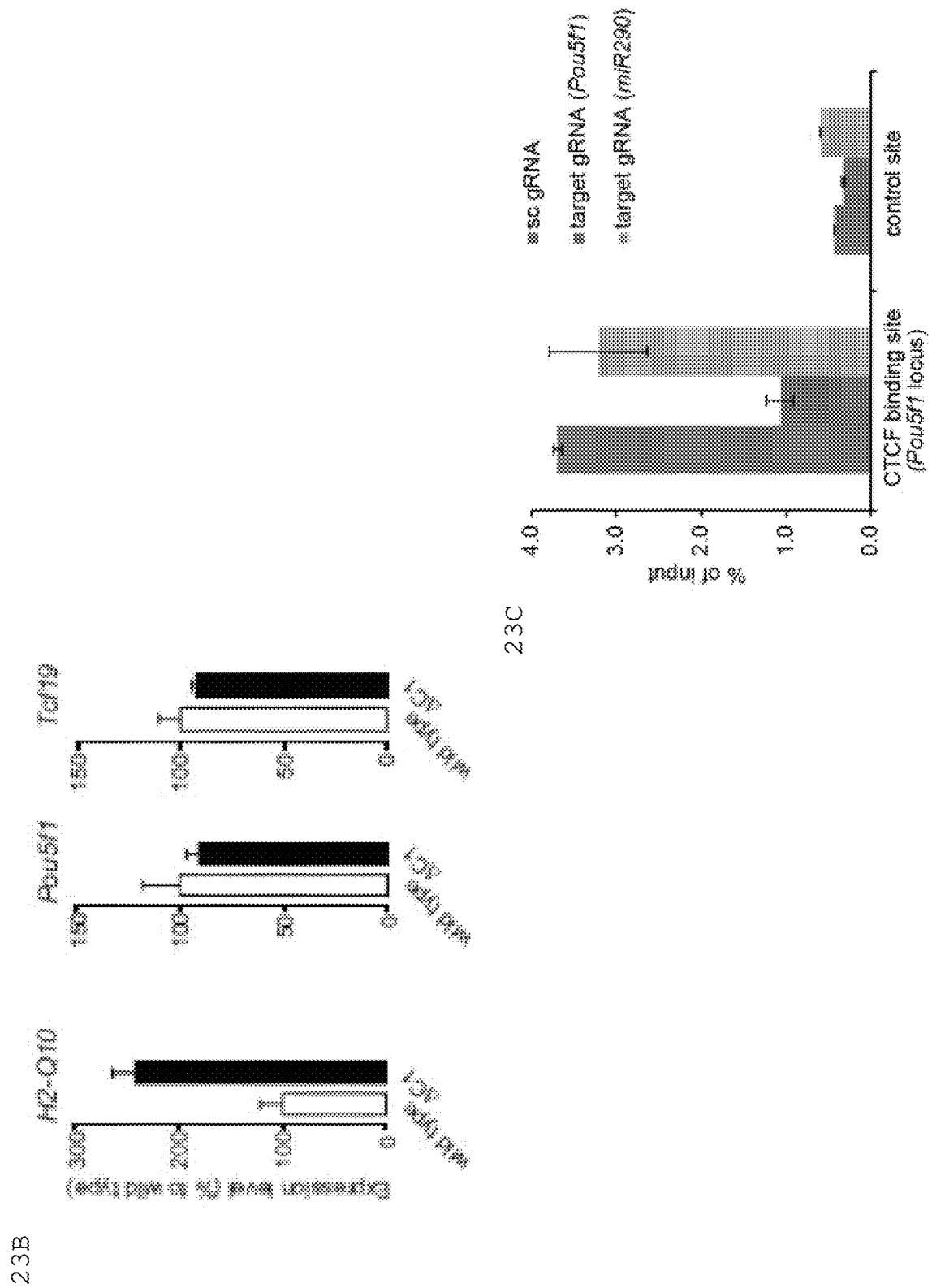

To evaluate the specificity of dCas9-Tet1/Dnmt3a-mediated methylation editing, we performed dCas9 ChIP-seq assay and identified 9 binding sites in the presence of gRNAs targeting the Dazl-Snrpn region described in FIGS. 9A and 18 binding sites in the presence of gRNAs targeting CTCF binding sites adjacent to the miR290 locus (see below FIG. 13A). FIG. 10D shows that among the identified binding sites for each group of gRNAs, the targeted locus (Dazl-Snrpn or miR290) showed the highest level of binding for dCas9-Dnmt3a (Table S1). The second and third strongest binding sites for each targeted locus were illustrated in FIG. 10E, and bisulfite sequencing analysis of these loci showed only marginal change in methylation level (FIGS. 10F-10G), likely due to the significantly lower binding affinity of dCas9- Dnmt3a/Tet1 at these off-target loci compared to the targeted loci. These results indicate that dCas9-based epigenetic editing can be highly specific.

Targeted Demethylation of BDNF Promoter IV Activates BDNF in Neurons

Figure 3A:
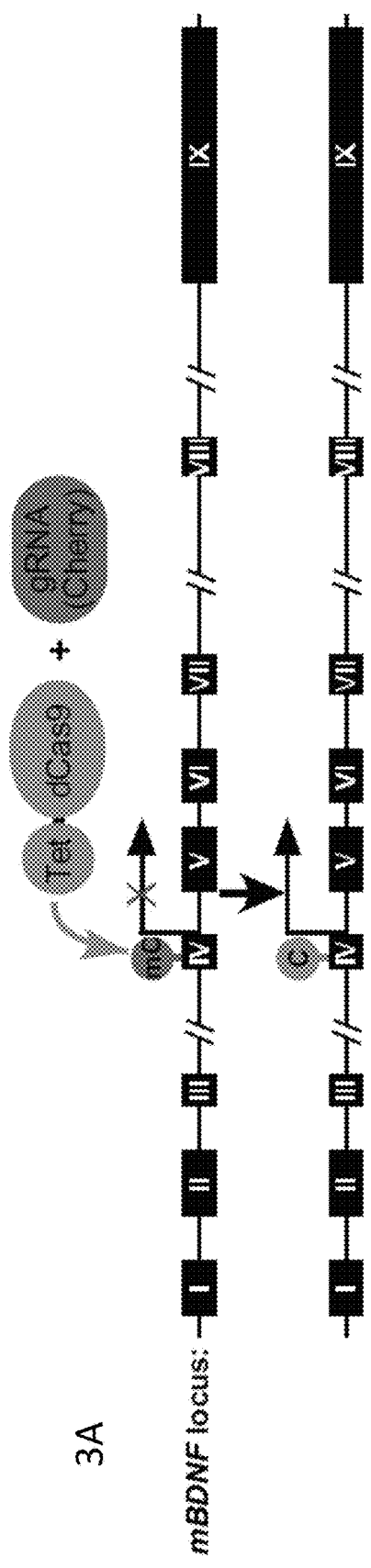
FIGS. 3A-3E depict targeted demethylation of BDNF promoter IV by dCas9-Tet1 to activate BDNF in neurons.

DNA replication-independent active demethylation has been proposed to operate in post-mitotic neurons (Guo et al., 2011; Martinowich et al., 2003). To test whether active demethylation can be induced in post-mitotic neurons, we applied the dCas9-Tet1 system to study the regulation of the BDNF gene. BDNF expression can be induced by neuronal activity accompanied by demethylation of its promoter IV (Chen et al., 2003; Martinowich et al., 2003). We designed 4 gRNAs targeting 11 CpGs in BDNF promoter IV (FIG. 11A) to determine whether dCas9-Tet1 can activate BDNF by inducing demethylation of this promoter (FIG. 3A).

Figure 3B:
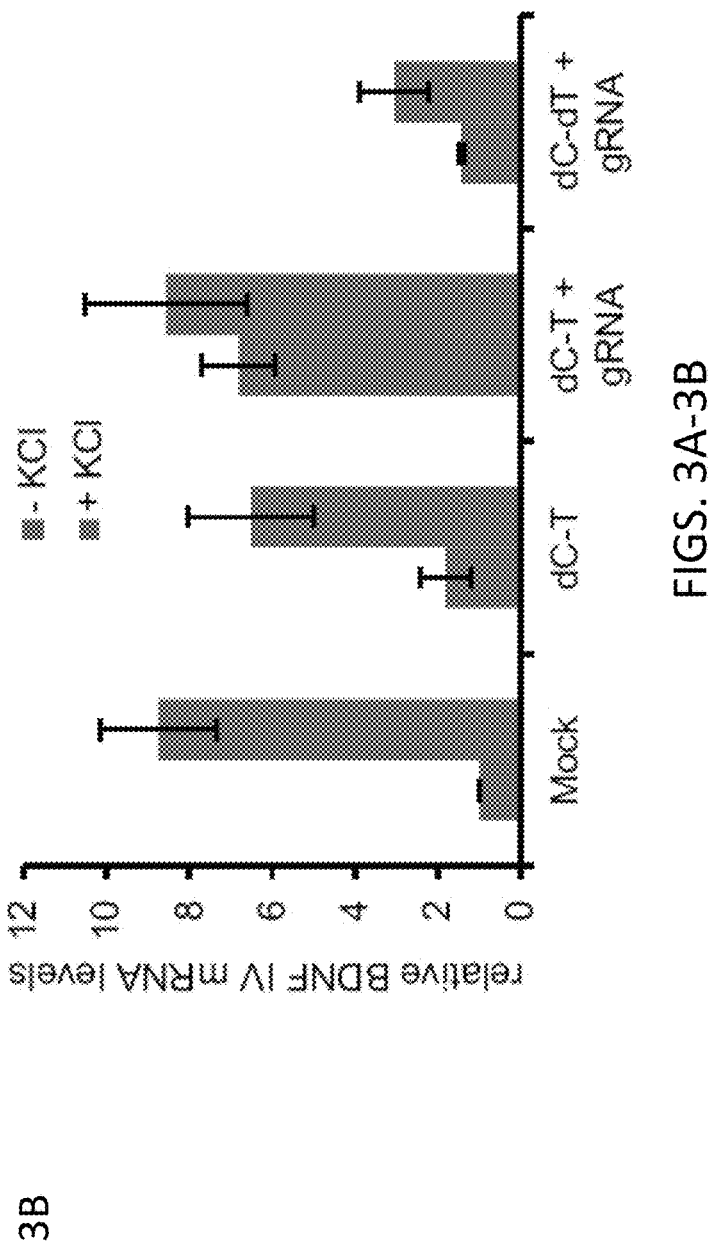
Figure 3C:
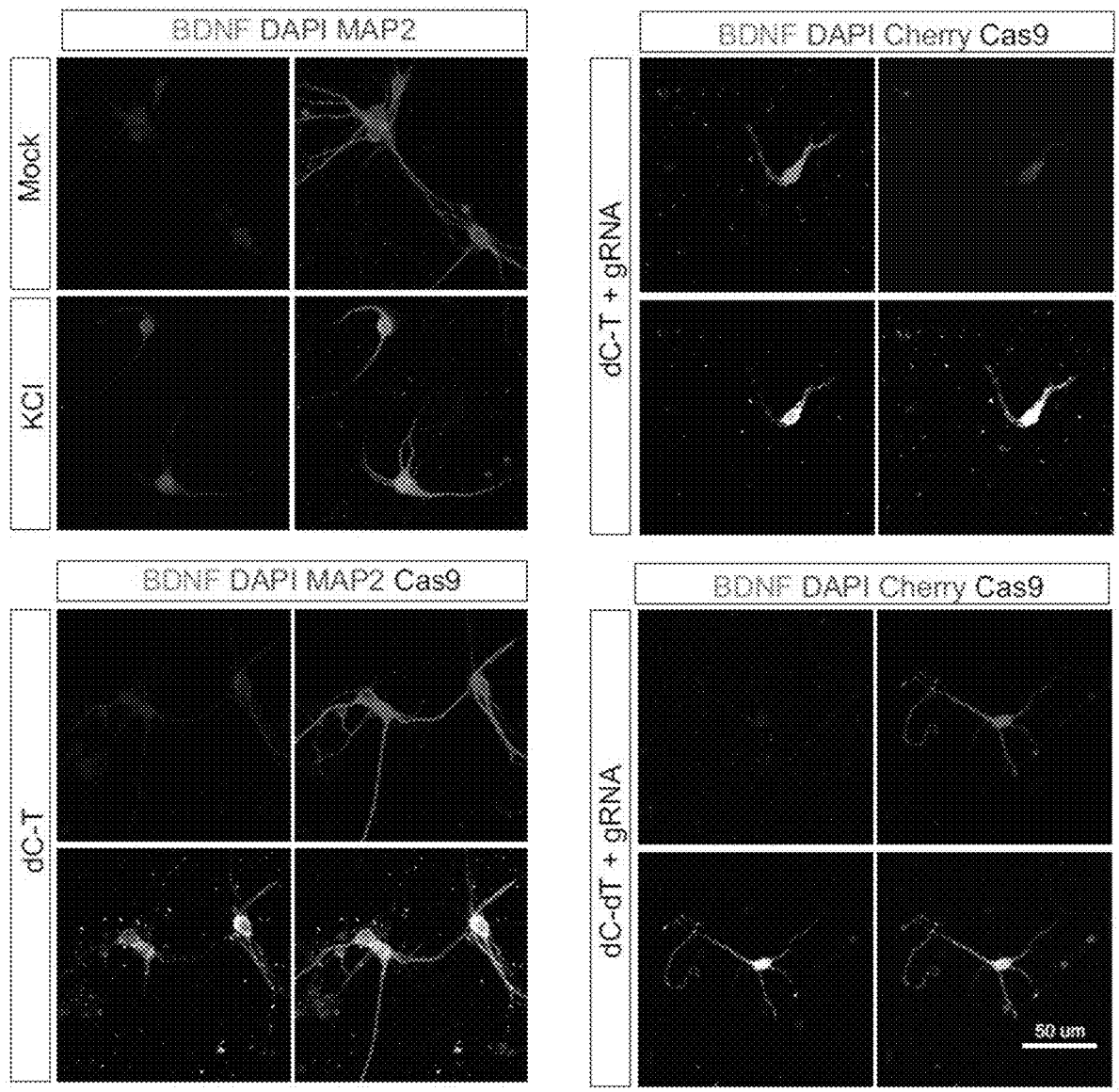
Figures 3D, 3E:
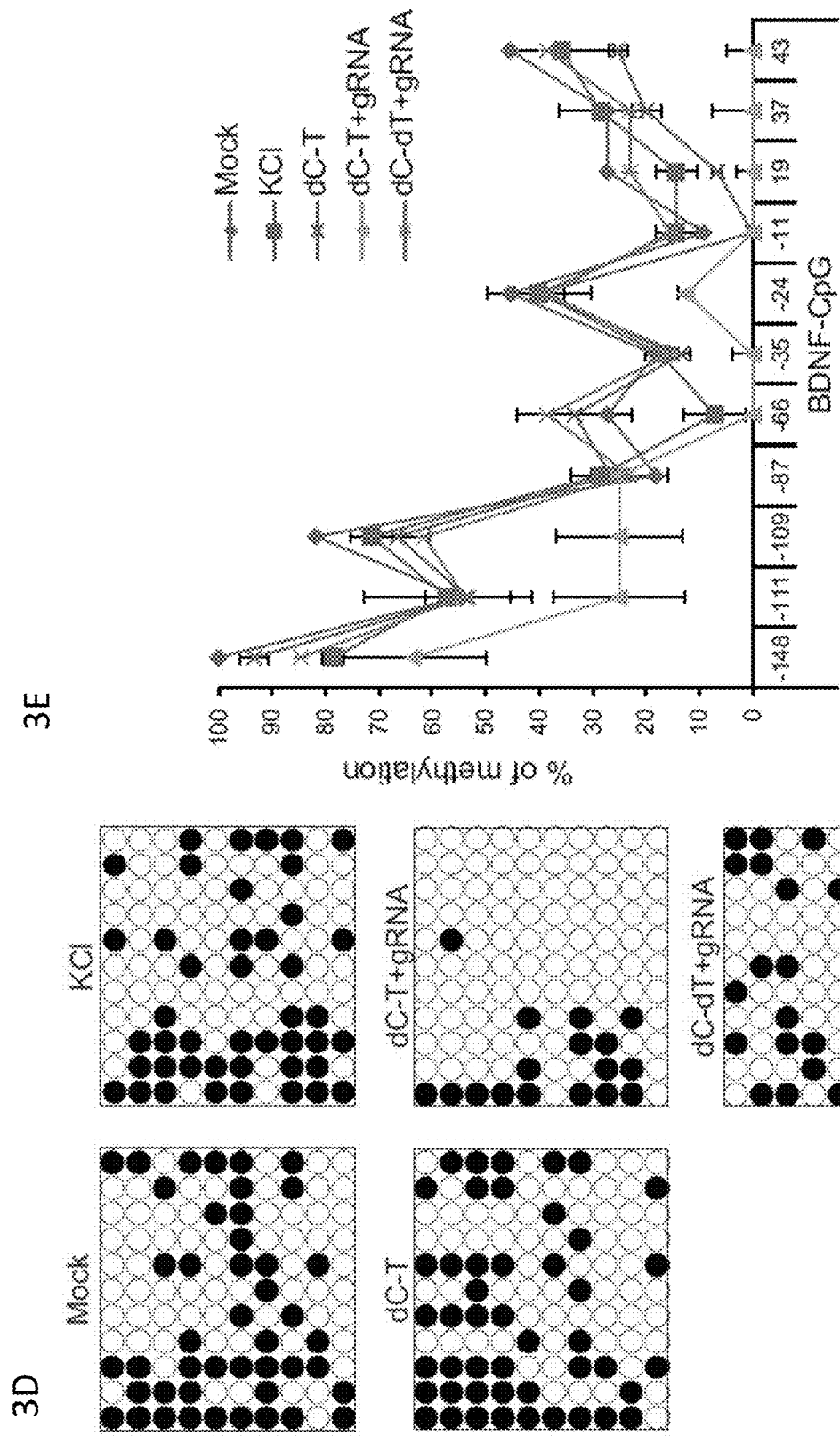
Figures 11A, 11B, 11C, 11D, 11E:
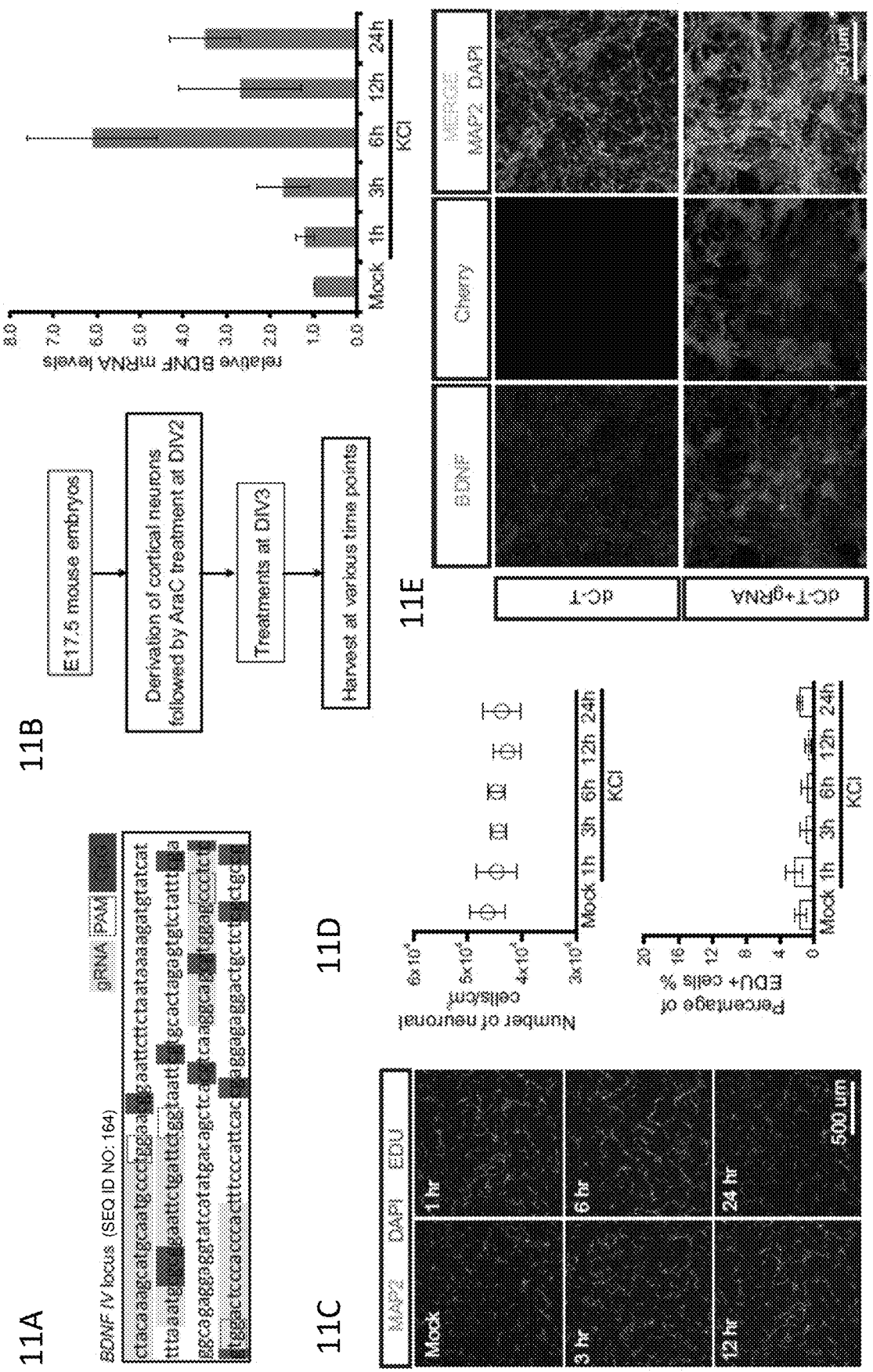
FIGS. 11A-11L depict targeted demethylation of BDNF promoter IV by dCas9-Tet1 in neurons.
Figures 11F, 11G, 11H, 11I:
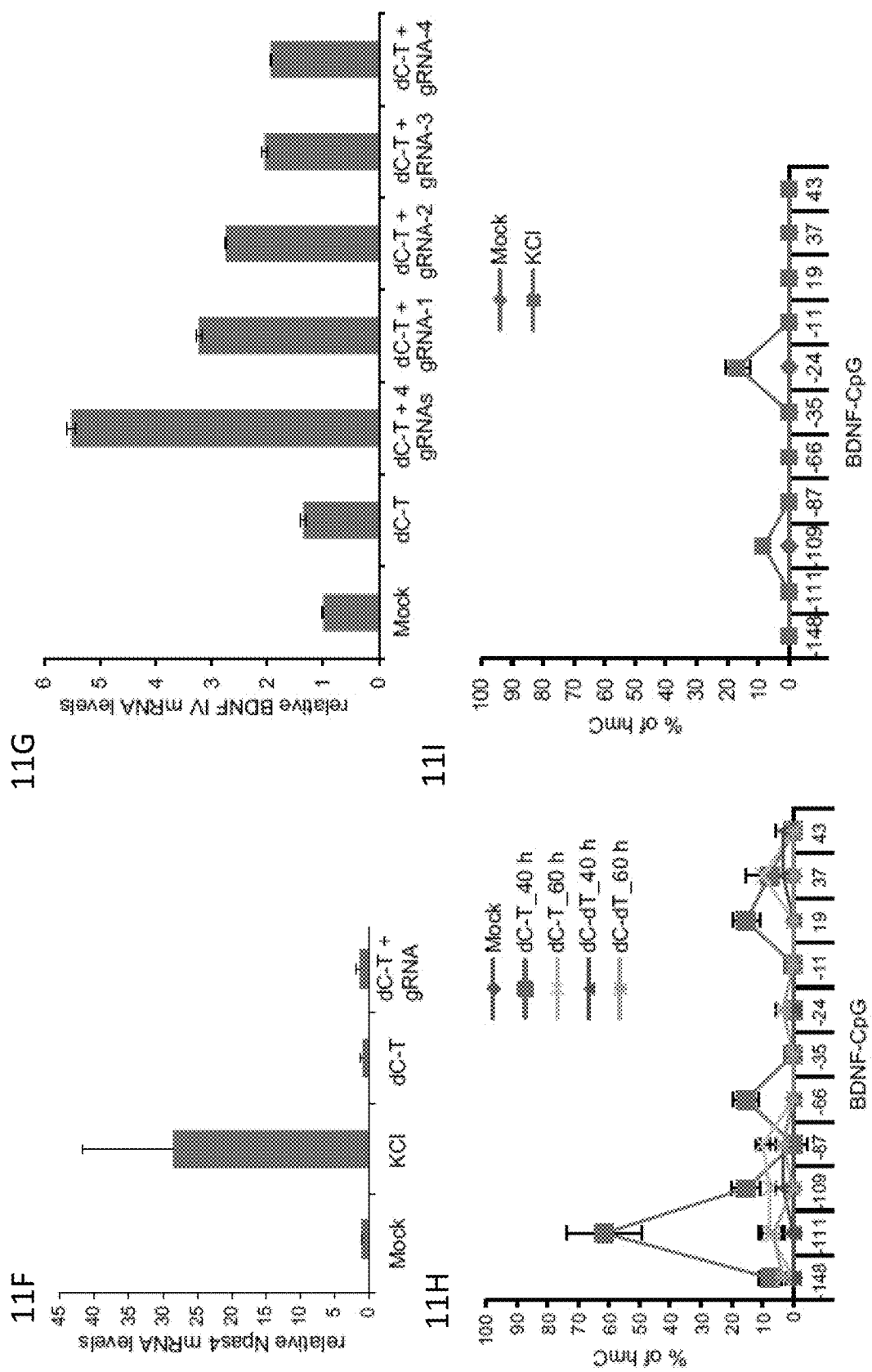

Mouse cortical neurons were isolated from E17.5 embryos and cultured for two days in vitro (DIV2) following a well-established experimental procedure for producing primary neuronal culture (Ebert et al., 2013). As shown in FIGS. 11B-11D, KCl treatment induced BDNF expression in these neurons with no detectable cell proliferation. Neurons at day 3 in culture (DIV3) were infected with lentiviral vectors expressing dCas9-Tet1 with or without the 4 gRNAs at almost 100% transduction efficiency (FIG. 11E). At 48-hour post infection some of the cultures were treated with KCl to induce neuronal activity. As shown in FIGS. 3B-3C, dCas9-Tet1/gRNAs induced BDNF expression by about 6-fold, whereas dCas9-Tet1 in the absence of gRNAs showed only a slight induction (less than 2-fold) and a catalytically dead form of Tet1 (dC-dT) showed no induction. Importantly, the same group of dCas9-Tet1/gRNAs did not induce Npas4 expression (FIG. 11F), another neuronal activity-inducible gene (Lin et al., 2008). Co-transduction of dCas9-Tet1 with each individual gRNA targeting the BDNF promoter IV showed a 2-3 fold induction of BDNF (FIG. 11G). We performed bisulfite sequencing to examine the methylation state of BDNF promoter IV. As shown in FIGS. 3D-3E, dCas9-Tet1/gRNAs significantly reduced methylation in this region in contrast to gRNA negative controls while KCl treatment also induced demethylation of CpGs at positions of −148, −66 and 19 (relative to transcription start site).

Figure 11J:
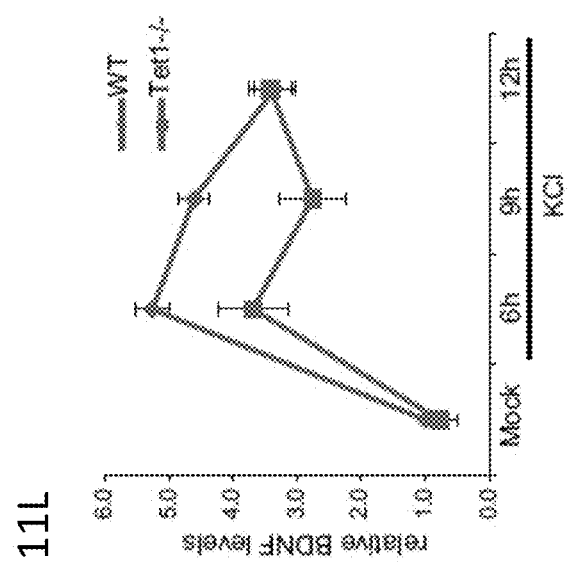

Our results demonstrate that demethylation of the BDNF promoter IV can be induced by dCas9-Tet1/gRNAs and is sufficient to activate BDNF expression. Because post-mitotic neurons were used for these experiments, loss of methylation was likely due to active demethylation. To further support this conclusion, we examined 5-hmC level in the BDNF promoter IV during the time course of dCas9-Tet1 induced demethylation by Tet-assisted Bisulfite sequencing (TAB-seq) analysis. As shown in FIG. 11H, 5-hmC was detected 40-hour post infection with dCas9-Tet1 and gRNA lentiviruses and diminished after 60 hours. Similarly, 5-hmC was also detected after KCl treatment (FIG. 11I). As bisulfite sequencing method does not distinguish unmethylated 5-cytosine (5-C) and 5-formlycytosine/5-carboxylcytosin (5-fC/5-caC) generated from 5-hmC, it is possible that some CpGs were 5-fC/5-caC modified after targeting with dCas9-Tet1/gRNA. Nevertheless, inhibition of the base excision repair pathway by treatment with ABT-888 (an inhibitor of PARP) reduced the activation of BDNF by KCl treatment (FIG. 11J), suggesting that demethylation of BDNF promoter IV contributes to BDNF activation.

Figure 11K:
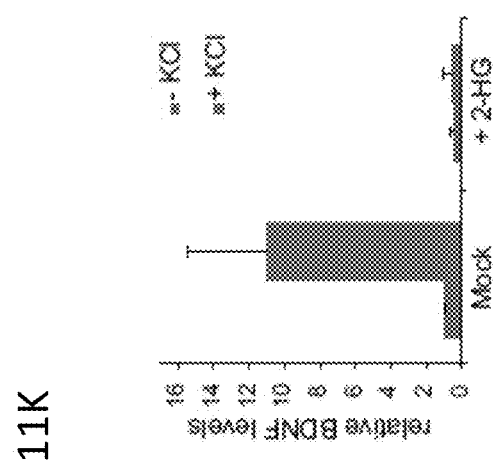
Figure 11L:
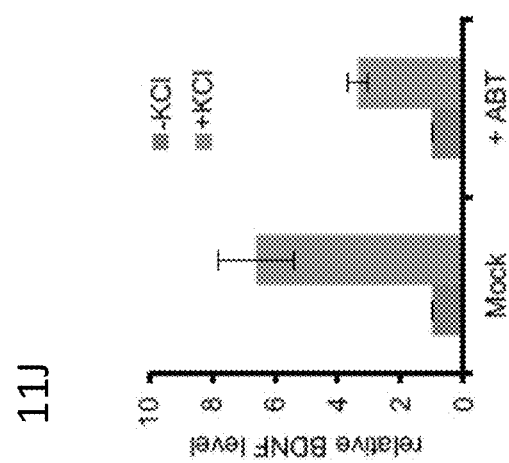

To test whether endogenous Tet activity was required to regulate BDNF expression upon neuronal activity stimulation, we treated DIV3 neurons with 2-hydroxygluterate, a competitive inhibitor for α-ketoglutarate-dependent dioxygenases including Tet enzymes (Xu et al., 2011). As shown in FIG. 11K, pharmacological inhibition of Tet enzymatic activity completely abolished the induction of BDNF expression by KCl treatment. Furthermore, mouse primary cortical neurons carrying a Tet1 null mutant showed significantly attenuated activation kinetics of BDNF (FIG. 11L), supporting a role of endogenous Tet for induction of neuronal activity.

Figures 4A, 4B, 4C:
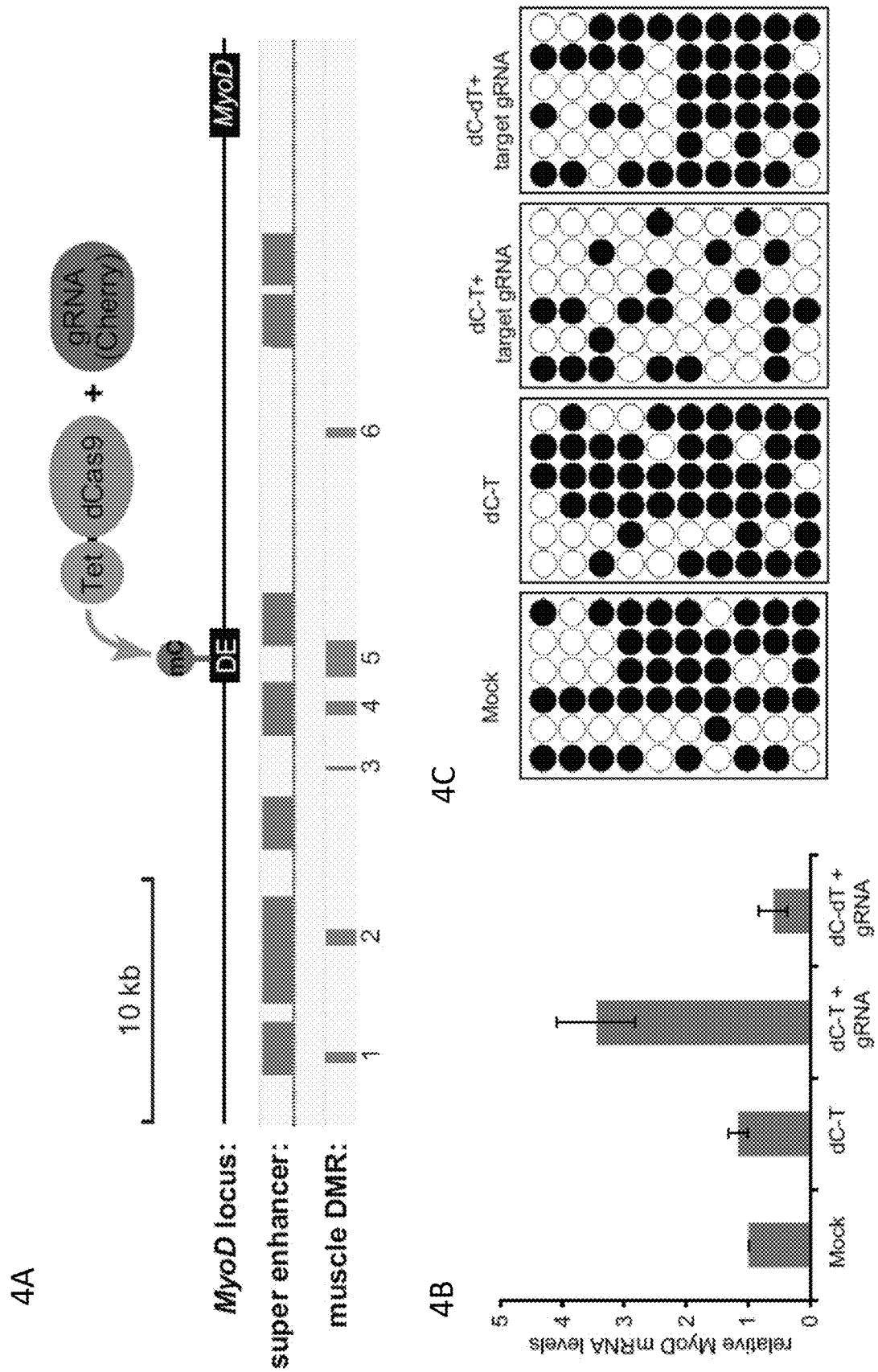
FIGS. 4A-4H depict targeted demethylation of the MyoD distal enhancer by dCas9-Tet1 to facilitate conversion of fibroblasts to myoblasts.
Figure 4D:
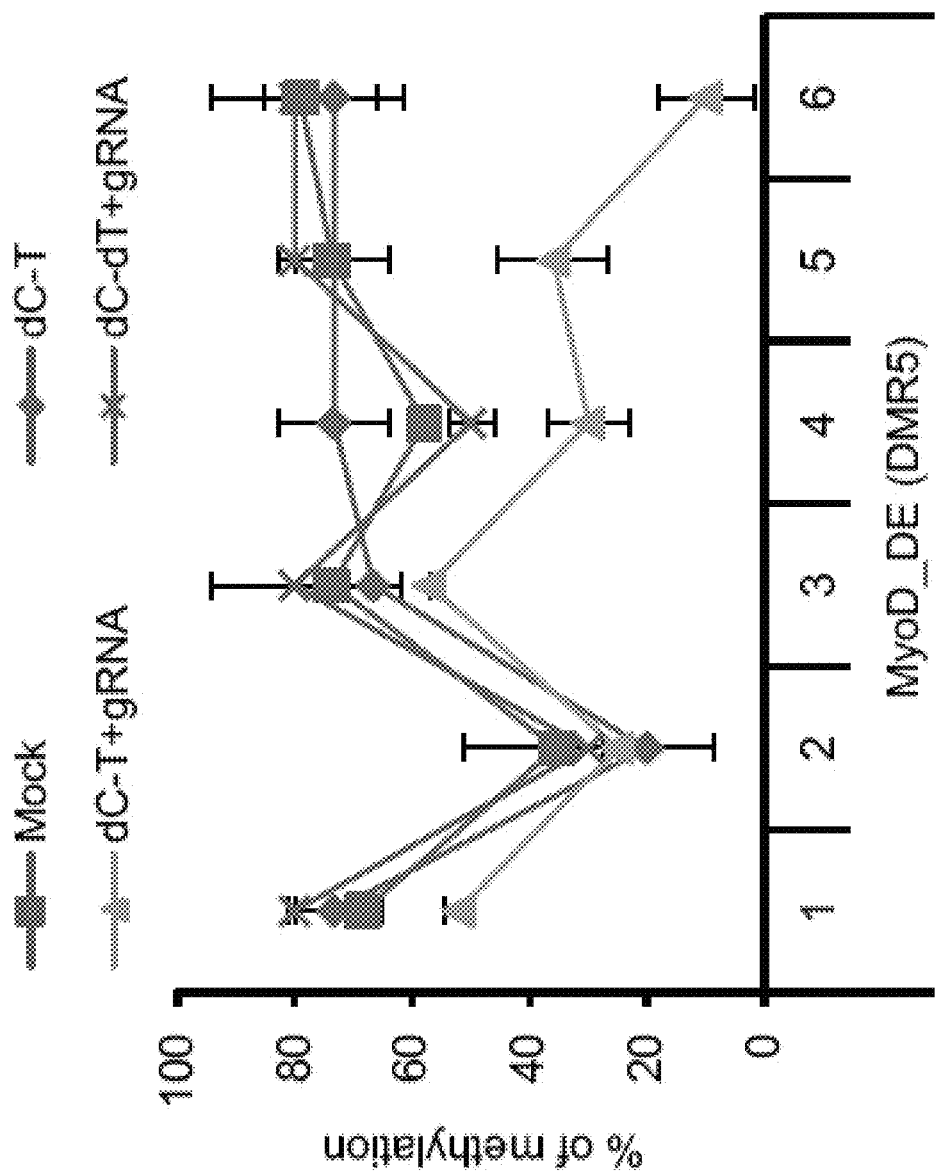
Figure 4E:
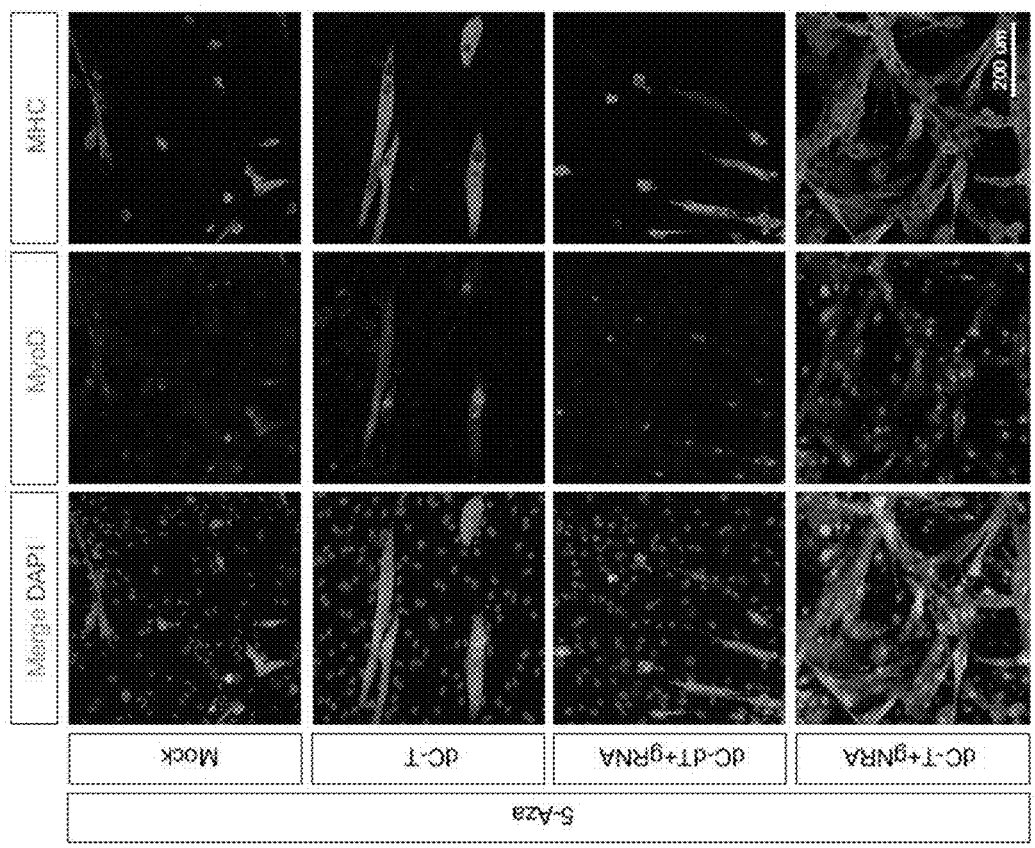
Figure 4E:
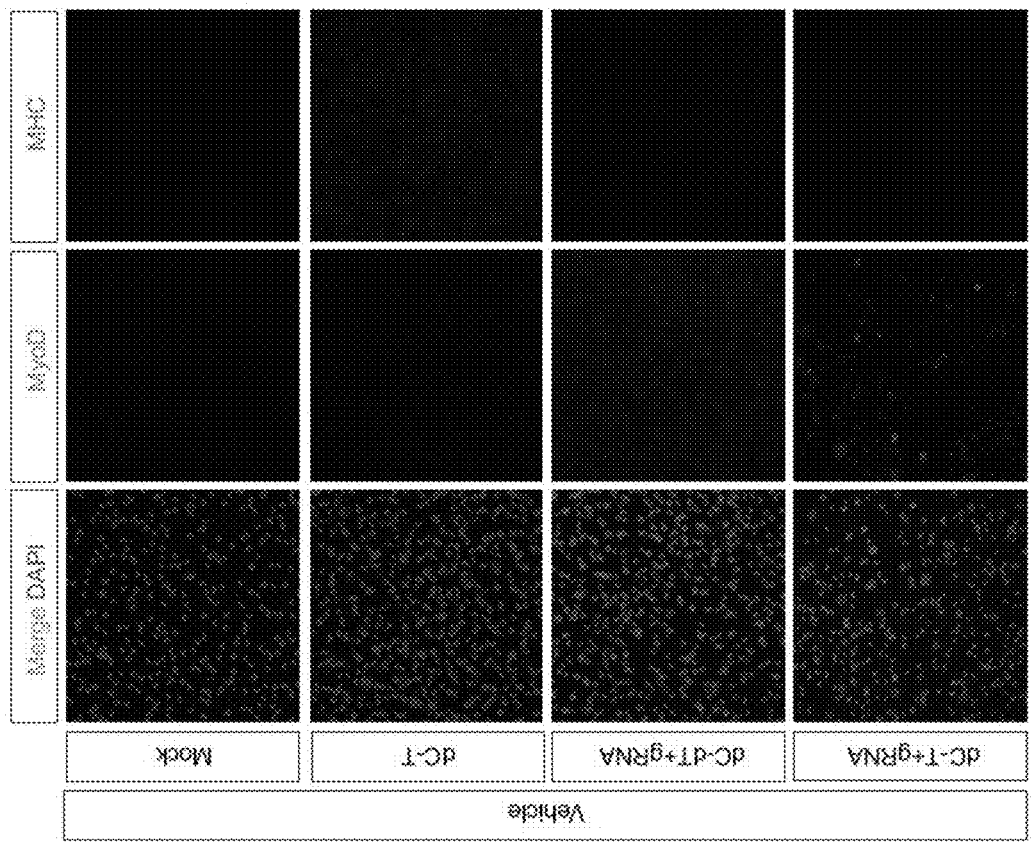
Figures 4F, 4G, 4H:
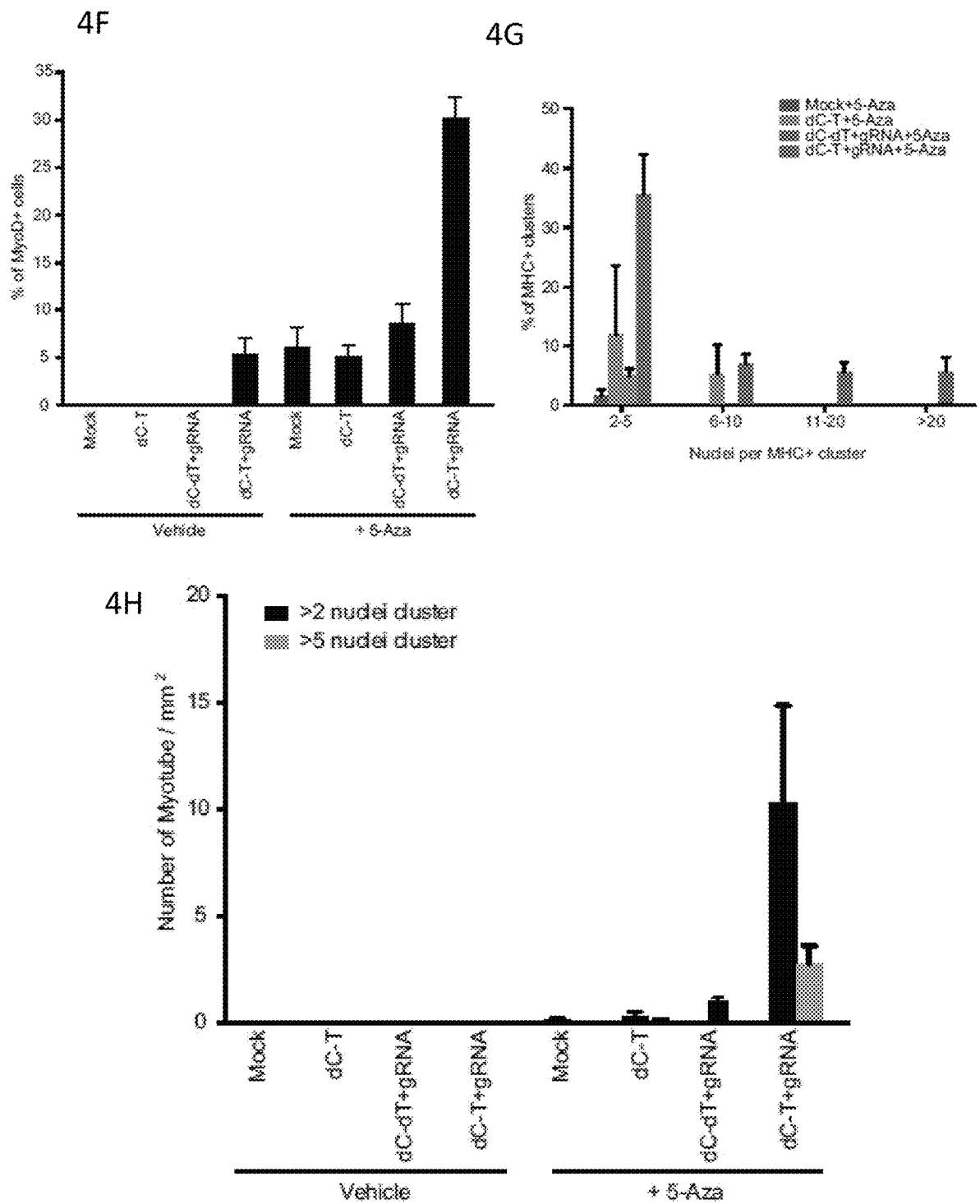
Figures 12F, 12G:
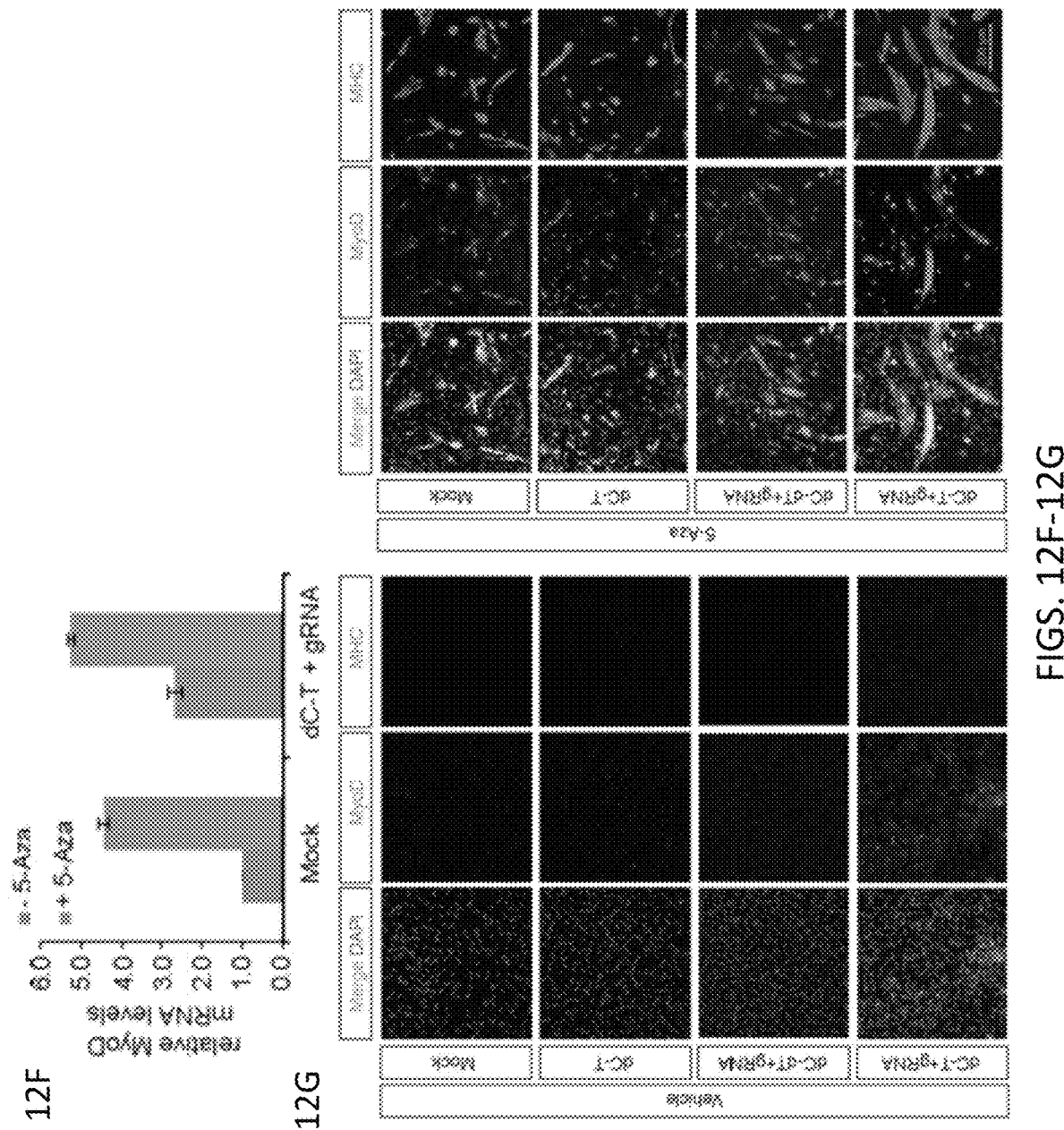
Figures 12H, 12I, 12J:
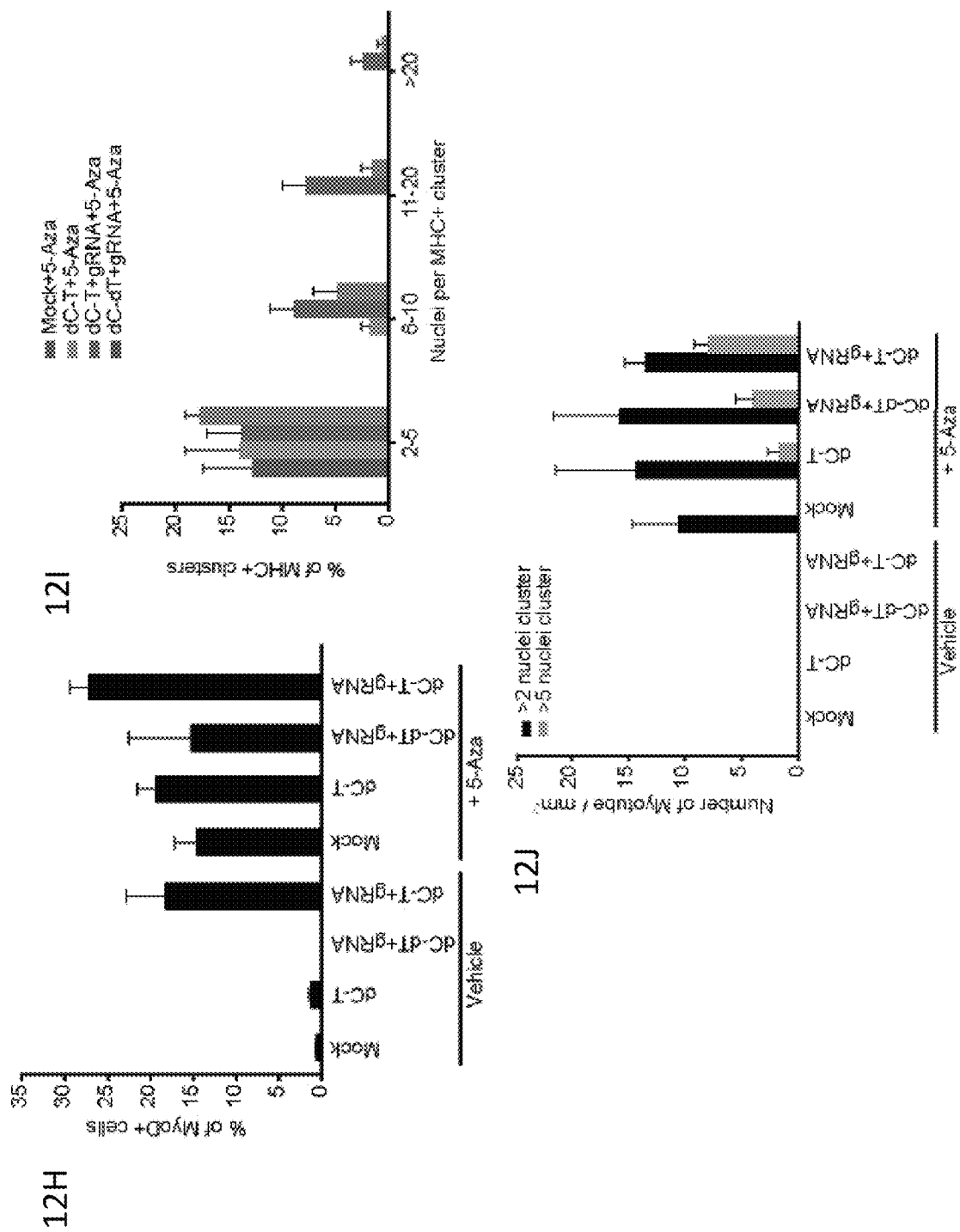

Targeted Demethylation of the MyoD Distal Enhancer Facilitates Myogenic Reprogramming of Fibroblasts The role of MyoD as a master regulator for muscle development was initially defined by the observations that demethylation of DNA in fibroblasts by 5-Aza (5-Aza-2'-deoxycytidine) treatment resulted in activation of MyoD and subsequent myoblast conversion and myotube formation (Constantinides et al., 1977; Davis et al., 1987; Lassar et al., 1986). Six muscle-specific DMRs have been described within the 50 kb upstream region of MyoD gene (Schultz et al., 2015), and DMR-5 overlaps with a known distal enhancer of MyoD (Brunk et al., 1996) as shown in FIG. 4A. To test whether demethylation of DMR-5 would activate MyoD in fibroblasts, we designed 4 gRNAs targeting this DMR (FIG. 12A). Co-expression of dCas9-Tet1 with these gRNAs in C3H10T1/2 cells, a sub-clone from mouse embryonic fibroblasts previously used for 5-Aza mediated MyoD activation (Constantinides et al., 1977), resulted in a moderate induction of MyoD expression (3-fold) as shown in FIG. 4B. Combination of dCas9- Tet1/MyoD DMR-5 gRNAs with 5-Aza treatment resulted in a higher induction of MyoD as shown in FIG. 12F. Bisulfite sequencing showed a substantial reduction of methylation in the DMR-5 region of sorted infection-positive cells transduced with dCas9-Tet1 and target gRNAs lentiviruses, but not with a catalytically dead Tet1 (dC-dT) or a scrambled gRNA (FIGS. 4C-4D). To investigate whether demethylation of the MyoD distal enhancer region could reprogram fibroblasts into muscle cells, we infected C3H10T1/2 cells with lentiviruses expressing dCas9-Tet1 and gRNAs. The cells were cultured for 14 days and analyzed for MyoD and MHC (Myosin Heavy chain, a myotube specific marker) expression. As shown in FIGS. 4E-4F, co-expression of dCas9-Tet1 with gRNAs targeting DMR-5 induced a moderate expression level of MyoD, but was not sufficient to induce myotube formation in the absence of 5-Aza treatment.

We then investigated whether targeted demethylation of DMR-5 would synergize with 5-Aza treatment to induce myotube formation (FIG. 12B). To follow the process of myotube formation after 5-Aza treatment, a time-course experiment was performed. Multi-nucleated myotube (MHC-positive) with heterogeneous sizes began to form 14 days post treatment, and both MyoD-positive cell ratio and myotube density and size then increased up to day-25 (FIGS. 12C-12E). Co-expression of dCas9-Tet1 with gRNAs targeting MyoD DMR-5 facilitated the myotube formation 14 days post-treatment as evidenced by significantly more mature, multi-nucleated MHC+ clusters (>2 nuclei per MHC+ cluster) compared to cells expressing only dCas9-Tet1 or dC-dT with MyoD DMR-5 gRNAs (FIG. 4E, FIGS. 4G-4H). A similar observation was made when the cells were analyzed at a later time point (16-day) post-treatment (FIGS. 12G-12J). Our results suggest that demethylation of the MyoD distal enhancer by dCas9-Tet1/gRNA synergizes with 5-Aza in C3H10T1/2 cells to substantially facilitate myoblast conversion and myotube formation.

Figures 5D, 5E, 5F:
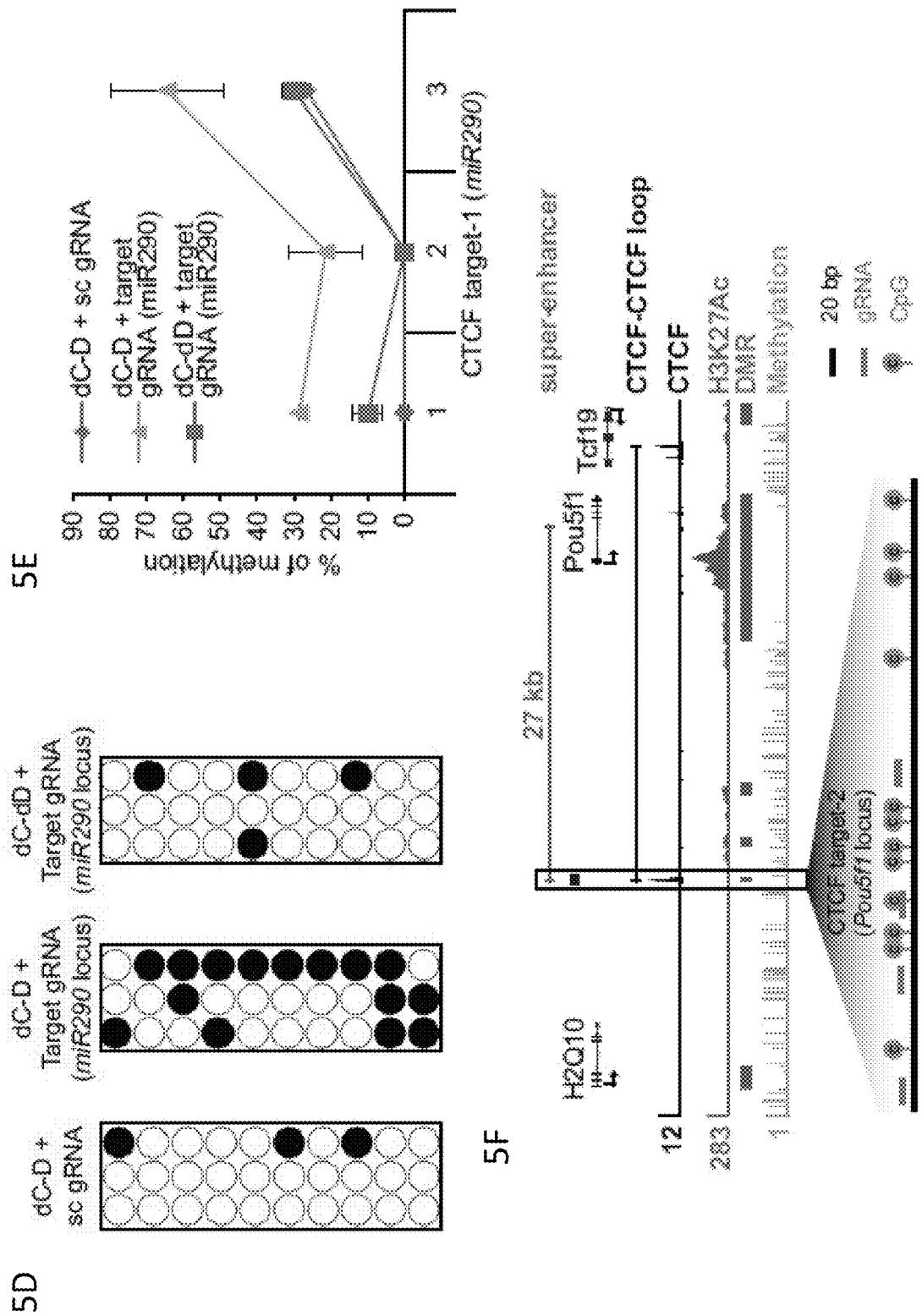
Figure 13B:
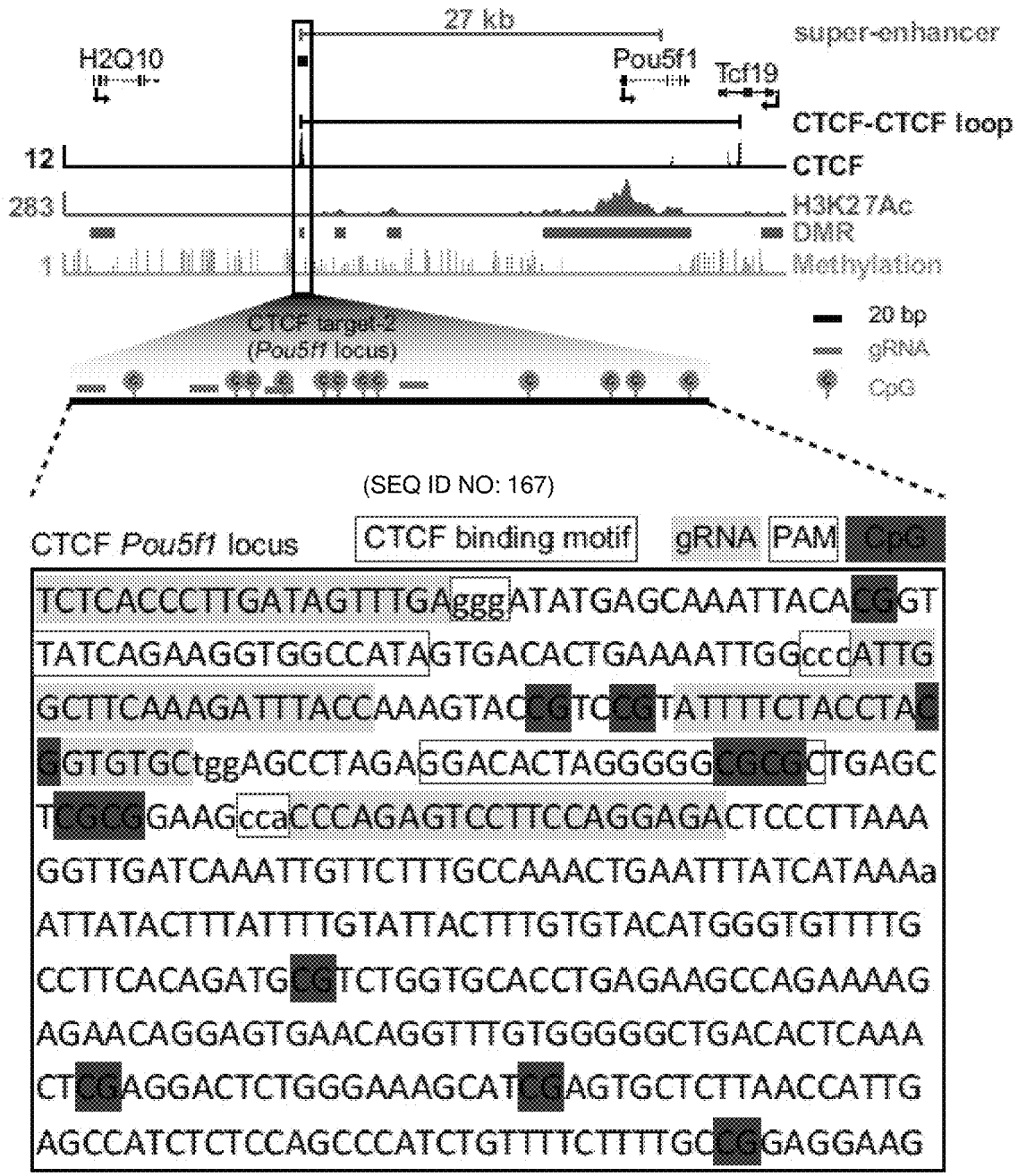

Targeted De Novo Methylation of CTCF Binding Sites Alters CTCF-Mediated Chromatin Loops CTCF is a highly conserved zinc finger protein that plays a primary role in the global organization of chromatin architecture (Phillips and Corces, 2009). Transcriptional enhancers normally interact with their target genes through the formation of DNA loops (Gibcus and Dekker, 2013; Gorkin et al., 2014; Kagey et al., 2010), which typically are constrained within larger CTCF-mediated loops called insulated neighborhoods (Dowen et al., 2014; Ji et al., 2016; Phillips-Cremins et al., 2013), which in turn can form clusters of loops that contribute to topologically associating domains (TADs) (Dixon et al., 2012; Nora et al., 2012). Deletion of the CTCF loop anchor sites of insulated neighborhoods can cause enhancers to interact inappropriately with genes located outside the loop and thus increase their expression (Dowen et al., 2014). Interestingly, methylation of the DNA recognition site of CTCF has been reported to block CTCF binding (Bell and Felsenfeld, 2000; Wang et al., 2012). To study whether methylation of specific CTCF sites could alter CTCF-mediated chromatin loops, we applied the dCas9-Dnmt3a system to target CTCF anchor sites (FIG. 5A). We designed specific gRNAs (FIG. 13) targeting dCas9-Dnmt3a to two CTCF sites to investigate whether de novo methylation would interfere with the looping function of CTCF (FIG. 5B and FIG. 5F). Doxycycline-inducible dCas9-Dnmt3a mES cells (FIG. 9H) were infected with lentiviruses expressing the gRNAs and transduced cells were FACS sorted for subsequent analysis.

Figure 5G:
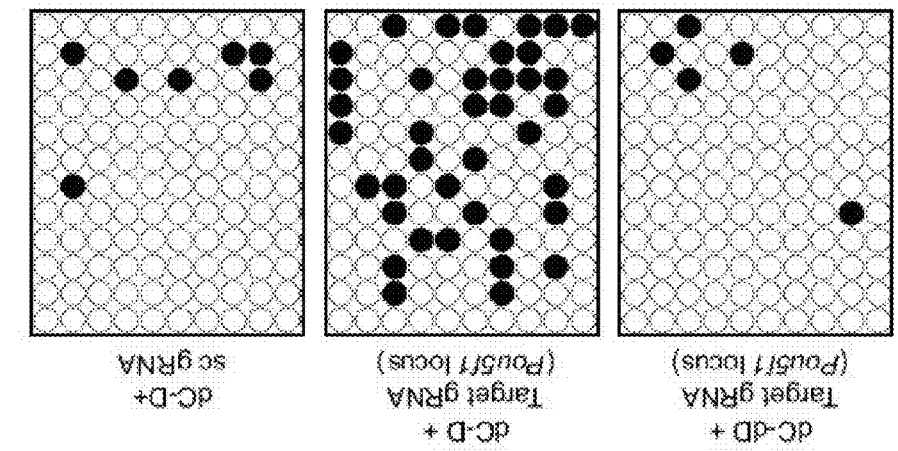
Figure 5H:
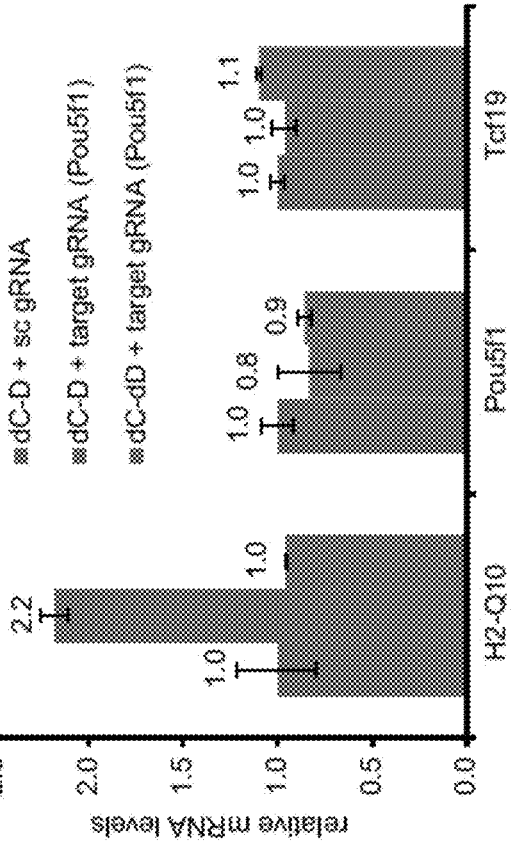
Figure 5I:
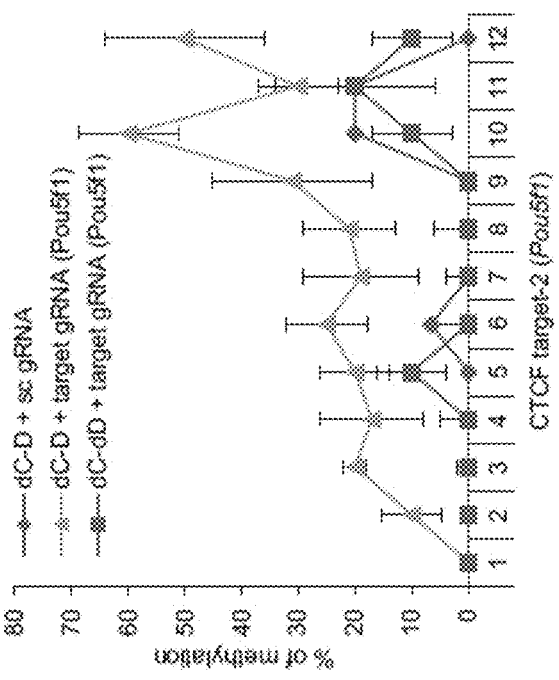

Targeting of dCas9-Dnmt3a to the CTCF binding site bordering the miR290 loop that harbors a super-enhancer (FIG. 5B) induced de novo methylation of CpGs at this site (FIGS. 5D-5E). Gene expression analysis of transduced cells showed a significant elevation of Nirp12 gene, which is outside of this super-enhancer-containing insulated neighborhood and next to the targeted CTCF site, but did not affect the expression of genes that are located inside the miR290 loop or of genes in other neighboring loops including AU01801 and Myadm (FIG. 5C). Similarly, targeting of dCas9-Dnmt3a to the CTCF binding site bordering the Pou5f1 gene loop that harbors another super-enhancer (FIG. 5F) induced methylation of CpGs in the CTCF binding sequence (FIGS. 5H-5I), and increased the expression of H2Q10, which is located in a neighboring loop and next to the targeted CTCF site, but did not affect the expression of Pou5f1 gene itself or Tcf19 gene in the other neighboring loop (FIG. 5G). For either targeted CTCF sites, a catalytically inactive Dnmt3a form (dC-dD) did not induce changes in methylation level or gene expression as did by dC-D (FIGS. 5C-5E and FIGS. 5G-5I). These observations are consistent with the results obtained when these CTCF sites were deleted (Dowen et al., 2014), and support the notion that methylation of the CTCF binding site interferes with its insulator function.

Figure 6A:
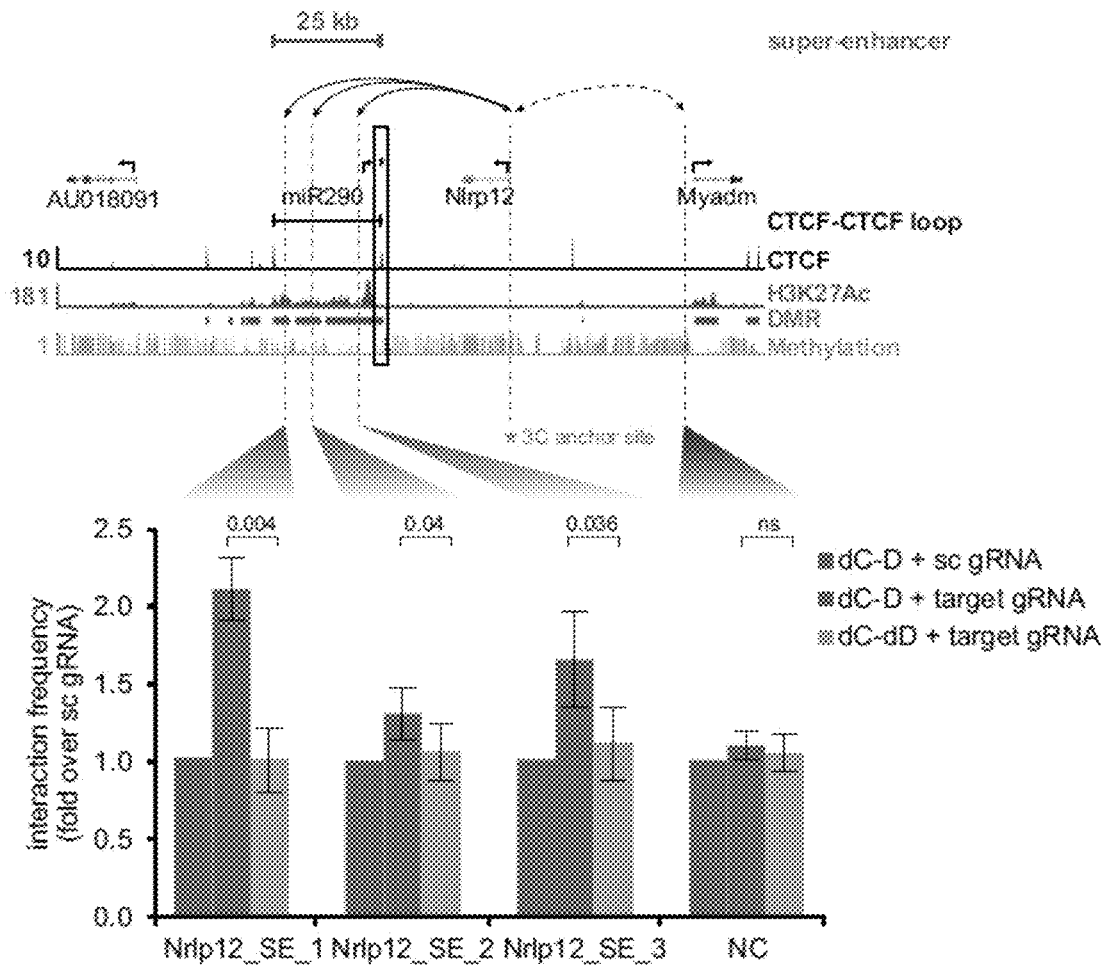
FIGS. 6A-6D depict targeted methylation of CTCF binding sites to manipulate CTCF loops.
Figure 6B:
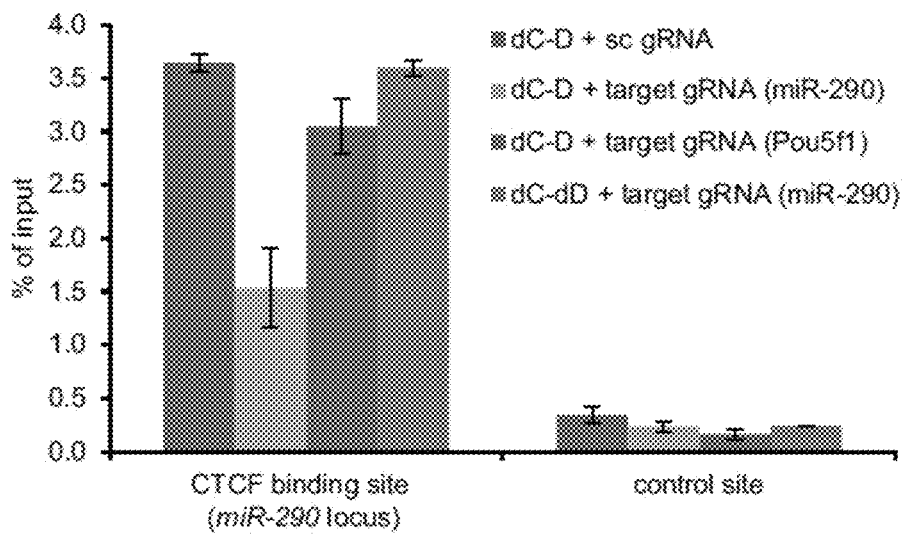
Figure 6C:
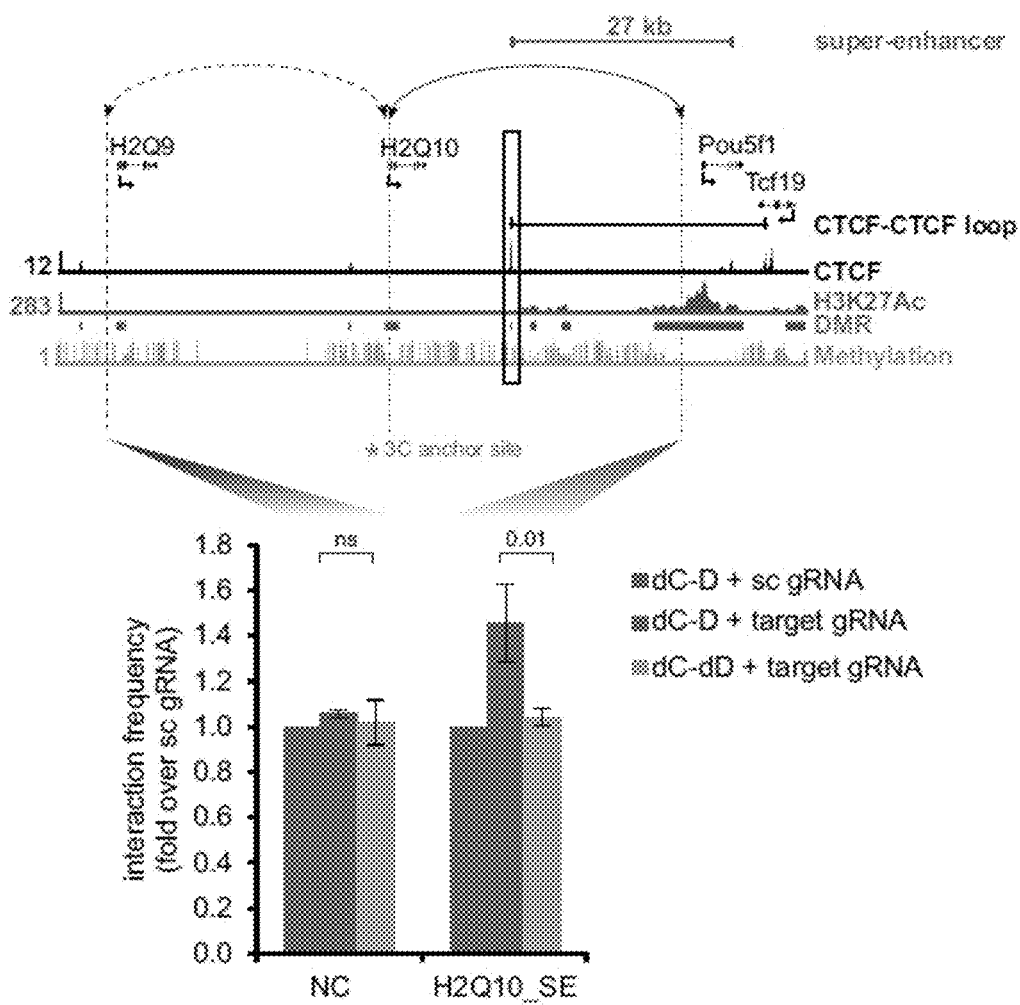
Figure 6D:
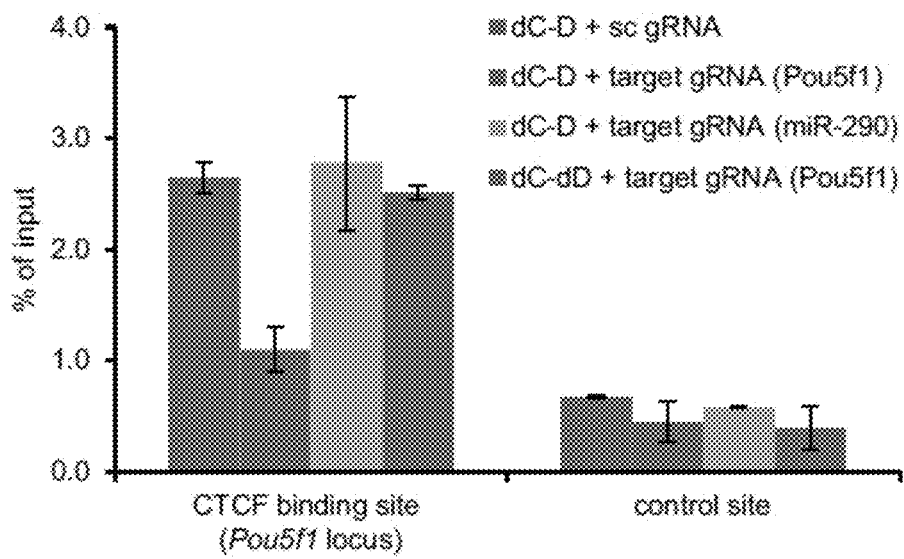

To test whether targeted methylations of CTCF binding sites would result in increased interaction frequencies between insulated super-enhancers and activated genes, Chromosome Conformation Capture (3C) assay was performed at these loci. As shown in FIG. 6A, the interaction frequency between super-enhancers in the miR290 loop and the newly activated gene (Nirp12) in the neighboring loop was significantly increased but the interaction between Nirp12 and Myadm genes remained the same, indicating an open conformation for this targeted CTCF loop. To confirm that the increased interaction frequency was due to blocking CTCF anchoring, we performed a CTCF ChIP assay. Binding of CTCF to the targeted genomic site was significantly reduced in the sample with miR290 target gRNAs as compared to the sample with a scrambled gRNA, gRNAs targeting other CTCF binding sites or a catalytically inactive dC-dD with miR290 target gRNAs (FIG. 6B), supporting the notion that DNA methylation blocks CTCF anchoring and thus alters the CTCF loop conformation. A similar set of experiments was performed for the second CTCF loop (PouSf1 loop) demonstrating increased interaction frequency between the insulated super-enhancers and the newly activated gene (H2Q10), and decreased binding of CTCF after targeted methylation of its binding site (FIGS. 6C-6D).

In summary, our results demonstrate that the dCas9-Dnmt3a system can be used to change the methylation state of specific CTCF anchor sites and thus to interfere with the CTCF looping function.

In Vivo Demethylation of an Endogenous Locus for Gene Activation by dCas9-Tet1

Figures 7A, 7B, 7C:
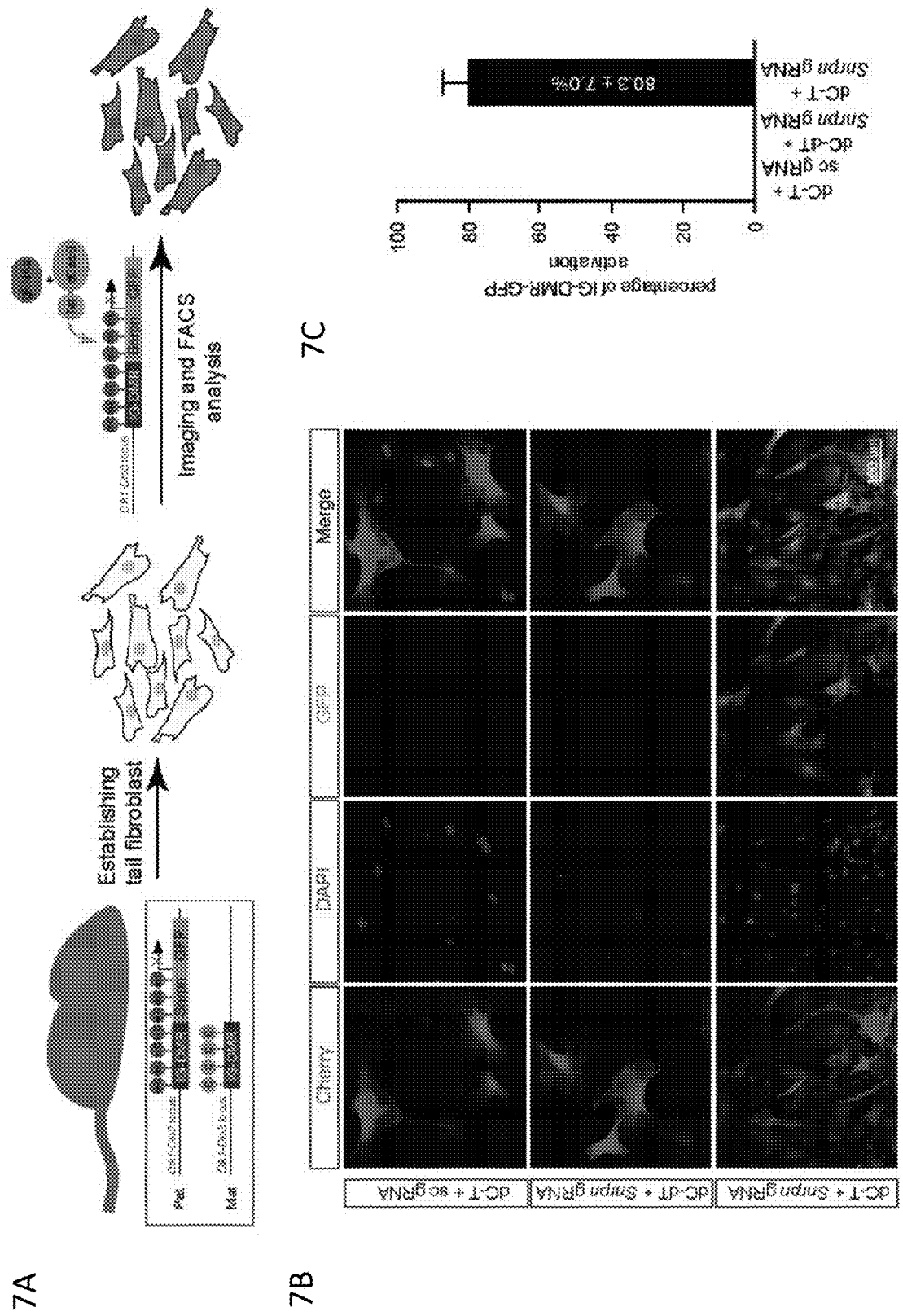
FIGS. 7A-7H depict targeted ex vivo and in vivo DNA methylation editing by dCas9-Tet1 to activate a silenced GFP reporter.

To test whether the dCas9-mediated DNA methylation-editing tools could be used to alter methylation in vivo we utilized a methylation sensitive reporter mouse previously generated (FIG. 7A, Ref: Stelzer et al., Parent-of-origin DNA methylation dynamics during mouse development, Developmental Cell, under editorial consideration). In these transgenic mice, a methylation sensitive Snrpn-GFP cassette was inserted into the Dlk1-Dio3 locus to report the methylation status of its intergenic-differentially methylated region (IG-DMR). As the IG-DMR of this locus acquires paternal methylation during spermatogenesis, the GFP reporter (IG-DMR$^{GF/Pat}$) is constitutively repressed in heterozygous mice carrying the paternal Snrpn-GFP allele (See the Ref: Stelzer et al., Parent-of-origin DNA methylation dynamics during mouse development, Developmental Cell, under editorial consideration). As shown above the GFP reporter in the Dad locus was activated by targeted promoter demethylation in mES cells (FIG. 1). To assess whether the Dlk1-Dio3 locus GFP reporter could be activated by dCas9-Tet1 in differentiated cells we derived adult mouse skin fibroblast cells from the tails of IG-DMR$^{GFP/Pat}$ transgenic mice, which were then transduced by lentiviruses expressing dCas9-Tet1 with Snrpn target gRNAs or a scrambled gRNA, or a catalytically dead form of Tet1 (dC-dT) with Snrpn target gRNAs (FIG. 7A). The results in FIGS. 7B-7C reveal GFP reporter activation in about 80% of Cherry (gRNA) positive fibroblasts but only when transduced by both dCas9-Tet1 and Snrpn gRNAs lentiviruses. FACS analysis of these cells further confirmed this notion (FIGS. 14A-14C).

Figures 7D, 7E:
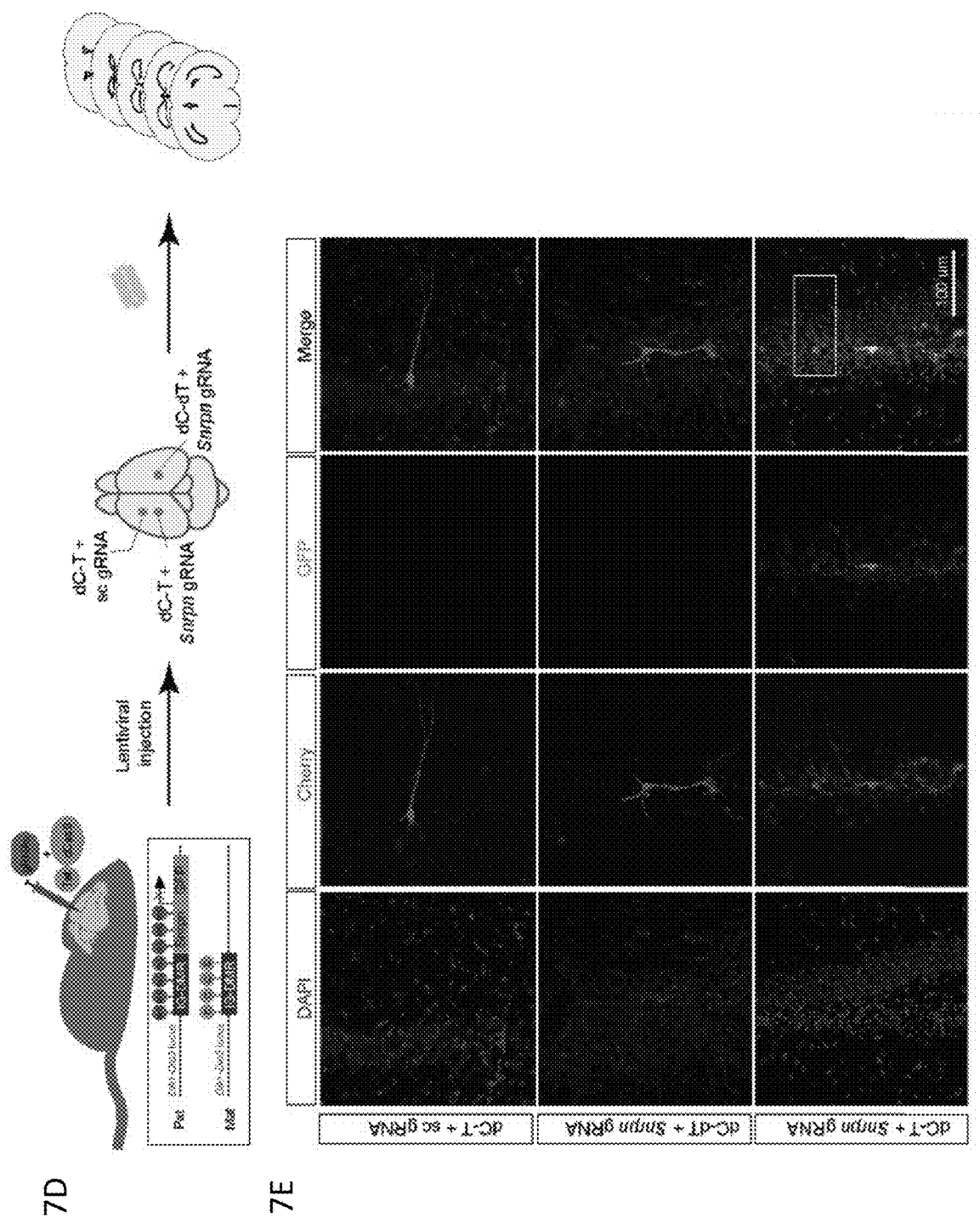
Figure 7F:
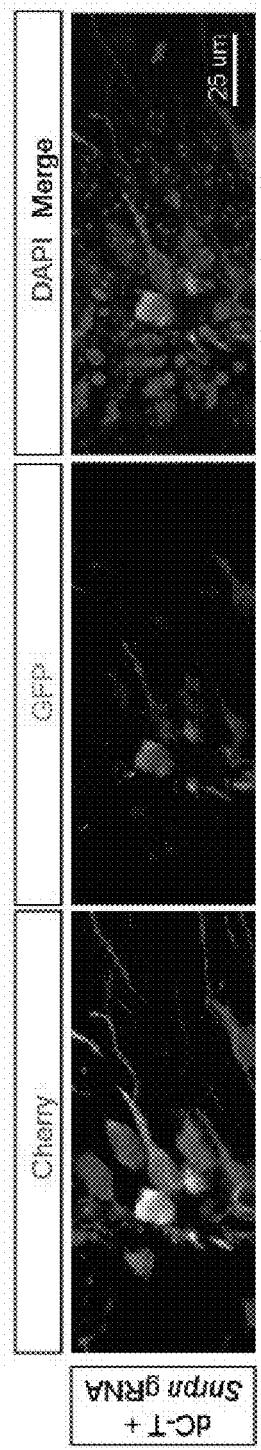
Figure 7G:
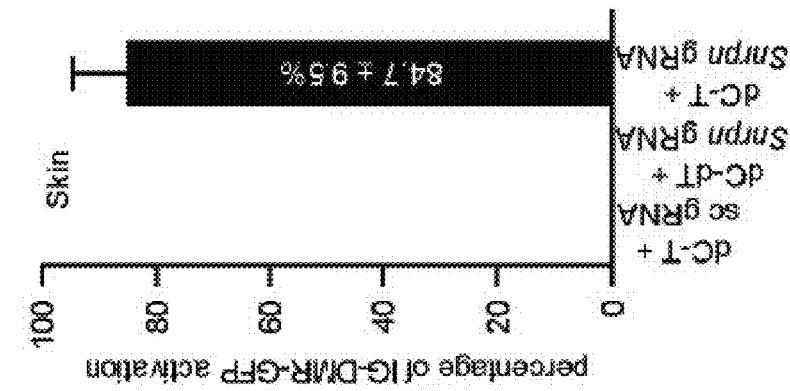
Figure 7H:
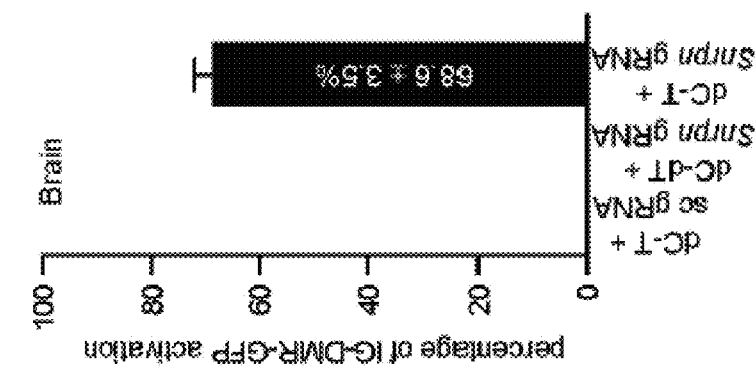
Figures 14A, 14B, 14C, 14D:
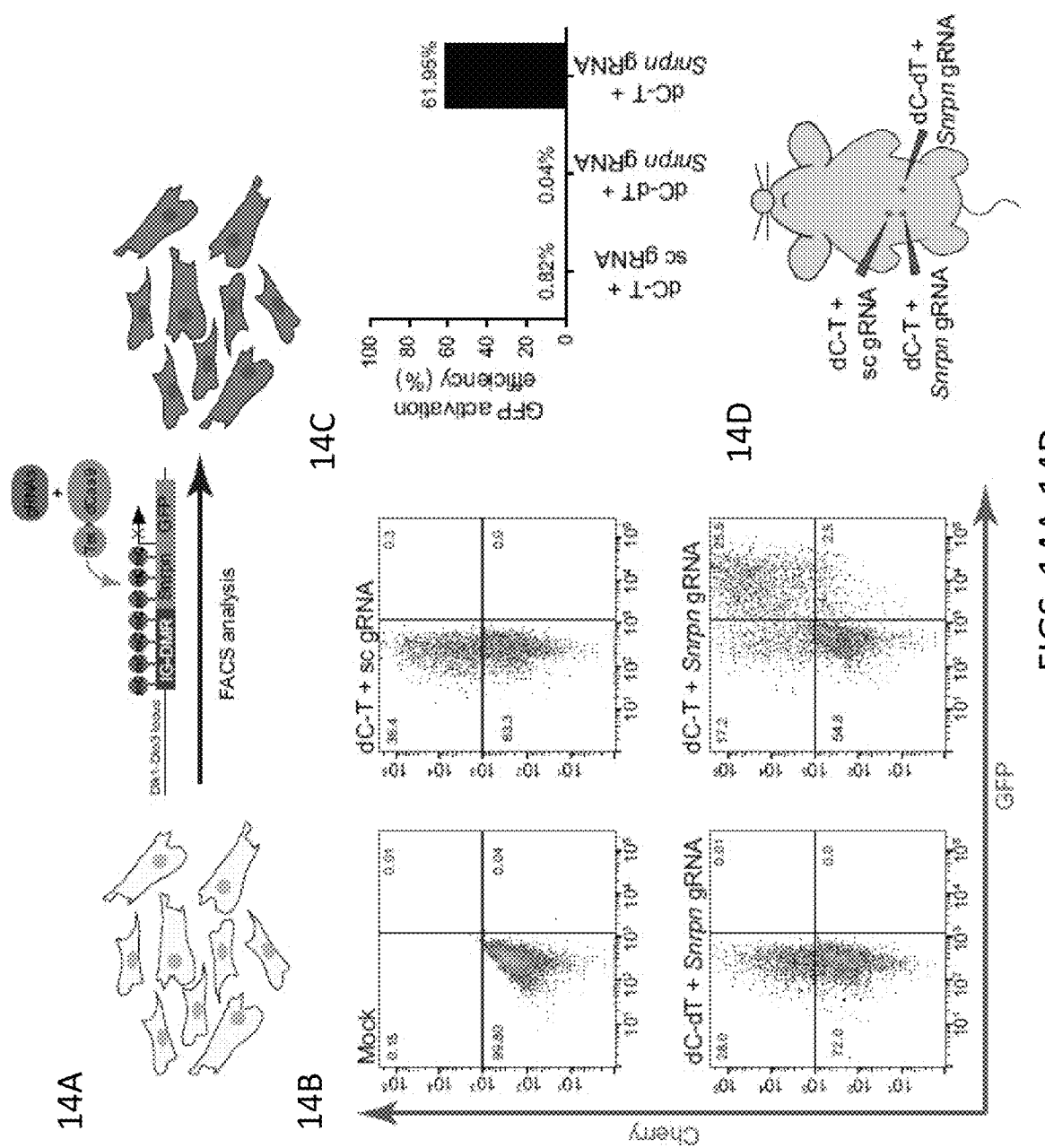
FIGS. 14A-14F depict activation of IG-DMR$^{GFP/Pat}$ reporter in mouse skin cells by dCas9-Tet1 mediated demethylation.
Figure 14E:
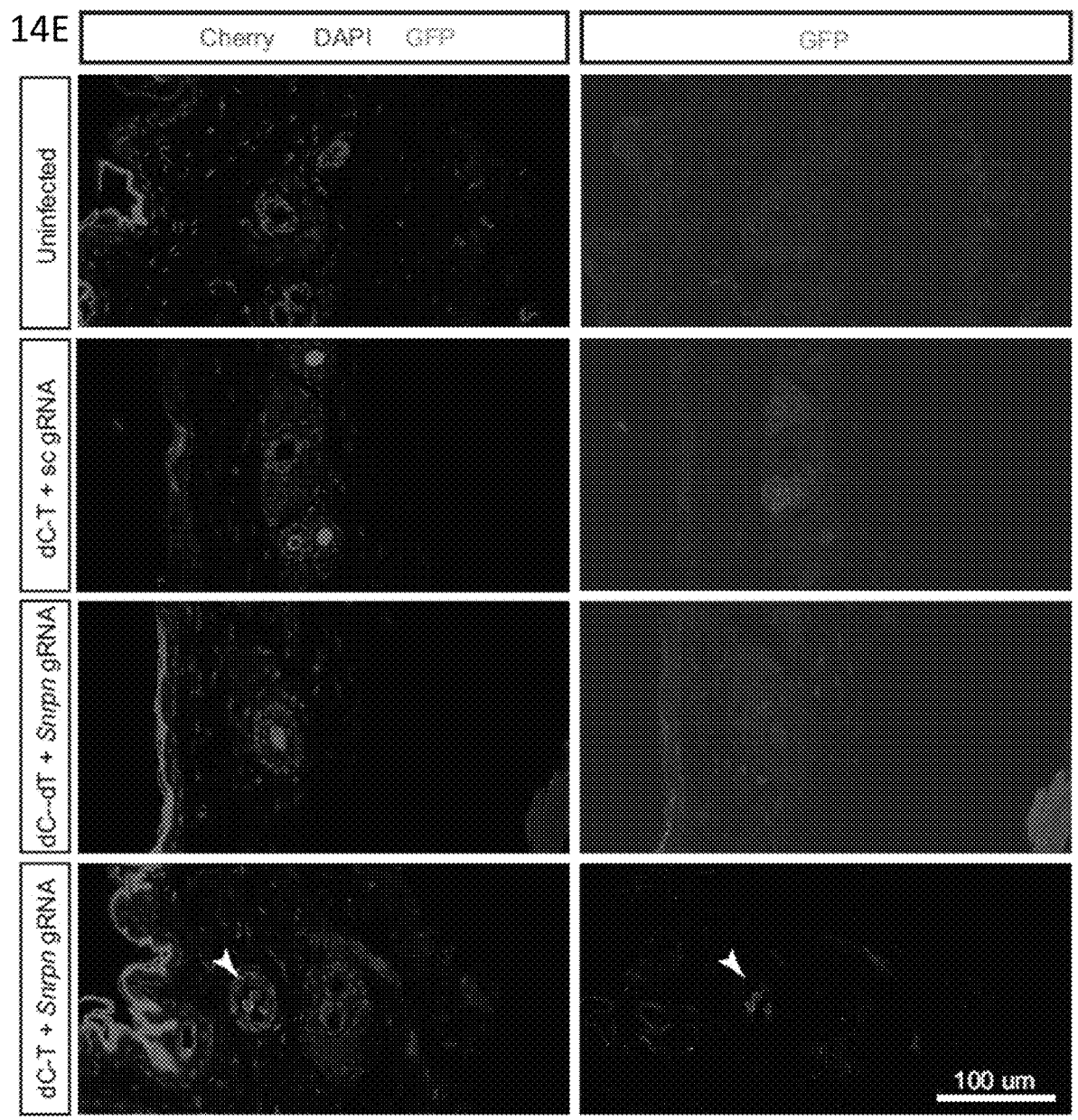
Figure 14F:
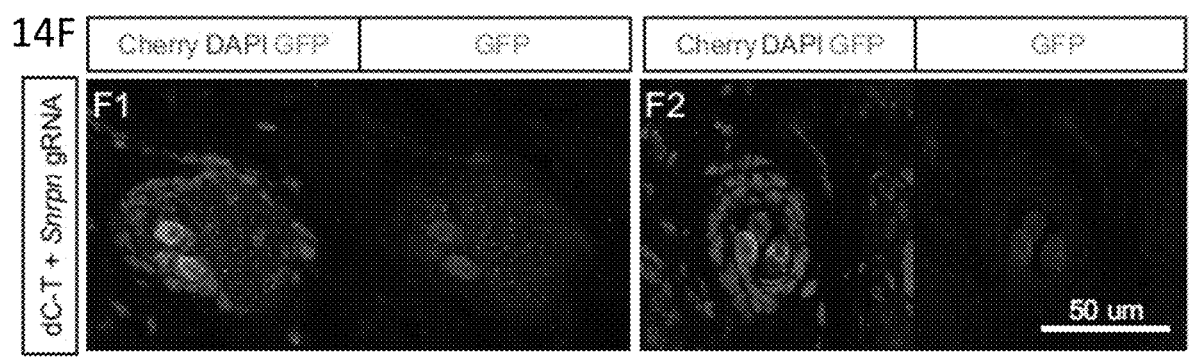
Figure 15:
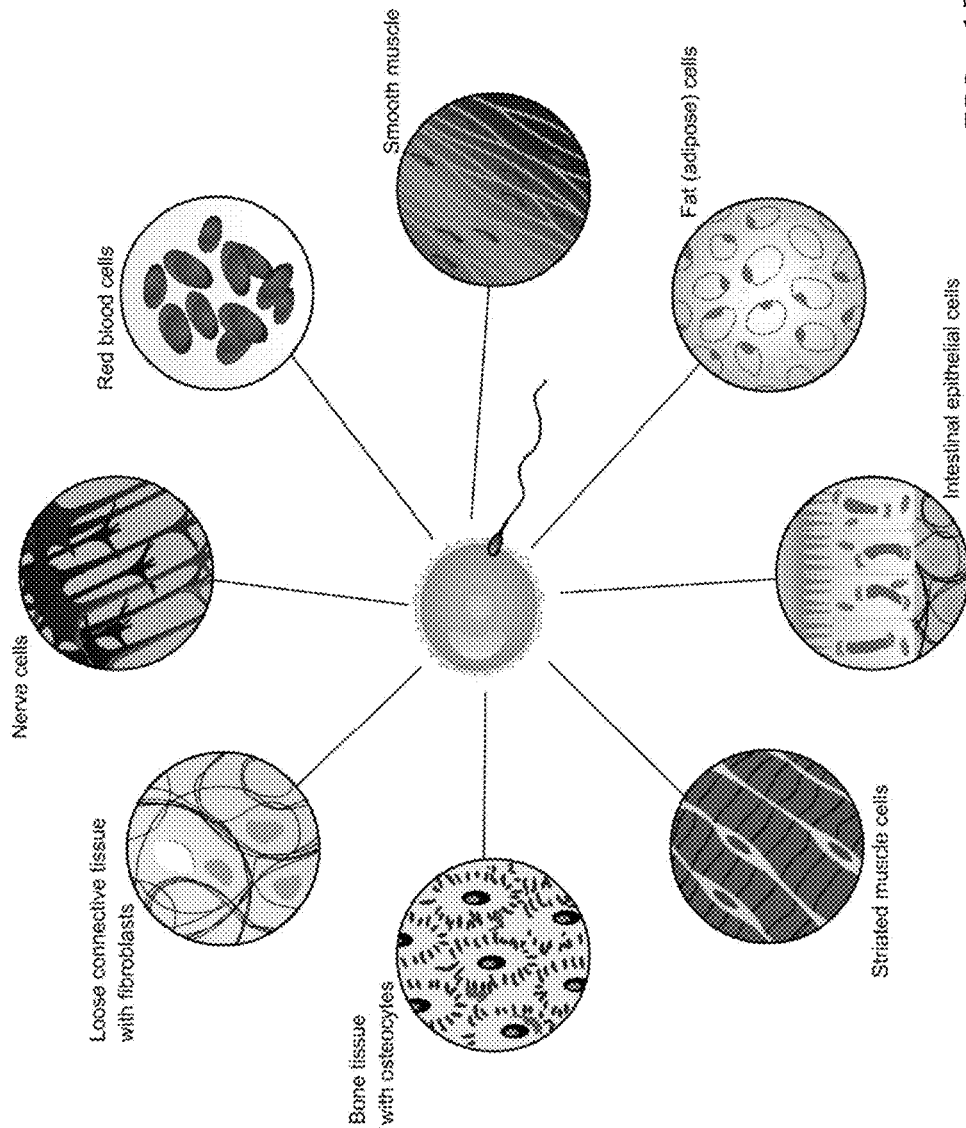
FIG. 15 demonstrates various examples of cell types.
Figure 16:
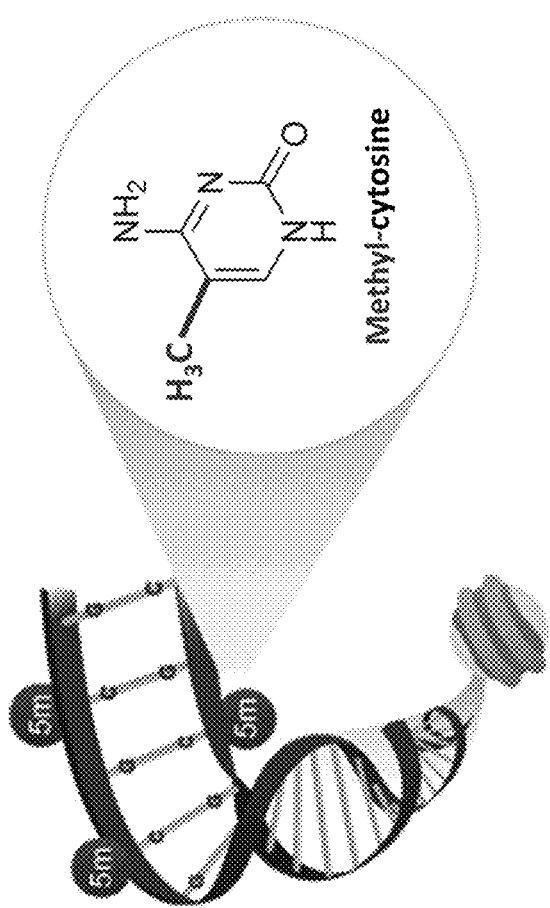
FIG. 16 depicts DNA methylation.
Figure 17:
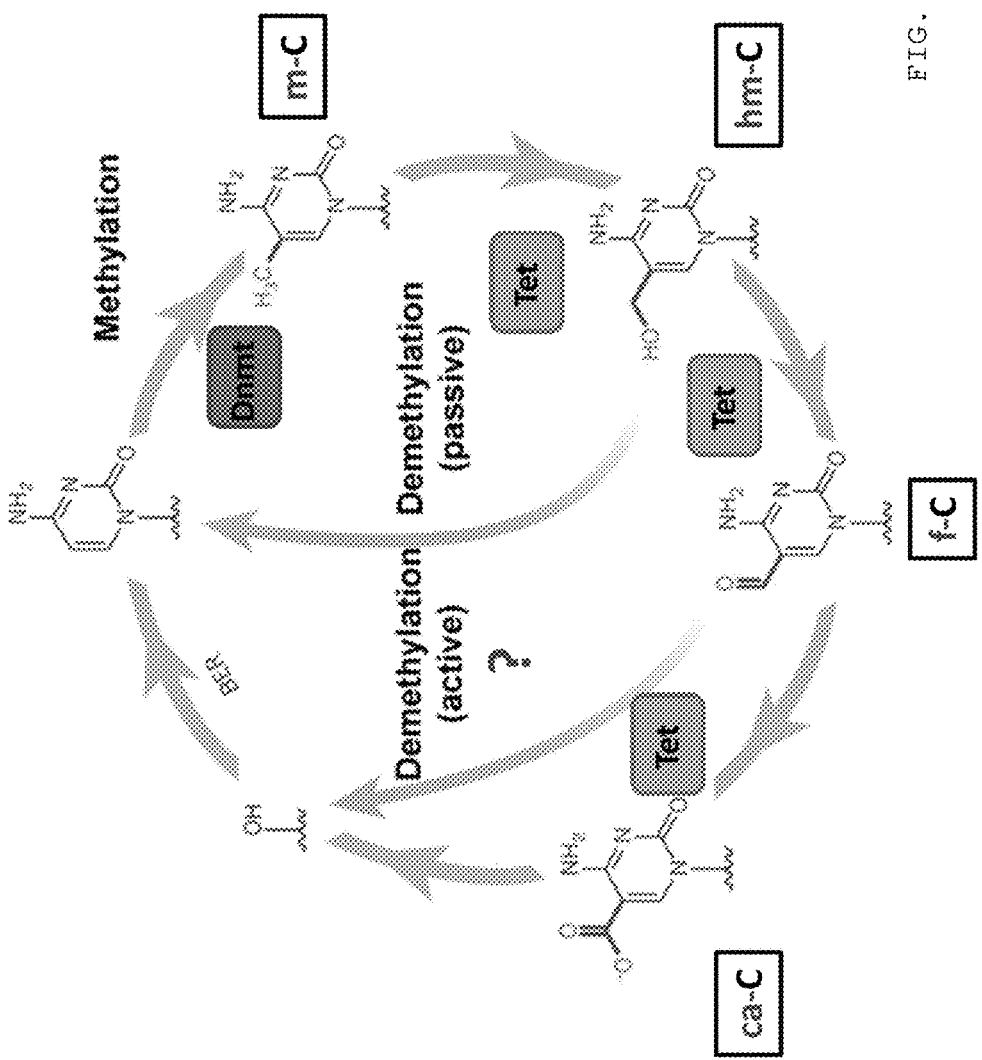
FIG. 17 shows a DNA methylation cycle including DNA methylation and reversing DNA methylation.

To investigate whether the DNA methylation status can be modified in vivo, we infected 3 epidermal sites on the ventral side of an IG-DMR$^{GFP/Pat}$ transgenic mouse with the dCas9-Tet1 and Snrpn gRNAs (FIG. 14D). Cells were sparsely infected with cherry expression seen only in some of the hair follicles. dCas9-Tet1 with Snrpn gRNAs, but not dCas9-Tet1 with the scrambled gRNA or dC-dT with Snrpn gRNAs, was able to activate GFP reporter expression in about 85% infected skin dermal cells in vivo (FIG. 7H, FIGS. 14E-14F). In addition we infected the brain of an IG-DMR$^{GFP/Pat}$ transgenic mouse with lentiviral vectors using a stereotaxic setup and analyzed the effect on targeted DNA methylation in brain slices by confocal microscopy. To eliminate possible inter-individual variability, we injected lentiviral vectors expressing dCas9-Tet1 and Snrpn gRNAs, as well as the two negative control vector combinations into different regions of the same brain (FIG. 7D). As shown in FIGS. 7E-7F, after infection with all three lentiviral combinations as indicated by Cherry expression, only lentiviral vectors expressing dCas9-Tet1 with Snrpn gRNAs, but not vectors expressing dCas9-Tet1 with sc gRNA or dC-dT with Snrpn gRNAs, activated the GFP reporter with an activation efficiency of about 70% (FIG. 7G).

Discussion

In this study we have repurposed the CRISPR/Cas9 system to edit the methylation status of genomic sequences. The catalytically inactive Cas9 protein (dCas9) was fused either to the catalytic domain of Tet1 (dCas9-Tet1) or to Dnmt3a (dCas9-Dnmt3a) to predictably alter the epigenetic state of target sequences. A GFP reporter inserted into the promoter region of the methylated and silenced Dazl gene was demethylated and activated when targeted by dCas9-Tet1 whereas the GFP reporter inserted into the promoter region of the active and unmethylated Gapdh gene was de novo methylated and silenced when targeted by dCas9-

Dnmt3a. When the dCas9-Tet1 was targeted to the inactive BDNF promoter IV in post-mitotic neurons, the promoter became demethylated and activated. Importantly, this tool predictably altered the methylation state and activity of regulatory regions: Targeted demethylation of the inactive distal enhancer of MyoD activated the gene and facilitated muscle differentiation and targeted methylation of CTCF anchor sites inhibited CTCF binding and interfered with its function as an insulator between chromatin loops. Finally, the editing tools can in vivo alter the methylation state of regulatory sequences as injection of the lentiviral vectors of dCas9-Tet1 with target gRNAs into the dermis or brain of transgenic mice demethylated the methylated Snrpn promoter in the Dlk1-Dio3 imprinted locus and activated the methylation-sensing GFP reporter.

Dynamic DNA methylation has been proposed to decode neuronal activities (Sweatt, 2013). For instance, treatment of neurons with KCl has been shown to de-silence promoter IV of BDNF and induce BDNF expression associated with demethylation of some methylated CpGs in the promoter region (Chen et al., 2003; Martinowich et al., 2003). When the BDNF promoter IV was targeted by dCas9-Tet1, extensive demethylation of methylated CpGs was observed, and BDNF was activated to a similar level as when the cultures were treated with KCl. Because the neurons were post-mitotic, the dCas9-Tet1-mediated demethylation of the promoter sequences was likely the result of active demethylation as has been proposed previously (Wu and Zhang, 2014). Although it is possible that some CpGs in the BDNF promoter were 5-fC/5-caC modified after targeting with dCas9-Tet1/gRNA, blocking restoration of 5-fC/5-caC into unmethylated cytosine by inhibition of the BER pathway reduced BDNF expression, suggesting that demethylation of the BDNF promoter IV contributes to the activation of BDNF. Importantly, our results establish a causal relationship between demethylation of BDNF promoter IV and gene activation.

The role of DNA methylation as a barrier between cell lineages is consistent with the previous observation that demethylation of DNA in fibroblasts by treatment with 5-Aza can activate MyoD and mediate myotube formation (Constantinides et al., 1977; Davis et al., 1987; Lassar et al., 1986). Targeting of dCas9-Tet1 to the methylated distal enhancer of MyoD in fibroblasts induced demethylation of CpGs and resulted in a moderate activation of MyoD but failed to generate myoblasts. However, when dCas9-Tet1/gRNA lentiviral transduction was combined with 5-Aza treatment, a significantly enhanced myoblast and myotube formation was observed as compared to 5-Aza treatment alone. Additional DMRs upstream of MyoD have been identified (Schultz et al., 2015) and it is possible that demethylation of these sites in combination with the distal enhancer may be required to induce efficient conversion of fibroblasts to myoblasts.

Recent studies of mammalian chromosome structure reveal that chromatin is organized in topologically associating domains and gene loops mediated by chromatin architecture proteins such as Cohesin and CTCF (Ji et al., 2016; Seitan et al., 2013; Sofueva et al., 2013; Tang et al., 2015; Zuin et al., 2014). Emerging data suggest that higher-order chromatin structures confer epigenetic information during development and are frequently altered in cancer (Flavahan et al., 2016; Ji et al., 2016; Narendra et al., 2015). It has been reported that binding of CTCF is inhibited when its recognition sequence is methylated (Bell and Felsenfeld, 2000; Kang et al., 2015; Wang et al., 2012). Targeting of dCas9-Dnmt3a to two CTCF binding sites induced de novo methylation of CpGs in these sites and interfered with the insulator function of the protein as evidenced by increased interaction frequencies between insulated super-enhancers in the targeted loop and genes in the neighboring loop causing up-regulation of these genes. This suggests that the dCas9-Dnmt3a system is a useful tool to manipulate chromatin structure and to assess its functional significance during development and in disease context.

Our results indicate that dCas9 fused to the epigenetic effectors Tet1 and Dnmt3a represent a powerful toolbox to edit DNA methylation of specific genomic sequences. Comparison of these tools with TALE-based method showed a higher efficacy and resolution for methylation editing, and dCas9 ChIP-seq followed by bisulfite sequencing of potential off-target binding loci revealed marginal changes in methylation levels, suggesting that high specificity can be achieved with properly designed gRNAs. These dCas9-Dnmt3a/Tet1 tools will be useful to gain insight into the functional significance of DNA methylation in diverse biological processes such as gene expression, cell fate determination, and organization of high-order chromatin structures.

Experimental Procedures

Plasmid Design and Construction

PCR amplified Tet1 catalytic domain from pJFA344C7 (Addgene plasmid: 49236), Tet1 inactive catalytic domain from MLM3739 (Addgene plasmid: 49959), or Dnmt3a from pcDNA3-hDNMT3A (Addgene plasmid: 35521) were cloned in modified pdCas9 plasmid (Addgene plasmid: 44246) with BamHI and EcoRI sites. Then dCas9-NLS-Tet1 or dCas9-NLS-Dnmt3a were PCR amplified and cloned into FUW vector (Addgene plasmid: 14882) with AscI and EcoRI to package lentiviruses. NLS-dCas9-NLS-Tet1 was cloned by inserting annealed oligos (NLS) into FUW-dCas9-NLS-Tet1 with XbaI and AscI. The gRNA expression plasmids were cloned by inserting annealed oligos into modified pgRNA plasmid (Addgene plasmid: 44248) with AarI site. The PiaggyBac-dCas9-Tet1 and -dCas9-Dnmt3a were cloned by ligation of PCR amplified dCas9-NLS-Tet1 or dCas9-NLS-Dnmt3a from FUW constructs with modified PiggyBac transposon vector (Wilson et al., 2007) with NheI and EcoRI. All constructs were sequenced before transfection. Primer information for gRNA design and construction is listed in Supplemental Table S2. Related plasmids have been deposited into Addgene plasmid database. TALE-Dnmt3a construct targeting p16 locus is a gift from Dr. Klaus Kaestner, and TALE-Tet1 targeting RHOXF2 locus is from Addgene (Plasmid #49943). Full length protein sequences of dCas9-Dnmt3a and dCas9-Tet1CD and their mutants are listed in Supplemental Table S6.

Cell Culture, Lentivirus Production, and Stable Cell Line Generation

Mouse embryonic stem cells (mESCs) were cultured on irradiated mouse embryonic fibroblasts (MEFs) with standard ESCs medium: (500 ml) DMEM supplemented with 10% FBS (Hyclone), 10 ug recombinant leukemia inhibitory factor (LIF), 0.1 mM ß-mercaptoethanol (Sigma-Aldrich), penicillin/streptomycin, 1 mM L-glutamine, and 1% nonessential amino acids (all from Invitrogen). C3H10T1/2 cells were cultured in standard DEME medium with 10% FBS. Lentiviruses expressing dCas9-Tet1, dCas9-Dnmt3a, and gRNAs were produced by transfecting HEK293T cells with FUW constructs or pgRNA constructs together with standard packaging vectors (pCMV-dR8.74 and pCMV-VSVG) followed by ultra-centrifugation-based concentration. Virus titer (T) was calculated based on the infection efficiency for 293T cells, where T=(P*N)/(V), T=titer (TU/ul), P=% of infection positive cells according to the fluorescence marker, N=number of cells at the time of transduction, V=total volume of virus used. Note TU stands for transduction unit. To generate stable cell lines with integrated Doxycycline-inducible dCas9-Tet1 or dCas9-Dnmt3a transgenes, PiggyBac-dCas9-Tet1 or -dCas9-Dnmt3a construct, with a helper plasmid expressing transposase, were transfected into C3H10T1/2 cell using X-tremeGENE 9 transfection reagent (Roche) or into mESCs cells using Xfect transfection reagent (Clontech), according to the provider's protocol. Stably integrated cells were selected with G418 (400 ug/ml) for 10 days. Adult mouse fibroblasts were derived from tails of IG-DMR$^{GFP/Pat}$ reporter mice. Briefly, ~2 cm-long mouse tail was obtained from 3 month old mouse carrying paternally transmitted IG-DMR-Snrpn-GFP methylation reporter, and sterilized by 70% EtOH. ~2 mm×2 mm minced tail pieces were digested with 5 ml of 1 mg/ml Collagenase IV at 37° C. for 90 min in a 15 ml Falcon tube. 5 ml MEF medium were added into the tube to terminate the digestion. Dissociated cells were extruded through a 40 um cell strainer with gentle grind using a syringe plug. Cells were then collected and cultured for viral infection. Cells were analyzed 3 days post-infection in this study.

Mouse Lines and Breeding Strategies

Tet1 mutant mice were previously generated in our lab (Dawlaty et al., 2011). Tet1 KO mice in the study were maintained in a mixed 129 and C57BL/6 background. To obtain Tet1 KO mice, male and female mice heterozygous for Tet1 were crossed. To obtain wild type mouse primary cortical neurons, male and female C57BL/6 mice were mated. IG-DMR$^{GFP/Pat}$ methylation reporter mouse line was generated as described (Ref: Stelzer et al., Parent-of-origin DNA methylation dynamics during mouse development, Developmental Cell, under editorial consideration). Male mice with IG-DMR$^{GFP/Pat}$ reporter allele were crossed with C57BL/6 females to generate adult offsprings carrying the paternally transmitted allele for in vivo DNA methylation editing analysis. Mice were handled in accordance with institutional guidelines and approved by the Committee on Animal Care (CAC) and Department of Comparative Medicine (DCM) of Massachusetts Institute of Technology.

Viral Infection of Mice and Tissue Sample Preparation

Mice were infected with appropriate lentiviral cocktails in accordance with institutional guidelines and approved by the Committee on Animal Care (CAC) and Department of Comparative Medicine (DCM) of Massachusetts Institute of Technology. Specifically, to infect mouse skin, lentiviruses expressing dCas9-Tet1 with sc gRNA, an inactive mutant of dC-dT with target gRNAs, and dCas9-Tet1 with target gRNAs were delivered by Hamilton syringe into multiple dermal sites on the ventral side of the deeply anesthetized mouse carrying the Paternal IG-DMR$^{GFP/Pat}$ reporter allele (FIG. 14D). To infect mouse brain, various lentiviral mixtures were delivered by stereotaxic setup (Leica BIOSYSTEMS, BenchMark Digital Stereotaxic with Manual Fine Drive) into the following locations (relative to the Franklin and Paxinos mouse brain atlas) of the deeply anesthetized mouse carrying the paternal IG-DMR$^{GFP/Pat}$ reporter allele (FIG. 7D): dCas9-Tet1 with sc gRNA (A-P 0.70 mm, M-L 1.50 mm, D-V 1.50 mm), an inactive mutant of dC-dT with Snrpn gRNAs (A-P—1.90 mm, M-L −1.50 mm, D-V 1.50 mm), and dCas9-Tet1 with Snrpn gRNAs (A-P—1.90 mm, M-L 1.50 mm, D-V 1.50 mm). The titers for dC-T/dC-dT and gRNA lentiviruses are 1.2×10$^4$ TU/ul and 1.2×10$^5$ TU/ul respectively. Mice were sacrificed 3 days after infection. The animals were fixed by transcardial perfusion with 4% paraformaldehyde (PFA)/PBS. Fixed skin pads and brain samples were dissected and post fixed with 4% paraformaldehyde (PFA)/PBS overnight at 4° C. The brain samples were sectioned with a vibratome (Leica VT1100) at 150 um thickness and the skin samples were sectioned with a cryostat (Leica) at 10 um thickness followed by immunohistochemical analysis. For vibratome sectioning, tissues were embedded in 3% agarose gel. For cryosectioning, tissues were equilibrated in 30% sucrose/PBS prior to embedding in Optimal Cutting Temperature (OCT) compound.

Immunohistochemistry, Microscopy, and Image Analysis

Neurons, HEK293T cells, mouse ES cells and C3H10T1/2 cells were fixed with 4% paraformaldehyde (PFA) for 10 min at room temperature. Cells were permeablized with PBST (1×PBS solution with 0.1% Triton X-100) before blocking with 10% Normal Donkey Serum (NDS) in PBST. Cells were then incubated with appropriately diluted primary antibodies in PBST with 5% NDS for 1 hours at room temperature or 12 hours at 4° C., washed with PBST for 3 times at room temperature and then incubated with desired secondary antibodies in TBST with 5% NDS and DAPI to counter stain the nuclei. Cells were washed 3 times with PBST before mounted onto slides with Fluoromount G (SouthernBiotech). Immunostaining procedures for tissue sections were previously described (Wu et al., 2014a). Briefly, sections were permeablized with PBST (1×PBS solution with 0.5% Triton X-100) for 1 hour at RT before blocking with 10% Normal Donkey Serum (NDS) in PBST. Slices were then incubated with desired primary antibodies in PBST with 5% NDS for 24 hours at 4° C., washed with PBST for 3 times at room temperature and then incubated with secondary antibodies in TBST with 5% NDS and DAPI to counter stain the nuclei. Sections were washed 3 times with PBST before slide mounting. The following antibodies were used in this study: Chicken anti-GFP (1:1000, Aves Labs), Mouse anti-Cas9 (7A9, 1:1000, EMD Millipore), Rabbit anti-BDNF (1:1000, Thermo Fisher), Chicken anti-MAP2 (1:1000, Sigma Aldrich), Mouse anti-Tuj1 (1:1000, R&D system), Rabbit anti-MyoD (C-20, 1:1000, Santa Cruz Biotechnology), Mouse anti-MHC (MF20, 1:1000, Fisher Scientific), Mouse anti-MyoG (F5G, 1:1000, Life Technologies). Images were captured on a Zeiss LSM710 confocal microscope and processed with Zen software, ImageJ/Fiji, and Adobe Photoshop. For imaging based quantification, unless otherwise specified, 3-5 representative images were quantified and data were plotted as mean±SD with Excel or Graphpad.

FACS Analysis

To assess the proportion of GFP and/or Cherry positive cells after treatment, the treated cells were dissociated with trypsin and single-cell suspensions were prepared in growth medium subject to a BD FACSAria cell sorter according to the manufacture's protocol at the Whitehead Institute Flow Cytometry Core. Data were analyzed with FlowJo software.

Mouse Primary Cortical Neuron Culture, EDU Labeling and Neural Induction

Dissociated E17.5 cortical neuron cultures were generated from wild type or Tet1 KO mouse embryos as described previously (Ebert et al., 2013). Briefly, E17.5 cortices were dissected in ice-cold 1×HBSS (Gibco 14185-052) containing 1× pen/strep (Gibco: 15140122), 1× pyruvate (Gibco: 11360070) and 30 mM Glucose. Tissues were minced into around 1 mm3 and dissociated with Papain neural tissue dissociation system (Worthington Biochemicals) following the manufacturer's instruction. Cells were resuspended in NM5 media (%5 FBS (Hyclone), 2% B27 supplement (Gibco 17504044), 1×pen/strep and 1×glutamax I (Gibco 35050-061)). $1 \times 10^6$ cells were plated per well of a 6-well plate coated with poly-D-lysine (PDL, Sigma). On DIV2, cells were treated with 2.5 uM AraC overnight (Sigma C-6645) to eliminate the excessive cell division of mitotic astrocytes and neural progenitor cells. Cultures were fed at DIV3 with fresh NM5 media and subsequently membrane depolarized with 50 mM KCl or infected with preferred lentivirus. We started the treatment at the very beginning of the in vitro culture so the step of AP5 and TTX (tetrodotoxin) treatment to silence basal activity in the culture before KCl treatment was omitted. For EDU labeling, primary neuronal culture were treated with EDU at a final concentration of 10 uM for 24 hours followed by Click-it EDU labeling procedure according to the manufacturer's instruction (Thermo Fisher Scientific). Cells were fixed for immunohistochemical analysis, lysed in Trizol to extract total RNA for RT-qPCR or lysed to extract DNA for bisulfite sequencing analysis.

Fibroblast-to-Myoblast Conversion Assay

Myoblast conversion assay was described previously (Constantinides et al., 1977). Briefly, C3H10T1/2 mouse embryonic fibroblast cells were plated as $1 \times 10^4$ cells per well in 6-well plate, and then infected with lentiviruses expressing dCas9-Tet1 and target gRNAs. 24-hour post infection, cells were treated with vehicle control (HEPES buffer) or 5-Azacytidine (1 uM) for 24-hour, and harvested at different time points for subsequently analysis. DMRs upstream of mouse MyoD gene were defined based on human/mouse genome homology (Schultz et al., 2015).

Western Blot

HEK293T cells were transfected with various constructs by X-tremeGENE 9 reagent following manufacturer's protocol. 2-day post transfection, cells were lysed by RIPA buffer with proteinase inhibitor (Invitrogen), and subject to standard immunoblotting analysis. Mouse anti-Cas9 (1:1000, Active Motif) and mouse α-Tubulin (1:1000, Sigma) antibodies were used.

RT-qPCR

Cells were harvested using Trizol followed by Direct-zol (Zymo Research), according to manufacturer's instructions. RNA was converted to cDNA using First-strand cDNA synthesis (Invitrogen SuperScript III). Quantitative PCR reactions were prepared with SYBR Green (Invitrogen), and performed in 7900HT Fast ABI instrument. Primer information for RT-qPCR is listed in Supplemental Table S3.

ChIP Assay

ChIP experiment was performed as previously described (Dowen et al., 2014). Briefly, cells were cross-linked by 1% formaldehyde in the medium for 10 min in room temperature, and then quenched by adding 0.125 M Glycine for 5 min. Collected cells were washed with PBS twice, and then re-suspended in 3.5 ml of sonication buffer. Sonication was performed for 10 cycles with 0.5 min pulse on and 1 min rest, and 24 watts in ice-water mixture. Then cell lysate was spun down with $14,000 \times$ rpm for 10 min at 4° C. 50 ul of supernatant was saved as input for gDNA. 10 ul of anti-CTCF antibody (EMD Millipore: 07729) or anti-Cas9 antibody (Active Motif) was added and incubate overnight at 4° C. 50 ul protein G dynabeads was added into antibody-cell lysate mixture and incubate overnight at 4° C. Then beads were washed with sonication buffer, sonication buffer with high salt (500 mM NaCl), LiCl wash buffer, and TE buffer. Bound protein-DNA complex was eluted from beads by incubation in a 65° C. oven for 15 min, and then reverse cross-linked under 65° C. over-night. The bound DNA was purified with Qiagen QIAquick PCR Purification Kit, and then subject to qPCR analysis or sequencing.

ChIP-Seq Data Analysis

Sequencing data was analyzed with a previously reported method (Wu et al., 2014b). Reads are de-multiplexed and the first 25 bases are mapped to mouse genome (mm10) using STAR (Dobin et al., 2013), requiring unique mapping allowing one mismatch. Mapped reads are collapsed and the same number of reads (about 15 million) are randomly sampled from each sample to match sequencing depth. Peaks are called using MACS (Zhang et al., 2008) with default settings. For each sample, the other five samples are each used as a control and only peaks called over all five controls are defined as candidate peaks. Candidate peaks are filtered by fold of enrichment over background and the threshold is chosen such that no peaks pass this threshold in the four control samples (input, mock IP, dCas9 alone, and scrambled gRNA). Note that six candidate peaks in input mapped to 45S rRNA and mitochondria DNA are excluded from the analysis. Raw data is available in the following link: ncbi.nlm.nih.gov/geo/query/acc.cgi?token=ktohskmgnhudhud&acc=GSE83890.

Bisulfite Conversion, PCR and Sequencing

Bisulfite conversion of DNA was established using the EpiTect Bisulfite Kit (Qiagen) following the manufacturer's instructions. The resulting modified DNA was amplified by first round of nested PCR, following a second round using loci specific PCR primers (Supplemental Table S3). The first round of nested PCR was done as follows: 94° C. for 4 min; 55° C. for 2 min; 72° C. for 2 min; Repeat steps 1-3 1×; 94° C. for 1 min; 55° C. for 2 min; 72° C. for 2 min; Repeat steps 5-7 35×; 72° C. for 5 min; Hold 12° C. The second round of PCR was as follows: 95° C. for 4 min; 94° C. for 1 min; 55° C. for 2 min; 72° C. for 2 min; Repeat steps 2-4 35×; 72° C. for 5 min; Hold 12° C. The resulting amplified products were gel-purified, sub-cloned into a pCR2.1-TOPO-TA cloning vector (Life technologies), and sequenced. Primer information for bisulfite sequencing is listed in Supplemental Table S4.

Locus-Specific TAB-Seq

TAB-Seq was performed as described previously (Yu et al., 2012). Briefly, 1 ug of genomic DNA from treated mouse cortical neuron was glucosylated in a solution containing 50 mM HEPES buffer (pH 8.0), 25 mM $MgCl_2$, 100 ng/ml model DNA, 200 mM UDP-Glc, and 1 mM bGT at 37C for 1 hr. After the reaction, the DNA was column purified. The oxidation reactions were performed in a solution containing 50 mM HEPES buffer (pH 8.0), 100 mM ammonium iron (II) sulfate, 1 mM a-ketoglutarate, 2 mM ascorbic acid, 2.5 mM DTT, 100 mM NaCl, 1.2 mM ATP, 15 ng/ml glucosylated DNA, and 3 mM recombinant mTet1. The reactions were incubated at 37 C for 1 hr. After proteinase K treatment, the DNA was column purified and then applied to EpiTect Bisulfite Kit (QIAGEN) following the supplier's instruction. The resulting modified DNA was amplified by first round of nested PCR, following a second round using loci specific PCR primers (Supplemental Table S3). The resulting amplified products were gel-purified, sub-cloned into a pJET cloning vector (Life technologies), and sequenced. Primer information for bisulfite sequencing is listed in Supplemental Table S4.

Chromosome Conformation Capture (3C) Assay $5 \times 10^6$ mESCs were fixed with 1% formaldehyde for 20 min at room temperature, and the reaction was quenched by 0.125 M glycine for 5 min at room temperature. Cross-linked cells were collected and washed with 1 ml ice cold PBS. Cell pellet was re-suspended with 550 µl lysis buffer (10 mM Tris-HCl with pH 8.0, 10 mM NaCl, and 0.2% IGEPAL CA630 with proteinase inhibitor), and incubated on ice for 20 min. Cell pellet was then washed twice with 1×NEB buffer 2 (NEB, B7002S), then incubated with 50 µl 0.5% SDS for 10 min at 62° C. After heating, 145 µl H$_2$O and 25 µl 10% Triton X-100 were added into the mixture and incubate for 15 min at 37° C. 25 µl 10×NEB buffer 2 and 100 U BglII (NEB, R0144S) were added to digest chromatin over night at 37° C. The digest reaction was inactivated by incubation for 20 min at 62° C. Then 713 µl H$_2$O, 120 µl 10 µl×T4 DNA ligase buffer (NEB, B0202), 100 µl 10% Triton X-100, 12 µl 10 mg/ml BSA, and 5 µl T4 DNA ligase (NEB, M0202) were added and incubated for 22 hour at 16° C. The chromatin was reverse cross-linked, and DNA was purified by phenol:chloroform:isoamyl alcohol (Sigma, P3803) extraction. The 3C interactions at the miR290 and Pou5f1 loci (FIG. 6A and FIG. 6C) were analyzed by quantitative real-time PCR using custom Taqman probes. The amount of DNA in the qPCR reactions was normalized across 3C libraries using a custom Taqman probe directed against the Actb locus. Primer and probe sequences are listed in Supplemental Table S5.

Supplemental Tables:

Supplemental TABLE S1

| | | | | | | | | |
|---|---|---|---|---|---|---|---|---|
| dCas9 ChIP-Seq (SEQ ID NOs: 1-35) | | | | | | | | |
| peak (miR290) | position | start | end | guide_match | guide_match + NGG | peak score | peak_summit_height | relative binding |
| 1 | chr7 (mir290) | 5221269 | 3222647 | 20 | GTTTTGAGGCCTCATTTGTAAGG, TTTTTGAAAAATTACCTTGTGGG, CAGAGTCCTAGACATTTCCATGG | 5100 | 55 | 1.00 |
| 2 | chr8 (Vac14) | 110658179 | 110659329 | 16, 12 | GgagaGAGGCCTCATTTGTAGGG, gTTgTcAgAgcaTAgCTTGTAGG | 3147 | 52 | 0.80 |
| 3 | chr16 (Tenm4) | 92920310 | 92920851 | 9 | CtaAagCgatGttccTTCCAGGG | 1240 | 27 | 0.42 |
| 4 | chr7 | 96797181 | 96798058 | 13 | ttGctctCaAGACATTTCCAGGG | 1371 | 23 | 0.35 |
| 5 | chr8 | 47746475 | 47748820 | 9 | ttGctTtCcAttttcTTCCAGGG | 346 | 17 | 0.26 |
| 6 | chr8 | 119845496 | 119848845 | 10 | agcTTctAgctcACCTTCcTAGG | 582 | 17 | 0.26 |
| 7 | chr2 | 60720846 | 60721662 | 12 | tcTgcGAGtCCTtAaTTtTAGGG | 779 | 17 | 0.26 |
| 8 | chr4 | 134701902 | 134752180 | 8 | aAagcattTtcttcTTCCCAGGG | 212 | 15 | 0.23 |
| 9 | chr3 | 35405566 | 35406124 | 6 | agttGctgctctttTgTCCAGGG | 447 | 15 | 0.23 |
| 10 | chr3 | 116425072 | 116425343 | 9 | acGcaaCtgcGAgcTTTCaAAGG | 220 | 15 | 0.23 |
| 11 | chr11 | 113612406 | 113612832 | 7 | tttAaagCcccttccTTCCAGGG | 227 | 15 | 0.23 |
| 12 | chr15 | 58022874 | 58023358 | 10 | acTgTcttcAAcTtCCTTGgGGG | 143 | 14 | 0.22 |
| 13 | chr3 | 116748072 | 116748683 | 12 | ggactaCtgAGACATTTCCAGGG | 793 | 13 | 0.20 |
| 14 | chr2 | 122357139 | 122357691 | 13 | tcaAccCtgAGACATTTCCAGGG | 326 | 13 | 0.20 |
| 15 | chr1 | 191708537 | 191708741 | 14 | CcaAGattgAGACATTTCCAGGG | 205 | 13 | 0.20 |
| 16 | chr8 | 84471283 | 84471659 | 12 | tAaAGTCCcAGtCcccTCCcTGG | 345 | 12 | 0.18 |
| 17 | chr4 | 125502946 | 125503352 | 10 | CtaAGctGTgtgttgTTCCAGGG | 219 | 12 | 0.18 |
| 18 | chr2 | 152112091 | 152112284 | 9 | GTagaGcatgtTgAgcTGTAGGS | 84 | 12 | 0.18 |

Supplemental TABLE S1-continued

| dCas9 ChIP-Seq (SEQ ID NOs: 1-35) | | | | | | | | |
|---|---|---|---|---|---|---|---|---|
| peak (Dazl-Snrpn) | position | start | end | guide_match | guide_match + NGG | peak score | peak_summit_height | relative binding |
| 1 | ch17 (Dazl) | 50293768 | 50295107 | 20 | GAGCCGAGCTGTAGGGTGCTTGG | 3100 | 64 | 1.00 |
| 2 | chr12 (Vrk1) | 105962219 | 105963255 | 14, 5 | cgGgCagcCTGTAGGGTGCTGGG, gcgcaagGgttgtcgTGCCTTGG | 3100 | 53 | 0.83 |
| 3 | Chr7 (Snrpn) | 60004859 | 60005472 | 20, 20, 20 | CGCATGTGCAGCCATTGCCTGGG, TTTGGTAGCTGCCTTTTGGCAGG, ACAAACCTGAGCCATTGCGG | 1251 | 35 | 0.55 |
| 4 | chr5 (Gm42 619) | 148500582 | 143501113 | 14, 8 | ccctgcAGCTGAGGGTGCTAGG, tctcTcagtGtaATTGgCTTGG | 657 | 21 | 0.33 |
| 5 | chr5 | 103341125 | 103341731 | 13, 10 | tccatttGCTGTAGGGTGCTAGG, tgctaatGttCCaTTTGGCAGG | 1073 | 19 | 0.30 |
| 6 | chr18 | 82149068 | 82149284 | 15 | GcaCaGcaCTGTAGGGTGCTGGG | 377 | 17 | 0.27 |
| 7 | chr1 | 127220317 | 127220836 | 13 | ccatCtctCTGTAGGGTGCTGGG | 521 | 17 | 0.27 |
| 8 | chr19 | 46897110 | 46897668 | 15 | GtGagctGCTGTAGGGTGCTAGG | 386 | 23 | 0.20 |
| 9 | chr6 | 93599579 | 23599815 | 16 | GAatgGAcCTGTAGGGTGCTTGG | 205 | 12 | 0.19 |

Table legends:
chr: chromsosome
start: start coordinate of the peak
end: end coordinate of the peak
guide_match: number of base match to the gudie
guide_match + NGG: guide match sequence + NGG within the peak (mismatched seqeuence in lower case)
peak_score: MACS peak score(log-transformed:- 10*log10(p value))
peak_summit_height: MACS peak summit height
relative binding: normalized to peek summit heigh of target gRNAs Supplemental TABLE S2

| Primer sequences to construct guide RNAs | |
|---|---|
| 5' to 3' | |
| scrambled gRNA | |
| SL-289_dCas9-effector_scramble gRNA_For | TTGG cccccggggaaaaattttt (SEQ ID NO: 36) |
| SL-290_dCas9-effector_scramble gRNA_Rev | AAAC aaaaattttccccggggg (SEQ ID NO: 37) |
| gRNAs targeting the BDNF promoter IV | |
| SL-64_mBDNF_Exon IV_gRNA-1_For | TTGG ctacaaagcatgcaatgccc (SEQ ID NO: 38) |
| SL-65 mBDNF Exon IV gRNA-1 Rev | AAAC gggcattgcatgcttttgtag (SEQ ID NO: 39) |
| SL-66_mBDNF Exon IV_gRNA-2_For | TTGG aatgcgcggaattctgattc (SEQ ID NO: 40) |
| SL-67_mBDNF_Exon IV_gRNA-2_Rev | AAAC gaatcagaattccgcgcatt (SEQ ID NO: 41) |
| SL-68_mBDNF_Exon IV_gRNA-3_For | TTGG gtgggtgggagtccacgaga (SEQ ID NO: 42) |
| SL-69_mBDNF_Exon IV_gRNA-3_Rev | AAAC tctcgtggactccacccac (SEQ ID NO: 43) |
| SL-70_mBDNF_Exon IV_gRNA-4_For | TTGG ggcagcgtggagccctctcg (SEQ ID NO: 44) |
| SL-71 mBDNF Exon IV gRNA-4 Rev | AAAC cgagagggctccacgctgcc (SEQ ID NO: 45) |
| gRNAs targeting the Snrpn promoter | |
| SL-127_mSnrpn_gRNA-1_For | TTGG GAGCCGAGCTGTAGGGTGCT (SEQ ID NO: 46) |
| SL-128_mSnrpn_gRNA-1_Rev | AAAC AGCACCCTACAGCTCGGCTC (SEQ ID NO: 47) |

Supplemental TABLE S2-continued

| Primer sequences to construct guide RNAs | |
|---|---|
| | 5' to 3' |
| SL-129_mSnrpn_gRNA-2_For | TTGG TTTGGTAGCTGCCTTTTGGC (SEQ ID NO: 48) |
| SL-130_mSnrpn_gRNA-2_Rev | AAAC GCCAAAAGGCAGCTACCAAA (SEQ ID NO: 49) |
| SL-131_mSnrpn_gRNA-3_For | TTGG CGCATGTGCAGCCATTGCCT (SEQ ID NO: 50) |
| SL-132_mSnrpn_gRNA-3_Rev | AAAC AGGCAATGGCTGCACATGCG (SEQ ID NO: 51) |
| SL-133_mSnrpn_gRNA-4_For | TTGG ACAAACCTGAGCCATTG (SEQ ID NO: 52) |
| SL-134_mSnrpn_gRNA-4_Rev | AAAC CAATGGCTCAGGTTTGT (SEQ ID NO: 53) |
| gRNAs targeting MyoD DMR-5 (distal enhancer region) | |
| SL-174_mMyoD_gRNA-1_For | TTGG agcatttgggggcatttatg (SEQ ID NO: 54) |
| SL-175_mMyoD_gRNA-1_Rev | AAAC cataaatgcccccaaatgct (SEQ ID NO: 55) |
| SL-176_mMyoD_gRNA-2_For | TTGG aagtatcctcctccagcagc (SEQ ID NO: 56) |
| SL-177_mMyoD_gRNA-2_Rev | AAAC gctgctggaggaggatactt (SEQ ID NO: 57) |
| SL-178_mMyoD_gRNA-3_For | TTGG acacagccagttgggggaag (SEQ ID NO: 58) |
| SL-179_mMyoD_gRNA-3_Rev | AAAC cttcccccaactggctgtgt (SEQ ID NO: 59) |
| SL-180_mMyoD_gRNA-4_For | TTGG ccagagtcagctgttcct (SEQ ID NO: 60) |
| SL-181_mMyoD_gRNA-4_Rev | AAAC aggaacagctgactctgg (SEQ ID NO: 61) |
| gRNAs targeting miR290 locus (CTCF target-1) | |
| SL-357_miR290-Nlrp12_gRNA-1_For | TTGG GTTTTGAGGCCTCATTTGTA (SEQ ID NO: 62) |
| SL-358_miR290-Nlrp12_gRNA-1_Rev | AAAC TACAAATGAGGCCTCAAAAC (SEQ ID NO: 63) |
| SL-359_miR290-Nlrp12_gRNA-2_For | TTGG TTTTTGAAAAATTACCTTGT (SEQ ID NO: 64) |
| SL-360_miR290-Nlrp12_gRN A-2_Rev | AAAC ACAAGGTAATTTTTCAAAAA (SEQ ID NO: 65) |
| SL-361_miR290-Nlrp12_gRNA-3_For | TTGG CAGAGTCCTAGACATTTCCA (SEQ ID NO: 66) |
| SL-362_miR290Nlrp12_gRN A-3_Rev | AAAC TGGAAATGTCTAGGACTCTG (SEQ ID NO: 67) |
| gRNAs targeting Pou5f1_locus (CTCF target-2) | |
| SL-377_Pou5f1_gRNA-1_For | TTGG TCTCACCCTTGATAGTTTGA (SEQ ID NO: 68) |
| SL-378_Pou5f1_gRNA-1_Rev | AAAC TCAAACTATCAAGGGTGAGA (SEQ ID NO: 69) |
| SL-379_Pou5f1_gRNA-2_For | TTGG GGTAAATCTTTGAAGCCAAT (SEQ ID NO: 70) |
| SL-380_Pou5f1_gRNA-2_Rev | AAAC ATTGGCTTCAAAGATTTACC (SEQ ID NO: 71) |
| SL-381_Pou5f1_gRNA-3_For | TTGG ATTTTCTACCTACGGTGTGC (SEQ ID NO: 72) |
| SL-382_Pou5f1_gRNA-3_Rev | AAAC GCACACCGTAGGTAGAAAAT (SEQ ID NO: 73) |
| SL-383_Pou5f1_gRNA-4_For | TTGG TCTCCTGGAAGGACTCTGGG (SEQ ID NO: 74) |
| SL-384_Pou5f1_gRNA-4_Rev | AAAC CCCAGAGTCCTTCCAGGAGA (SEQ ID NO: 75) |
| gRNA targeting p16 locus | |
| SL-504_p16 promoter_sgRNA-1_For | TTGG tcctccttccttgccaacgc (SEQ ID NO: 76) |
| SL-505_p16 promoter_sgRNA-1_Rev | AAAC gcgttggcaaggaaggagga (SEQ ID NO: 77) |

Supplemental TABLE S2-continued

Primer sequences to construct guide RNAs

5' to 3' gRNA targeting RHOXF2 locus

| | |
|---|---|
| SL-506_RHOXF2 promoter sgRNA-1_For | TTGG cccgctatttgctgtgggtt (SEQ ID NO: 78) |
| SL-507_RHOXF2 promoter sgRNA-1_Rev | AAAC aacccacagcaaatagcggg (SEQ ID NO: 79) |

SUPPLEMENTAL TABLE S3

| qPCR primers | |
|---|---|
| mBDNF_Exon IV_qPCR_For | CAG GAG TAC ATA TCG GCC ACC A (SEQ ID NO: 80) |
| mBDNF_Exon IV_GPCR_Rev | GTA GGC CAA GTT GCC TTG TCC GT (SEQ ID NO: 81) |
| P-Actin_qPCR_For primer | GCC TTC CTT CTT GGG TAT G (SEQ ID NO: 82) |
| P-Actin_qPCR_Rev primer | ACC ACC AGA CAA CAC TGT G (SEQ ID NO: 83) |
| mNpas4_qPCR_For primer | GCTATACTCAGAAGGTCCAGAAGGC (SEQ ID NO: 84) |
| mNpas4_qPCR_Rev primer | TCAGAGAATGAGGGTAGCACAGC (SEQ ID NO: 85) |
| mMyoD_qPCR_For | ACT TTC TGG AGC CCT CCT GGC A (SEQ ID NO: 86) |
| mMyoD_qPCR_Rev | TTT GTT GCA CTA CAC AGC ATG (SEQ ID NO: 87) |
| CTCF target-1 | |
| SL-401_AU018091_for | AGGGGATTCTCCGTGGTACA (SEQ ID NO: 88) |
| SL-402_AU018091_rev | CTCTTCCCCTGTACTCGCAA (SEQ ID NO: 89) |
| SL-411_Pri-miR290-295_for | CGAGACGCGGATGGATGTAA (SEQ ID NO: 90) |
| SL-412_Pri-miR290-295_rev | GCGGCACTTTTCTTCCGATG (SEQ ID NO: 91) |
| SL-397_Nlrp12_for | CCAGACCCTGCATGAGCTTTA (SEQ ID NO: 92) |
| SL-398_Nlrp12_rev | AAACAGCCACAGGACTCGAA (SEQ ID NO: 93) |
| SL-429_Myadm_new_F | TCTGTTAAGGGAGCAGCCATGC (SEQ ID NO: 94) |
| SL-430_Myadm_new_R | GGATATTAGCTGCAGGAGGCG (SEQ ID NO: 95) |
| CTCF target-2 | |
| SL-423_H2Q10_CDS_F | CAGAGAGCCAAGGGCAATGA (SEQ ID NO: 96) |
| SL-424_H2Q10_CDS_R | GGACCCCACTTTACAGCCAT (SEQ ID NO: 97) |
| SL-421_Pou5f1_new_F | GCGTTCTCTTTGGAAAGGTGT (SEQ ID NO: 98) |
| SL-422_Pou5f1_new_R | TTGTTGTCGGCTTCCTCCAC (SEQ ID NO: 99) |
| SL-395_Tcf19_for | ATCTCTGGAGTCCATGCGGA (SEQ ID NO: 100) |
| SL-396_Tcf19_rev | CAAAGTCCCTTGGCTGCTGT (SEQ ID NO: 101) |
| ChIP-qPCR primers for CTCF target-1 | |
| SL-456_mCTCF_ChIP-qPCR_T1_2_For | CAGGTGTGCAAATCTTGGGT (SEQ ID NO: 102) |
| SL-457_mCTCF_ChIP-qPCR_T1_2_Rev | TGGTGGCTTGCAATCATCTG (SEQ ID NO: 103) |
| SL-458_mCTCF_ChIP-qPCR_T1_control_1_For | TGAGTCCTTGCTCGGTTCTT (SEQ ID NO: 104) |
| SL-459_mCTCF_ChIP-qPCR_T1_control_1_Rev | CAGGCACATTGCTGTGAGTT (SEQ ID NO: 105) |

SUPPLEMENTAL TABLE S3-continued qPCR primers

ChIP-qPCR primers for CTCF target-2

| | |
|---|---|
| SL-446_mCTCF_ChIP-qPCR_T2_1_For | TGGCCTTGTACTGTTGCAAC (SEQ ID NO: 106) |
| SL-447_mCTCF_ChIP-qPCR_T2_1_Rev | AGTGTCACTATGGCCACCTT (SEQ ID NO: 107) |
| SL-452_mCTCF_ChIP-qPCR_T2_control_2_For | AATCTTCCCTTGGGGTATG (SEQ ID NO: 108) |
| SL-453_mCTCF_ChIP-qPCR_T2_control_2_Rev | TAAGGAGCCATGCTGTACCC (SEQ ID NO: 109) |

Supplemental Table S4

Bisulfite sequencing primers

Dazl-Snrpn-GFP locus

| | |
|---|---|
| Dazl Nested F | GAAGTTTTTGTGAAATAAGTTTT GGGTAGG (SEQ ID NO: 110) |
| GFP Nested R | CTCGACCAAAATAAACACCACCCC (SEQ ID NO: 111) |
| Dazl-Snrpn F | CGAGTTGTAGGGTGTTTGGTAATTG (SEQ ID NO: 112) |
| Dazl-Snrpn R | ACGTTACAAATCACTCCTCAAAACC (SEQ ID NO: 113) |

Gapdh-Snrpn-GFP locus

| | |
|---|---|
| Gapdh Nested F | GGTTGTAGGAGAAGAAAATGAGATTAG (SEQ ID NO: 114) |
| GFP Nested R | CTCGACCAAAATAAACACCACCCC (SEQ ID NO: 115) |
| Gapdh-Snrpn F | TAGTTTAAGGGCGTAGAGGTTTGAG (SEQ ID NO: 116) |
| Gapdh-Snrpn R | ACGTTACAAATCACTCCTCAAAACC (SEQ ID NO: 117) |

BDNF promoter IV

| | |
|---|---|
| SL-108_hBDNF_Exon IV_Nest_For | TTATTTATTGGTTGGATTAGAGGGGT (SEQ ID NO: 118) |
| SL-109_hBDNF_Exon IV_Nest_Rev | CATATACTTCCCAACAAACCAAAC (SEQ ID NO: 119) |
| SL-110_hBDNF_Exon IV_BS-Seq_For | GTGAATTTGTTAGGATTGGAAGTGAA (SEQ ID NO: 120) |
| SL-111_hBDNF_Exon IV_BS-Seq_Rev | ACTCTTACTATATATTTCCCCTTCTCTTCA (SEQ ID NO: 121) |

DMR-5 for MyoD distal enhancer

| | |
|---|---|
| SL-253_mMyoD_DMR-5_Nest_For | GGTTTGAGGTAGGTAGGGGTTAGG (SEQ ID NO: 122) |
| SL-254_mMyoD_DMR-5_Nest_Rev | CCAACTCACTTTCTCCCAAAATTACACTAA (SEQ ID NO: 123) |
| SL-255_mMyoD_DMR-5_BS_For | GTAGAATTTGTTAGGTGGGTGAAAGGAAG (SEQ ID NO: 124) |
| SL-256_mMyoD_DMR-5_BS_Rev | CCTTCCTCCCAAAATACTAACCTCTCATAC (SEQ ID NO: 125) |

CTCF target-1 locus (miR290)

| | |
|---|---|
| SL-431_miR290-Nlrp12 locus_Nest_For | GATTTTTGGGTATTGTATTGGAAGTGGG (SEQ ID NO: 126) |
| SL-432_miR290-Nlrp12 locus_Nest_Rev | CCAAAATATTTATTCCCTCTACTTTAAAACAC (SEQ ID NO: 127) |
| SL-433_miR290-Nlrp12 locus_BS_For | TTTAGGATAGGATGGGAGTATTGGTTG (SEQ ID NO: 128) |
| SL-434_miR290-Nlrp12 locus_BS_Rev | CAAAATCACTCAAAATCATCCTATTACATAAAAC (SEQ ID NO: 129) |

CTCF target-2 locus (Pou5f1)

| | |
|---|---|
| SL-440_H2Q10-Pou5f1_locus_Nest_For | ATTAAGAGGTTAGGGGTTTTTAGTTGGTTTTGTATTG (SEQ ID NO: 130) |
| SL-441_H2Q10-Pou5f12 locus_Nest_Rev | AAAAAAAACCTTCATCACATAATAAACTAAACCAACC (SEQ ID NO: 131) |
| SL-442_H2Q10-Pou5f1_locus_BS_For | GAAAGGATGTAATTAGAGGGTTTTTGGG (SEQ ID NO: 132) |
| SL-443_H2Q10-Pou5f1_locus_BS_Rev | AATCCTTTCTCAAAACCCCTTCCTC (SEQ ID NO: 133) |

Supplemental Table S4-continued

Bisulfite sequencing primers p16

| | |
|---|---|
| SL-510_p16 promoter_Nest_For | Gtggggttttataattaggaaagaatag (SEQ ID NO: 134) |
| SL-511_p16 promoter_Nest_Rev | ATTACAAACCCCTTCTAAAAACTCC (SEQ ID NO: 135) |
| SL-512_p16 promoter_BS_For | Atttggtagttaggaaggttgta (SEQ ID NO: 136) |
| SL-513_p16 promote _BS _Rev | CCAAAAAACCTCCCCTTTTTCC (SEQ ID NO: 137) |

RHOXF2 RHOXF2 BS-seq

| | |
|---|---|
| SL-514_RHOXF2 promoter_Nest_For | GTGGATTTTTTTAAGGAGTGTGTTG (SEQ ID NO: 138) |
| SL-515_RHOXF2 promoter_Nest_Rev | CTTCTAATATCTAAACTCAACAACAATATATCCAC (SEQ ID NO: 139) |
| SL-516_RHOXF2 promoter_BS _For | GGAGATTTAGGAAGTATGGGGTTAGTG (SEQ ID NO: 140) |
| SL-517_RHOXF2 promoter_BS _Rev | AAAACCTCCTCTCTTACTTTT CTACTTC (SEQ ID NO: 141) |

SUPPLEMENTAL TABLE S5

3C assay primers

| | |
|---|---|
| SL-471_3Cassay_Nlrp12_Rev | CACATCTTCAAAGCAAACACTATTGTT (SEQ ID NO: 142) |
| SL-472_3Cassay_Nlrp12_SE_1_For | TTCCTGGAACCTGGGCAA (SEQ ID NO: 143) |
| SL-473_3Cassay_Nlrp12_SE_2_For | TGATACAGCACAGCTTTCCTTCA (SEQ ID NO: 144) |
| SL-474_3Cassay_Nlrp12_SE_3_For | CAGATTTTTTATTTCCTTCAGTTCTGTG (SEQ ID NO: 145) |
| SL-475_3C assay_Nlrp12_Taqman Probe | TCTCCTACCCATTGCTTCTCTGCTACCTGC (SEQ ID NO: 146) |
| 3Cassay_Nlrp12_NC_1_For | TGAAGTTTGAGGAGATGCCATGGTTG (SEQ ID NO: 147) |
| 3Cassay_Nlrp12_NC_1_Rev | CACGCTAGGCTGAACACTGTGTCACTG (SEQ ID NO: 148) |
| SL-476_3C assay_H2Q10_For | AGGATGGCTCAGCGGTTAAG (SEQ ID NO: 149) |
| SL-477_3C assay_H2Q10_SE_Rev | AGGGCTCACCTTCAGTCAAGTT (SEQ ID NO: 150) |
| SL-478_3C assay_H2Q10_Taqman Probe | CGGCCTGTCTACTTTAGCCTCAGACTCCA (SEQ ID NO: 151) |
| 3C assay_H2Q10_NC-3_For | TGCCTTCCCTCTTACAAGGAGTTTTCTT (SEQ ID NO: 152) |
| 3C assay_H2Q10_NC-3_Rev | CGGTTAAGAAGAGCTCTTCTGGAGGCC (SEQ ID NO: 153) |
| SL-483_3C assay_Actin_For | GGGAGTGACTCTCTGTCCATTCA (SEQ ID NO: 154) |
| SL-484_3C assay_Actin_Rev | ATTTGTGTGGCCTCTTGTTTGA (SEQ ID NO: 155) |
| SL-485_3C assay_Actin_Taqman Probe | TCCAGGCCCCGCGTGTCC (SEQ ID NO: 156) |

SUPPLEMENTAL TABLE S6

Full length protein sequences of dCas9-Dnmt3a/Tet and mutants dCas9-Dnmt3a (dC-D)
(SEQ ID NO: 157)
MDKKYSIGLAIGTNSVGWAVITDEYKVPSKKFKVL
GNTDRHSIKKNLIGALLFDSGETAEATRLKRTARR
RYTRRKNRICYLQEIFSNEMAKVDDSFFHRLEESF
LVEEDKKHERHPIFGNIVDEVAYHEKYPTIYHLRK
KLVDSTDKADLRLIYLALAHMIKFRGHFLIEGDLN
PDNSDVDKLFIQLVQTYNQLFEENPINASGVDAKA
ILSARLSKSRRLENLIAQLPGEKKNGLFGNLIALS
LGLTPNFKSNFDLAEDAKLQLSKDTYDDDLDNLLA
QIGDQYADLFLAAKNLSDAILLSDILRVNTEITKA
PLSASMIKRYDEHHQDLTLLKALVRQQLPEKYKEI
FFDQSKNGYAGYIDGGASQEEFYKFIKPILEKMDG
TEELLVKLNREDLLRKQRTFDNGSIPHQIHLGELH
AILRRQEDFYPFLKDNREKIEKILTFRIPYYVGPL
ARGNSRFAWMTRKSEETITPWNFEEVVDKGASAQS
FIERMTNFDKNLPNEKVLPKHSLLYEYFTVYNELT
KVKYVTEGMRKPAFLSGEQKKAIVDLLFKTNRKVT
VKQLKEDYFKKIECFDSVEISGVEDRFNASLGTYH
DLLKIIKDKDFLDNEENEDILEDIVLTLTLFEDRE
MIEERLKTYAHLFDDKVMKQLKRRRYTGWGRLSRK
LINGIRDKQSGKTILDFLKSDGFANRNFMQLIHDD
SLTFKEDIQKAQVSGQGDSLHEHIANLAGSPAIKK
GILQTVKVVDELVKVMGRHKPENIVIEMARENQTT
QKGQKNSRERMKRIEEGIKELGSQILKEHPVENTQ
LQNEKLYLYYLQNGRDMYVDQELDINRLSDYDVDA
IVPQSFLKDDSIDNKVLTRSDKNRGKSDNVPSEEV
VKKMKNYWRQLLNAKLITQRKFDNLTKAERGGLSE
LDKAGFIKRQLVETRQITKHVAQILDSRMNTKYDE
NDKLIREVKVITLKSKLVSDFRKDFQFYKVREINN
YHHAHDAYLNAVVGTALIKKYPKLESEFVYGDYKV
YDVRKMIAKSEQEIGKATAKYFFYSNIMNFFKTEI
TLANGEIRKRPLIETNGETGEIVWDKGRDFATVRK
VLSMPQVNIVKKTEVQTGGFSKESILPKRNSDKLI
ARKKDWDPKKYGGFDSPTVAYSVLVVAKVEKGKSK
KLKSVKELLGITIMERSSFEKNPIDFLEAKGYKEV SUPPLEMENTAL TABLE S6-continued Full length protein sequences of dCas9-Dnmt3a/Tet and mutants KKDLIIKLPKYSLFELENGRKRMLASAGELQKGNE
LALPSKYVNFLYLASHYEKLKGSPEDNEQKQLFVE
QHKHYLDEIIEQISEFSKRVILADANLDKVLSAYN
KHRDKPIREQAENIIHLFTLTNLGAPAAFKYFDTT
IDRKRYTSTKEVLDATLIHQSITGLYETRIDLSQL
GGDEGADPKKKRKVDPKKKRKVDPKKKRKVGSMPA
MPSSGPGDTSSSAAEREEDRKDGEEQEEPRGKEER
QEPSTTARKVGRPGRKRKHPPVESGDTPKDPAVIS
KSPSMAQDSGASELLPNGDLEKRSEPQPEEGSPAG
GQKGGAPAEGEGAAETLPEASRAVENGCCTPKEGR
GAPAEAGKEQKETNIESMKMEGSRGRLRGGLGWES
SLRQRPMPRLTFQAGDPYYISKRKRDEWLARWKRE
AEKKAKVIAGMNAVEENQGPGESQKVEEASPPAVQ
QPTDPASPTVATTPEPVGSDAGDKNATKAGDDEPE
YEDGRGFGIGELVWGKLRGFSWWPGRIVSWWMTGR
SRAAEGTRWVMWFGDGKFSVVCVEKLMPLSSFCSA
FHQATYNKQPMYRKAIYEVLQVASSRAGKLFPVCH
DSDESDTAKAVEVQNKPMIEWALGGFQPSGPKGLE
PPEEEKNPYKEVYTDMWVEPEAAAYAPPPPAKKPR
KSTAEKPKVKEIIDERTRERLVYEVRQKCRNIEDI
CISCGSLNVTLEHPLFVGGMCQNCKNCFLECAYQY
DDDGYQSYCTICCGGREVLMCGNNNCCRCFCVECV
DLLVGPGAAQAAIKEDPWNCYMCGHKGTYGLLRRR
EDWPSRLQMFFANNHDQEFDPPKVYPPVPAEKRKP
IRVLSLFDGIATGLLVLKDLGIQVDRYIASEVCED
SITVGMVRHQGKIMYVGDVRSVTQKHIQEWGPFDL
VIGGSPCNDLSIVNPARKGLYEGTGRLFFEFYRLL
HDARPKEGDDRPFFWLFENVVAMGVSDKRDISRFL
ESNPVMIDAKEVSAAHRARYFWGNLPGMNRPLAST
VNDKLELQECLEHGRIAKFSKVRTITTRSNSIKQG
KDQHFPVFMNEKEDILWCTEMERVFGFPVHYTDVS
NMSRLARQRLLGRSWSVPVIRHLFAPLKEYFACV dCas9-Dnmt3a_IM (dC-dD, an inactive
mutant form of Dnmt3a)
(SEQ ID NO: 158)
MDKKYSIGLAIGTNSVGWAVITDEYKVPSKKFKVL
GNTDRHSIKKNLIGALLFDSGETAEATRLKRTARR
RYTRRKNRICYLQEIFSNEMAKVDDSFFHRLEESF
LVEEDKKHERHPIFGNIVDEVAYHEKYPTIYHLRK
KLVDSTDKADLRLIYLALAHMIKFRGHFLIEGDLN
PDNSDVDKLFIQLVQTYNQLFEENPINASGVDAKA
ILSARLSKSRRLENLIAQLPGEKKNGLFGNLIALS
LGLTPNFKSNFDLAEDAKLQLSKDTYDDDLDNLLA
QIGDQYADLFLAAKNLSDAILLSDILRVNTEITKA
PLSASMIKRYDEHHQDLTLLKALVRQQLPEKYKEI
FFDQSKNGYAGYIDGGASQEEFYKFIKPILEKMDG
TEELLVKLNREDLLRKQRTFDNGSIPHQIHLGELH
AILRRQEDFYPFLKDNREKIEKILTFRIPYYVGPL
ARGNSRFAWMTRKSEETITPWNFEEVVDKGASAQS
FIERMTNFDKNLPNEKVLPKHSLLYEYFTVYNELT
KVKYVTEGMRKPAFLSGEQKKAIVDLLFKTNRKVT
VKQLKEDYFKKIECFDSVEISGVEDRFNASLGTYH
DLLKIIKDKDFLDNEENEDILEDIVLTLTLFEDRE
MIEERLKTYAHLFDDKVMKQLKRRRYTGWGRLSRK
LINGIRDKQSGKTILDFLKSDGFANRNFMQLIHDD
SLTFKEDIQKAQVSGQGDSLHEHIANLAGSPAIKK
GILQTVKVVDELVKVMGRHKPENIVIEMARENQTT
QKGQKNSRERMKRIEEGIKELGSQILKEHPVENTQ
LQNEKLYLYYLQNGRDMYVDQELDINRLSDYDVDA
IVPQSFLKDDSIDNKVLTRSDKNRGKSDNVPSEEV
VKKMKNYWRQLLNAKLITQRKFDNLTKAERGGLSE
LDKAGFIKRQLVETRQITKHVAQILDSRMNTKYDE
NDKLIREVKVITLKSKLVSDFRKDFQFYKVREINN
YHHAHDAYLNAVVGTALIKKYPKLESEFVYGDYKV
YDVRKMIAKSEQEIGKATAKYFFYSNIMNFFKTEI
TLANGEIRKRPLIETNGETGEIVWDKGRDFATVRK
VLSMPQVNIVKKTEVQTGGFSKESILPKRNSDKLI
ARKKDWDPKKYGGFDSPTVAYSVLVVAKVEKGKSK
KLKSVKELLGITIMERSSFEKNPIDFLEAKGYKEV
KKDLIIKLPKYSLFELENGRKRMLASAGELQKGNE
LALPSKYVNFLYLASHYEKLKGSPEDNEQKQLFVE
QHKHYLDEIIEQISEFSKRVILADANLDKVLSAYN
KHRDKPIREQAENIIHLFTLTNLGAPAAFKYFDTT
IDRKRYTSTKEVLDATLIHQSITGLYETRIDLSQL
GGDEGADPKKKRKVDPKKKRKVDPKKKRKVGSMPA
MPSSGPGDTSSSAAEREEDRKDGEEQEEPRGKEER
QEPSTTARKVGRPGRKRKHPPVESGDTPKDPAVIS
KSPSMAQDSGASELLPNGDLEKRSEPQPEEGSPAG
GQKGGAPAEGEGAAETLPEASRAVENGCCTPKEGR
GAPAEAGKEQKETNIESMKMEGSRGRLRGGLGWES
SLRQRPMPRLTFQAGDPYYISKRKRDEWLARWKRE
AEKKAKVIAGMNAVEENQGPGESQKVEEASPPAVQ
QPTDPASPTVATTPEPVGSDAGDKNATKAGDDEPE
YEDGRGFGIGELVWGKLRGFSWWPGRIVSWWMTGR
SRAAEGTRWVMWFGDGKFSVVCVEKLMPLSSFCSA
FHQATYNKQPMYRKAIYEVLQVASSRAGKLFPVCH
DSDESDTAKAVEVQNKPMIEWALGGFQPSGPKGLE
PPEEEKNPYKEVYTDMWVEPEAAAYAPPPPAKKPR
KSTAEKPKVKEIIDERTRERLVYEVRQKCRNIEDI
CISCGSLNVTLEHPLFVGGMCQNCKNCFLECAYQY
DDDGYQSYCTICCGGREVLMCGNNNCCRCFCVECV
DLLVGPGAAQAAIKEDPWNCYMCGHKGTYGLLRRR
EDWPSRLQMFFANNHDQEFDPPKVYPPVPAEKRKP
IRVLSLFDGIATGLLVLKDLGIQVDRYIASAVCED
SITVGMVRHQGKIMYVGDVRSVTQKHIQEWGPFDL
VIGGSPCNDLSIVNPARKGLYEGTGRLFFEFYRLL
HDARPKEGDDRPFFWLFANVVAMGVSDKRDISRFL
ESNPVMIDAKEVSAAHRARYFWGNLPGMNRPLAST
VNDKLELQECLEHGRIAKFSKVRTITTRSNSIKQG
KDQHFPVFMNEKEDILWCTEMERVFGFPVHYTDVS
NMSRLARQRLLGRSWSVPVIRHLFAPLKEYFACV dCas9-Tet1CD (dC-T)
(SEQ ID NO: 159)
MDKKYSIGLAIGTNSVGWAVITDEYKVPSKKFKVL
GNTDRHSIKKNLIGALLFDSGETAEATRLKRTARR
RYTRRKNRICYLQEIFSNEMAKVDDSFFHRLEESF
LVEEDKKHERHPIFGNIVDEVAYHEKYPTIYHLRK
KLVDSTDKADLRLIYLALAHMIKFRGHFLIEGDLN
PDNSDVDKLFIQLVQTYNQLFEENPINASGVDAKA
ILSARLSKSRRLENLIAQLPGEKKNGLFGNLIALS
LGLTPNFKSNFDLAEDAKLQLSKDTYDDDLDNLLA
QIGDQYADLFLAAKNLSDAILLSDILRVNTEITKA
PLSASMIKRYDEHHQDLTLLKALVRQQLPEKYKEI
FFDQSKNGYAGYIDGGASQEEFYKFIKPILEKMDG
TEELLVKLNREDLLRKQRTFDNGSIPHQIHLGELH
AILRRQEDFYPFLKDNREKIEKILTFRIPYYVGPL
ARGNSRFAWMTRKSEETITPWNFEEVVDKGASAQS
FIERMTNFDKNLPNEKVLPKHSLLYEYFTVYNELT
KVKYVTEGMRKPAFLSGEQKKAIVDLLFKTNRKVT
VKQLKEDYFKKIECFDSVEISGVEDRFNASLGTYH
DLLKIIKDKDFLDNEENEDILEDIVLTLTLFEDRE
MIEERLKTYAHLFDDKVMKQLKRRRYTGWGRLSRK
LINGIRDKQSGKTILDFLKSDGFANRNFMQLIHDD
SLTFKEDIQKAQVSGQGDSLHEHIANLAGSPAIKK
GILQTVKVVDELVKVMGRHKPENIVIEMARENQTT
QKGQKNSRERMKRIEEGIKELGSQILKEHPVENTQ
LQNEKLYLYYLQNGRDMYVDQELDINRLSDYDVDA
IVPQSFLKDDSIDNKVLTRSDKNRGKSDNVPSEEV
VKKMKNYWRQLLNAKLITQRKFDNLTKAERGGLSE
LDKAGFIKRQLVETRQITKHVAQILDSRMNTKYDE
NDKLIREVKVITLKSKLVSDFRKDFQFYKVREINN
YHHAHDAYLNAVVGTALIKKYPKLESEFVYGDYKV
YDVRKMIAKSEQEIGKATAKYFFYSNIMNFFKTEI
TLANGEIRKRPLIETNGETGEIVWDKGRDFATVRK
VLSMPQVNIVKKTEVQTGGFSKESILPKRNSDKLI
ARKKDWDPKKYGGFDSPTVAYSVLVVAKVEKGKSK
KLKSVKELLGITIMERSSFEKNPIDFLEAKGYKEV
KKDLIIKLPKYSLFELENGRKRMLASAGELQKGNE
LALPSKYVNFLYLASHYEKLKGSPEDNEQKQLFVE
QHKHYLDEIIEQISEFSKRVILADANLDKVLSAYN
KHRDKPIREQAENIIHLFTLTNLGAPAAFKYFDTT
IDRKRYTSTKEVLDATLIHQSITGLYETRIDLSQL
GGDEGADPKKKRKVDPKKKRKVDPKKKRKVGSMPA
CSCLDRVIQKDKGPYYTHLGAGPSVAAVREIMENR
YGQKGNAIRIEIVVYTGKEGKSSHGCPIAKWVLRR
SSDEEKVLCLVRQRTGHHCPTAVMVVLIMVWDGIP
LPMADRLYTELTENLKSYNGHPTDRRCTLNENRTC
TCQGIDPETCGASFSFGCSWSMYFNGCKFGRSPSP
RRFRIDPSSPLHEKNLEDNLQSLATRLXPIYKQYA
PVAYQNQVEYENVARECRLGSKEGRPFSGVTACLD
FCAHPHRDIHNMMNGSTVVCTLTREDNRSLGVIPQ
DEQLHVLPLYKLSDTDEFGSKEGMEAKIKSGAIEV SUPPLEMENTAL TABLE S6-continued Full length protein sequences of
dCas9-Dnmt3a/Tet and mutants LAPRRKKRTCFTQPVPRSGKKRAAMMTEVLAHKIR
AVEKKPIPRIKRKNNSTTTNNSKPSSLPTLGSNTE
TVQPEVKSETEPHFILKSSDNTKTYSLMPSAPHPV
KEASPGFSWSPKTASATPAPLKNDATASCGFSERS
STPHCTMPSGRLSGANAAAADGPGISQLGEVAPLP
TLSAPVMEPLINSEPSTGVTEPLTPHQPNHQPSFL
TSPQDLASSPMEEDEQHSEADEPPSDEPLSDDPLS
PAEEKLPHIDEYWSDSEHIFLDANIGGVAIAPAHG
SVLIECARRELHATTPVEHPNRNHPTRLSLVFYQH
KNLNKPQHGFELNKIKFEAKEAKNKKMKASEQKDQ
AANEGPEQSSEVNELNQIPSHKALTLTHDNVVTVS
PYALTHVAGPYNHWV dCas9-Tet1CD_IM (dC-dT, an inactive
mutant form of Tet1)

(SEQ ID NO: 160)
MDKKYSIGLAIGTNSVGWAVITDEYKVPSKKFKVL
GNTDRHSIKKNLIGALLFDSGETAEATRLKRTARR
RYTRRKNRICYLQEIFSNEMAKVDDSFFHRLEESF
LVEEDKKHERHPIFGNIVDEVAYHEKYPTIYHLRK
KLVDSTDKADLRLIYLALAHMIKFRGHFLIEGDLN
PDNSDVDKLFIQLVQTYNQLFEENPINASGVDAKA
ILSARLSKSRRLENLIAQLPGEKKNGLFGNLIALS
LGLTPNFKSNFDLAEDAKLQLSKDTYDDDLDNLLA
QIGDQYADLFLAAKNLSDAILLSDILRVNTEITKA
PLSASMIKRYDEHHQDLTLLKALVRQQLPEKYKEI
FFDQSKNGYAGYIDGGASQEEFYKFIKPILEKMDG
TEELLVKLNREDLLRKQRTFDNGSIPHQIHLGELH
AILRRQEDFYPFLKDNREKIEKILTFRIPYYVGPL
ARGNSRFAWMTRKSEETITPWNFEEVVDKGASAQS
FIERMTNFDKNLPNEKVLPKHSLLYEYFTVYNELT
KVKYVTEGMRKPAFLSGEQKKAIVDLLFKTNRKVT
VKQLKEDYFKKIECFDSVEISGVEDRFNASLGTYH
DLLKIIKDKDFLDNEENEDILEDIVLTLTLFEDRE
MIEERLKTYAHLFDDKVMKQLKRRRYTGWGRLSRK
LINGIRDKQSGKTILDFLKSDGFANRNFMQLIHDD
SLTFKEDIQKAQVSGQGDSLHEHIANLAGSPAIKK
GILQTVKVVDELVKVMGRHKPENIVIEMARENQTT
QKGQKNSRERMKRIEEGIKELGSQILKEHPVENTQ
LQNEKLYLYYLQNGRDMYVDQELDINRLSDYDVDA
IVPQSFLKDDSIDNKVLTRSDKNRGKSDNVPSEEV
VKKMKNYWRQLLNAKLITQRKFDNLTKAERGGLSE
LDKAGFIKRQLVETRQITKHVAQILDSRMNTKYDE
NDKLIREVKVITLKSKLVSDFRKDFQFYKVREINN
YHHAHDAYLNAVVGTALIKKYPKLESEFVYGDYKV
YDVRKMIAKSEQEIGKATAKYFFYSNIMNFFKTEI
TLANGEIRKRPLIETNGETGEIVWDKGRDFATVRK
VLSMPQVNIVKKTEVQTGGFSKESILPKRNSDKLI
ARKKDWDPKKYGGFDSPTVAYSVLVVAKVEKGKSK
KLKSVKELLGITIMERSSFEKNPIDFLEAKGYKEV
KKDLIIKLPKYSLFELENGRKRMLASAGELQKGNE
LALPSKYVNFLYLASHYEKLKGSPEDNEQKQLFVE
QHKHYLDEIIEQISEFSKRVILADANLDKVLSAYN
KHRDKPIREQAENIIHLFTLTNLGAPAAFKYFDTT
IDRKRYTSTKEVLDATLIHQSITGLYETRIDLSQL
GGDEGADPKKKRKVDPKKKRKVDPKKKRKVGSLPT
CSCLDRVIQKDKGPYYTHLGAGPSVAAVREIMENR
YGQKGNAIRIEIVVYTGKEGKSSHGCPIAKWVLRR
SSDEEKVLCLVRQRTGHHCPTAVMVVLIMVWDGIP
LPMADRLYTELTENLKSYNGHPTDRRCTLNENRTC
TCQGIDPETCGASFSFGCSWSMYFNGCKFGRSPSP
RRFRIDPSSPLHEKNLEDNLQSLATRXUXPIYKQYA
PVAYQNQVEYENVARECRLGSKEGRPFSGVTACLD
FCAHPYRAIHNMNNGSTVVCTLTREDNRSLGVIPQ
DEQLHVLPLYKLSDTDEFGSKEGMEAKIKSGAIEV
LAPRRKKRTCFTQPVPRSGKKRAAMMTEVLAHKIR
AVEKKPIPRIKRKNNSTTTNNSKPSSLPTLGSNTE
TVQPEVKSETEPHFILKSSDNTKTYSLMPSAPHPV
KEASPGFSWSPKTASATPAPLKNDATASCGFSERS
STPHCTMPSGRLSGANAAAADGPGISQLGEVAPLP
TLSAPVMEPLINSEPSTGVTEPLTPHQPNHQPSFL
TSPQDLASSPMEEDEQHSEADEPPSDEPLSDDPLS
PAEEKLPHIDEYWSDSEHIFLDANIGGVAIAPAHG
SVLIECARRELHATTPVEHPNRNHPTRLSLVFYQH
KNLNKPQHGFELNKIKFEAKEAKNKKMKASEQKDQ
AANEGPEQSSEVNELNQIPSHKALTLTHDNVVTVS
PYALTHVAGPYNHWV dCas9-Dnmt3a-P2A-BFP (SEQ ID NO: 161)
MDKKYSIGLAIGTNSVGWAVITDEYKVPSKKFKVL
GNTDRHSIKKNLIGALLFDSGETAEATRLKRTARR
RYTRRKNRICYLQEIFSNEMAKVDDSFFHRLEESF
LVEEDKKHERHPIFGNIVDEVAYHEKYPTIYHLRK
KLVDSTDKADLRLIYLALAHMIKFRGHFLIEGDLN
PDNSDVDKLFIQLVQTYNQLFEENPINASGVDAKA
ILSARLSKSRRLENLIAQLPGEKKNGLFGNLIALS
LGLTPNFKSNFDLAEDAKLQLSKDTYDDDLDNLLA
QIGDQYADLFLAAKNLSDAILLSDILRVNTEITKA
PLSASMIKRYDEHHQDLTLLKALVRQQLPEKYKEI
FFDQSKNGYAGYIDGGASQEEFYKFIKPILEKMDG
TEELLVKLNREDLLRKQRTFDNGSIPHQIHLGELH
AILRRQEDFYPFLKDNREKIEKILTFRIPYYVGPL
ARGNSRFAWMTRKSEETITPWNFEEVVDKGASAQS
FIERMTNFDKNLPNEKVLPKHSLLYEYFTVYNELT
KVKYVTEGMRKPAFLSGEQKKAIVDLLFKTNRKVT
VKQLKEDYFKKIECFDSVEISGVEDRFNASLGTYH
DLLKIIKDKDFLDNEENEDILEDIVLTLTLFEDRE
MIEERLKTYAHLFDDKVMKQLKRRRYTGWGRLSRK
LINGIRDKQSGKTILDFLKSDGFANRNFMQLIHDD
SLTFKEDIQKAQVSGQGDSLHEHIANLAGSPAIKK
GILQTVKVVDELVKVMGRHKPENIVIEMARENQTT
QKGQKNSRERMKRIEEGIKELGSQILKEHPVENTQ
LQNEKLYLYYLQNGRDMYVDQELDINRLSDYDVDA
IVPQSFLKDDSIDNKVLTRSDKNRGKSDNVPSEEV
VKKMKNYWRQLLNAKLITQRKFDNLTKAERGGLSE
LDKAGFIKRQLVETRQITKHVAQILDSRMNTKYDE
NDKLIREVKVITLKSKLVSDFRKDFQFYKVREINN
YHHAHDAYLNAVVGTALIKKYPKLESEFVYGDYKV
YDVRKMIAKSEQEIGKATAKYFFYSNIMNFFKTEI
TLANGEIRKRPLIETNGETGEIVWDKGRDFATVRK
VLSMPQVNIVKKTEVQTGGFSKESILPKRNSDKLI
ARKKDWDPKKYGGFDSPTVAYSVLVVAKVEKGKSK
KLKSVKELLGITIMERSSFEKNPIDFLEAKGYKEV
KKDLIIKLPKYSLFELENGRKRMLASAGELQKGNE
LALPSKYVNFLYLASHYEKLKGSPEDNEQKQLFVE
QHKHYLDEIIEQISEFSKRVILADANLDKVLSAYN
KHRDKPIREQAENIIHLFTLTNLGAPAAFKYFDTT
IDRKRYTSTKEVLDATLIHQSITGLYETRIDLSQL
GGDEGADPKKKRKVDPKKKRKVDPKKKRKVGSMPA
MPSSGPGDTSSSAAEREEDRKDGEEQEEPRGKEER
QEPSTTARKVGRPGRKRKHPPVESGDTPKDPAVIS
KSPSMAQDSGASELLPNGDLEKRSEPQPEEGSPAG
GQKGGAPAEGEGAAETLPEASRAVENGCCTPKEGR
GAPAEAGKEQKETNIESMKMEGSRGRLRGGLGWES
SLRQRPMPRLTFQAGDPYYISKRKRDEWLARWKRE
AEKKAKVIAGMNAVEENQGPGESQKVEEASPPAVQ
QPTDPASPTVATTPEPVGSDAGDKNATKAGDDEPE
YEDGRGFGIGELVWGKLRGFSWWPGRIVSWWMTGR
SRAAEGTRWVMWFGDGKFSVVCVEKLMPLSSFCSA
FHQATYNKQPMYRKAIYEVLQVASSRAGKLFPVCH
DSDESDTAKAVEVQNKPMIEWALGGFQPSGPKGLE
PPEEEKNPYKEVYTDMWVEPEAAAYAPPPAKKPR
KSTAEKPKVKEIIDERTRERLVYEVRQKCRNIEDI
CISCGSLNVTLEHPLFVGGMCQNCKNCFLECAYQY
DDDGYQSYCTICCGGREVLMCGNNNCCRCFCVECV
DLLVGPGAAQAAIKEDPWNCYMCGHKGTYGLLRRR
EDWPSRLQMFFANNHDQEFDPPKVYPPVPAEKRKP
IRVLSLFDGIATGLLVLKDLGIQVDRYIASEVCED
SITVGMVRHQGKIMYVGDVRSVTQKHIQEWGPFDL
VIGGSPCNDLSIVNPARKGLYEGTGRLFFEFYRLL
HDARPKEGDDRPFFWLFENVVAMGVSDKRDISRFL
ESNPVMIDAKEVSAAHRARYFWGNLPGMNRPLAST
VNDKLELQECLEHGRIAKFSKVRTITTRSNSIKQG
KDQHFPVFMNEKEDILWCTEMERVFGFPVHYTDVS
NMSRLARQRLLGRSWSVPVIRHLFAPLKEYFACVE
FAYPYDVPDYAATNFSLLKQAGDVEENGPMSELI
KENMHMKLYMEGTVDNHHFKCTSEGEGKPYEGTQT
MRIKVVEGGPLPFAFDILATSFLYGSKTFINHTQG
IPDFFKQSFPEGFTWERVTTYEDGGVLTATQDTSL SUPPLEMENTAL TABLE S6-continued Full length protein sequences of
dCas9-Dnmt3a/Tet and mutants QDGCLIYNVKIRGVNFTSNGPVMQKKTLGWEAFTE
TLYPADGGLEGRNDMALKLVGGSHLIANIKTTYRS
KKPAKNLKMPGVYYVDYRLERIKEANNETYVEQHE
VAVARYCDLPSKLGHKLN

REFERENCES (THE CONTENTS OF WHICH ARE HEREBY INCORPORATED BY REFERENCE IN THEIR ENTIRETY)

Bell, A. C., and Felsenfeld, G. (2000). Methylation of a CTCF-dependent boundary controls imprinted expression of the Igf2 gene. Nature 405, 482-485.

Bernstein, D. L., Le Lay, J. E., Ruano, E. G., and Kaestner, K. H. (2015). TALE-mediated epigenetic suppression of CDKN2A increases replication in human fibroblasts. J Clin Invest 125, 1998-2006.

Bird, A. (2002). DNA methylation patterns and epigenetic memory. Genes Dev 16, 6-21. Boch, J., and Bonas, U. (2010). *Xanthomonas* AvrBs3 family-type III effectors: discovery and function. Annual review of phytopathology 48, 419-436.

Brunk, B. P., Goldhamer, D. J., and Emerson, C. P., Jr. (1996). Regulated demethylation of the myoD distal enhancer during skeletal myogenesis. Dev Biol 177, 490-503.

Carroll, D. (2008). Progress and prospects: zinc-finger nucleases as gene therapy agents. Gene Ther 15, 1463-1468.

Cedar, H., and Bergman, Y. (2012). Programming of DNA methylation patterns. Annu Rev Biochem 81, 97-117.

Chen, B., Gilbert, L. A., Cimini, B. A., Schnitzbauer, J., Zhang, W., Li, G. W., Park, J., Blackburn, E. H., Weissman, J. S., Qi, L. S., et al. (2013). Dynamic imaging of genomic loci in living human cells by an optimized CRISPR/Cas system. Cell 155, 1479-1491.

Chen, W. G., Chang, Q., Lin, Y., Meissner, A., West, A. E., Griffith, E. C., Jaenisch, R., and Greenberg, M. E. (2003). Derepression of BDNF transcription involves calcium-dependent phosphorylation of MeCP2. Science 302, 885-889.

Choudhury, S. R., Cui, Y., Lubecka, K., Stefanska, B., and Irudayaraj, J. (2016). CRISPR-dCas9 mediated TET1 targeting for selective DNA demethylation at BRCA1 promoter. Oncotarget.

Cong, L., Ran, F. A., Cox, D., Lin, S. L., Barretto, R., Habib, N., Hsu, P. D., Wu, X. B., Jiang, W. Y., Marraffini, L. A., et al. (2013). Multiplex Genome Engineering Using CRISPR/Cas Systems. Science 339, 819-823.

Constantinides, P. G., Jones, P. A., and Gevers, W. (1977). Functional striated muscle cells from non-myoblast precursors following 5-azacytidine treatment. Nature 267, 364-366.

Davis, R. L., Weintraub, H., and Lassar, A. B. (1987). Expression of a single transfected cDNA converts fibroblasts to myoblasts. Cell 51, 987-1000.

Dawlaty, M. M., Breiling, A., Le, T., Barrasa, M. I., Raddatz, G., Gao, Q., Powell, B. E., Cheng, A. W., Faull, K. F., Lyko, F., et al. (2014). Loss of Tet enzymes compromises proper differentiation of embryonic stem cells. Dev Cell 29, 102-111.

Dawlaty, M. M., Ganz, K., Powell, B. E., Hu, Y. C., Markoulaki, S., Cheng, A. W., Gao, Q., Kim, J., Choi, S. W., Page, D. C., et al. (2011). Tet1 is dispensable for maintaining pluripotency and its loss is compatible with embryonic and postnatal development. Cell Stem Cell 9, 166-175.

De Jager, P. L., Srivastava, G., Lunnon, K., Burgess, J., Schalkwyk, L. C., Yu, L., Eaton, M. L., Keenan, B. T., Ernst, J., McCabe, C., et al. (2014). Alzheimer's disease: early alterations in brain DNA methylation at ANK1, BIN1, RHBDF2 and other loci. Nat Neurosci 17, 1156-1163.

Dixon, J. R., Selvaraj, S., Yue, F., Kim, A., Li, Y., Shen, Y., Hu, M., Liu, J. S., and Ren, B. (2012). Topological domains in mammalian genomes identified by analysis of chromatin interactions. Nature 485, 376-380.

Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21.

Doi, A., Park, I. H., Wen, B., Murakami, P., Aryee, M. J., Irizarry, R., Herb, B., Ladd-Acosta, C., Rho, J., Loewer, S., et al. (2009). Differential methylation of tissue- and cancer-specific CpG island shores distinguishes human induced pluripotent stem cells, embryonic stem cells and fibroblasts. Nat Genet 41, 1350-1353.

Dowen, J. M., Fan, Z. P., Hnisz, D., Ren, G., Abraham, B. J., Zhang, L. N., Weintraub, A. S., Schuijers, J., Lee, T. I., Zhao, K., et al. (2014). Control of cell identity genes occurs in insulated neighborhoods in mammalian chromosomes. Cell 159, 374-387.

Ebert, D. H., Gabel, H. W., Robinson, N. D., Kastan, N. R., Hu, L. S., Cohen, S., Navarro, A. J., Lyst, M. J., Ekiert, R., Bird, A. P., et al. (2013). Activity-dependent phosphorylation of MeCP2 threonine 308 regulates interaction with NCoR. Nature 499, 341-345.

Flavahan, W. A., Drier, Y., Liau, B. B., Gillespie, S. M., Venteicher, A. S., Stemmer-Rachamimov, A. O., Suva, M. L., and Bernstein, B. E. (2016). Insulator dysfunction and oncogene activation in IDH mutant gliomas. Nature 529, 110-114.

Gibcus, J. H., and Dekker, J. (2013). The hierarchy of the 3D genome. Mol Cell 49, 773-782.

Gilbert, L. A., Larson, M. H., Morsut, L., Liu, Z., Brar, G. A., Torres, S. E., Stern-Ginossar, N., Brandman, O., Whitehead, E. H., Doudna, J. A., et al. (2013). CRISPR-mediated modular RNA-guided regulation of transcription in eukaryotes. Cell 154, 442-451.

Gorkin, D. U., Leung, D., and Ren, B. (2014). The 3D genome in transcriptional regulation and pluripotency. Cell Stem Cell 14, 762-775.

Guo, J. U., Su, Y., Zhong, C., Ming, G. L., and Song, H. (2011). Hydroxylation of 5-methylcytosine by TET1 promotes active DNA demethylation in the adult brain. Cell 145, 423-434.

Hilton, I. B., D'Ippolito, A. M., Vockley, C. M., Thakore, P. I., Crawford, G. E., Reddy, T. E., and Gersbach, C. A. (2015). Epigenome editing by a CRISPR-Cas9-based acetyltransferase activates genes from promoters and enhancers. Nat Biotechnol 33, 510-517.

Hockemeyer, D., Soldner, F., Beard, C., Gao, Q., Mitalipova, M., DeKelver, R. C., Katibah, G. E., Amora, R., Boydston, E. A., Zeitler, B., et al. (2009). Efficient targeting of expressed and silent genes in human ESCs and iPSCs using zinc-finger nucleases. Nat Biotechnol 27, 851-857.

Hockemeyer, D., Wang, H., Kiani, S., Lai, C. S., Gao, Q., Cassady, J. P., Cost, G. J., Zhang, L., Santiago, Y., Miller, J. C., et al. (2011). Genetic engineering of human pluripotent cells using TALE nucleases. Nat Biotechnol 29, 731-734.

Jaenisch, R., and Bird, A. (2003). Epigenetic regulation of gene expression: how the genome integrates intrinsic and environmental signals. Nat Genet 33 Suppl, 245-254.

Ji, X., Dadon, D. B., Powell, B. E., Fan, Z. P., Borges-Rivera, D., Shachar, S., Weintraub, A. S., Hnisz, D., Pegoraro, G., Lee, T. I., et al. (2016). 3D Chromosome Regulatory Landscape of Human Pluripotent Cells. Cell Stem Cell 18, 262-275.

Jinek, M., Chylinski, K., Fonfara, I., Hauer, M., Doudna, J. A., and Charpentier, E. (2012). A programmable dual-RNA-guided DNA endonuclease in adaptive bacterial immunity. Science 337, 816-821.

Kagey, M. H., Newman, J. J., Bilodeau, S., Zhan, Y., Orlando, D. A., van Berkum, N. L., Ebmeier, C. C., Goossens, J., Rahl, P. B., Levine, S. S., et al. (2010). Mediator and cohesin connect gene expression and chromatin architecture. Nature 467, 430-435.

Kang, J. Y., Song, S. H., Yun, J., Jeon, M. S., Kim, H. P., Han, S. W., and Kim, T. Y. (2015). Disruption of CTCF/cohesin-mediated high-order chromatin structures by DNA methylation downregulates PTGS2 expression. Oncogene 34, 5677-5684.

Konermann, S., Brigham, M. D., Trevino, A. E., Joung, J., Abudayyeh, O. O., Barcena, C., Hsu, P. D., Habib, N., Gootenberg, J. S., Nishimasu, H., et al. (2015). Genome-scale transcriptional activation by an engineered CRISPR-Cas9 complex. Nature 517, 583-U332.

Laird, P. W., and Jaenisch, R. (1996). The role of DNA methylation in cancer genetics and epigenetics. Annual Review of Genetics 30, 441-464.

Landau, D. A., Clement, K., Ziller, M. J., Boyle, P., Fan, J., Gu, H., Stevenson, K., Sougnez, C., Wang, L., Li, S., et al. (2014). Locally disordered methylation forms the basis of intratumor methylome variation in chronic lymphocytic leukemia. Cancer Cell 26, 813-825.

Lassar, A. B., Paterson, B. M., and Weintraub, H. (1986). Transfection of a DNA locus that mediates the conversion of 10T1/2 fibroblasts to myoblasts. Cell 47, 649-656.

Li, E., Bestor, T. H., and Jaenisch, R. (1992). Targeted mutation of the DNA methyltransferase gene results in embryonic lethality. Cell 69, 915-926.

Lin, Y., Bloodgood, B. L., Hauser, J. L., Lapan, A. D., Koon, A. C., Kim, T. K., Hu, L. S., Malik, A. N., and Greenberg, M. E. (2008). Activity-dependent regulation of inhibitory synapse development by Npas4. Nature 455, 1198-1204.

Lister, R., Mukamel, E. A., Nery, J. R., Urich, M., Puddifoot, C. A., Johnson, N. D., Lucero, J., Huang, Y., Dwork, A. J., Schultz, M. D., et al. (2013). Global Epigenomic Reconfiguration During Mammalian Brain Development. Science 341, 629-+.

Lister, R., Pelizzola, M., Dowen, R. H., Hawkins, R. D., Hon, G., Tonti-Filippini, J., Nery, J. R., Lee, L., Ye, Z., Ngo, Q. M., et al. (2009). Human DNA methylomes at base resolution show widespread epigenomic differences. Nature 462, 315-322.

Maeder, M. L., Angstman, J. F., Richardson, M. E., Linder, S. J., Cascio, V. M., Tsai, S. Q., Ho, Q. H., Sander, J. D., Reyon, D., Bernstein, B. E., et al. (2013). Targeted DNA demethylation and activation of endogenous genes using programmable TALE-TET1 fusion proteins. Nat Biotechnol 31, 1137-1142.

Mali, P., Yang, L., Esvelt, K. M., Aach, J., Guell, M., DiCarlo, J. E., Norville, J. E., and Church, G. M. (2013). RNA-guided human genome engineering via Cas9. Science 339, 823-826.

Martinowich, K., Hattori, D., Wu, H., Fouse, S., He, F., Hu, Y., Fan, G., and Sun, Y. E. (2003). DNA methylation-related chromatin remodeling in activity-dependent BDNF gene regulation. Science 302, 890-893.

Narendra, V., Rocha, P. P., An, D., Raviram, R., Skok, J. A., Mazzoni, E. O., and Reinberg, D. (2015). CTCF establishes discrete functional chromatin domains at the Hox clusters during differentiation. Science 347, 1017-1021.

Nora, E. P., Lajoie, B. R., Schulz, E. G., Giorgetti, L., Okamoto, I., Servant, N., Piolot, T., van Berkum, N. L., Meisig, J., Sedat, J., et al. (2012). Spatial partitioning of the regulatory landscape of the X-inactivation centre. Nature 485, 381-385.

Phillips-Cremins, J. E., Sauria, M. E., Sanyal, A., Gerasimova, T. I., Lajoie, B. R., Bell, J. S., Ong, C. T., Hookway, T. A., Guo, C., Sun, Y., et al. (2013). Architectural protein subclasses shape 3D organization of genomes during lineage commitment. Cell 153, 1281-1295.

Phillips, J. E., and Corces, V. G. (2009). CTCF: master weaver of the genome. Cell 137, 1194-1211.

Qi, L. S., Larson, M. H., Gilbert, L. A., Doudna, J. A., Weissman, J. S., Arkin, A. P., and Lim, W. A. (2013). Repurposing CRISPR as an RNA-guided platform for sequence-specific control of gene expression. Cell 152, 1173-1183.

Robertson, K. D. (2005). DNA methylation and human disease. Nat Rev Genet 6,597-610.

Schultz, M. D., He, Y., Whitaker, J. W., Hariharan, M., Mukamel, E. A., Leung, D., Rajagopal, N., Nery, J. R., Urich, M. A., Chen, H., et al. (2015). Human body epigenome maps reveal noncanonical DNA methylation variation. Nature 523, 212-216.

Seitan, V. C., Faure, A. J., Zhan, Y., McCord, R. P., Lajoie, B. R., Ing-Simmons, E., Lenhard, B., Giorgetti, L., Heard, E., Fisher, A. G., et al. (2013). Cohesin-based chromatin interactions enable regulated gene expression within preexisting architectural compartments. Genome Res 23, 2066-2077.

Smith, Z. D., and Meissner, A. (2013). DNA methylation: roles in mammalian development. Nat Rev Genet 14, 204-220.

Sofueva, S., Yaffe, E., Chan, W. C., Georgopoulou, D., Vietri Rudan, M., Mira-Bontenbal, H., Pollard, S. M., Schroth, G. P., Tanay, A., and Hadjur, S. (2013). Cohesin-mediated interactions organize chromosomal domain architecture. EMBO J 32, 3119-3129.

Stelzer, Y., Shivalila, C. S., Soldner, F., Markoulaki, S., and Jaenisch, R. (2015). Tracing dynamic changes of DNA methylation at single-cell resolution. Cell 163, 218-229.

Sweatt, J. D. (2013). The emerging field of neuroepigenetics. Neuron 80, 624-632.

Tang, Z., Luo, O. J., Li, X., Zheng, M., Zhu, J. J., Szalaj, P., Trzaskoma, P., Magalska, A., Wlodarczyk, J., Ruszczycki, B., et al. (2015). CTCF-Mediated Human 3D Genome Architecture Reveals Chromatin Topology for Transcription. Cell 163, 1611-1627.

Vojta, A., Dobrinic, P., Tadic, V., Bockor, L., Korac, P., Julg, B., Klasic, M., and Zoldos, V. (2016). Repurposing the CRISPR-Cas9 system for targeted DNA methylation. Nucleic Acids Res 44, 5615-5628.

Wang, H., Maurano, M. T., Qu, H., Varley, K. E., Gertz, J., Pauli, F., Lee, K., Canfield, T., Weaver, M., Sandstrom, R., et al. (2012). Widespread plasticity in CTCF occupancy linked to DNA methylation. Genome Res 22, 1680-1688.

Wilson, M. H., Coates, C J., and George, A. L., Jr. (2007). PiggyBac transposon-mediated gene transfer in human cells. Mol Ther 15, 139-145.

Wu, H., Luo, J., Yu, H., Rattner, A., Mo, A., Wang, Y., Smallwood, P. M., Erlanger, B., Wheelan, S J., and Nathans, J. (2014a). Cellular resolution maps of X chromosome inactivation: implications for neural development, function, and disease. Neuron 81, 103-119.

Wu, H., and Zhang, Y. (2014). Reversing DNA methylation: mechanisms, genomics, and biological functions. Cell 156, 45-68.

Wu, X., Scott, D. A., Kriz, A. J., Chiu, A. C., Hsu, P. D., Dadon, D. B., Cheng, A. W., Trevino, A. E., Konermann, S., Chen, S., et al. (2014b). Genome-wide binding of the CRISPR endonuclease Cas9 in mammalian cells. Nat Biotechnol 32, 670-676.

Xu, W., Yang, H., Liu, Y., Yang, Y., Wang, P., Kim, S. H., Ito, S., Yang, C., Wang, P., Xiao, M. T., et al. (2011). Oncometabolite 2-hydroxyglutarate is a competitive inhibitor of alpha-ketoglutarate-dependent dioxygenases. Cancer Cell 19, 17-30.

Xu, X., Tao, Y., Gao, X., Zhang, L., Li, X., Zou, W., Ruan, K., Wang, F., Xu, G. L., and Hu, R. (2016). A CRISPR-based approach for targeted DNA demethylation. Cell discovery 2, 16009.

Yu, M., Hon, G. C., Szulwach, K. E., Song, C. X., Zhang, L., Kim, A., Li, X., Dai, Q., Shen, Y., Park, B., et al. (2012). Base-resolution analysis of 5-hydroxymethylcytosine in the mammalian genome. Cell 149, 1368-1380.

Zhang, Y., Liu, T., Meyer, C. A., Eeckhoute, J., Johnson, D. S., Bernstein, B. E., Nusbaum, C., Myers, R. M., Brown, M., Li, W., et al. (2008). Model-based analysis of ChIP-Seq (MACS). Genome Biol 9, R137.

Zuin, J., Dixon, J. R., van der Reijden, M. I., Ye, Z., Kolovos, P., Brouwer, R. W., van de Corput, M. P., van de Werken, H. J., Knoch, T. A., van, I. W. F., et al. (2014). Cohesin and CTCF differentially affect chromatin architecture and gene expression in human cells. Proc Natl Acad Sci USA 111, 996-1001.

PCT Application No. PCT/US2014/034387, filed Apr. 16, 2014, and U.S. application Ser. No. 15/078,851, filed Mar. 23, 2016.

What is claimed is:

1. A method of modulating the methylation of one or more genomic sequences in an individual, the method comprising administering to the individual: a. a nucleic acid that encodes a polypeptide comprising a catalytically inactive site specific nuclease fused to an effector domain having methylation or demethylation activity; b. a guide sequence or a nucleic acid that encodes a guide sequence, wherein the genomic sequence comprises a CTCF binding site or an enhancer of MyoD, and wherein the effector domain comprises Tet1 or Dnmt3a.

2. The method of claim 1, wherein the guide sequence targets the polypeptide to the one or more genomic sequences.

3. The method of claim 1, wherein the genomic sequence further comprises a differentially methylated region or a promoter.

4. The method of claim 1, wherein the method comprises modulating the methylation of at least two genomic sequences in a cell, wherein the genomic sequences are selected from differentially methylated regions, enhancers, promoters, and CTCF binding sites.

5. The method of claim 1, wherein the genomic sequence further comprises an enhancer or a promoter.

6. The method of claim 1, wherein the promoter is a BDNF promoter.

7. The method of claim 1, wherein the catalytically inactive site specific nuclease is a catalytically inactive Cas protein.

8. The method of claim 1, wherein the catalytically inactive site specific nuclease is a catalytically inactive Cas9 protein.

9. The method of claim 1, wherein the catalytically inactive site specific nuclease is a catalytically inactive Cpf1 protein.

10. The method of claim 1, wherein the guide sequence is a ribonucleic acid guide sequence.

11. The method of claim 1, wherein the guide sequence is from about 10 base pairs to about 150 base pairs in length.

12. The method of claim 1, wherein 2, 3, 4, 5, 6, 7, 8, 9, 10, 11, 12, 13, 14, 15, 16, 17, 18, 19, or 20 genomic sequences are modified in the individual.

13. The method of claim 1, wherein the individual is a human.

14. The method of claim 1, wherein the individual has a disease, disorder, or condition.

* * * * *

SEQUENCE LISTING

```
Sequence total quantity: 167
SEQ ID NO: 1            moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 1
gttttgaggc ctcatttgta agg                                                 23

SEQ ID NO: 2            moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 2
tttttgaaaa attaccttgt ggg                                                 23

SEQ ID NO: 3            moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 3
cagagtccta gacatttcca tgg                                                 23

SEQ ID NO: 4            moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 4
ggagagaggc ctcatttgta ggg                                                 23

SEQ ID NO: 5            moltype = DNA  length = 23
FEATURE                 Location/Qualifiers
misc_feature            1..23
                        note = guide RNA sequence
source                  1..23
                        mol_type = other DNA
                        organism = synthetic construct
```

```
SEQUENCE: 5
gttgtcagag catagcttgt agg                                               23

SEQ ID NO: 6            moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 6
ctaaagcgat gttccttcca ggg                                               23

SEQ ID NO: 7            moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 7
ttgctctcaa gacatttcca ggg                                               23

SEQ ID NO: 8            moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 8
ttgctttcca ttttcttcca ggg                                               23

SEQ ID NO: 9            moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 9
agcttctagc tctaccttct agg                                               23

SEQ ID NO: 10           moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 10
tctgcgagtc cttaatttta ggg                                               23

SEQ ID NO: 11           moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 11
aaagcatttt cttctttcca ggg                                               23

SEQ ID NO: 12           moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 12
agttgctgct cttttgtcca ggg                                               23

SEQ ID NO: 13           moltype = DNA  length = 23
FEATURE                 Location/Qualifiers
misc_feature            1..23
                        note = guide RNA sequence
source                  1..23
                        mol_type = other DNA
```

```
                        organism = synthetic construct
SEQUENCE: 13
acgcaactgc gagctttcaa agg                                              23

SEQ ID NO: 14           moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 14
tttaaagccc cttccttcca ggg                                              23

SEQ ID NO: 15           moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 15
actgtcttca acttccttgg ggg                                              23

SEQ ID NO: 16           moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 16
ggactactga gacatttcca ggg                                              23

SEQ ID NO: 17           moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 17
tcaaccctga gacatttcca ggg                                              23

SEQ ID NO: 18           moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 18
ccaagattga gacatttcca ggg                                              23

SEQ ID NO: 19           moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 19
taaagtccca gtccctccc tgg                                               23

SEQ ID NO: 20           moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 20
ctaagctctg tgttgttcca ggg                                              23

SEQ ID NO: 21           moltype = DNA  length = 23
FEATURE                 Location/Qualifiers
misc_feature            1..23
                        note = guide RNA sequence
source                  1..23
```

```
                        mol_type = other DNA
                        organism = synthetic construct
SEQUENCE: 21
gtagagcatg ttgagctgta ggg                                                23

SEQ ID NO: 22           moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 22
gagccgagct gtagggtgct tgg                                                23

SEQ ID NO: 23           moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 23
cgggcagcct gtagggtgct ggg                                                23

SEQ ID NO: 24           moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 24
gcgcaagggt tgtcgtgcct tgg                                                23

SEQ ID NO: 25           moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 25
cgcatgtgca gccattgcct ggg                                                23

SEQ ID NO: 26           moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 26
tttggtagct gccttttggc agg                                                23

SEQ ID NO: 27           moltype = DNA  length = 20
FEATURE                 Location/Qualifiers
misc_feature            1..20
                        note = guide RNA sequence
source                  1..20
                        mol_type = other DNA
                        organism = synthetic construct
SEQUENCE: 27
acaaacctga gccattgcgg                                                    20

SEQ ID NO: 28           moltype = DNA  length = 23
FEATURE                 Location/Qualifiers
misc_feature            1..23
                        note = guide RNA sequence
source                  1..23
                        mol_type = other DNA
                        organism = synthetic construct
SEQUENCE: 28
ccctgcagct gtagggtgct agg                                                23

SEQ ID NO: 29           moltype = DNA  length = 23
FEATURE                 Location/Qualifiers
misc_feature            1..23
                        note = guide RNA sequence
```

```
                        source              1..23
                                            mol_type = other DNA
                                            organism = synthetic construct
SEQUENCE: 29
tctcttcagt gtaattggct tgg                                                    23

SEQ ID NO: 30           moltype = DNA   length = 23
FEATURE                 Location/Qualifiers
misc_feature            1..23
                        note = guide RNA sequence
source                  1..23
                        mol_type = other DNA
                        organism = synthetic construct
SEQUENCE: 30
tccatttgct gtagggtgct agg                                                    23

SEQ ID NO: 31           moltype = DNA   length = 23
FEATURE                 Location/Qualifiers
misc_feature            1..23
                        note = guide RNA sequence
source                  1..23
                        mol_type = other DNA
                        organism = synthetic construct
SEQUENCE: 31
tgctaatgtc cccatttggc agg                                                    23

SEQ ID NO: 32           moltype = DNA   length = 23
FEATURE                 Location/Qualifiers
misc_feature            1..23
                        note = guide RNA sequence
source                  1..23
                        mol_type = other DNA
                        organism = synthetic construct
SEQUENCE: 32
gcacagcact gtagggtgct ggg                                                    23

SEQ ID NO: 33           moltype = DNA   length = 23
FEATURE                 Location/Qualifiers
misc_feature            1..23
                        note = guide RNA sequence
source                  1..23
                        mol_type = other DNA
                        organism = synthetic construct
SEQUENCE: 33
ccatctctct gtagggtgct ggg                                                    23

SEQ ID NO: 34           moltype = DNA   length = 23
FEATURE                 Location/Qualifiers
misc_feature            1..23
                        note = guide RNA sequence
source                  1..23
                        mol_type = other DNA
                        organism = synthetic construct
SEQUENCE: 34
gtgagctgct gtagggtgct agg                                                    23

SEQ ID NO: 35           moltype = DNA   length = 23
FEATURE                 Location/Qualifiers
misc_feature            1..23
                        note = guide RNA sequence
source                  1..23
                        mol_type = other DNA
                        organism = synthetic construct
SEQUENCE: 35
gaatggacct gtagggtgct tgg                                                    23

SEQ ID NO: 36           moltype = DNA   length = 24
FEATURE                 Location/Qualifiers
misc_feature            1..24
                        note = guide RNA primer sequence
source                  1..24
                        mol_type = other DNA
                        organism = synthetic construct
SEQUENCE: 36
ttggcccccg ggggaaaaat tttt                                                   24

SEQ ID NO: 37           moltype = DNA   length = 24
FEATURE                 Location/Qualifiers
misc_feature            1..24
```

```
                    note = guide RNA primer sequence
source              1..24
                    mol_type = other DNA
                    organism = synthetic construct
SEQUENCE: 37
aaacaaaaat ttttcccccg gggg                                              24

SEQ ID NO: 38           moltype = DNA  length = 24
FEATURE                 Location/Qualifiers
misc_feature            1..24
                        note = guide RNA primer sequence
source                  1..24
                        mol_type = other DNA
                        organism = synthetic construct
SEQUENCE: 38
ttggctacaa agcatgcaat gccc                                              24

SEQ ID NO: 39           moltype = DNA  length = 24
FEATURE                 Location/Qualifiers
misc_feature            1..24
                        note = guide RNA primer sequence
source                  1..24
                        mol_type = other DNA
                        organism = synthetic construct
SEQUENCE: 39
aaacgggcat tgcatgcttt gtag                                              24

SEQ ID NO: 40           moltype = DNA  length = 24
FEATURE                 Location/Qualifiers
misc_feature            1..24
                        note = guide RNA primer sequence
source                  1..24
                        mol_type = other DNA
                        organism = synthetic construct
SEQUENCE: 40
ttggaatgcg cggaattctg attc                                              24

SEQ ID NO: 41           moltype = DNA  length = 24
FEATURE                 Location/Qualifiers
misc_feature            1..24
                        note = guide RNA primer sequence
source                  1..24
                        mol_type = other DNA
                        organism = synthetic construct
SEQUENCE: 41
aaacgaatca gaattccgcg catt                                              24

SEQ ID NO: 42           moltype = DNA  length = 24
FEATURE                 Location/Qualifiers
misc_feature            1..24
                        note = guide RNA primer sequence
source                  1..24
                        mol_type = other DNA
                        organism = synthetic construct
SEQUENCE: 42
ttgggtgggt gggagtccac gaga                                              24

SEQ ID NO: 43           moltype = DNA  length = 24
FEATURE                 Location/Qualifiers
misc_feature            1..24
                        note = guide RNA primer sequence
source                  1..24
                        mol_type = other DNA
                        organism = synthetic construct
SEQUENCE: 43
aaactctcgt ggactcccac ccac                                              24

SEQ ID NO: 44           moltype = DNA  length = 24
FEATURE                 Location/Qualifiers
misc_feature            1..24
                        note = guide RNA primer sequence
source                  1..24
                        mol_type = other DNA
                        organism = synthetic construct
SEQUENCE: 44
ttggggcagc gtggagccct ctcg                                              24

SEQ ID NO: 45           moltype = DNA  length = 24
FEATURE                 Location/Qualifiers
```

```
misc_feature              1..24
                          note = guide RNA primer sequence
source                    1..24
                          mol_type = other DNA
                          organism = synthetic construct
SEQUENCE: 45
aaaccgagag ggctccacgc tgcc                                              24

SEQ ID NO: 46             moltype = DNA  length = 24
FEATURE                   Location/Qualifiers
misc_feature              1..24
                          note = guide RNA primer sequence
source                    1..24
                          mol_type = other DNA
                          organism = synthetic construct
SEQUENCE: 46
ttgggagccg agctgtaggg tgct                                              24

SEQ ID NO: 47             moltype = DNA  length = 24
FEATURE                   Location/Qualifiers
misc_feature              1..24
                          note = guide RNA primer sequence
source                    1..24
                          mol_type = other DNA
                          organism = synthetic construct
SEQUENCE: 47
aaacagcacc ctacagctcg gctc                                              24

SEQ ID NO: 48             moltype = DNA  length = 24
FEATURE                   Location/Qualifiers
misc_feature              1..24
                          note = guide RNA primer sequence
source                    1..24
                          mol_type = other DNA
                          organism = synthetic construct
SEQUENCE: 48
ttggtttggt agctgccttt tggc                                              24

SEQ ID NO: 49             moltype = DNA  length = 24
FEATURE                   Location/Qualifiers
misc_feature              1..24
                          note = guide RNA primer sequence
source                    1..24
                          mol_type = other DNA
                          organism = synthetic construct
SEQUENCE: 49
aaacgccaaa aggcagctac caaa                                              24

SEQ ID NO: 50             moltype = DNA  length = 24
FEATURE                   Location/Qualifiers
misc_feature              1..24
                          note = guide RNA primer sequence
source                    1..24
                          mol_type = other DNA
                          organism = synthetic construct
SEQUENCE: 50
ttggcgcatg tgcagccatt gcct                                              24

SEQ ID NO: 51             moltype = DNA  length = 24
FEATURE                   Location/Qualifiers
misc_feature              1..24
                          note = guide RNA primer sequence
source                    1..24
                          mol_type = other DNA
                          organism = synthetic construct
SEQUENCE: 51
aaacaggcaa tggctgcaca tgcg                                              24

SEQ ID NO: 52             moltype = DNA  length = 21
FEATURE                   Location/Qualifiers
misc_feature              1..21
                          note = guide RNA primer sequence
source                    1..21
                          mol_type = other DNA
                          organism = synthetic construct
SEQUENCE: 52
ttggacaaac ctgagccatt g                                                 21

SEQ ID NO: 53             moltype = DNA  length = 21
```

```
FEATURE                 Location/Qualifiers
misc_feature            1..21
                        note = guide RNA primer sequence
source                  1..21
                        mol_type = other DNA
                        organism = synthetic construct
SEQUENCE: 53
aaaccaatgg ctcaggtttg t                                              21

SEQ ID NO: 54           moltype = DNA   length = 24
FEATURE                 Location/Qualifiers
misc_feature            1..24
                        note = guide RNA primer sequence
source                  1..24
                        mol_type = other DNA
                        organism = synthetic construct
SEQUENCE: 54
ttggagcatt tgggggcatt tatg                                           24

SEQ ID NO: 55           moltype = DNA   length = 24
FEATURE                 Location/Qualifiers
misc_feature            1..24
                        note = guide RNA primer sequence
source                  1..24
                        mol_type = other DNA
                        organism = synthetic construct
SEQUENCE: 55
aaaccataaa tgcccccaaa tgct                                           24

SEQ ID NO: 56           moltype = DNA   length = 24
FEATURE                 Location/Qualifiers
misc_feature            1..24
                        note = guide RNA primer sequence
source                  1..24
                        mol_type = other DNA
                        organism = synthetic construct
SEQUENCE: 56
ttggaagtat cctcctccag cagc                                           24

SEQ ID NO: 57           moltype = DNA   length = 24
FEATURE                 Location/Qualifiers
misc_feature            1..24
                        note = guide RNA primer sequence
source                  1..24
                        mol_type = other DNA
                        organism = synthetic construct
SEQUENCE: 57
aaacgctgct ggaggaggat actt                                           24

SEQ ID NO: 58           moltype = DNA   length = 24
FEATURE                 Location/Qualifiers
misc_feature            1..24
                        note = guide RNA primer sequence
source                  1..24
                        mol_type = other DNA
                        organism = synthetic construct
SEQUENCE: 58
ttggacacag ccagttgggg gaag                                           24

SEQ ID NO: 59           moltype = DNA   length = 24
FEATURE                 Location/Qualifiers
misc_feature            1..24
                        note = guide RNA primer sequence
source                  1..24
                        mol_type = other DNA
                        organism = synthetic construct
SEQUENCE: 59
aaaccttccc ccaactggct gtgt                                           24

SEQ ID NO: 60           moltype = DNA   length = 22
FEATURE                 Location/Qualifiers
misc_feature            1..22
                        note = guide RNA primer sequence
source                  1..22
                        mol_type = other DNA
                        organism = synthetic construct
SEQUENCE: 60
ttggccagag tcagctgttc ct                                             22
```

-continued

```
SEQ ID NO: 61         moltype = DNA   length = 22
FEATURE               Location/Qualifiers
misc_feature          1..22
                      note = guide RNA primer sequence
source                1..22
                      mol_type = other DNA
                      organism = synthetic construct
SEQUENCE: 61
aaacaggaac agctgactct gg                                                  22

SEQ ID NO: 62         moltype = DNA   length = 24
FEATURE               Location/Qualifiers
misc_feature          1..24
                      note = guide RNA primer sequence
source                1..24
                      mol_type = other DNA
                      organism = synthetic construct
SEQUENCE: 62
ttgggttttg aggcctcatt tgta                                                24

SEQ ID NO: 63         moltype = DNA   length = 24
FEATURE               Location/Qualifiers
misc_feature          1..24
                      note = guide RNA primer sequence
source                1..24
                      mol_type = other DNA
                      organism = synthetic construct
SEQUENCE: 63
aaactacaaa tgaggcctca aaac                                                24

SEQ ID NO: 64         moltype = DNA   length = 24
FEATURE               Location/Qualifiers
misc_feature          1..24
                      note = guide RNA primer sequence
source                1..24
                      mol_type = other DNA
                      organism = synthetic construct
SEQUENCE: 64
ttggttttg aaaaattacc ttgt                                                 24

SEQ ID NO: 65         moltype = DNA   length = 24
FEATURE               Location/Qualifiers
misc_feature          1..24
                      note = guide RNA primer sequence
source                1..24
                      mol_type = other DNA
                      organism = synthetic construct
SEQUENCE: 65
aaacacaagg taatttttca aaaa                                                24

SEQ ID NO: 66         moltype = DNA   length = 24
FEATURE               Location/Qualifiers
misc_feature          1..24
                      note = guide RNA primer sequence
source                1..24
                      mol_type = other DNA
                      organism = synthetic construct
SEQUENCE: 66
ttggcagagt cctagacatt tcca                                                24

SEQ ID NO: 67         moltype = DNA   length = 24
FEATURE               Location/Qualifiers
misc_feature          1..24
                      note = guide RNA primer sequence
source                1..24
                      mol_type = other DNA
                      organism = synthetic construct
SEQUENCE: 67
aaactggaaa tgtctaggac tctg                                                24

SEQ ID NO: 68         moltype = DNA   length = 24
FEATURE               Location/Qualifiers
misc_feature          1..24
                      note = guide RNA primer sequence
source                1..24
                      mol_type = other DNA
                      organism = synthetic construct
SEQUENCE: 68
ttggtctcac ccttgatagt ttga                                                24
```

```
SEQ ID NO: 69          moltype = DNA  length = 24
FEATURE                Location/Qualifiers
misc_feature           1..24
                       note = guide RNA primer sequence
source                 1..24
                       mol_type = other DNA
                       organism = synthetic construct
SEQUENCE: 69
aaactcaaac tatcaagggt gaga                                         24

SEQ ID NO: 70          moltype = DNA  length = 24
FEATURE                Location/Qualifiers
misc_feature           1..24
                       note = guide RNA primer sequence
source                 1..24
                       mol_type = other DNA
                       organism = synthetic construct
SEQUENCE: 70
ttggggtaaa tctttgaagc caat                                         24

SEQ ID NO: 71          moltype = DNA  length = 24
FEATURE                Location/Qualifiers
misc_feature           1..24
                       note = guide RNA primer sequence
source                 1..24
                       mol_type = other DNA
                       organism = synthetic construct
SEQUENCE: 71
aaacattggc ttcaaagatt tacc                                         24

SEQ ID NO: 72          moltype = DNA  length = 24
FEATURE                Location/Qualifiers
misc_feature           1..24
                       note = guide RNA primer sequence
source                 1..24
                       mol_type = other DNA
                       organism = synthetic construct
SEQUENCE: 72
ttggattttc tacctacggt gtgc                                         24

SEQ ID NO: 73          moltype = DNA  length = 24
FEATURE                Location/Qualifiers
misc_feature           1..24
                       note = guide RNA primer sequence
source                 1..24
                       mol_type = other DNA
                       organism = synthetic construct
SEQUENCE: 73
aaacgcacac cgtaggtaga aaat                                         24

SEQ ID NO: 74          moltype = DNA  length = 24
FEATURE                Location/Qualifiers
misc_feature           1..24
                       note = guide RNA primer sequence
source                 1..24
                       mol_type = other DNA
                       organism = synthetic construct
SEQUENCE: 74
ttggtctcct ggaaggactc tggg                                         24

SEQ ID NO: 75          moltype = DNA  length = 24
FEATURE                Location/Qualifiers
misc_feature           1..24
                       note = guide RNA primer sequence
source                 1..24
                       mol_type = other DNA
                       organism = synthetic construct
SEQUENCE: 75
aaaccccaga gtccttccag gaga                                         24

SEQ ID NO: 76          moltype = DNA  length = 24
FEATURE                Location/Qualifiers
misc_feature           1..24
                       note = guide RNA primer sequence
source                 1..24
                       mol_type = other DNA
                       organism = synthetic construct
SEQUENCE: 76
```

```
ttggtcctcc ttccttgcca acgc                                          24

SEQ ID NO: 77          moltype = DNA   length = 24
FEATURE                Location/Qualifiers
misc_feature           1..24
                       note = guide RNA primer sequence
source                 1..24
                       mol_type = other DNA
                       organism = synthetic construct
SEQUENCE: 77
aaacgcgttg gcaaggaagg agga                                          24

SEQ ID NO: 78          moltype = DNA   length = 24
FEATURE                Location/Qualifiers
misc_feature           1..24
                       note = guide RNA primer sequence
source                 1..24
                       mol_type = other DNA
                       organism = synthetic construct
SEQUENCE: 78
ttggcccgct atttgctgtg ggtt                                          24

SEQ ID NO: 79          moltype = DNA   length = 24
FEATURE                Location/Qualifiers
misc_feature           1..24
                       note = guide RNA primer sequence
source                 1..24
                       mol_type = other DNA
                       organism = synthetic construct
SEQUENCE: 79
aaacaaccca cagcaaatag cggg                                          24

SEQ ID NO: 80          moltype = DNA   length = 22
FEATURE                Location/Qualifiers
misc_feature           1..22
                       note = qPCR primer sequence
source                 1..22
                       mol_type = other DNA
                       organism = synthetic construct
SEQUENCE: 80
caggagtaca tatcggccac ca                                            22

SEQ ID NO: 81          moltype = DNA   length = 23
FEATURE                Location/Qualifiers
misc_feature           1..23
                       note = qPCR primer sequence
source                 1..23
                       mol_type = other DNA
                       organism = synthetic construct
SEQUENCE: 81
gtaggccaag ttgccttgtc cgt                                           23

SEQ ID NO: 82          moltype = DNA   length = 19
FEATURE                Location/Qualifiers
misc_feature           1..19
                       note = qPCR primer sequence
source                 1..19
                       mol_type = other DNA
                       organism = synthetic construct
SEQUENCE: 82
gccttccttc ttgggtatg                                                19

SEQ ID NO: 83          moltype = DNA   length = 19
FEATURE                Location/Qualifiers
misc_feature           1..19
                       note = qPCR primer sequence
source                 1..19
                       mol_type = other DNA
                       organism = synthetic construct
SEQUENCE: 83
accaccagac aacactgtg                                                19

SEQ ID NO: 84          moltype = DNA   length = 25
FEATURE                Location/Qualifiers
misc_feature           1..25
                       note = qPCR primer sequence
source                 1..25
                       mol_type = other DNA
                       organism = synthetic construct
```

```
SEQUENCE: 84
gctatactca gaaggtccag aaggc                                              25

SEQ ID NO: 85           moltype = DNA  length = 23
FEATURE                 Location/Qualifiers
misc_feature            1..23
                        note = qPCR primer sequence
source                  1..23
                        mol_type = other DNA
                        organism = synthetic construct
SEQUENCE: 85
tcagagaatg agggtagcac agc                                                23

SEQ ID NO: 86           moltype = DNA  length = 22
FEATURE                 Location/Qualifiers
misc_feature            1..22
                        note = qPCR primer sequence
source                  1..22
                        mol_type = other DNA
                        organism = synthetic construct
SEQUENCE: 86
actttctgga gccctcctgg ca                                                 22

SEQ ID NO: 87           moltype = DNA  length = 21
FEATURE                 Location/Qualifiers
misc_feature            1..21
                        note = qPCR primer sequence
source                  1..21
                        mol_type = other DNA
                        organism = synthetic construct
SEQUENCE: 87
tttgttgcac tacacagcat g                                                  21

SEQ ID NO: 88           moltype = DNA  length = 20
FEATURE                 Location/Qualifiers
misc_feature            1..20
                        note = qPCR primer sequence
source                  1..20
                        mol_type = other DNA
                        organism = synthetic construct
SEQUENCE: 88
aggggattct ccgtggtaca                                                    20

SEQ ID NO: 89           moltype = DNA  length = 20
FEATURE                 Location/Qualifiers
misc_feature            1..20
                        note = qPCR primer sequence
source                  1..20
                        mol_type = other DNA
                        organism = synthetic construct
SEQUENCE: 89
ctcttcccct gtactcgcaa                                                    20

SEQ ID NO: 90           moltype = DNA  length = 20
FEATURE                 Location/Qualifiers
misc_feature            1..20
                        note = qPCR primer sequence
source                  1..20
                        mol_type = other DNA
                        organism = synthetic construct
SEQUENCE: 90
cgagacgcgg atggatgtaa                                                    20

SEQ ID NO: 91           moltype = DNA  length = 20
FEATURE                 Location/Qualifiers
misc_feature            1..20
                        note = qPCR primer sequence
source                  1..20
                        mol_type = other DNA
                        organism = synthetic construct
SEQUENCE: 91
gcggcactttt tcttccgatg                                                   20

SEQ ID NO: 92           moltype = DNA  length = 21
FEATURE                 Location/Qualifiers
misc_feature            1..21
                        note = qPCR primer sequence
source                  1..21
                        mol_type = other DNA
```

```
                              organism = synthetic construct
SEQUENCE: 92
ccagaccctg catgagcttt a                                              21

SEQ ID NO: 93             moltype = DNA   length = 20
FEATURE                   Location/Qualifiers
misc_feature              1..20
                          note = qPCR primer sequence
source                    1..20
                          mol_type = other DNA
                          organism = synthetic construct
SEQUENCE: 93
aaacagccac aggactcgaa                                                20

SEQ ID NO: 94             moltype = DNA   length = 22
FEATURE                   Location/Qualifiers
misc_feature              1..22
                          note = qPCR primer sequence
source                    1..22
                          mol_type = other DNA
                          organism = synthetic construct
SEQUENCE: 94
tctgttaagg gagcagccat gc                                             22

SEQ ID NO: 95             moltype = DNA   length = 21
FEATURE                   Location/Qualifiers
misc_feature              1..21
                          note = qPCR primer sequence
source                    1..21
                          mol_type = other DNA
                          organism = synthetic construct
SEQUENCE: 95
ggatattagc tgcaggaggc g                                              21

SEQ ID NO: 96             moltype = DNA   length = 20
FEATURE                   Location/Qualifiers
misc_feature              1..20
                          note = qPCR primer sequence
source                    1..20
                          mol_type = other DNA
                          organism = synthetic construct
SEQUENCE: 96
cagagagcca aggcaatga                                                 20

SEQ ID NO: 97             moltype = DNA   length = 20
FEATURE                   Location/Qualifiers
misc_feature              1..20
                          note = qPCR primer sequence
source                    1..20
                          mol_type = other DNA
                          organism = synthetic construct
SEQUENCE: 97
ggaccccact ttacagccat                                                20

SEQ ID NO: 98             moltype = DNA   length = 21
FEATURE                   Location/Qualifiers
misc_feature              1..21
                          note = qPCR primer sequence
source                    1..21
                          mol_type = other DNA
                          organism = synthetic construct
SEQUENCE: 98
gcgttctctt tggaaaggtg t                                              21

SEQ ID NO: 99             moltype = DNA   length = 20
FEATURE                   Location/Qualifiers
misc_feature              1..20
                          note = qPCR primer sequence
source                    1..20
                          mol_type = other DNA
                          organism = synthetic construct
SEQUENCE: 99
ttgttgtcgg cttcctccac                                                20

SEQ ID NO: 100            moltype = DNA   length = 20
FEATURE                   Location/Qualifiers
misc_feature              1..20
                          note = qPCR primer sequence
source                    1..20
```

```
                        mol_type = other DNA
                        organism = synthetic construct
SEQUENCE: 100
atctctggag tccatgcgga                                                 20

SEQ ID NO: 101          moltype = DNA  length = 20
FEATURE                 Location/Qualifiers
misc_feature            1..20
                        note = qPCR primer sequence
source                  1..20
                        mol_type = other DNA
                        organism = synthetic construct
SEQUENCE: 101
caaagtccct tggctgctgt                                                 20

SEQ ID NO: 102          moltype = DNA  length = 20
FEATURE                 Location/Qualifiers
misc_feature            1..20
                        note = qPCR primer sequence
source                  1..20
                        mol_type = other DNA
                        organism = synthetic construct
SEQUENCE: 102
caggtgtgca aatcttgggt                                                 20

SEQ ID NO: 103          moltype = DNA  length = 20
FEATURE                 Location/Qualifiers
misc_feature            1..20
                        note = qPCR primer sequence
source                  1..20
                        mol_type = other DNA
                        organism = synthetic construct
SEQUENCE: 103
tggtggcttg caatcatctg                                                 20

SEQ ID NO: 104          moltype = DNA  length = 20
FEATURE                 Location/Qualifiers
misc_feature            1..20
                        note = qPCR primer sequence
source                  1..20
                        mol_type = other DNA
                        organism = synthetic construct
SEQUENCE: 104
tgagtccttg ctcggttctt                                                 20

SEQ ID NO: 105          moltype = DNA  length = 20
FEATURE                 Location/Qualifiers
misc_feature            1..20
                        note = qPCR primer sequence
source                  1..20
                        mol_type = other DNA
                        organism = synthetic construct
SEQUENCE: 105
caggcacatt gctgtgagtt                                                 20

SEQ ID NO: 106          moltype = DNA  length = 20
FEATURE                 Location/Qualifiers
misc_feature            1..20
                        note = qPCR primer sequence
source                  1..20
                        mol_type = other DNA
                        organism = synthetic construct
SEQUENCE: 106
tggccttgta ctgttgcaac                                                 20

SEQ ID NO: 107          moltype = DNA  length = 20
FEATURE                 Location/Qualifiers
misc_feature            1..20
                        note = qPCR primer sequence
source                  1..20
                        mol_type = other DNA
                        organism = synthetic construct
SEQUENCE: 107
agtgtcacta tggccacctt                                                 20

SEQ ID NO: 108          moltype = DNA  length = 20
FEATURE                 Location/Qualifiers
misc_feature            1..20
                        note = qPCR primer sequence
```

```
source                      1..20
                            mol_type = other DNA
                            organism = synthetic construct
SEQUENCE: 108
aatcttccct tgggggtatg                                                    20

SEQ ID NO: 109              moltype = DNA   length = 20
FEATURE                     Location/Qualifiers
misc_feature                1..20
                            note = qPCR primer sequence
source                      1..20
                            mol_type = other DNA
                            organism = synthetic construct
SEQUENCE: 109
taaggagcca tgctgtaccc                                                    20

SEQ ID NO: 110              moltype = DNA   length = 30
FEATURE                     Location/Qualifiers
misc_feature                1..30
                            note = bisulfite sequencing primer sequence
source                      1..30
                            mol_type = other DNA
                            organism = synthetic construct
SEQUENCE: 110
gaagttttg tgaaataagt tttgggtagg                                          30

SEQ ID NO: 111              moltype = DNA   length = 24
FEATURE                     Location/Qualifiers
misc_feature                1..24
                            note = bisulfite sequencing primer sequence
source                      1..24
                            mol_type = other DNA
                            organism = synthetic construct
SEQUENCE: 111
ctcgaccaaa ataaacacca cccc                                               24

SEQ ID NO: 112              moltype = DNA   length = 25
FEATURE                     Location/Qualifiers
misc_feature                1..25
                            note = bisulfite sequencing primer sequence
source                      1..25
                            mol_type = other DNA
                            organism = synthetic construct
SEQUENCE: 112
cgagttgtag ggtgtttggt aattg                                              25

SEQ ID NO: 113              moltype = DNA   length = 25
FEATURE                     Location/Qualifiers
misc_feature                1..25
                            note = bisulfite sequencing primer sequence
source                      1..25
                            mol_type = other DNA
                            organism = synthetic construct
SEQUENCE: 113
acgttacaaa tcactcctca aaacc                                              25

SEQ ID NO: 114              moltype = DNA   length = 27
FEATURE                     Location/Qualifiers
misc_feature                1..27
                            note = bisulfite sequencing primer sequence
source                      1..27
                            mol_type = other DNA
                            organism = synthetic construct
SEQUENCE: 114
ggttgtagga gaagaaatg agattag                                             27

SEQ ID NO: 115              moltype = DNA   length = 24
FEATURE                     Location/Qualifiers
misc_feature                1..24
                            note = bisulfite sequencing primer sequence
source                      1..24
                            mol_type = other DNA
                            organism = synthetic construct
SEQUENCE: 115
ctcgaccaaa ataaacacca cccc                                               24

SEQ ID NO: 116              moltype = DNA   length = 25
FEATURE                     Location/Qualifiers
misc_feature                1..25
```

```
                        note = bisulfite sequencing primer sequence
source                  1..25
                        mol_type = other DNA
                        organism = synthetic construct
SEQUENCE: 116
tagtttaagg gcgtagaggt ttgag                                             25

SEQ ID NO: 117          moltype = DNA   length = 25
FEATURE                 Location/Qualifiers
misc_feature            1..25
                        note = bisulfite sequencing primer sequence
source                  1..25
                        mol_type = other DNA
                        organism = synthetic construct
SEQUENCE: 117
acgttacaaa tcactcctca aaacc                                             25

SEQ ID NO: 118          moltype = DNA   length = 26
FEATURE                 Location/Qualifiers
misc_feature            1..26
                        note = bisulfite sequencing primer sequence
source                  1..26
                        mol_type = other DNA
                        organism = synthetic construct
SEQUENCE: 118
ttatttattg gttggattag aggggt                                            26

SEQ ID NO: 119          moltype = DNA   length = 24
FEATURE                 Location/Qualifiers
misc_feature            1..24
                        note = bisulfite sequencing primer sequence
source                  1..24
                        mol_type = other DNA
                        organism = synthetic construct
SEQUENCE: 119
catatacttc ccaacaaacc aaac                                              24

SEQ ID NO: 120          moltype = DNA   length = 26
FEATURE                 Location/Qualifiers
misc_feature            1..26
                        note = bisulfite sequencing primer sequence
source                  1..26
                        mol_type = other DNA
                        organism = synthetic construct
SEQUENCE: 120
gtgaatttgt taggattgga agtgaa                                            26

SEQ ID NO: 121          moltype = DNA   length = 30
FEATURE                 Location/Qualifiers
misc_feature            1..30
                        note = bisulfite sequencing primer sequence
source                  1..30
                        mol_type = other DNA
                        organism = synthetic construct
SEQUENCE: 121
actcttacta tatatttccc cttctcttca                                        30

SEQ ID NO: 122          moltype = DNA   length = 24
FEATURE                 Location/Qualifiers
misc_feature            1..24
                        note = bisulfite sequencing primer sequence
source                  1..24
                        mol_type = other DNA
                        organism = synthetic construct
SEQUENCE: 122
ggtttgaggt aggtaggggt tagg                                              24

SEQ ID NO: 123          moltype = DNA   length = 30
FEATURE                 Location/Qualifiers
misc_feature            1..30
                        note = bisulfite sequencing primer sequence
source                  1..30
                        mol_type = other DNA
                        organism = synthetic construct
SEQUENCE: 123
ccaactcact ttctcccaaa attacactaa                                        30

SEQ ID NO: 124          moltype = DNA   length = 29
FEATURE                 Location/Qualifiers
```

```
misc_feature          1..29
                      note = bisulfite sequencing primer sequence
source                1..29
                      mol_type = other DNA
                      organism = synthetic construct
SEQUENCE: 124
gtagaatttg ttaggtgggt gaaaggaag                                    29

SEQ ID NO: 125        moltype = DNA   length = 30
FEATURE               Location/Qualifiers
misc_feature          1..30
                      note = bisulfite sequencing primer sequence
source                1..30
                      mol_type = other DNA
                      organism = synthetic construct
SEQUENCE: 125
ccttcctccc aaaatactaa cctctcatac                                   30

SEQ ID NO: 126        moltype = DNA   length = 28
FEATURE               Location/Qualifiers
misc_feature          1..28
                      note = bisulfite sequencing primer sequence
source                1..28
                      mol_type = other DNA
                      organism = synthetic construct
SEQUENCE: 126
gatttttggg tattgtattg gaagtggg                                     28

SEQ ID NO: 127        moltype = DNA   length = 32
FEATURE               Location/Qualifiers
misc_feature          1..32
                      note = bisulfite sequencing primer sequence
source                1..32
                      mol_type = other DNA
                      organism = synthetic construct
SEQUENCE: 127
ccaaaatatt tattccctct actttaaaac ac                                32

SEQ ID NO: 128        moltype = DNA   length = 27
FEATURE               Location/Qualifiers
misc_feature          1..27
                      note = bisulfite sequencing primer sequence
source                1..27
                      mol_type = other DNA
                      organism = synthetic construct
SEQUENCE: 128
tttaggatag gatgggagta ttggttg                                      27

SEQ ID NO: 129        moltype = DNA   length = 34
FEATURE               Location/Qualifiers
misc_feature          1..34
                      note = bisulfite sequencing primer sequence
source                1..34
                      mol_type = other DNA
                      organism = synthetic construct
SEQUENCE: 129
caaaatcact caaaatcatc ctattacata aaac                              34

SEQ ID NO: 130        moltype = DNA   length = 38
FEATURE               Location/Qualifiers
misc_feature          1..38
                      note = bisulfite sequencing primer sequence
source                1..38
                      mol_type = other DNA
                      organism = synthetic construct
SEQUENCE: 130
attaagaggt tagggttttt ttagttggtt ttgtattg                          38

SEQ ID NO: 131        moltype = DNA   length = 37
FEATURE               Location/Qualifiers
misc_feature          1..37
                      note = bisulfite sequencing primer sequence
source                1..37
                      mol_type = other DNA
                      organism = synthetic construct
SEQUENCE: 131
aaaaaaaacc ttcatcacat aataaactaa accaacc                           37

SEQ ID NO: 132        moltype = DNA   length = 28
```

```
FEATURE                 Location/Qualifiers
misc_feature            1..28
                        note = bisulfite sequencing primer sequence
source                  1..28
                        mol_type = other DNA
                        organism = synthetic construct
SEQUENCE: 132
gaaaggatgt aattagaggg tttttggg                                       28

SEQ ID NO: 133          moltype = DNA  length = 25
FEATURE                 Location/Qualifiers
misc_feature            1..25
                        note = bisulfite sequencing primer sequence
source                  1..25
                        mol_type = other DNA
                        organism = synthetic construct
SEQUENCE: 133
aatcctttct caaacccct tcctc                                           25

SEQ ID NO: 134          moltype = DNA  length = 29
FEATURE                 Location/Qualifiers
misc_feature            1..29
                        note = bisulfite sequencing primer sequence
source                  1..29
                        mol_type = other DNA
                        organism = synthetic construct
SEQUENCE: 134
gtggggtttt tataattagg aaagaatag                                      29

SEQ ID NO: 135          moltype = DNA  length = 25
FEATURE                 Location/Qualifiers
misc_feature            1..25
                        note = bisulfite sequencing primer sequence
source                  1..25
                        mol_type = other DNA
                        organism = synthetic construct
SEQUENCE: 135
attacaaacc ccttctaaaa actcc                                          25

SEQ ID NO: 136          moltype = DNA  length = 23
FEATURE                 Location/Qualifiers
misc_feature            1..23
                        note = bisulfite sequencing primer sequence
source                  1..23
                        mol_type = other DNA
                        organism = synthetic construct
SEQUENCE: 136
atttggtagt taggaaggtt gta                                            23

SEQ ID NO: 137          moltype = DNA  length = 22
FEATURE                 Location/Qualifiers
misc_feature            1..22
                        note = bisulfite sequencing primer sequence
source                  1..22
                        mol_type = other DNA
                        organism = synthetic construct
SEQUENCE: 137
ccaaaaaacc tcccctttt cc                                              22

SEQ ID NO: 138          moltype = DNA  length = 25
FEATURE                 Location/Qualifiers
misc_feature            1..25
                        note = bisulfite sequencing primer sequence
source                  1..25
                        mol_type = other DNA
                        organism = synthetic construct
SEQUENCE: 138
gtggattttt ttaaggagtg tgttg                                          25

SEQ ID NO: 139          moltype = DNA  length = 35
FEATURE                 Location/Qualifiers
misc_feature            1..35
                        note = bisulfite sequencing primer sequence
source                  1..35
                        mol_type = other DNA
                        organism = synthetic construct
SEQUENCE: 139
cttctaatat ctaaactcaa caacaatata tccac                               35
```

-continued

```
SEQ ID NO: 140           moltype = DNA   length = 27
FEATURE                  Location/Qualifiers
misc_feature             1..27
                         note = bisulfite sequencing primer sequence
source                   1..27
                         mol_type = other DNA
                         organism = synthetic construct
SEQUENCE: 140
ggagatttag gaagtatggg gttagtg                                        27

SEQ ID NO: 141           moltype = DNA   length = 28
FEATURE                  Location/Qualifiers
misc_feature             1..28
                         note = bisulfite sequencing primer sequence
source                   1..28
                         mol_type = other DNA
                         organism = synthetic construct
SEQUENCE: 141
aaaacctcct ctcttacttt tctacttc                                       28

SEQ ID NO: 142           moltype = DNA   length = 27
FEATURE                  Location/Qualifiers
misc_feature             1..27
                         note = 3C assay primer sequence
source                   1..27
                         mol_type = other DNA
                         organism = synthetic construct
SEQUENCE: 142
cacatcttca aagcaaacac tattgtt                                        27

SEQ ID NO: 143           moltype = DNA   length = 18
FEATURE                  Location/Qualifiers
misc_feature             1..18
                         note = 3C assay primer sequence
source                   1..18
                         mol_type = other DNA
                         organism = synthetic construct
SEQUENCE: 143
ttcctggaac ctgggcaa                                                  18

SEQ ID NO: 144           moltype = DNA   length = 23
FEATURE                  Location/Qualifiers
misc_feature             1..23
                         note = 3C assay primer sequence
source                   1..23
                         mol_type = other DNA
                         organism = synthetic construct
SEQUENCE: 144
tgatacagca cagctttcct tca                                            23

SEQ ID NO: 145           moltype = DNA   length = 28
FEATURE                  Location/Qualifiers
misc_feature             1..28
                         note = 3C assay primer sequence
source                   1..28
                         mol_type = other DNA
                         organism = synthetic construct
SEQUENCE: 145
cagattttt atttccttca gttctgtg                                        28

SEQ ID NO: 146           moltype = DNA   length = 30
FEATURE                  Location/Qualifiers
misc_feature             1..30
                         note = 3C assay primer sequence
source                   1..30
                         mol_type = other DNA
                         organism = synthetic construct
SEQUENCE: 146
tctcctaccc attgcttctc tgctacctgc                                     30

SEQ ID NO: 147           moltype = DNA   length = 26
FEATURE                  Location/Qualifiers
misc_feature             1..26
                         note = 3C assay primer sequence
source                   1..26
                         mol_type = other DNA
                         organism = synthetic construct
SEQUENCE: 147
tgaagtttga ggagatgcca tggttg                                         26
```

```
SEQ ID NO: 148          moltype = DNA   length = 27
FEATURE                 Location/Qualifiers
misc_feature            1..27
                        note = 3C assay primer sequence
source                  1..27
                        mol_type = other DNA
                        organism = synthetic construct
SEQUENCE: 148
cacgctaggc tgaacactgt gtcactg                                           27

SEQ ID NO: 149          moltype = DNA   length = 20
FEATURE                 Location/Qualifiers
misc_feature            1..20
                        note = 3C assay primer sequence
source                  1..20
                        mol_type = other DNA
                        organism = synthetic construct
SEQUENCE: 149
aggatggctc agcggttaag                                                   20

SEQ ID NO: 150          moltype = DNA   length = 22
FEATURE                 Location/Qualifiers
misc_feature            1..22
                        note = 3C assay primer sequence
source                  1..22
                        mol_type = other DNA
                        organism = synthetic construct
SEQUENCE: 150
agggctcacc ttcagtcaag tt                                                22

SEQ ID NO: 151          moltype = DNA   length = 29
FEATURE                 Location/Qualifiers
misc_feature            1..29
                        note = 3C assay primer sequence
source                  1..29
                        mol_type = other DNA
                        organism = synthetic construct
SEQUENCE: 151
cggcctgtct actttagcct cagactcca                                         29

SEQ ID NO: 152          moltype = DNA   length = 28
FEATURE                 Location/Qualifiers
misc_feature            1..28
                        note = 3C assay primer sequence
source                  1..28
                        mol_type = other DNA
                        organism = synthetic construct
SEQUENCE: 152
tgccttccct cttacaagga gttttctt                                          28

SEQ ID NO: 153          moltype = DNA   length = 27
FEATURE                 Location/Qualifiers
misc_feature            1..27
                        note = 3C assay primer sequence
source                  1..27
                        mol_type = other DNA
                        organism = synthetic construct
SEQUENCE: 153
cggttaagaa gagctcttct ggaggcc                                           27

SEQ ID NO: 154          moltype = DNA   length = 23
FEATURE                 Location/Qualifiers
misc_feature            1..23
                        note = 3C assay primer sequence
source                  1..23
                        mol_type = other DNA
                        organism = synthetic construct
SEQUENCE: 154
gggagtgact ctctgtccat tca                                               23

SEQ ID NO: 155          moltype = DNA   length = 22
FEATURE                 Location/Qualifiers
misc_feature            1..22
                        note = 3C assay primer sequence
source                  1..22
                        mol_type = other DNA
                        organism = synthetic construct
SEQUENCE: 155
```

```
atttgtgtgg cctcttgttt ga                                               22

SEQ ID NO: 156              moltype = DNA   length = 18
FEATURE                     Location/Qualifiers
misc_feature                1..18
                            note = 3C assay primer sequence
source                      1..18
                            mol_type = other DNA
                            organism = synthetic construct
SEQUENCE: 156
tccaggcccc gcgtgtcc                                                    18

SEQ ID NO: 157              moltype = AA   length = 2309
FEATURE                     Location/Qualifiers
REGION                      1..2309
                            note = dCAS9-Dnmt3a (protein)
source                      1..2309
                            mol_type = protein
                            organism = synthetic construct
SEQUENCE: 157
MDKKYSIGLA IGTNSVGWAV ITDEYKVPSK KFKVLGNTDR HSIKKNLIGA LLFDSGETAE    60
ATRLKRTARR RYTRRKNRIC YLQEIFSNEM AKVDDSFFHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEHP VENTQLQNEK LYLYYLQNGR DMYVDQELDI NRLSDYDVDA   840
IVPQSFLKDD SIDNKVLTRS DKNRGKSDNV PSEEVVKKMK NYWRQLLNAK LITQRKFDNL   900
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDEG ADPKKKRKVD  1380
PKKKRKVDPK KKRKVGSMPA MPSSGPGDTS SSAAEREEDR KDGEEQEEPR GKEERQEPST  1440
TARKVGRPGR KRKHPPVESG DTPKDPAVIS KSPSMAQDSG ASELLPNGDL EKRSEPQPEE  1500
GSPAGGQKGG APAEGEGAAE TLPEASRAVE NGCCTPKEGR GAPAEAGKEQ KETNIESMKM  1560
EGSRGRLRGG LGWESSLRQR PMPRLTFQAG DPYYISKRKR DEWLARWKRE AEKKAKVIAG  1620
MNAVEENQGP GESQKVEEAS PPAVQQPTDP ASPTVATTPE PVGSDAGDKN ATKAGDDEPE  1680
YEDGRGFGIG ELVWGKLRGF SWWPGRIVSW WMTGRSRAAE GTRWVMWFGD GKFSVVCVEK  1740
LMPLSSFCSA FHQATYNKQP MYRKAIYEVL QVASSRAGKL FPVCHDSDES DTAKAVEVQN  1800
KPMIEWALGG FQPSGPKGLE PPEEEKNPYK EVYTDMWVEP EAAAYAPPPP AKKPRKSTAE  1860
KPKVKEIIDE RTRERLVYEV RQKCRNIEDI CISCGSLNVT LEHPLFVGGM CQNCKNCFLE  1920
CAYQYDDDGY QSYCTICCGG REVLMCGNNN CCRCFCVECV DLLVGPGAAQ AAIKEDPWNC  1980
YMCGHKGTYG LLRRREDWPS RLQMFFANNH DQEFDPPKVY PPVPAEKRKP IRVLSLFDGI  2040
ATGLLVLKDL GIQVDRYIAS EVCEDSITVG MVRHQGKIMY VGDVRSVTQK HIQEWGPFDL  2100
VIGGSPCNDL SIVNPARKGL YEGTGRLFFE FYRLLHDARP KEGDDRPFFW LFENVVAMGV  2160
SDKRDISRFL ESNPVMIDAK EVSAAHRARY FWGNLPGMNR PLASTVNDKL ELQECLEHGR  2220
IAKFSKVRTI TTRSNSIKQG KDQHFPVFMN EKEDILWCTE MERVFGFPVH YTDVSNMSRL  2280
ARQRLLGRSW SVPVIRHLFA PLKEYFACV                                    2309

SEQ ID NO: 158              moltype = AA   length = 2309
FEATURE                     Location/Qualifiers
REGION                      1..2309
                            note = dCAS9-Dnmt3a_IM
source                      1..2309
                            mol_type = protein
                            organism = unidentified
SEQUENCE: 158
MDKKYSIGLA IGTNSVGWAV ITDEYKVPSK KFKVLGNTDR HSIKKNLIGA LLFDSGETAE    60
ATRLKRTARR RYTRRKNRIC YLQEIFSNEM AKVDDSFFHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
```

```
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEHP VENTQLQNEK LYLYYLQNGR DMYVDQELDI NRLSDYDVDA   840
IVPQSFLKDD SIDNKVLTRS DKNRGKSDNV PSEEVVKKMK NYWRQLLNAK LITQRKFDNL   900
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDEG ADPKKKRKVD  1380
PKKKRKVDPK KKRKVGSMPA MPSSGPGDTS SSAAEREEDR KDGEEQEEPR GKEERQEPST  1440
TARKVGRPGR KRKHPPVESG DTPKDPAVIS KSPSMAQDSG ASELLPNGDL EKRSEPQPEE  1500
GSPAGGQKGG APAEGEGAAE TLPEASRAVE NGCCTPKEGR GAPAEAGKEQ KETNIESMKM  1560
EGSRGRLRGG LGWESSLRQR PMPRLTFQAG DPYYISKRKR DEWLARWKRE AEKKAKVIAG  1620
MNAVEENQGP GESQKVEEAS PPAVQQPTDP ASPTVATTPE PVGSDAGDKN ATKAGDDEPE  1680
YEDGRGFGIG ELVWGKLRGF SWWPGRIVSW WMTGRSRAAE GTRWVMWFGD GKFSVVCVEK  1740
LMPLSSFCSA FHQATYNKQP MYRKAIYEVL QVASSRAGKL FPVCHDSDES DTAKAVEVQN  1800
KPMIEWALGG FQPSGPKGLE PPEEEKNPYK EVYTDMWVEP EAAAYAPPPP AKKPRKSTAE  1860
KPKVKEIIDE RTRERLVYEV RQKCRNIEDI CISCGSLNVT LEHPLFVGGM CQNCKNCFLE  1920
CAYQYDDDGY QSYCTICCGG REVLMCGNNN CCRCFCVRCV DLLVGPGAAQ AAIKEDPWNC  1980
YMCGHKGTYG LLRRREDWPS RLQMFFANNH DQEFDPPKVY PPVPAEKRKP IRVLSLFDGI  2040
ATGLLVLKDL GIQVDRYIAS AVCEDSITVG MVRHQGKIMY VGDVRSVTQK HIQEWGPFDL  2100
VIGGSPCNDL SIVNPARKGL YEGTGRLFFE FYRLLHDARP KEGDDRPFFW LFANVVAMGV  2160
SDKRDISRFL ESNPVMIDAK EVSAAHRARY FWGNLPGMNR PLASTVNDKL ELQECLEHGR  2220
IAKFSKVRTI TTRSNSIKQG KDQHFPVFMN EKEDILWCTE MERVFGFPVH YTDVSNMSRL  2280
ARQRLLGRSW SVPVIRHLFA PLKEYFACV                                  2309

SEQ ID NO: 159           moltype = AA   length = 2115
FEATURE                  Location/Qualifiers
REGION                   1..2115
                         note = dCAS9-Tet1CD
source                   1..2115
                         mol_type = protein
                         organism = unidentified
SEQUENCE: 159
MDKKYSIGLA IGTNSVGWAV ITDEYKVPSK KFKVLGNTDR HSIKKNLIGA LLFDSGETAE    60
ATRLKRTARR RYTRRKNRIC YLQEIFSNEM AKVDDSFFHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEHP VENTQLQNEK LYLYYLQNGR DMYVDQELDI NRLSDYDVDA   840
IVPQSFLKDD SIDNKVLTRS DKNRGKSDNV PSEEVVKKMK NYWRQLLNAK LITQRKFDNL   900
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDEG ADPKKKRKVD  1380
PKKKRKVDPK KKRKVGSLPT CSCLDRVIQK DKGPYYTHLG AGPSVAAVRE IMENRYGQKG  1440
NAIRIEIVVY TGKEGKSSHG CPIAKWVLRR SSDEEKVLCL VRQRTGHHCP TAVMVVLIMV  1500
WDGIPLPMAD RLYTELTENL KSYNGHPTDR RCTLNENRTC TCQGIDPETC GASFSFGCSW  1560
SMYFNGCKFG RSPSPRRFRI DPSSPLHEKN LEDNLQSLAT RLAPIYKQYA PVAYQNQVEY  1620
ENVARECRLG SKEGRPFSGV TACLDFCAHP HRDIHNMNNG STVVCTLTRE DNRSLGVIPQ  1680
DEQLHVLPLY KLSDTEFGS KEGMEAKIKS GAIEVLAPRR KKRTCFTQPV PRSGKKRAAM  1740
MTEVLAHKIR AVEKKPIPRI KRKNNSTTTN NSKPSSLPTL GSNTETVQPE VKSETEPHFI  1800
LKSSDNTKTY SLMPSAPHPV KEASPGFSWS PKTASATPAP LKNDATASCG FSERSSTPHC  1860
TMPSGRLSGA NAAADGPGI SQLGEVAPLP TLSAPVMEPL INSEPSTGVT EPLTPHQPNH  1920
QPSFLTSPQD LASSPMEEDE QHSEADEPPS DEPLSDDPLS PAEEKLPHID EYWSDSEHIF  1980
LDANIGGVAI APAHGSVLIE CARRELHATT PVEHPNRNHP TRLSLVFYQH KNLNKPQHGF  2040
ELNKIKFEAK EAKNKKMKAS EQKDQAANEG PEQSSEVNEL NQIPSHKALT LTHDNVVTVS  2100
PYALTHVAGP YNHWV                                                  2115

SEQ ID NO: 160           moltype = AA   length = 2115
FEATURE                  Location/Qualifiers
REGION                   1..2115
                         note = dCAS9-Tet1CD_IM
source                   1..2115
```

```
                        mol_type = protein
                        organism = unidentified
SEQUENCE: 160
MDKKYSIGLA IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDA  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKHYLDEII EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGDEG ADPKKKRKVD 1380
PKKKRKVDPK KKRKVGSLPT CSCLDRVIQK DKGPYYTHLG AGPSVAAVRE IMENRYGQKG 1440
NAIRIEIVVY TGKEGKSSHG CPIAKWVLRR SSDEEKVLCL VRQRTGHHCP TAVMVVLIMV 1500
WDGIPLPMAD RLYTELTENL KSYNGHPTDR RCTLNENRTC TCQGIDPETC GASFSFGCSW 1560
SMYFNGCKFG RSPSPRRFRI DPSSPLHEKN LEDNLQSLAT RLAPIYKQYA PVAYQNGYKY 1620
ENVARECRLG SKEGRPFSGV TACLDFCAHP YRAIHNMNNG STVVCTLTRE DNRSLGVIPQ 1680
DEQLHVLPLY KLSDTDEFGS KEGMEAKIKS GAIEVLAPRR KKRTCFTQPV PRSGKKRAAM 1740
MTEVLAHKIR AVEKKPIPRI KRKNNSTTTN NSKPSSLPTL GSNTETVQPE VKSETEPHFI 1800
LKSSDNTKTY SLMPSAPHPV KEASPGFSWS PKTASATPAP KLNDATASCG FSERSSTPHC 1860
TMPSGRLSGA NAAADGPGI SQLGEVAPLP TLSAPVMEPL INSEPSTGVT EPLTPHQPNH 1920
QPSFLTSPQD LASSPMEEDE QHSEADEPPS DEPLSDDPLS PAEEKLPHID EYWSDSEHIF 1980
LDANIGGVAI APAHGSVLIE CARRELHATT PVEHPNRNHP TRLSLVFYQH KNLNKPQHGF 2040
ELNKIKFEAK EAKNKKMKAS EQKDQAANEG PEQSSEVNEL NQIPSHKALT LTHDNVVTVS 2100
PYALTHVAGP YNHWV                                                 2115

SEQ ID NO: 161          moltype = AA   length = 2573
FEATURE                 Location/Qualifiers
REGION                  1..2573
                        note = dCAS-Dnmt3a-P2A-BFP
source                  1..2573
                        mol_type = protein
                        organism = unidentified
SEQUENCE: 161
MDKKYSIGLA IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDA  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKHYLDEII EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGDEG ADPKKKRKVD 1380
PKKKRKVDPK KKRKVGSMPA MPSSGPGDTS SSAAEREEDR KDGEEQEEPR GKEERQEPST 1440
TARKVGRPGR KRKHPPVESG DTPKDPAVIS KSPSMAQDSG ASELLPNGDL EKRSEPQPEE 1500
GSPAGGQKGG APAEGEGAAE TLPEASRAVE NGCCTPKEGR GAPAEAGKEQ KETNIESKSM 1560
EGSRGRLRGG LGWESSLRQR PMPRLTFQAG DPYYISKRKR DEWLARWKRE AEKKAKVIAG 1620
MNAVEENQGP GESQKVEEAS PPAVQQPTDP ASPTVATTPE PVGSDAGDKN ATKAGDDEPE 1680
YEDGRGFGIG ELVWGKLRGF SWWPGRIVSW WMTGRSRAAE GTRWVMWFGD GKFSVVCVEK 1740
LMPLSSFCSA FHQATYNKQP MYRKAIYEVL QVASSRAGKL FPVCHDSDES DTAKAVEVQN 1800
KPMIEWALGG FQPSGPKGLE PPEEEKNPYK EVYTDMWVEP EAAAYAPPPP AKKPRKSTAE 1860
```

```
KPKVKEIIDE RTRERLVYEV RQKCRNIEDI CISCGSLNVT LEHPLFVGGM CQNCKNCFLE  1920
CAYQYDDDGY QSYCTICCGG REVLMCGNNN CCRCFCVECV DLLVGPGAAQ AAIKEDPWNC  1980
YMCGHKGTYG LLRRREDWPS RLQMFFANNH DQEFDPPKVY PPVPAEKRKP IRVLSLFDGI  2040
ATGLLVLKDL GIQVDRYIAS EVCEDSITVG MVRHQGKIMY VGDVRSVTQK HIQEWGPFDL  2100
VIGGSPCNDL SIVNPARKGL YEGTGRLFFE FYRLLHDARP KEGDDRPFFW LFENVVAMGV  2160
SDKRDISRFL ESNPVMIDAK EVSAAHRARY FWGNLPGMNR PLASTVNDKL ELQECLEHGR  2220
IAKFSKVRTI TTRSNSIKQG KDQHFPVFMN EKEDILWCTE MERVFGFPVH YTDVSNMSRL  2280
ARQRLLGRSW SVPVIRHLFA PLKEYFACVE FAYPYDVPDY AATNFSLLKQ AGDVEENPGP  2340
MSELIKENMH MKLYMEGTVD NHHFKCTSEG EGKPYEGTQT MRIKVVEGGP LPFAFDILAT  2400
SFLYGSKTFI NHTQGIPDFF KQSFPEGFTW ERVTTYEDGG VLTATQDTSL QDGCLIYNVK  2460
IRGVNFTSNG PVMQKKTLGW EAFTETLYPA DGGLEGRNDM ALKLVGGSHL IANIKTTYRS  2520
KKPAKNLKMP GVYYVDYRLE RIKEANNETY VEQHEVAVAR YCDLPSKLGH KLN         2573

SEQ ID NO: 162          moltype = DNA  length = 579
FEATURE                 Location/Qualifiers
misc_feature            1..579
                        note = Daz1-Snrpn locus
source                  1..579
                        mol_type = other DNA
                        organism = unidentified
SEQUENCE: 162
cgactagaga gcaggccgcc tggccgggcc cccaccctct cagccacaga gaagggagtc   60
cgggtgcatg tggaaggcgc acctcatgcc tcacgggccg gcccgtcagc catcaggaca  120
gtcccgctcc ccccccccg ccccaaata aatgcccgaa atccggtaca aaggacacag    180
cagtgaccag accacacgag agaatatccc tccccgtgga ataggcagt gtgagcgtct   240
cgtaggctac agaaacaagc taggccagct gagagaacta gaacactcaa gctcagagaa  300
acggggccta cctacctaca gcagagccga gctgtagggt gcttggcaag acgctcaaat  360
ttccgcagta ggaatgctca agcattcctt ttggtagctg cctttggca ggacattccg   420
gtcagaggga cagagacccc tgcattgcgg caaaaatgtg cgcatgtgca gccattgcct  480
gggacgcatg cgtagggagc cgcgcgacaa acctgagcca ttgcggcaag actagcgcag  540
agaggagagg gagccggaga tgccagacgc ttggttctg                         579

SEQ ID NO: 163          moltype = DNA  length = 274
FEATURE                 Location/Qualifiers
misc_feature            1..274
                        note = Gapdh-Snrpn locus
source                  1..274
                        mol_type = other DNA
                        organism = unidentified
SEQUENCE: 163
ctacgtgcac ccgtaaagcc gcgagtagct gggcctctct ccaagacgct caaatttccg   60
cagtaggaat gctcaagcat tccttttggt agctgccttt tggcaggaca ttccggtcag  120
agggacagag acccctgcat tgcggcaaaa atgtgcgcat gcagcgccat tgcctgggac  180
gcatgcgtag ggagccgcgc gacaaacctg agccattgcg gcaagactag cgcagagagg  240
agagggagcc ggagatgcca gacgcttggt tctg                              274

SEQ ID NO: 164          moltype = DNA  length = 199
FEATURE                 Location/Qualifiers
misc_feature            1..199
                        note = BDNF IV locus
source                  1..199
                        mol_type = other DNA
                        organism = unidentified
SEQUENCE: 164
ctacaaagca tgcaatgccc tggaacggaa cctaataaaa gatgtatcat taaatgcgcg   60
gaactgactg gtaacgtgca ctagagtgtc tatcgaggca gaggaggtat catatgacag  120
ctcacgtcaa ggcagcgtgg agccctctcg tggactccca cccactccca caccgaggag  180
aggactgctc tcgctgccg                                               199

SEQ ID NO: 165          moltype = DNA  length = 253
FEATURE                 Location/Qualifiers
misc_feature            1..253
                        note = MyoD DE (DMR-5) locus
source                  1..253
                        mol_type = other DNA
                        organism = unidentified
SEQUENCE: 165
ccacagcatt tgggggcatt tatgggtctt cctataaact tctgagacag taattttatc   60
ctgcttcttt cggccaagta tcctcctcca gcagctggtc acaaagccag ttaatctccc  120
agagtgctca gcttaaaacc cgtgactcac aacacagcca gttggggggaa gggacagcc  180
gcctccaaac gtggcgccca gactcagctg ttcctgggtc ttctccggtt tctctagctc  240
aggcctaggg ctg                                                     253

SEQ ID NO: 166          moltype = DNA  length = 543
FEATURE                 Location/Qualifiers
misc_feature            1..543
                        note = CTCF miR290 locus
source                  1..543
                        mol_type = other DNA
```

```
                        organism = unidentified
SEQUENCE: 166
gttttgaggc ctcatttgta aggtgcctta tacctttagc cccagcccac ttttttttcc    60
ccctgctgta taaaattcag gtgtgagtac aatttttctt tttaaagatt tataagtgtt   120
ctgtagctat cttcagattc acccaaagaa ggcattggat cccattacag atgattgcaa   180
gccaccatgt agttgctggg aattgaactc aggacctctg acttaaccac tccagccctt   240
gagtacaatt tttgaaaaat taccttgtgg gtctttatgc tgtgacttgg ccagtagatg   300
gcagtcttgg tccatggaaa tgtctaggac tctggatatt tttccttttc tgtggtcttt   360
actgatcttc aaacctgcta accagccaat ccccgtccta aattatctgc gtggaatcta   420
catcaaaccc agtgagctcc atcaaaggtt gagtgtttag gtctcaagca gaacaatttt   480
gtcaacctgc acttactggg cctcctgacc taagacggtc ccatgtaaca ggatgacctt   540
gag                                                                  543

SEQ ID NO: 167         moltype = DNA  length = 461
FEATURE                Location/Qualifiers
misc_feature           1..461
                       note = CTCF Pou5f1 locus
source                 1..461
                       mol_type = other DNA
                       organism = unidentified
SEQUENCE: 167
tctcaccctt gatagtttga gggatatgag caaattacac ggttatcaga aggtggccat    60
agtgacactg aaaattggcc cattggcttc aaagatttac caaagtaccg tccgtatttt   120
ctacctacgg tgtgctggag cctagaggac actaggggc gcgctgagct cgcggaagcc   180
acccagagtc cttccaggag actcccttaa aggttgatca aattgttctt tgccaaactg   240
aattttatcat aaaaattata ctttattttg tattactttg tgtacatggg tgttttgcct   300
tcacagatgc gtctggtgca cctgagaagc cagaaaagag aacaggagtg aacaggtttg   360
tggggggctga cactcaaact cgaggactct gggaaagcat cgagtgctct taaccattga   420
gccatctctc cagcccatct gttttctttt gccggaggaa g                       461
```

UNITED STATES PATENT AND TRADEMARK OFFICE
CERTIFICATE OF CORRECTION

PATENT NO. : 12,060,588 B2
APPLICATION NO. : 17/858758
DATED : August 13, 2024
INVENTOR(S) : Rudolf Jaenisch et al.

Page 1 of 1

It is certified that error appears in the above-identified patent and that said Letters Patent is hereby corrected as shown below:

In the Claims

Claim 1, Column 121, Line 34, "activity;" should read --activity; and--;

Claim 1, Column 121, Lines 35-36, "wherein the genomic sequence comprises" should read --wherein the one or more genomic sequences comprise--;

Claim 3, Column 121, Line 42, "the genomic sequence" should read --the one or more genomic sequences--;

Claim 4, Column 121, Line 47, "the genomic sequences" should read --the at least two genomic sequences--;

Claim 5, Column 121, Lines 50-51, "the genomic sequence further comprises" should read --the one or more genomic sequences further comprise--.

Signed and Sealed this
Third Day of December, 2024

Katherine Kelly Vidal
*Director of the United States Patent and Trademark Office*